United States Patent
Waugh et al.

(10) Patent No.: US 9,278,089 B2
(45) Date of Patent: Mar. 8, 2016

(54) METHOD OF TREATING HCV INFECTION WITH A SMALL MOLECULE CHK2 INHIBITOR

(71) Applicants: The United States of America, as Represented by The Secretary, Department of Health and Human Service, Bethesda, MD (US); Provid Pharmaceuticals, Inc., Monmouth Junction, NJ (US)

(72) Inventors: David Waugh, Walkersville, MD (US); Christopher Self, West Caldwell, NJ (US); Guangtao Zhang, Princeton, NJ (US); Yves Pommier, Bethesda, MD (US); Robert H. Shoemaker, Boyds, MD (US); Michael Currens, Frederick, MD (US); John Cardellina, Walkersville, MD (US); Andrew Jobson, Coventry (GB); George Lountos, Frederick, MD (US); Dominic Scudiero, Frederick, MD (US)

(73) Assignee: THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 0 days.

(21) Appl. No.: 14/353,976

(22) PCT Filed: Oct. 26, 2012

(86) PCT No.: PCT/US2012/062212
§ 371 (c)(1),
(2) Date: Apr. 24, 2014

(87) PCT Pub. No.: WO2013/063462
PCT Pub. Date: May 2, 2013

(65) Prior Publication Data
US 2014/0294767 A1 Oct. 2, 2014

Related U.S. Application Data

(60) Provisional application No. 61/551,742, filed on Oct. 26, 2011.

(51) Int. Cl.
| | | |
|---|---|---|
| *A61K 31/454* | (2006.01) | |
| *A61K 45/06* | (2006.01) | |
| *C07D 403/12* | (2006.01) | |
| *C12N 9/96* | (2006.01) | |
| *A61K 31/4184* | (2006.01) | |
| *A61K 31/404* | (2006.01) | |
| *A61K 31/4178* | (2006.01) | |
| *A61K 31/4709* | (2006.01) | |

(Continued)

(52) U.S. Cl.
CPC .......... *A61K 31/4184* (2013.01); *A61K 31/404* (2013.01); *A61K 31/4178* (2013.01); *A61K 31/454* (2013.01); *A61K 31/4709* (2013.01); *A61K 45/06* (2013.01); *C07D 209/42* (2013.01); *C07D 401/12* (2013.01); *C07D 403/12* (2013.01); *C12N 9/96* (2013.01)

(58) Field of Classification Search
CPC ............ A61K 31/454; A61K 31/4184; A61K 31/1404; A61K 45/06; A61K 31/4709; A61K 31/4178; C07D 403/12; C07D 401/12; C12N 9/96
USPC ................. 514/313, 323, 394, 397, 414, 419; 424/85.4; 435/188
See application file for complete search history.

(56) References Cited

U.S. PATENT DOCUMENTS

| | | |
|---|---|---|
| 5,684,032 A | 11/1997 | Elliott et al. |
| 5,981,762 A | 11/1999 | Froshauer et al. |

(Continued)

FOREIGN PATENT DOCUMENTS

| | | |
|---|---|---|
| DE | 102005025906 A1 | 12/2006 |
| WO | 2008156573 A1 | 12/2008 |

OTHER PUBLICATIONS

Ariumi et al., "The DNA Damage Sensors Ataxia-Telangiectasia Mutated Kinase and Checkpoint Kinase 2 Are Required for Hepatitis C Virus RNA Replication", Journal of Virology, vol. 82, No. 19, p. 9639-9646 (Oct. 2008).

(Continued)

*Primary Examiner* — Raymond Henley, III
(74) *Attorney, Agent, or Firm* — Cantor Colburn LLP

(57) ABSTRACT

A method of treating an Hepatitis C Virus infection in a patient, comprising providing a therapeutically effective amount, to a patient in need thereof, of a compound of Formula (I) or a pharmaceutically acceptable salt thereof, wherein: $G_1$ is a group of the formula or where n is 0, 1, 2, 3, or 4 and Het is a 5- or 6-membered heteroaryl group containing 1 to 4 heteroatoms independently chosen from N, O, and S, which Het is optionally substituted.

(I)

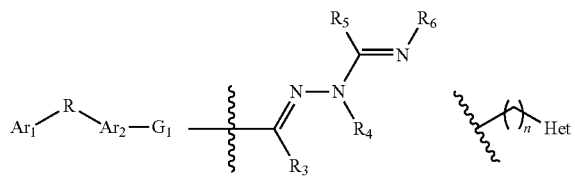

23 Claims, 4 Drawing Sheets

(51) Int. Cl.
*C07D 401/12* (2006.01)
*C07D 209/42* (2006.01)

(56) References Cited

U.S. PATENT DOCUMENTS

| | | | |
|---|---|---|---|
| 2007/0004711 | A1 | 1/2007 | Zhang et al. |
| 2009/0018141 | A1 | 1/2009 | Shoemaker et al. |
| 2009/0041720 | A1 | 2/2009 | Wang et al. |
| 2009/0041721 | A1 | 2/2009 | Wang et al. |
| 2009/0170890 | A1 | 7/2009 | Kinch et al. |

OTHER PUBLICATIONS

International Preliminary Report on Patentability; International Application No. PCT/US2012/062212; International Filing Date Oct. 26, 2012; 10 pages.

International Search Report; International Application No. PCT/US2012/062212; Oct. 26, 2012; 7 pages.

Jobson A, et al, "Identification of a Bis-guanylhydrazone [4,4*-Diacetyldiphenylurea-bis (guanylhydrazone) ; NSC 109555] as a Novel Chemotype for Inhibition of Chk2 Kinase", Molecular Pharmacol., 72(4): 876-84 (Oct. 2007).

Jobson, A, "Cellular Inhibition of Checkpoint Kinase 2 (Chk2) and Potentiation of Camptothecins and Radiation by the Novel Chk2 Inhibitor PV1019 [7-Nitro-1H-indole-2-carboxylic acid {4[1-(guanidinohydrazone)-ethyl]-phenyl}-amide]", J Pharmacol. Exp. The.

Lountos, G, et al, "Crystal Structure of Checkpoint Kinase 2 in Complex With NSC 109555, a Potent and Selective Inhibitor", Protein Sci., 18(1):92-100 (2009).

Lountos, G., et al, "Structural Characterization of Inhibitor Complexes With Checkpoint Kinase 2 (Chk2), a Drug Target for Cancer Therapy", Journal of Structural Biology, 292-301 (2011).

Lountos, G., et al, "X-ray Structures of Checkpoint Kinase 2 in Complex With Inhibitors That Target Its Gatekeeper-Dependent Hydrophobic Pocket", EEBS Letters, 3245-3249 (2011).

Written Opinion; International Application No. PCT/US2012/062212; Oct. 26, 2012; 9 pages.

Jobson, A, "Cellular Inhibition of Checkpoint Kinase 2 (Chk2) and Potentiation of Camptothecins and Radiation by the Novel Chk2 Inhibitor PV1019 [7-Nitro-1H-indole-2-carboxylic acid {4-[1-(guanidinohydrazone)-ethyl]-phenyl}-amide]", J Pharmacol. Exp. Ther., 816-826 (2009).

METHOD OF TREATING HCV INFECTION WITH A SMALL MOLECULE CHK2 INHIBITOR

CROSS REFERENCE TO RELATED APPLICATIONS

This application is a National Stage of International Patent Application No. PCT/US2012/062212 filed Oct. 26, 2012, which claims the benefit of U.S. Provisional Application No. 61/551,742, filed 26 Oct. 2011, both of which are incorporated herein by reference in their entirety.

STATEMENT OF GOVERNMENT INTEREST

Research supporting this disclosure was performed in part with support from United States of America as represented by the Secretary of the Department of Health and Human Services. The federal government has certain rights in this disclosure.

FIELD OF THE DISCLOSURE

The present disclosure provides a method of treating an HCV (Hepatitis C Virus) infection in a patient comprising administering a therapeutically effective amount of a Chk2 (Checkpoint kinase 2) inhibitor to a patient infected with an HCV virus. In certain embodiments, the Chk2 inhibitor is a hydrazine-carbamimide containing compound of Formula I (shown below). The Chk2 inhibitor may be the only active agent or may be administered together with one or more additional active agents that are not CHk2 inhibitors. The disclosure also provides methods of inhibiting HCV replication in vitro and in vivo by contacting HCV infected cells with a Chk2 inhibitor.

BACKGROUND

An estimated 3% of the world's population is infected with the hepatitis C virus. Of those exposed to HCV, 80% to 85% become chronically infected, at least 30% develop cirrhosis of the liver, and 1-4% develop hepatocellular carcinoma. Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. Chronic HCV infection is the most common cause of liver transplantation in the U.S., Australia, and most of Europe. Hepatitis C causes an estimated 10,000 to 12,000 deaths annually in the United States. While the acute phase of HCV infection is usually associated with mild symptoms, some evidence suggests that only about 15% to 20% of infected people will spontaneously clear HCV.

HCV is an enveloped, single-stranded RNA virus that contains a positive-stranded genome of about 9.6 kb. HCV is classified as a member of the Hepacivirus genus of the family Flaviviridae. At least 4 strains of HCV, GT-1-GT-4, have been characterized.

The HCV lifecycle includes entry into host cells; translation of the HCV genome, polyprotein processing, and replicase complex assembly; RNA replication, and virion assembly and release. Translation of the HCV RNA genome yields a more than 3000 amino acid long polyprotein that is processed by at least two cellular and two viral proteases. The HCV polyprotein is: NH2-C-E1-E2-p7-NS2-NS3-NS4A-NS4B-NS5A-NS5B-COOH.

The cellular signal peptidase and signal peptide peptidase have been reported to be responsible for cleavage of the N-terminal third of the polyprotein (C-E1-E2-p7) from the nonstructural proteins (NS2-NS3-NS4A-NS4B-NS5A-NS5B). The NS2-NS3 protease mediates a first cis cleavage at the NS2-NS3 site. The NS3-NS4A protease then mediates a second cis-cleavage at the NS3-NS4A junction. The NS3-NS4A complex then cleaves at three downstream sites to separate the remaining nonstructural proteins. Accurate processing of the polyprotein is asserted to be essential for forming an active HCV replicase complex.

Once the polyprotein has been cleaved, the replicase complex comprising at least the NS3-NS5B nonstructural proteins assembles. The replicase complex is cytoplasmic and membrane-associated. Major enzymatic activities in the replicase complex include serine protease activity and NTPase helicase activity in NS3, and RNA-dependent RNA polymerase activity of NS5B. In the RNA replication process, a complementary negative strand copy of the genomic RNA is produced. The negative strand copy is used as a template to synthesize additional positive strand genomic RNAs that may participate in translation, replication, packaging, or any combination thereof to produce progeny virus. Assembly of a functional replicase complex has been described as a component of the HCV replication mechanism. U.S. Provisional Application No. 60/669,872 "Pharmaceutical Compositions and Methods of Inhibiting HCV Replication" filed Apr. 11, 2005, is hereby incorporated by reference in its entirety for its disclosure related to assembly of the replicase complex.

Current treatment of hepatitis C infection typically includes administration of an interferon, such as pegylated interferon (IFN), in combination with ribavirin. The success of current therapies as measured by sustained virologic response (SVR) depends on the strain of HCV with which the patient is infected and the patient's adherence to the treatment regimen. Only 50% of patients infected with HCV strain GT-1 exhibit a sustained virological response. Direct acting antiviral agents such as BI 201335 (Boehringer Ingelheim), TMC435 (Tibotec), Telaprevir (Vertex), and Boceprevir (Merck) may be used for treatment of chronic HCV. Each of these drugs, may be used in combination with an immune modulator, such as interferon, or an additional anti-viral agent. Due to the high mutation rate of HCV and dearth of effective HCV therapeutics, new therapies are needed. Compounds that inhibit HCV replication via a different mechanism than those currently employed are particularly desirable.

HCV infection and the expression of the HCV non-structural protein NS3 has been proposed as a cause of double-stranded DNA breaks, possibly leading to the enhanced mutation rate of cellular genes in HCV-infected cells. DNA damage sensors, such as ataxia-telangiectasia mutated kinase (ATM), ATM- and Rad3-related kinase (ATR), poly(ADP-ribose) polymerase 1 (PARP-1) and checkpoint kinase 2 (Chk2) play central roles in the response to genotoxic stress. Ariumi, et al. determined that replication of genome-length HCV RNA and subgenomic HCV replicon RNA was suppressed in ATM- and Chk2-knockdown cells. (*J. Virology*, (2008) 82(19): 9639-9646). Ariumi identified the ATM-signaling pathway as a possible target for novel therapeutics useful for treating chronic HCV infection.

The present disclosure fulfills the need for HCV replication inhibitors that act via a novel mechanism, in this case Chk2 inhibition, and provides additional advantages, which are described herein.

SUMMARY

Chk2 inhibitors useful as HCV replication inhibitors are provided herein. The compounds of Formula I provided in this disclosure possess antiviral activity.

The disclosure provides certain novel compounds of Formula I, useful as Chk2 inhibitors. In a one aspect the disclosure provides a method of treating a hepatitis C (HCV) infection in a patient, comprising providing a therapeutically effective amount, to a patient in need thereof, of a Chk2 inhibitor. The disclosure also provides a method of inhibiting replication of a Hepatitis C Virus comprising contacting the virus, in vivo or in vitro with a concentration a Chk2 inhibitor sufficient to inhibit Hepatitis C Virus replication in vitro. The Chk2 inhibitor may be compound of Formula I

Formula I or a pharmaceutically acceptable salt thereof.

Within Formula I the variables $Ar_1$, R, $Ar_2$, and $G_1$ carry the following definitions.

$G_1$ is a group of the formula

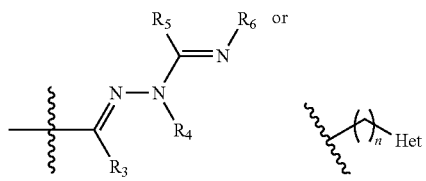

where n is 0, 1, 2, 3, or 4 and Het is a 5- or 6-membered heteroaryl group containing 1 to 4 heteroatoms independently chosen from N, O, and S; which Het is optionally substituted.

$Ar_1$ is a 6,6-fused or 6,5 bicyclic aromatic ring system containing only carbon ring atoms or containing 1, 2, or 3 nitrogen ring atoms with remaining atoms being carbon, which $Ar_1$ is optionally substituted.

$Ar_2$ is phenyl, a 6-membered heteroaryl ring containing 1 or 2 nitrogen ring atoms, or a 6,5 bicyclic aromatic ring system containing 1, 2, or 3 nitrogen atoms, with remaining atoms being carbon, which $Ar_2$ is optionally substituted.

R is a group of the formula —NH(C=O)— or —(O=C) NH—; $R_3$ is hydrogen or $C_1$-$C_6$alkyl.

$R_3$ is taken together with an $Ar_2$ substituent to form a 5- or 6-membered unsaturated or aromatic $R_3$/$Ar_2$ ring having 0, 1, or 2 heteroatoms independently chosen from N, O, and S, which $R_3$/$Ar_2$ ring is optionally substituted.

$R_4$ is hydrogen or $C_1$-$C_6$alkyl.

$R_5$ is amino, —NHOH, or optionally substituted mono- or di-alkylamino, and $R_6$ is hydrogen or hydroxyl; or $R_5$ and $R_6$ are taken together to form a 5 or 6-membered heterocyclic ring, which is unsaturated or aromatic and which contains 0, 1 or 2 additional heteroatoms chosen from N, S, and O, which 5 or 6-membered heterocyclic ring is optionally substituted.

Within Formula I the variables $Ar_1$, $Ar_2$, $R_3$, and $R_4$ carry the following definitions.

$Ar_1$ is a 6,6-fused bicyclic aromatic ring system containing only carbon ring atoms or containing 1, 2, or 3 nitrogen ring atoms with remaining atoms being carbon, which $Ar_1$ is optionally substituted.

$Ar_2$ is phenyl or a 6-membered heteroaryl ring containing 1 or 2 nitrogen ring atoms, which $Ar_2$ is optionally substituted.

$R_3$ is hydrogen or $C_1$-$C_6$alkyl.

$R_4$ is hydroxyl or amino.

The disclosure also provides a method of inhibiting replication of an HCV, in vivo or in vitro, comprising contacting HCV infected cells with a therapeutically effective amount of a compound of Formula I.

In either of the preceding methods the compound or salt of Formula I may be administered as the only active agent or together with a therapeutically effective amount of at least one additional active agent. The additional active agent can be another compound of Formula I or an active agent that is not a compound of Formula I such as an interferon or non-Chk2 directed anti-HCV agent.

The disclosure provides compounds of Formula I that are potent and/or selective inhibitors of Hepatitis C virus replication. Without being bound to any particular theory it is believed the present compounds are potent and selective inhibitors of Chk2 Pharmaceutical compositions containing one or more compounds or salts of Formula I, together with pharmaceutically acceptable carriers are also provided herein.

Certain compounds of Formula I disclosed herein exhibit good activity in an HCV replication assay, such as the HCV replicon assay set forth in Example 2, which follows. Preferred compounds of Formula I exhibit an $EC_{50}$ of about 10 micromolar or less, or more preferably an $EC_{50}$ of about 1.5 micromolar or less. Preferred compounds Chk2 inhibitors that inhibit HCV replication exhibit a cytotoxicity $IC_{50}$ of greater than 10 micromolar in a standard assay of cytotoxicity such as the assay of Example 3, which follows. Preferred Chk2 inhibitor/anti-HCV compounds also exhibit $IC_{50}/EC_{50}$ (Selectivity ratio) of 4 or greater.

BRIEF DESCRIPTION OF THE DRAWINGS

The present patent application contains at least one drawing executed in color. Copies of this application with color drawing(s) will be provided by the Office upon request and payment of the necessary fee.

DETAILED DESCRIPTION

Chemical Description and Terminology

Figure 1:
FIG. 1 shows the structure of the HCV Replicon from the Huh7 ET cell line. The HCV RNA replicon ET contains the 5' NTR (IRES) of HCV (5') which drives the production of a firefly luciferase (Luc), ubiquitin (Ubiq), and neomycin phosphotransferase (Neo) fusion protein. Ubiquitin cleavage releases the LUC and Neo genes. The EMCV IRES element (E-I) controls the translation of the HCV structural proteins NS3-NS5. The NS3 protein cleaves the HCV polyprotein to release the mature NS3, NS4A, NS4B, NS5A, and NS5B proteins that are required for HCV replication. At the 3' end of the replicon is the authentic 3' NTR of HCV.

Prior to setting forth the invention in detail, it may be helpful to provide definitions of certain terms to be used in this disclosure. Compounds are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well as all pharmaceutically acceptable salts of the compound.

The term "compounds of Formula I" encompasses all compounds that satisfy Formula I, including any enantiomers, racemates and stereoisomers, as well as all pharmaceutically acceptable salts of such compounds. The phrase "a compound of Formula I" includes all subgeneric groups of Formula I, including compounds of Formula IA, IB, and IC, and also includes pharmaceutically acceptable salts of a compound of Formula I, unless clearly contraindicated by the context in which this phrase is used.

The terms "a" and "an" do not denote a limitation of quantity, but rather denote the presence of at least one of the referenced item. The term "or" means "and/or." The open-ended transitional phrase "comprising" encompasses the intermediate transitional phrase "consisting essentially of" and the close-ended phrase "consisting of" Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in any suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including a compound disclosed herein), element, or mixture that when administered to a patient, alone or in combination with another compound, element, or mixture, confers, directly or indirectly, a physiological effect on the patient. The indirect physiological effect may occur via a metabolite or other indirect mechanism.

A dash ("-") that is not between two letters or symbols is used to indicate a point of attachment for a substituent. For example, —(C=O)OH is attached through carbon of the keto (C=O) group.

"Alkanoyl" is an alkyl group as defined herein, covalently bound to the group it substitutes by a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

"Alkyl" is a branched or straight chain saturated aliphatic hydrocarbon group, having the specified number of carbon atoms, generally from 1 to about 12 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, (mono- or di-$C_1$-$C_4$alkylamino)$C_0$-$C_4$ alkyl, the indicated group, in this case alkylamino, is either directly bound by a single covalent bond ($C_0$alkyl), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Haloalkyl" includes both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined herein attached through an oxygen bridge (oxygen of an alcohol radical).

"Halo" or "halogen" indicates any of fluoro, chloro, bromo, and iodo.

"Mono- and/or di-alkylamino" is a secondary or tertiary alkyl amino group, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino. In some instances the mono- and/or di-alkyl amino group is attached to the group it substitutes via a $C_0$-$C_4$alkyl linker "Optionally substituted mono- and/or di-alkylamino" includes mono- and di-alkylamino groups as described in this paragraph, optionally substituted with the substituents chosen from the group of optional substituents listed in this section. In certain embodiments the "optionally substituted mono- and/or di-alkylamino" optionally contains one or more double or triple bonds in its alkyl groups, and is optionally substituted one or more substituents independently chosen from halogen, hydroxyl, amino, oxo, $C_1$-$C_4$ alkoxy, $C_1$-$C_4$alkylamino, and $C_3$-$C_7$cycloalkyl.

The term "substituted" means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example, a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is listed as a possible substituent the point of attachment of this substituent to the core structure is in the alkyl portion.

Groups that may be present on a "substituted" or "optionally substituted" position include, but are not limited to, e.g., halogen; cyano; hydroxyl; nitro; azido; alkanoyl (such as a $C_2$-$C_6$ alkanoyl group); carboxamide; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms.

In certain embodiments, an "optionally substituted" group is substituted with one or more substituents independently selected from halogen, hydroxyl, amino, nitro, cyano, oxo, —NHOH, —COOH, —CONH$_2$, $C_1$-$C_6$alkyl, $C_1$-$C_6$alkoxy, $C_2$-$C_6$alkanoyl, $C_2$-$C_6$alkylester, $C_3$-$C_7$cycloalkyl, phenyl, (mono- or di-$C_1$-$C_4$alkylamino)$C_0$-$C_4$alkyl, which may be optionally substituted, $C_1$-$C_2$haloalkyl, and $C_1$-$C_2$haloalkoxy.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt of Formula I, and at least one other substance, such as a carrier. Pharmaceutical compositions optional contain one or more additional active agents. When specified, pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided. To be pharmaceutically acceptable a carrier must be safe, non-toxic and neither biologically nor otherwise undesirable.

A "patient" is a human or non-human animal in need of medical treatment. Medical treatment can include treatment of an existing condition, such as a disease or disorder, prophylactic or preventative treatment, or diagnostic treatment. In certain embodiments disclosed herein, "medical treatment" means treatment of existing acute or chronic HCV infections. In certain embodiments, the patient is a human patient.

"Provided together with at least one additional active agent" means the Chk2 inhibitor and the additional active agent(s) are provided simultaneously in a single dosage form, provided concomitantly in separate dosage forms, or provided in separate dosage forms for administration separated by some amount of time that is within the time in which both the Chk2 inhibitor and the at least one additional active agent are within the blood stream of a patient. In certain embodiments, the Chk2 inhibitor and the additional active agent need not be prescribed for a patient by the same medical care worker. In certain embodiments, the additional active agent or agents need not require a prescription. Administration of the Chk2 inhibitor or the at least one additional active agent can occur via any appropriate route, for example, oral tablets, oral capsules, oral liquids, inhalation, injection, suppositories or topical contact.

"Treatment" as used herein includes providing a compound of Formula I, either as the only active agent or together with at least one additional active agent sufficient to: (a) prevent a disease or a symptom of a disease from occurring in a patient who may be predisposed to the disease but has not yet been diagnosed as having it (e.g. including diseases that may be associated with or caused by a primary disease (as in liver fibrosis that can result in the context of chronic HCV infection); (b) inhibiting the disease, i.e. arresting its development; and (c) relieving the disease, i.e., causing regression of the disease. "Treating" and "treatment" also means providing a therapeutically effective amount of a Chk2 inhibitor as the only active agent or together with at least one additional active agent to a patient having or susceptible to a hepatitis C infection.

A "therapeutically effective amount" of a pharmaceutical composition/combination means an amount effective, when administered to a patient, to provide a therapeutic benefit such as an amelioration of symptoms, e.g., an amount effective to decrease the symptoms of a HCV infection. For example, a patient infected with HCV may present elevated levels of certain liver enzymes, including AST and ALT. Normal levels of AST are from 5 to 40 units per liter of serum (the liquid part of the blood) and normal levels of ALT are from 7 to 56 units per liter of serum. A therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues. One method of determining treatment efficacy includes measuring HCV RNA levels by a conventional method for determining viral RNA levels such as the Roche TaqMan assay. In certain preferred embodiments treatment reduces HCV RNA levels below the limit of quantitation (30 IU/mL, as measured by the Roche TaqMan® assay) or more preferably below the limit of detection (10 IU/mL, Roche TaqMan).

A significant increase or reduction in the detectable level of virus or viral antibodies is any detectable change that is statistically significant in a standard parametric test of statistical significance such as Student's T-test, where p<0.05.

Chemical Description

The disclosure provides a method of treating HCV infection in a patient, comprising administering a therapeutically effective amount of a Chk2 inhibitor to a patient in need of such treatment. Chk2 inhibitors have been disclosed previously. Chk2 inhibitors particularly useful for treating HCV include compounds disclosed in U.S. application Ser. No. 11/989,737 filed 3 Sep. 2009, which is hereby incorporated by reference at pages 12-14 for its disclosure of particular Chk2 inhibitor compounds and at pages 2-5 for its disclosure of a class of Chk2 inhibitor compounds. Chk2 inhibitors have also been disclosed in US 2009/0018141 (Ser. No. 13/557,508) filed 9 Jun. 2009, which is hereby incorporated by reference at paragraphs [0008]-[0009], [0054]-[0133], and [0135]-[0209] for its general description of Chk2 inhibitors and at paragraph [0210] (TABLE I) for its disclosure of specific Chk2 inhibitors.

Formula I includes all subformulae thereof. In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral HPLC column.

Where a compound exists in various tautomeric forms, the invention is not limited to any one of the specific tautomers, but rather includes all tautomeric forms.

The present disclosure includes all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The Chk2 inhibitors disclosed herein as useful for treating HCV infection include compounds and salts of Formula I, where

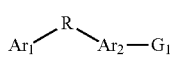

Formula I wherein in Formula I, $G_1$ is a group of the formula

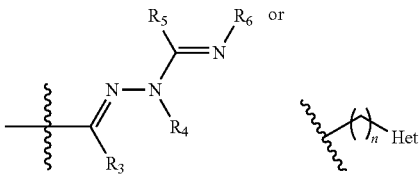

and the variables $Ar_1$, $Ar_3$, and R carry the definitions set forth in the "SUMMARY" section. Alternatively the variables carry any of the definitions set forth below. Any combination of the variables that results in a stable compound is within the scope of the disclosure.

(1) R is —NH(C=O)—.
(2) R is —(C=O)NH—.
(3) $G_1$ is a group of the formula

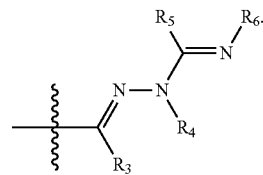

(4) $G_1$ is a group of the formula

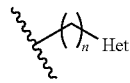

where n is 0, 1, 2, 3, or 4 and Het is a 5- or 6-membered heteroaryl group containing 1 to 3 heteroatoms independently chosen from N, O, and S; which Het is optionally substituted.

(4) $G_1$ is a group of the formula

where n is 0, 1, 2, 3, or 4 and Het is a 5- or 6-membered heteroaryl group containing 1 to 3 heteroatoms independently chosen from N, O, and S; which Het is optionally substituted with amino, —NHOH, or optionally substituted (mono- or di-$C_1$-$C_6$alkylamino)$C_0$-$C_4$alkyl.

(5) Het is a basic heteroaryl group or Het is a heteroaryl group that is substituted with a basic amino substituent such as an amino, NHOH, or optionally substituted mono- or di-$C_1$-$C_6$alkylamino)$C_0$-$C_4$alkyl.

(6) $G_1$ carries the definition set forth in (4) except n is 0 or 1 and Het is an optionally substituted imidazolyl group. In certain embodiments, the imidazolyl group is substituted with 0 to 2 substituents independently chosen from halogen, hydroxyl, amino, $C_1$-$C_4$alkyl, $C_1$-$C_4$alkoxy, and (mono- and di-$C_1$-$C_4$alkylamino)$C_0$-$C_2$alkyl.

(7) $Ar_1$ and $Ar_1$ are independently chosen from quinolinyl, isoquinolinyl, benzimidazolyl, indolyl, naphthyl, phenyl, pyridyl, and pyrimidinyl groups, wherein:

(i) $Ar_1$ is unsubstituted or substituted with one or more substituents independently chosen from halogen, hydroxyl, amino, nitro, cyano, —COOH, —CONH$_2$, $C_1$-$C_6$alkyl, $C_1$-$C_6$alkoxy, $C_2$-$C_6$alkanoyl, $C_3$-$C_7$cycloalkyl, 5- to 7-membered heterocycloalkyl, (mono- or di-$C_1$-$C_4$alkylamino)$C_0$-$C_4$alkyl, $C_1$-$C_2$haloalkyl, and $C_1$-$C_2$haloalkoxy; and (ii) $Ar_2$ is unsubstituted or substituted with one or more substituents independently chosen from halogen, hydroxyl, amino, nitro, cyano, $C_1$-$C_4$alkyl, $C_1$-$C_4$alkoxy, (mono- or di-$C_1$-$C_4$alkylamino)$C_0$-$C_4$alkyl, $C_1$-$C_2$haloalkyl, and $C_1$-$C_2$haloalkoxy.

(8) $A_1$ is chosen from quinolinyl, isoquinolinyl, benzimidazolyl, indolyl, naphthyl, phenyl, pyridyl, and pyrimidinyl groups, each of which is unsubstituted or substituted with one or more substituents independently chosen from halogen, hydroxyl, amino, nitro, cyano, —COOH, —CONH$_2$, $C_1$-$C_6$alkyl, $C_1$-$C_6$alkoxy, $C_2$-$C_6$alkanoyl, $C_3$-$C_7$cycloalkyl, 5- to 7-membered heterocycloalkyl, (mono- or di-$C_1$-$C_4$alkylamino)$C_0$-$C_4$alkyl, $C_1$-$C_2$haloalkyl, and $C_1$-$C_2$haloalkoxy; and $Ar_2$ is imidazolyl, which is unsubstituted or substituted with one or more substituents independently chosen from halogen, hydroxyl, nitro, amino, $C_1$-$C_2$alkyl, $C_1$-$C_2$alkoxy, (mono- or di-$C_1$-$C_2$alkylamino)$C_0$-$C_2$alkyl, $C_1$-$C_2$haloalkyl, and $C_1$-$C_2$haloalkoxy.

(9) The compound is a compound of Formula IA-IC.

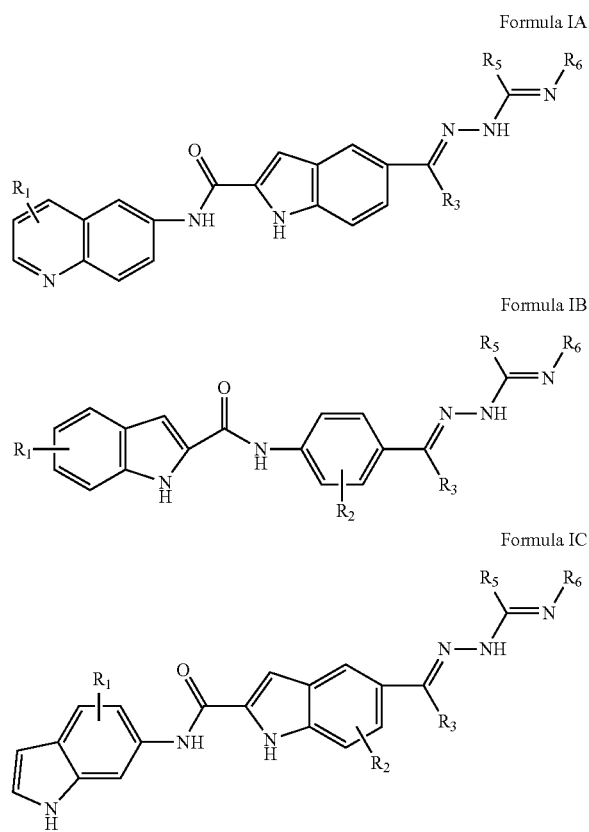

Formula IA

Formula IB

Formula IC

(10) Included herein are compounds of Formula I and IA-IC in which:

$R_1$ is absent or is 1 or more substituents bound to either ring of the bicyclic system and independently selected from halogen, hydroxyl, amino, nitro, cyano, —COOH, —CONH$_2$, $C_1$-$C_6$alkyl, $C_1$-$C_6$alkoxy, $C_2$-$C_6$alkanoyl, $C_3$-$C_7$cycloalkyl, 5- to 7-membered heterocycloalkyl, (mono- or di-$C_1$-$C_4$alkylamino)$C_0$-$C_4$alkyl, $C_1$-$C_2$haloalkyl, and $C_1$-$C_2$haloalkoxy; and $R_2$ is absent or is 1 or more substituents independently selected from halogen, hydroxyl, amino, nitro, cyano, —COOH, —CONH$_2$, $C_1$-$C_6$alkyl, $C_1$-$C_6$alkoxy, $C_2$-$C_6$alkanoyl, (mono- or di-$C_1$-$C_4$alkylamino)$C_0$-$C_4$alkyl, $C_1$-$C_2$haloalkyl, and $C_1$-$C_2$haloalkoxy.

(11) $R_3$ is methyl, $R_5$ is amino, and $R_6$ is hydrogen.

(12) $R_1$ is 1 or 2 substituents independently chosen from halogen, nitro, acetyl, $C_1$-$C_2$alkyl, and $C_1$-$C_2$alkoxy.

(13) $R_2$ is absent.

The following compounds and their pharmaceutically acceptable salts shown and described in Examples 1-15 are also included in this disclosure.

Pharmaceutical Preparations

Compounds disclosed herein can be administered as the neat chemical, but are preferably administered as a pharmaceutical composition. Accordingly, the disclosure provides pharmaceutical compositions comprising a compound or pharmaceutically acceptable salt of a Chk2 inhibitor, such as a compound of Formula I, together with at least one pharmaceutically acceptable carrier. The pharmaceutical composition/combination may contain a compound or salt of Formula I as the only active agent, but is preferably contains at least one additional active agent. In certain embodiments it is preferred that the additional active agent is an NS3 protease inhibitor. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form. The pharmaceutical composition may also include a molar ratio of a compound of Chk2 inhibitor, such as a compound of Formula I, and an additional active agent. For example, the pharmaceutical composition may contain a molar ratio of about 0.5:1, about 1:1, about 2:1, about 3:1 or from about 1.5:1 to about 4:1 of an NS3 protease inhibitor of Formula II to NS5a inhibitor of Formula I.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt. %) of a compound of Formula I and usually at least about 5 wt. % of a compound of Formula. Some embodiments contain from about 25 wt. % to about 50 wt. % or from about 5 wt. % to about 75 wt. % of the compound of Formula.

Methods of Treatment

The pharmaceutical compositions/combinations disclosed herein are useful for treating hepatitis C infections in patients.

This disclosure provides methods of treating viral infections, including hepatitis C infections, by providing an effective amount of a compound or pharmaceutically acceptable salt of Formula I to patient infected with a hepatitis C virus. A compound or salt of Formula I may be provided as the only active agent or may be provided together with one or more additional active agents. In certain embodiments, the Chk2 kinase inhibitor is administered together with interferon, a Hepatitis C Virus NS3 inhibitor, Hepatitis C Virus protease inhibitor, Hepatitis C Virus NS4a inhibitor, or a Hepatitis C Virus NS5a inhibitor, or other anti-Hepatitis C Virus compound.

In certain embodiments, the other anti-Hepatitis C Virus compound is not a Chk2 kinase inhibitor and/or is not a compound or salt of Formula I.

An effective amount of a pharmaceutical composition/combination of the invention may be an amount sufficient to (a) inhibit the progression of hepatitis C; (b) cause a regression of the hepatitis C infection; or (c) cause a cure of a hepatitis C infection such that HCV virus or HCV antibodies can no longer be detected in a previously infected patient's blood or plasma. An amount of a pharmaceutical composition/combination effective to inhibit the progress or cause a regression of hepatitis C includes an amount effective to stop the worsening of symptoms of hepatitis C or reduce the symptoms experienced by a patient infected with the hepatitis C virus. Alternatively, a halt in progression or regression of hepatitis C may be indicated by any of several markers for the disease. For example, a lack of increase or reduction in the hepatitis C viral load or a lack of increase or reduction in the number of circulating HCV antibodies in a patient's blood are markers of a halt in progression or regression of hepatitis C infection. Other hepatitis C disease markers include aminotransferase levels, particularly levels of the liver enzymes AST and ALT. Normal levels of AST are from 5 to 40 units per liter of serum (the liquid part of the blood) and normal levels of ALT are from 7 to 56 units per liter of serum. These levels will typically be elevated in a HCV infected patient. Disease regression is usually marked by the return of AST and ALT levels to the normal range.

Symptoms of hepatitis C that may be affected by an effective amount of a pharmaceutical composition/combination of the invention include decreased liver function, fatigue, flu-like symptoms: fever, chills, muscle aches, joint pain, and headaches, nausea, aversion to certain foods, unexplained weight loss, psychological disorders including depression, tenderness in the abdomen, and jaundice.

"Liver function" refers to a normal function of the liver, including, but not limited to, a synthetic function including synthesis of proteins such as serum proteins (e.g., albumin, clotting factors, alkaline phosphatase, aminotransferases (e.g., alanine transaminase, aspartate transaminase), 5'-nucleosidase, y glutaminyltranspeptidase, etc.), synthesis of bilirubin, synthesis of cholesterol, and synthesis of bile acids; a liver metabolic function, including carbohydrate metabolism, amino acid and ammonia metabolism, hormone metabolism, and lipid metabolism; detoxification of exogenous drugs; and a hemodynamic function, including splanchnic and portal hemodynamics.

An effective amount of a pharmaceutical composition/combination described herein will also provide a sufficient concentration of the active agents in the concentration when administered to a patient. A sufficient concentration of an active agent is a concentration of the agent in the patient's body necessary to prevent or combat the infection. Such an amount may be ascertained experimentally, for example by assaying blood concentration of the agent, or theoretically, by calculating bioavailability. The amount of an active agent sufficient to inhibit viral infection in vitro may be determined with a conventional assay for viral infectivity such as a replicon based assay, which has been described in the literature.

Pharmaceutical compositions/combinations and methods of treatment in which a compound or salt of Formula I is provided together with one or more additional active agents are included herein. In preferred embodiments a compound of Formula I is provided together with an NS3 protease inhibitor, either in a single pharmaceutical composition or a in separate dosage forms with instructions to the patient to use the compound of Formula I and additional active agent together. In certain embodiments, the additional active agent (or agents) is an HCV protease inhibitor or HCV polymerase inhibitor.

According to the methods of the invention, the compound or pharmaceutically acceptable salt of Formula I and at least one additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the compound or salt of Formula I and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Methods of treatment and pharmaceutical combinations including compounds or pharmaceutically acceptable salts of Formula I described herein together with any one or combination of the following compounds and substances as an additional active agent are provided by the disclosure:

Caspase inhibitors: IDN 6556 (Idun Pharmaceuticals).

Cyclophilin Inhibitors: for example, NIM811 (Novartis), SCY-635 (Scynexis), and DEBIO-025 (Debiopharm).

Cytochrome P450 monooxygenase inhibitors: ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole.

Glucocorticoids: hydrocortisone, cortisone, prednisone, prednisolone, methylprednisolone, triamcinolone, paramethasone, betamethasone, and dexamethasone.

HCV Protease Inhibitors: for example ACH-1625 and ACH-2684, ABT-450 (Abbott), ACL-181 and AVL-192

(Avila), BI-335 (Boehringer Ingelheim), BMS-032 (Bristol Meyers Squibb), boceprevir (Merck), TMC-435, MK-7152 (Merck), GS-9256 (Gilead), GS-9451 (Gilead), R7227 (Roche), VX-950 (telaprevir, Vertex), VX-985 (Vertex), TMC-435 (Tibotec), GW-433908 (prodrug of Amprenavir, Glaxo/Vertex), indinavir (CRIXIVAN, Merck), and ITMN-191 (Intermune/Array Biopharma).

Immunomodulatory compounds: thalidomide, IL-2, hematopoietins, IMPDH inhibitors, for example Merimepodib (Vertex Pharmaceuticals Inc.), interferon, including natural interferon (such as OMNIFERON, Viragen and SUMIFERON, Sumitomo, a blend of natural interferons), natural interferon alpha (ALFERON, Hemispherx Biopharma, Inc.), interferon alpha nl from lymphblastoid cells (WELLFERON, Glaxo Wellcome), oral alpha interferon, Peg-interferon, Peg-interferon alfa 2a (PEGASYS, Roche), recombinant interferon alfa 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alfa 2b (INTRON A, Schering), pegylated interferon alfa 2b (PEGINTRON, Schering, VIRAFERONPEG, Schering), interferon beta-1a (REBIF, Serono, Inc. and Pfizer), consensus interferon alpha (INFERGEN, Valeant Pharmaceutical), interferon gamma-1b (ACTIMMUNE, Intermune, Inc.), un-pegylated interferon alpha, alpha interferon, and its analogs, and synthetic thymosin alpha 1 (ZADAXIN, SciClone Pharmaceuticals Inc.), and lamdba interferon (BMS)

Immunosupressants: sirolimus (RAPAMUNE, Wyeth).

Interleukins: (IL-1, IL-3, IL-4, IL-5, IL-6, IL-10, IL-11, IL-12), LIF, TGF-beta, TNF-alpha) and other low molecular weight factors (e.g. AcSDKP, pEEDCK, thymic hormones, and minicytokines)

Interferon Enhancers: EMZ702 (Transition Therapeutics)

IRES inhibitors: VGX-410C (VGX Pharma)

Monoclonal and Polyclonal antibodies: XTL-6865 (XTL), HuMax-HepC (Genmab), Hepatitis C Immune Globin (human) (CIVACIR, Nabi Biopharmaceuticals)

Nucleoside analogues: IDX-184 (Idenix), PSI-7977 and PSI-938 (Pharmasset), INX-189 (Inhibitex), R7128 (Roche), R7348 (Roche), GS-6620 (Gilead), TMC-649 (Tibotec), Lamivudine (EPIVIR, 3TC, GlaxoSmithKline), MK-0608 (Merck), zalcitabine (HIVID, Roche US Pharmaceuticals), ribavirin (including COPEGUS (Roche), REBETOL (Schering), VILONA (ICN Pharmaceuticals, and VIRAZOLE (ICN Pharmaceuticals), and viramidine (Valeant Pharmaceuticals), an amidine prodrug of ribavirin. Combinations of nucleoside analogues may also be employed.

Non-nucleoside inhibitors: PSI-6130 (Roche/Pharmasset), ABT-333 and ABT-072 (Abbott), delaviridine (RESCRIPTOR, Pfizer), PF-868554 (Pfizer), GSK-852 (GlaxoSmithKline), IDX-325 (Idenix), ANA-598 (Anadys), VX-222 and VX-759 (Vertex), MK-3281 (Merck), BI-127 (Boehringer Ingelheim), BMS-325 (Bristol Meyers), and HCV-796 (Viropharm)

NS4a inhibitors: for example ACH-1095. US patent application no. US2007/0004711 is hereby incorporated by reference in its entirety for its teachings regarding HCV inhibitors and U.S. patent application Ser. No. 12/125,554 at pages 45-90 is hereby incorporated by reference for its teachings regarding HCV inhibitors.

NS5a inhibitors: ACH-2928 (Achillion), AZD7295 (Arrow Therapeutics), BMS-790052 (Bristol-Myers Squibb), EDP-239 (Enanta), PPI-461 and PPI-1301 (Presidio).

NS5b inhibitors: INX-181, IDX-375, MK-3281, PSI-7977, PSI-7851, PSI-938, RG-9190, VX-222 (Vertex), and BMS-791325 (Bristol Myers Squibb).

P7 protein inhibitor: amantadine (SYMMETREL, Endo Pharmaceuticals, Inc.)

Polymerase inhibitors: NM283 (valopicitabine) (Idenix) and NM 107 (Idenix).

Protease inhibitors: BILN-2061 (Boehringer Ingelheim), GW-433908 (prodrug of Amprenavir, Glaxo/Vertex), indinavir (CRIXIVAN, Merck), ITMN-191 (Intermune/Array Biopharma), VX950 (Vertex) and combinations comprising one or more of the foregoing protease inhibitors.

RNA interference: SIRNA-034 RNAi (Sirna Therapeutics)

Therapeutic Vaccines: IC41 (Intercell), IMN-0101 (Imnogenetics), GI 5005 (Globeimmune), Chronvac-C (Tripep/Inovio), ED-002 (Imnogenetics), Hepavaxx C (ViRex Medical)

TNF agonists: adalimumab (HUMIRA, Abbott), entanercept (ENBREL, Amgen and Wyeth), infliximab (REMICADE, Centocor, Inc.)

Tubulin inhibitors: Colchicine

Sphingosine-1-phosphate receptor modulators: FTY720 (Novartis)

TLR agonists: ANA-975 (Anadys Pharmaceuticals), ANA-773 (Anadys Pharmaceuticals), TLR7 agonist (Anadys Pharmaceuticals), CPG10101 (Coley), and TLR9 agonists including CPG 7909 (Coley)

Cyclophilin Inhibitors: NIM811 (Novartis) and DEBIO-025 (Debiopharm)

Patients receiving hepatitis C medications are typically given interferon together with another active agent. Thus, methods of treatment and pharmaceutical combinations in which a compound of the invention is provided together with an interferon, such as pegylated interferon alfa 2a, as the additional active agents are included as embodiments. Similarly, methods and pharmaceutical combinations in which ribavirin is an additional active agent are provided herein.

Additionally, methods and pharmaceutical combinations in which an NS3 protease inhibitor is the additional active agent are provided herein. The NS3 protease inhibitor may be selected from the group ACH-1625, ACH-2684, ABT-450, ACL-181, AVL-192, BI-335, BMS-032, boceprevir, TMC-435, MK-7152, GS-9256, GS-9451, R7227, VX-950, VX-985, TMC-435, GW-433908, indinavir, and ITMN-191.

Methods of inhibiting HCV replication in vivo comprising providing a compound or pharmaceutically acceptable salt of Formula I to a patient infected with HCV, a concentration of the compound or salt of Formula I sufficient to inhibit HCV replicon replication in vitro are included herein. In this instance the concentration includes an in vivo concentration, such as a blood or plasma concentration. The concentration of compound sufficient to inhibit HCV replicon replication in vitro may be determined from an assay of replicon replication such as the assay provided in Example 2, herein.

Methods of treatment include providing certain dosage amounts of a compound or pharmaceutically acceptable salt of Formula I to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single unit dosage form will vary depending upon the patient treated and the particular mode of administration. In certain embodiments about 0.1 mg to about 2000 mg, from about 10 mg to about 1500 mg, from about 100 mg to about 1000 mg, from about 200 mg to about 800 mg, or from about 300 to about 600 mg of a compound of Formula I and optionally from about 0.1 mg to about 2000 mg, from about 10 mg to about 1500 mg, from about 100 mg to about 1000 mg, from about 200 mg to about 800 mg, or from about 300 to about 600 mg of a compound of an additional active agent, for example an NS3 protease inhibitor such as a compound of Formula II are provided daily to a patient. It is preferred that each unit dosage form contains less than 1200 mg of active agent in total. Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

Packaged Formulations

Methods comprising providing a compound or salt of a Chk2 inhibitor, such as a compound of Formula I, in a container together with instructions for using the compound to treat a patient suffering from HCV infection are included herein.

Packaged pharmaceutical compositions/combinations are also included herein. Such packaged combinations include a Chk2 inhibitor, such as a compound of Formula I, in a container together with instructions for using the combination to treat or prevent a viral infection, such as a HCV infection, in a patient. Pharmaceutical combinations include at least one additional active agent. In certain embodiments, the additional active agent is an NS3 protease inhibitor.

The packaged pharmaceutical combination may include a Chk2 inhibitor, such as a compound of Formula I, and an additional active agent provided simultaneously in a single dosage form, concomitantly in separate dosage forms, or provided in separate dosage forms for administration separated by some amount of time that is within the time in which both the Chk2 inhibitor, such as a compound of Formula I, and the additional active agent are within the bloodstream of the patient.

EXAMPLES

General Methods

All chemicals used in synthetic examples 1-### were purchased from Sigma-Aldrich Chemicals, Co. or Fisher Scientific and directly used without further purification. $^1$H and $^{13}$C NMR spectra were acquired on Varian 300 spectrometer at 25° C., and chemical shifts (δ in ppm) are given relative to that of Me$_4$Si (TMS, δ 0.00 ppm) or with the solvent reference relative to TMS employed as the internal standard (CDCl$_3$δ 7.26; D$_6$-DMSO δ 2.50 ppm). Data are reported as follow: chemical shift (multiplicity [singlet (s), doublet (d), triplet (t), quartet (q), multiplet (m) broad (b)], coupling constants [Hz], integration. HPLC was performed on Rainin SD-300 or Varian ProStar equipped with a single wavelength UV detector at 214 nm and linear gradients. Analytical HPLC was performed on a Varian C$_{18}$ column (Microsorb 60-8, 4.6×250 mm) at a flow rate of 1 mL/min. Semi-preparative HPLC was performed on a Varian C$_{18}$ column (Microsorb 60-8, 10.0× 250 mm) at a flow rate of 5 mL/min. Preparative HPLC was routinely performed on a Varian C$_{18}$ column (Microsorb 60-8, 21.4×250 mm) at a flow rate of 20 mL/min. The solvent system used on linear gradients was water with 0.075% TFA (solvent A) vs. acetonitrile with 0.075% TFA (solvent B). Silica gel used in flash column chromatography was obtained from Sorbent Technologies (Atlanta, Ga.). Analytical thin-layer chromatography (TLC) was carried out using Silica Gel 60 F254 precoated plates G/UV254 plates (Merck, 0.25 mm thickness). TLC R$_f$ values are reported. Visualization was accomplished by irradiation with a UV lamp and/or staining with ceric ammonium molybdate (CAM) solution. LC-MS spectra were taken on Thermo Finnigan Navigator LC/MS-ESI or APCI.

GENERAL SYNTHETIC SCHEME 1

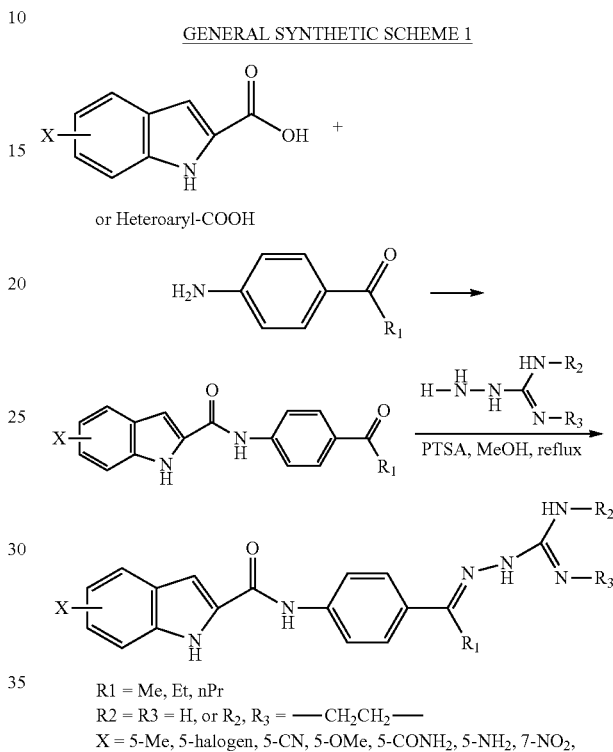

R1 = Me, Et, nPr
R2 = R3 = H, or R$_2$, R$_3$ = —CH$_2$CH$_2$—
X = 5-Me, 5-halogen, 5-CN, 5-OMe, 5-CONH$_2$, 5-NH$_2$, 7-NO$_2$, Example 1

Preparation of (E)-N-(4-(1-(2-carbamimidoylhydrazono)ethyl)phenyl)-5-methoxy-1H-indole-2-carboxamide

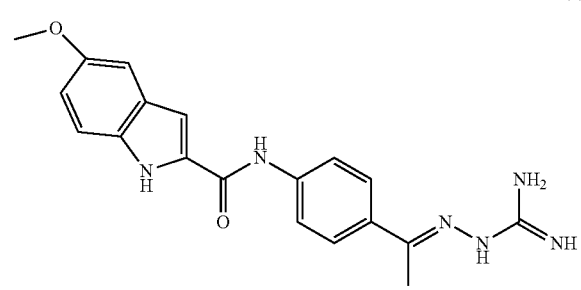

(1)

5-Methoxy-1H-indole-2-carboxylic acid and 4'-aminoacetophenone are combined according to general synthetic scheme 1 (steps (i) and (ii)), to obtain the product. t$_R$ 14.5 min (20-60%, CH$_3$CN, 20 min); MS (m/z) 365 (MH$^+$).

Example 2

Preparation of (E)-N-(4-(1-(2-carbamimidoylhydrazono)ethyl)phenyl)-7-nitro-1H-indole-2-carboxamide

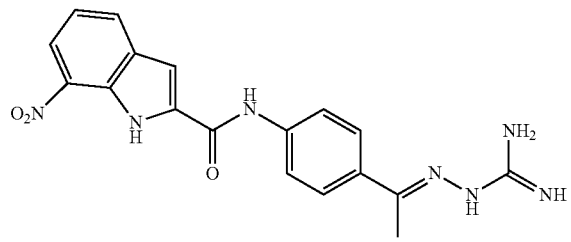

(2)

5-Nitro-1H-indole-2-carboxylic acid and 4'-aminoacetophenone were combined according to synthetic scheme 1 (steps (i) and (ii)), to obtain the product. $t_R$ 18.8 min (20-70%, CH$_3$CN, 25 min); MS (m/z) 397 (M$^+$).

Example 3

Preparation of (E)-N-(4-(1-(2-(4,5-dihydro-1H-imidazol-2-yl)hydrazono)ethyl)phenyl)-7-nitro-1H-indole-2-carboxamide

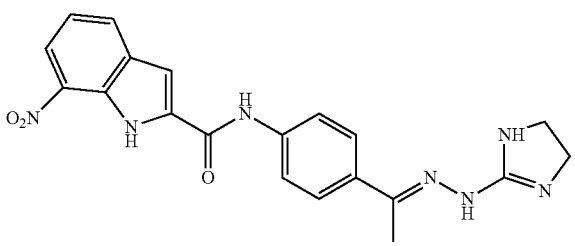

(3)

7-nitro-1H-indole-2-carboxylic acid and 4'-aminoacetophenone were combined according to general procedure B (steps (i) and (ii)), to obtain the product, $t_R$ 16.0 min (20-80%, CH$_3$CN, 20 min); MS (m/z) 405 (M$^+$).

Example 4

Preparation of (E)-N-(4-(1-(2-carbamimidoylhydrazono)ethyl)phenyl)-5-methoxy-7-nitro-1H-indole-2-carboxamide

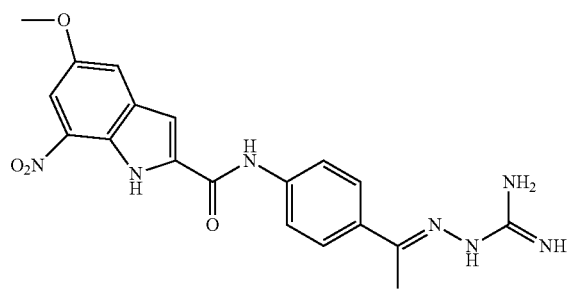

(4)

5-Acetyl-1H-indole-2-carboxylic acid and 4'-aminoacetophenone were combined according to synthetic scheme 1 B (steps (i) and (ii)), to obtain the product. $t_R$ 15.5 min (10-90% CH$_3$CN in H$_2$O, 20 min); MS (m/z) 410 (MH$^+$).

Example 5

Preparation of (E)-5-acetyl-N-(4-(1-(2-carbamimidoylhydrazono)ethyl)phenyl)-1H-indole-2-carboxamide

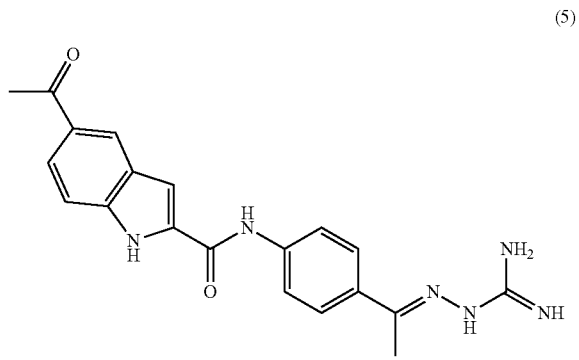 [SMILES: CC(=O)c1ccc2[nH]c(C(=O)Nc3ccc(/C(C)=N/NC(=N)N)cc3)cc2c1]

(5)

5-(2-Methyl-[1,3]dithian-2-yl)-1H-indole-2-carboxylic acid prepared by the method described by Kumar and Dev (*Tetrahedron Letters* (1983) 24(12):1289-1292) and 4'-aminoacetophenone were combined according to synthetic scheme 1 B (steps (i) and (ii)). After 1,3-dithiane deprotection by the DMP oxidation procedure described by Langille et al. (*J. S. Org. Lett.* (2003) 5(4:575-578), the pure monohydrozone was obtained by HPLC purification. $t_R$ 22.03 min (15-45% CH$_3$CN in H$_2$O, 40 min, semiprep); MS (m/z) 377 (MH$^+$).

Example 6

Preparation of (E)-N-(5-(2-carbamimidoylhydrazono)-5,6,7,8-tetrahydronaphthalen-2-yl)-7-nitro-1H-indole-2-carboxamide

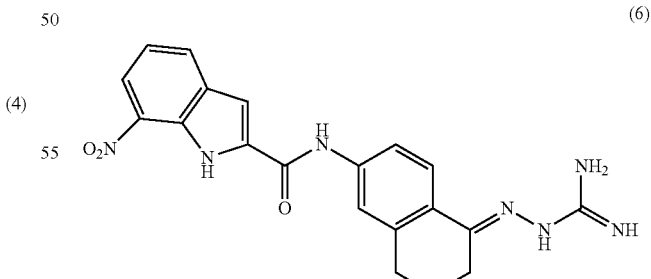

(6)

7-Nitro-1H-indole-2-carboxylic acid and 6-Amino-3,4-dihydro-2H-naphthalen-1-one were combined according to synthetic scheme 1 (steps (i) and (ii)), to obtain the product after HPLC purification. $t_R$ 15.71 min (20-70% CH$_3$CN in H$_2$O, 20 min); MS (m/z) 406 (MH$^+$).

Example 7

Preparation of (E)-5-(1-(2-carbamimidoylhydrazono)ethyl)-N-(quinolin-6-yl)-1H-indole-2-carboxamide

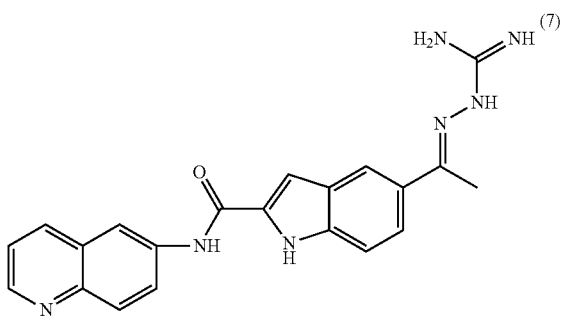 [SMILES: C/C(=N\NC(=N)N)c1ccc2[nH]c(C(=O)Nc3ccc4ncccc4c3)cc2c1]

(7)

5-Acetyl-1H-indole-2-carboxylic acid and 6-aminoquinoline were combined according to synthetic scheme 1 (steps (i) and (ii)) to obtain the pure product after HPLC purification. $t_R$ 13.77 min (10-50% $CH_3CN$ in $H_2O$, 20 min); MS (m/z) 386 (MH$^+$).

Example 8

Preparation of (E)-5-(1-(2-carbamimidoylhydrazono)ethyl)-N-(1H-indol-4-yl)-1H-indole-2-carboxamide

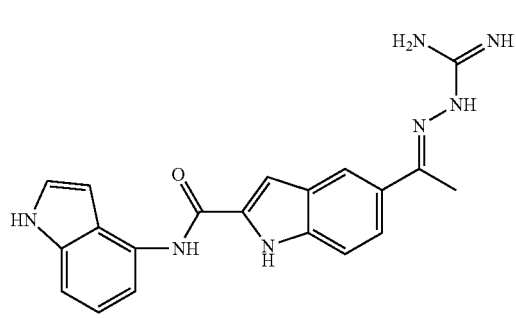

(8)

5-Acetyl-1H-indole-2-carboxylic acid and 4-amino-indole were combined according to synthetic scheme 1 (steps (i) and (ii)) to obtain the pure product after HPLC purification. $t_R$ 15.57 min (10-60% $CH_3CN$ in $H_2O$, 20 min); MS (m/z) 374 (MH$^+$).

Example 9

(E)-5-(1-(2-carbamimidoylhydrazono)ethyl)-N-(2-methyl-1H-indol-5-yl)-1H-indole-2-carboxamide

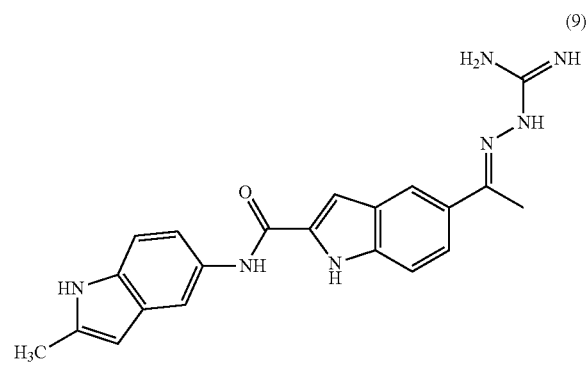 [SMILES: C/C(=N\NC(=N)N)c1ccc2[nH]c(C(=O)Nc3ccc4[nH]c(C)cc4c3)cc2c1]

(9)

5-Acetyl-1H-indole-2-carboxylic acid and 5-amino-2-methyl-1H-indole were combined according to synthetic scheme 1 (steps (i) and (ii)) to obtained the pure product after HPLC purification. $t_R$ 15.57 min (10-60% $CH_3CN$ in $H_2O$, 20 min); MS (m/z) 388 (MH$^+$).

Example 10

Preparation of 5-(1-(2-carbamimidoylhydrazono)butyl)-N-(1H-indol-6-yl)-1H-indole-2-carboxamide

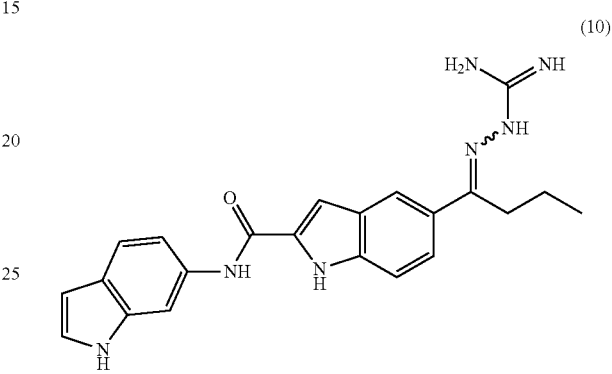

(10)

5-Butyryl-1H-indole-2-carboxylic acid and 6-amino-1H-indole were combined according to synthetic scheme 1 (steps (i) and (ii)) to obtained two pure isomers after HPLC purification. PV1518: $t_R$ 14.40 min, MS (m/z) 406 (MH$^+$) and PV1519: $t_R$ 16.73 min (30-50% $CH_3CN$ in $H_2O$, 20 min); MS (m/z) 406 (MH$^+$).

Example 11

Preparation of (E)-N-(4-(1-(2(N-hydroxycarbamimidoyl)hydrazono)ethylphenyl)-5-methoxy-1H-indole-2-carboxamide

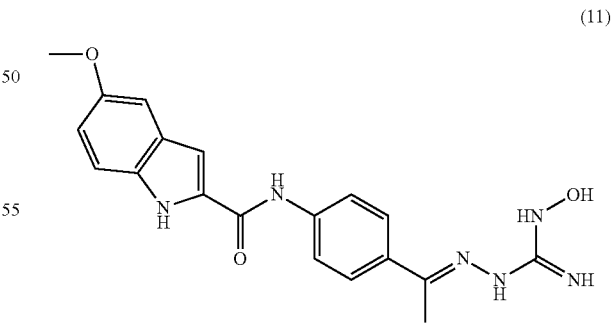

(11)

5-Methoxy-1H-indole-2-carboxylic acid (4-acetyl-phenyl)-amide, made from 5-Methoxy-1H-indole-2-carboxylic acid and 4-acetyl phenylamine, and N-hydroxy-N'-aminoguanidine PTSA salt, prepared by following method discussed in Tai, et al. (*J. Med. Chem.* (1983) 26:1326-1329) were combined according to synthetic scheme, to obtain the pure product after purification by reverse phase HPLC: $t_R$ 20.5 min (20-60% $CH_3CN$ in $H_2O$, 25 min); MS (m/z) 381 ($MH^+$).

Example 12

(Z)—N-(1H-benzo[D]imidazol-6-yl)-5-(1-(2-carbamimidoylhydrazono)ethyl)-1H-indole-2-carboxamide

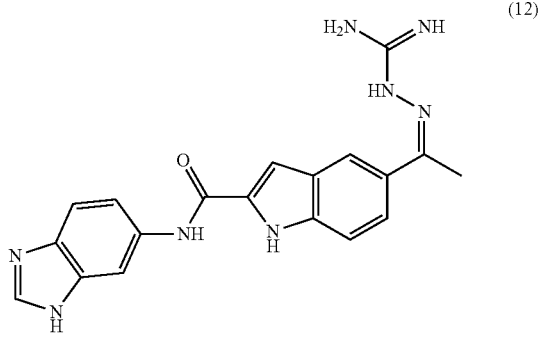 [SMILES: C/C(=N/NC(=N)N)c1ccc2[nH]c(C(=O)Nc3ccc4nc[nH]c4c3)cc2c1]

(12)

5-Acetyl-1H-indole-2-carboxylic acid and 5-amino-benzoimidazole were combined according to synthetic scheme 1 (steps (i) and (ii)) to obtain the pure product after HPLC purification. $t_R$ 14.71 min (10-40% $CH_3CN$ in $H_2O$, 20 min); MS (m/z) 375 ($MH^+$).

Example 13

Preparation of (E)-5-(1-(2-carbamimidoylhydrazono)-3-methylbutyl)-N-(1H-indol-6-yl)-1H-indole-2-carboxamide

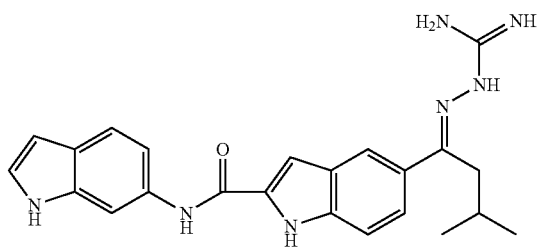

(13)

A. Synthesis of 5-(3-Methyl-butyryl)-1H-indole-2-carboxylic acid (Froshauer, S. A. et al., U.S. Pat. No. 5,981,762 (1999)): 3-Bromo-1H-indole-2-carboxylic acid ethyl ester (536 mg, 2.0 mmol), is prepared by following the method given by Elliott, J. D. et al., (U.S. Pat. No. 5,684,032 (1997)) is dissolved in nitromethane (10 mL) and cooled to 0° C. $AlCl_3$ is added to the flask. Then a solution of isovaleryl chloride (0.295 mL, 2.4 mmol) in nitromethane (2 mL) was added dropwise to the flask. The mixture is allowed to come to room temperature and stirred for 18 hours, and then cooled to 0° C. 20 mL ice-water is added and extracted with $CH_2Cl_2$ (4×20 mL). The combined organic phase is washed with saturated brine (20 mL), 1N $NaHCO_3$ (20 mL) and saturated brine (2×20 mL), dried over anhydrous $Na_2SO_4$, filtered, and concentrated under vacuum to give yellow solid. It is then purified by flash column chromatography eluted with hexane: ethyl acetate (6:1) to give 3-Bromo-5-(3-methyl-butyryl)-1H-indole-2-carboxylic acid ethyl ester (468 mg, 67%) as light yellow solid. $^1H$ NMR (300 MHz, DMSO-$d_6$) δ12.60 (brs, 1H); 8.20 (d, J=1.2 Hz, 1H), 7.97 (dd, J=8.7, 1.8 Hz, 1H), 7.57 (d, J=8.7 Hz, 1H), 4.41 (q, J=6.9 Hz, 2H), 2.98 (d, J=6.9 Hz, 2H), 2.20 (m, 1H), 1.39 (t, J=6.9 Hz, 3H), 0.97 (d, J=6.9 Hz, 6H). EIMS m/z 352.0 ($M^++H$).

B. Synthesis of 5-(3-Methyl-butyryl)-1H-indole-2-carboxylic acid. DMF (5 mL) and water (0.625 mL) are added to the mixture of 3-Bromo-5-(3-methyl-butyryl)-1H-indole-2-carboxylic acid ethyl ester (408 mg, 1.1 mmol), ammonium formate (110 mg, 1.7 mmol), and 10% Pd/C (200 mg). The mixture is slightly shaken at room temperature for 70 minutes and then filtered through celite. The solvent is evaporated under vacuum to give 5-(3-Methyl-butyryl)-1H-indole-2-carboxylic acid ethyl ester as light yellow liquid as crude product with the purity of 90%; EI-MS m/z 274.1 ($M^++H$). The crude ethyl ester is dissolved in dioxane (10 mL), then a solution of $LiOH.H_2O$ (195 mg, 4.6 mmol) in water (5 mL) is added to the flask. The mixture is stirred at room temperature for 2 days. Dioxane is stripped under vacuum. 10 mL water is added and extracted with $CH_2Cl_2$. The aqueous phase is then acidified with 6N HCl and extracted with $CH_2Cl_2$. The $CH_2Cl_2$ phase is then washed with saturated brine and dried over anhydrous $Na_2SO_4$. Solvent is removed under vacuum to give 5-(3-Methyl-butyryl)-1H-indole-2-carboxylic acid (250 mg, 88% for two steps) as white solid. EIMS m/z 246.1 ($M^++H$).

C. 5-(3-Methyl-butyryl)-1H-indole-2-carboxylic acid and 6-amino-1H-indole were combined according to synthetic scheme 1 (steps (i) and (ii)) to obtained two isomers after HPLC purification. (E)-5-(1-(2-carbamimidoylhydrazono)-3-methylbutyl)-N-(1H-indol-6-yl)-1H-indole-2-carboxamide: $t_R$ 14.85 min (20-80% $CH_3CN$ in $H_2O$, 20 min); MS (m/z) 416 ($MH^+$); (E)-5-(1-(2-carbamimidoylhydrazono)-3-methylbutyl)-N-(1H-indol-6-yl)-1H-indole-2-carboxamide Isomer: $t_R$ 16.23 min (20-80% $CH_3CN$ in $H_2O$, 20 min); MS (m/z) 416 ($MH^+$).

Example 14

Preparation of (E)-5-(1-(2-carbamimidoylhydrazono) ethyl)-N-(2-methylquinolin-7-yl)-1H-indole-2-carboxamide (PV-1549)

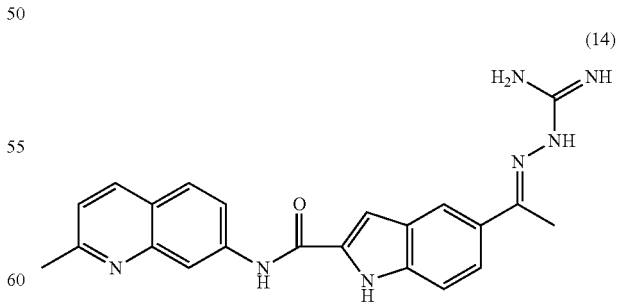

(14)

5-Acetyl-1H-indole-2-carboxylic acid and 6-amino-2-methyl-quinoline were combined according to synthetic scheme 1 (steps (i) and (ii)) to obtain the pure product after HPLC purification. $t_R$ 12.63 min (10-60% $CH_3CN$ in $H_2O$, 20 min); MS (m/z) 400 ($MH^+$).

Example 15

Additional Compounds

The following compounds have been prepared by the methods set forth in Examples 1-14 and Scheme 1.

Example 15a

N-(4-(2-amino-1H-imidazol-5-yl)phenyl)-5-methoxy-1H-indole-2-carboxamide (16)

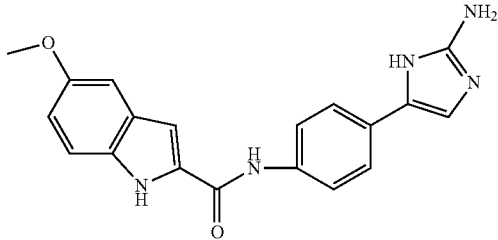

Example 15b (E)-5-(1-(2-carbamimidoylhydrazono)ethyl)-N-(4-(piperidin-1-yl)phenyl)-1H-indole-2-carboxamide (17)

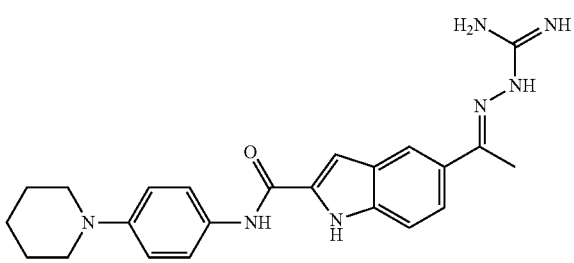

Example 15c 5-((E)-1-(2-((Z)—N'-hydroxycarbamimidoyl)hydrazono)ethyl)-N-(4-(piperidin-1-yl)phenyl)-1H-indole-2-carboxamide (18)

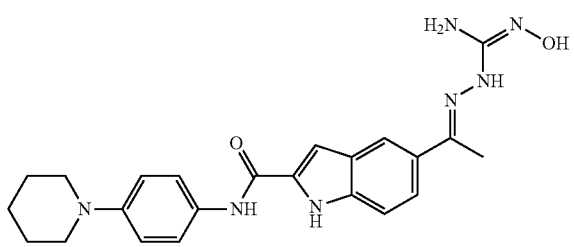

Example 16

Assay for Identifying Compounds which Inhibit HCV Replication

Compounds claimed herein are tested for the ability to inhibit viral replication of the Hepatitis C replicon in cultured cells in which the HCV replicon construct has been incorporated. The HCV replicon system was described by Bartenschlager, et al (*Science* (1999) 285:110-113) and Krieger, N. V. et al., (*J. Virol.* (2001) 75:4614-4624). The replicon system is predictive of in vivo anti-HCV activity; compounds that are active in humans uniformly evidence activity in the replicon assay.

The methods used to identify compounds are described at: http://niaid-aacf.org/protocols/HCV.htm.

The assay used the cell line Huh7 ET (luc-ubi-neo/ET), which contains a HCV RNA replicon with a stable luciferase (LUC) reporter. This particular construct is similar to the cell line 5-2 described by Krieger, but contains additional modifications that make the cell line more robust and provide stable LUC expression for antiviral screening. This composition of the replicon is shown diagrammatically in FIG. 1.

Primary HCV RNA Replicon Assay

Drugs are added in triplicate at a single high-test concentration of 20 μM and the effect on HCV RNA-derived LUC activity and cytotoxicity is determined. Human interferon alpha-2b is included in each run as a positive control compound. Subconfluent cultures of the ET line are plated out into 96-well plates that are dedicated for the analysis of cell numbers (cytotoxicity) or antiviral activity and the next day drugs are added to the appropriate wells. Cells are processed 72 hr later when the cells are still subconfluent. Compounds that reduced the LUC signal by 50% or more relative to the untreated cell controls are considered active. Compound cytotoxicity is assessed as the percent viable cells relative to the untreated cell controls.

HCV RNA Replicon Confirmatory Assay

The HCV RNA replicon confirmatory assay is used to examine the effects of compounds at five half-log concentrations each. Human interferon alpha-2b is included in each run as a positive control compound. Subconfluent cultures of the ET line are plated out into 96-well plates that are dedicated for the analysis of cell numbers (cytotoxicity) or antiviral activity and the next day drugs are added to the appropriate wells. Cells are processed 72 hr later when the cells are still subconfluent. Compound EC50 and EC90 values (antiviral activity) are derived from HCV RNA levels assessed as either HCV RNA replicon-derived LUC activity or as HCV RNA using TaqMan RT-PCR. Compound IC50 values (cytotoxicity) are calculated using CytoTox-1 (Promega), a colorimetric assay used as an indicator of cell numbers and cytotoxicity when the LUC assay system is employed, while ribosomal (rRNA) levels determined via TaqMan RT-PCR are used as an indication of cell numbers in the RNA-based assay.

HCV Replicon Assay Results

Figure 2:
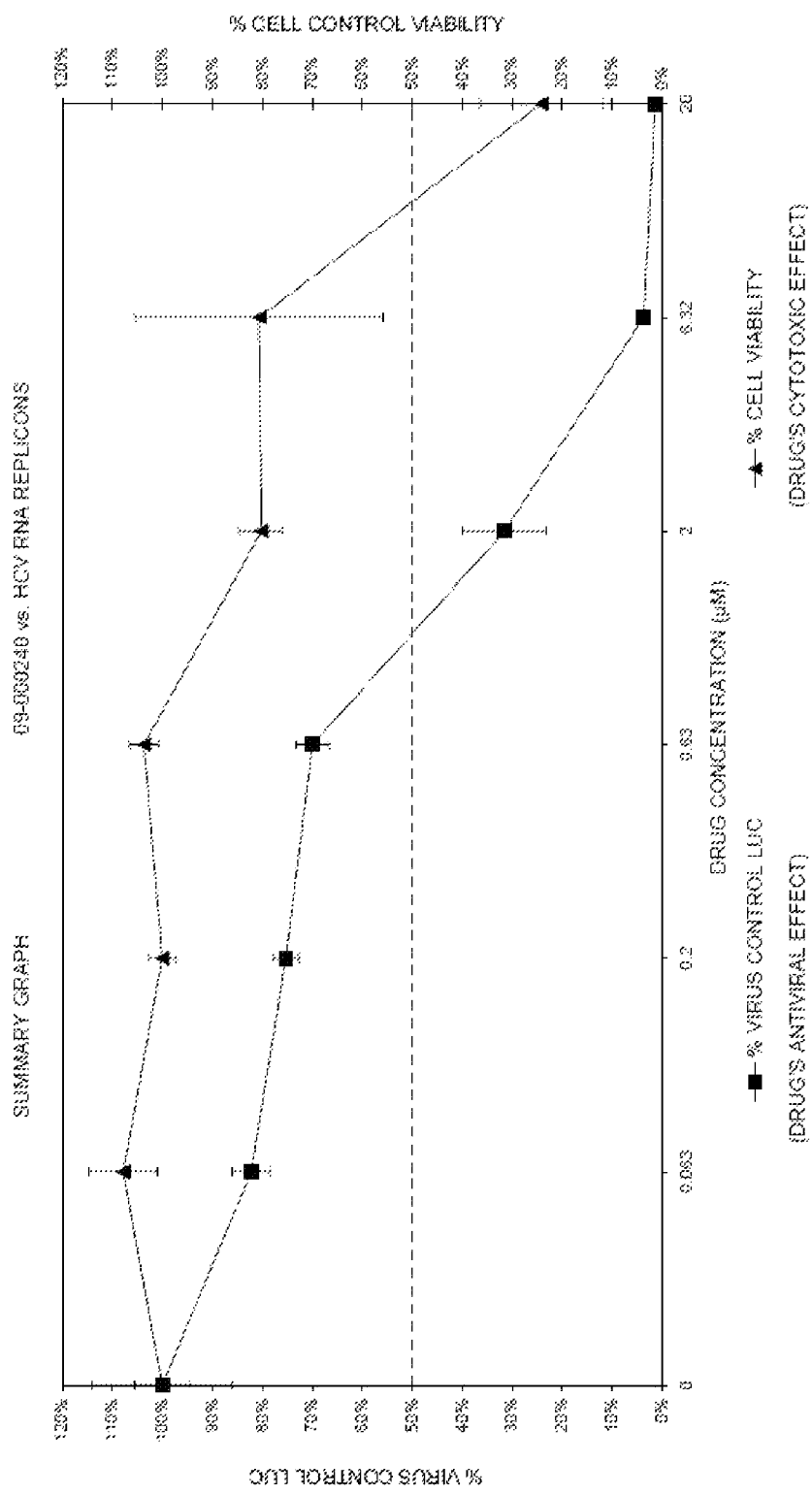
FIG. 2 shows the effect of increasing concentrations of Compound 14 on HCV replication and cell viability.
Figure 3:
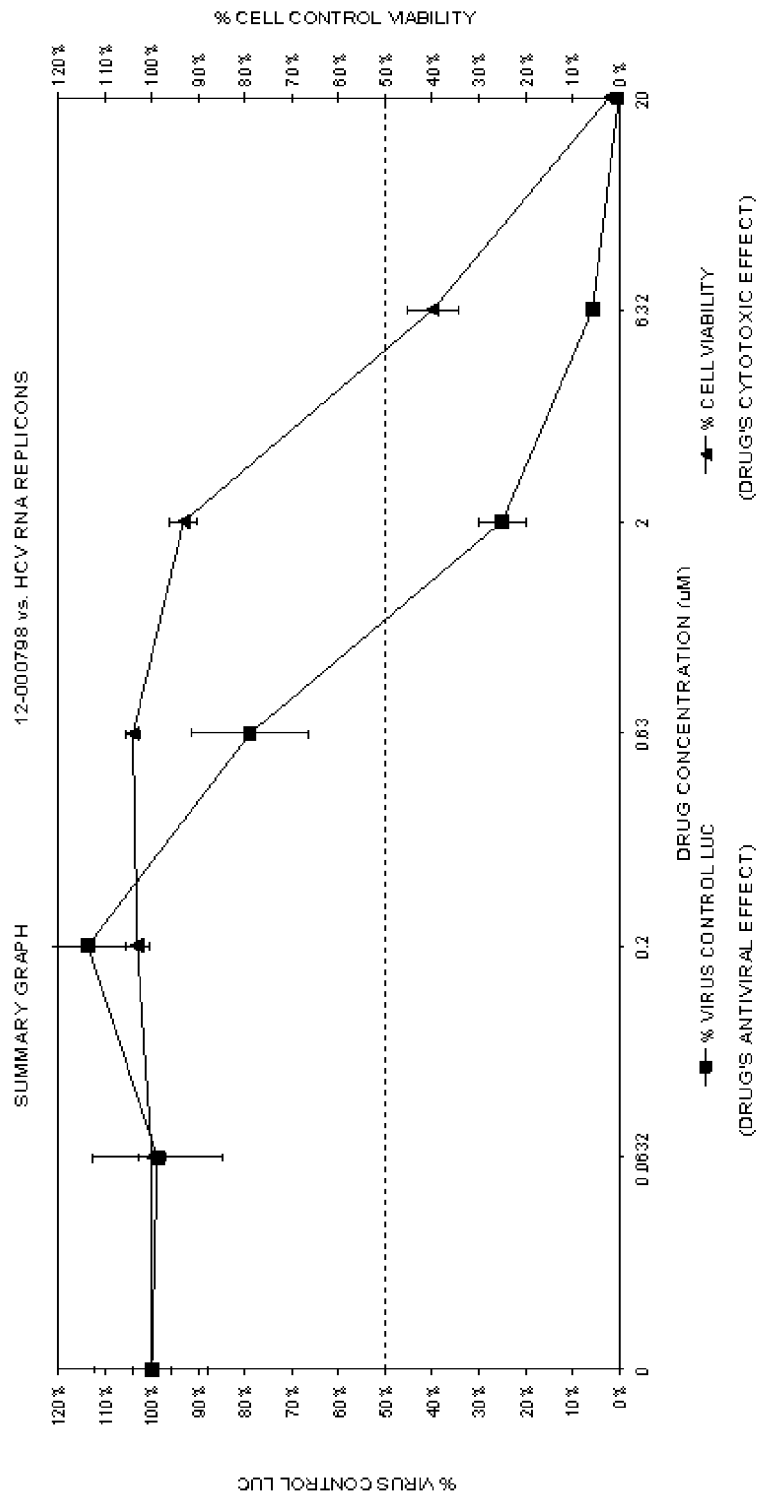
FIG. 3 shows the effect of increasing concentrations of Compound 10 on HCV replication and cell viability.

The concentration-response curves are presented in FIGS. 2 and 3 for select compounds tested in the luciferase based HCV replicon assay described in the preceding paragraph. FIG. 2 shows the effect of increasing concentrations of Compound 14 on HCV replication and cell viability. FIG. 3 shows the effect of increasing concentrations of Compound 10 on HCV replication and cell viability. Compound 10 was dissolved in dH$_2$O: DMSO. Compound 14 was dissolved in dH$_2$O.

Figure 4:
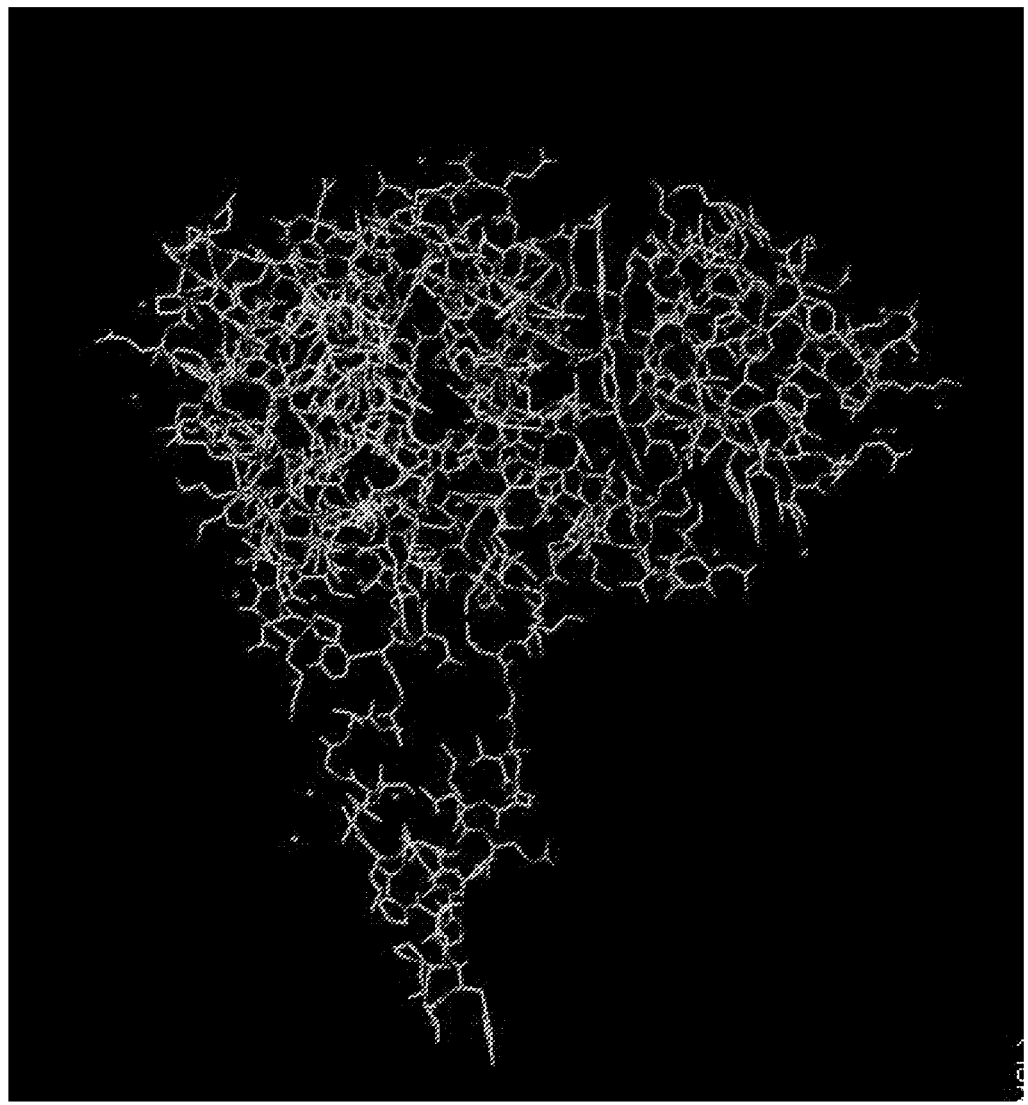
FIG. 4 shows co-crystal structure of Compound 14 (PV-1549) in the catalytic domain of the CHK2 kinase.

FIG. 4 shows a crystal structure of Compound 14 (PV-1549) in the catalytic domain of the CHK2 kinase. Crystallographic data processing, refinement statistics, and other details are givent in Table 1.

TABLE 1

REFINEMENT.
  PROGRAM: REFMAC 5.5.0104
  AUTHORS: MURSHUDOV, VAGIN, DODSON
  REFINEMENT TARGET: MAXIMUM LIKELIHOOD
DATA USED IN REFINEMENT.
  RESOLUTION RANGE HIGH (ANGSTROMS): 2.55
  RESOLUTION RANGE LOW (ANGSTROMS): 50.00
  DATA CUTOFF (SIGMA(F)): NONE
  COMPLETENESS FOR RANGE (%): 99.86
  NUMBER OF REFLECTIONS: 13938
FIT TO DATA USED IN REFINEMENT.
  CROSS-VALIDATION METHOD: THROUGHOUT
  FREE R VALUE TEST SET SELECTION: RANDOM
  R VALUE (WORKING + TEST SET): 0.22534
  R VALUE (WORKING SET): 0.22281
  FREE R VALUE: 0.27320
  FREE R VALUE TEST SET SIZE (%): 5.0
  FREE R VALUE TEST SET COUNT: 739
FIT IN THE HIGHEST RESOLUTION BIN.
  TOTAL NUMBER OF BINS USED: 20
  BIN RESOLUTION RANGE HIGH: 2.551
  BIN RESOLUTION RANGE LOW: 2.617
  REFLECTION IN BIN (WORKING SET): 998
  BIN COMPLETENESS (WORKING + TEST) (%): 98.79
  BIN R VALUE (WORKING SET): 0.353
  BIN FREE R VALUE SET COUNT: 62
  BIN FREE R VALUE: 0.413
NUMBER OF NON-HYDROGEN ATOMS USED IN REFINEMENT.
  ALL ATOMS: 2352
B VALUES.
  FROM WILSON PLOT (A$^{**}$2): NULL
  MEAN B VALUE (OVERALL, A$^{**}$2): 52.093
  OVERALL ANISOTROPIC B VALUE.
    B11 (A$^{**}$2): −0.20
    B22 (A$^{**}$2): −0.20
    B33 (A$^{**}$2): 0.30
    B12 (A$^{**}$2): −0.10
    B13 (A$^{**}$2): 0.00
    B23 (A$^{**}$2): 0.00
ESTIMATED OVERALL COORDINATE ERROR.
  ESU BASED ON R VALUE (A): 0.417
  ESU BASED ON FREE R VALUE (A): 0.291
  ESU BASED ON MAXIMUM LIKELIHOOD (A): 0.223
  ESU FOR B VALUES BASED (A$^{**}$2): 10.209
  ON MAXIMUM LIKELIHOOD
CORRELATION COEFFICIENTS.
  CORRELATION COEFFICIENT FO-FC: 0.945
  CORRELATION COEFFICIENT FO-FC FREE: 0.927

RMS DEVIATIONS FROM IDEAL VALUES | | COUNT | RMS | WEIGHT
---|---|---|---|---
BOND LENGTHS REFINED ATOMS | (A): | 2356; | 0.014; | 0.022
BOND LENGTHS OTHERS | (A): | 1623; | 0.001; | 0.020
BOND ANGLES REFINED ATOMS | (DEGREES): | 3182; | 1.349; | 1.998
BOND ANGLES OTHERS | (DEGREES): | 3980; | 0.849; | 3.005
TORSION ANGLES, PERIOD 1 | (DEGREES): | 283; | 5.657; | 5.000
TORSION ANGLES, PERIOD 2 | (DEGREES): | 99; | 36.895; | 24.848
TORSION ANGLES, PERIOD 3 | (DEGREES): | 444; | 17.076; | 15.000
TORSION ANGLES, PERIOD 4 | (DEGREES): | 10; | 20.741; | 15.000
CHIRAL-CENTER RESTRAINTS | (A$^{**}$3): | 359; | 0.073; | 0.200
GENERAL PLANES REFINED ATOMS | (A): | 2541; | 0.005; | 0.021
GENERAL PLANES OTHERS | (A): | 454; | 0.001; | 0.020

ISOTROPIC THERMAL FACTOR RESTRAINTS. | | COUNT | RMS | WEIGHT
---|---|---|---|---
MAIN-CHAIN BOND REFINED ATOMS | (A$^{**}$2): | 1419; | 0.743; | 1.500
MAIN-CHAIN BOND OTHER ATOMS | (A$^{**}$2): | 573; | 0.094; | 1.500
MAIN-CHAIN ANGLE REFINED ATOMS | (A$^{**}$2): | 2301; | 1.380; | 2.000
SIDE-CHAIN BOND REFINED ATOMS | (A$^{**}$2): | 937; | 1.519; | 3.000
SIDE-CHAIN ANGLE REFINED ATOMS | (A$^{**}$2): | 881; | 2.543; | 4.500

NCS RESTRAINTS STATISTICS
  NUMBER OF NCS GROUPS: NULL
TWIN DETAILS
  NUMBER OF TWIN DOMAINS: NULL
TLS DETAILS
  NUMBER OF TLS GROUPS: NULL
  BULK SOLVENT MODELLING.
    METHOD USED: MASK
    PARAMETERS FOR MASK CALCULATION
    VDW PROBE RADIUS: 1.20
    ION PROBE RADIUS: 0.80
    SHRINKAGE RADIUS: 0.80

TABLE 1-continued

```
OTHER REFINEMENT REMARKS:
  HYDROGENS HAVE BEEN ADDED
  IN THE RIDING POSITIONS
  U VALUES:   REFINED INDIVIDUALLY
LINKR   LYS A 253    ASN A 269    gap
CRYST1   90.322   90.322   92.977   90.00   90.00   120.00    P 32 2 1
SCALE1    0.011072   0.006392   0.000000    0.00000
SCALE2    0.000000   0.012784   0.000000    0.00000
SCALE3    0.000000   0.000000   0.010755    0.00000
```

TABLE 2

| | | | | | | | | | | | |
|---|---|---|---|---|---|---|---|---|---|---|---|
| ATOM | 1 | N | VAL | A | 211 | 9.704 | −66.509 | −3.990 | 1.00 | 59.69 | N |
| ATOM | 2 | CA | VAL | A | 211 | 10.385 | −66.598 | −2.646 | 1.00 | 60.04 | C |
| ATOM | 4 | CB | VAL | A | 211 | 10.989 | −68.012 | −2.359 | 1.00 | 59.80 | C |
| ATOM | 6 | CG1 | VAL | A | 211 | 9.891 | −69.035 | −2.116 | 1.00 | 59.27 | C |
| ATOM | 10 | CG2 | VAL | A | 211 | 11.946 | −68.457 | −3.489 | 1.00 | 59.03 | C |
| ATOM | 14 | C | VAL | A | 211 | 11.532 | −65.606 | −2.518 | 1.00 | 60.02 | C |
| ATOM | 15 | O | VAL | A | 211 | 11.997 | −65.062 | −3.514 | 1.00 | 60.65 | O |
| ATOM | 19 | N | TYR | A | 212 | 11.998 | −65.415 | −1.286 | 1.00 | 59.74 | N |
| ATOM | 20 | CA | TYR | A | 212 | 13.157 | −64.569 | −1.003 | 1.00 | 59.52 | C |
| ATOM | 22 | CB | TYR | A | 212 | 13.311 | −64.386 | 0.511 | 1.00 | 59.60 | C |
| ATOM | 25 | CG | TYR | A | 212 | 12.128 | −63.707 | 1.174 | 1.00 | 59.77 | C |
| ATOM | 26 | CD1 | TYR | A | 212 | 11.715 | −62.434 | 0.778 | 1.00 | 60.12 | C |
| ATOM | 28 | CE1 | TYR | A | 212 | 10.619 | −61.802 | 1.404 | 1.00 | 60.51 | C |
| ATOM | 30 | CZ | TYR | A | 212 | 9.940 | −62.452 | 2.434 | 1.00 | 60.56 | C |
| ATOM | 31 | OH | TYR | A | 212 | 8.878 | −61.832 | 3.046 | 1.00 | 62.98 | O |
| ATOM | 33 | CE2 | TYR | A | 212 | 10.326 | −63.714 | 2.843 | 1.00 | 59.39 | C |
| ATOM | 35 | CD2 | TYR | A | 212 | 11.421 | −64.333 | 2.213 | 1.00 | 60.77 | C |
| ATOM | 37 | C | TYR | A | 212 | 14.441 | −65.165 | −1.574 | 1.00 | 59.11 | C |
| ATOM | 38 | O | TYR | A | 212 | 14.550 | −66.377 | −1.718 | 1.00 | 59.78 | O |
| ATOM | 40 | N | PRO | A | 213 | 15.415 | −64.318 | −1.937 | 1.00 | 58.48 | N |
| ATOM | 41 | CA | PRO | A | 213 | 16.614 | −64.920 | −2.509 | 1.00 | 57.79 | C |
| ATOM | 43 | CB | PRO | A | 213 | 17.364 | −63.730 | −3.147 | 1.00 | 57.55 | C |
| ATOM | 46 | CG | PRO | A | 213 | 16.723 | −62.527 | −2.656 | 1.00 | 58.12 | C |
| ATOM | 49 | CD | PRO | A | 213 | 15.336 | −62.876 | −2.211 | 1.00 | 58.50 | C |
| ATOM | 52 | C | PRO | A | 213 | 17.461 | −65.610 | −1.464 | 1.00 | 57.37 | C |
| ATOM | 53 | O | PRO | A | 213 | 17.402 | −65.272 | −0.276 | 1.00 | 57.60 | O |
| ATOM | 54 | N | LYS | A | 214 | 18.261 | −66.556 | −1.927 | 1.00 | 56.63 | N |
| ATOM | 55 | CA | LYS | A | 214 | 19.101 | −67.370 | −1.056 | 1.00 | 56.21 | C |
| ATOM | 57 | CB | LYS | A | 214 | 19.924 | −68.363 | −1.892 | 1.00 | 56.25 | C |
| ATOM | 60 | CG | LYS | A | 214 | 20.776 | −69.324 | −1.085 | 1.00 | 55.36 | C |
| ATOM | 63 | CD | LYS | A | 214 | 21.099 | −70.544 | −1.909 | 1.00 | 55.57 | C |
| ATOM | 66 | CE | LYS | A | 214 | 21.812 | −71.608 | −1.117 | 1.00 | 55.87 | C |
| ATOM | 69 | NZ | LYS | A | 214 | 22.203 | −72.753 | −1.990 | 1.00 | 56.18 | N |
| ATOM | 73 | C | LYS | A | 214 | 20.042 | −66.551 | −0.189 | 1.00 | 55.96 | C |
| ATOM | 74 | O | LYS | A | 214 | 20.142 | −66.805 | 1.037 | 1.00 | 56.20 | O |
| ATOM | 76 | N | ALA | A | 215 | 20.744 | −65.593 | −0.809 | 1.00 | 54.77 | N |
| ATOM | 77 | CA | ALA | A | 215 | 21.747 | −64.802 | −0.079 | 1.00 | 53.99 | C |
| ATOM | 79 | CB | ALA | A | 215 | 22.507 | −63.912 | −1.011 | 1.00 | 53.78 | C |
| ATOM | 83 | C | ALA | A | 215 | 21.114 | −63.991 | 1.037 | 1.00 | 53.43 | C |
| ATOM | 84 | O | ALA | A | 215 | 21.740 | −63.742 | 2.042 | 1.00 | 54.14 | O |
| ATOM | 86 | N | LEU | A | 216 | 19.861 | −63.606 | 0.870 | 1.00 | 53.32 | N |
| ATOM | 87 | CA | LEU | A | 216 | 19.115 | −62.898 | 1.912 | 1.00 | 53.40 | C |
| ATOM | 89 | CB | LEU | A | 216 | 17.831 | −62.314 | 1.316 | 1.00 | 53.41 | C |
| ATOM | 92 | CG | LEU | A | 216 | 16.896 | −61.573 | 2.265 | 1.00 | 54.08 | C |
| ATOM | 94 | CD1 | LEU | A | 216 | 17.552 | −60.308 | 2.744 | 1.00 | 54.78 | C |
| ATOM | 98 | CD2 | LEU | A | 216 | 15.578 | −61.251 | 1.586 | 1.00 | 55.48 | C |
| ATOM | 102 | C | LEU | A | 216 | 18.750 | −63.845 | 3.062 | 1.00 | 53.13 | C |
| ATOM | 103 | O | LEU | A | 216 | 19.023 | −63.570 | 4.227 | 1.00 | 52.31 | O |
| ATOM | 105 | N | ARG | A | 217 | 18.112 | −64.959 | 2.715 | 1.00 | 52.97 | N |
| ATOM | 106 | CA | ARG | A | 217 | 17.702 | −65.955 | 3.712 | 1.00 | 52.47 | C |
| ATOM | 108 | CB | ARG | A | 217 | 16.960 | −67.106 | 3.051 | 1.00 | 51.91 | C |
| ATOM | 111 | CG | ARG | A | 217 | 15.582 | −66.743 | 2.529 | 1.00 | 50.50 | C |
| ATOM | 114 | CD | ARG | A | 217 | 15.006 | −67.879 | 1.647 | 1.00 | 49.87 | C |
| ATOM | 117 | NE | ARG | A | 217 | 15.044 | −69.171 | 2.358 | 1.00 | 46.94 | N |
| ATOM | 119 | CZ | ARG | A | 217 | 15.584 | −70.296 | 1.905 | 1.00 | 44.78 | C |
| ATOM | 120 | NH1 | ARG | A | 217 | 16.108 | −70.383 | 0.688 | 1.00 | 45.58 | N |
| ATOM | 123 | NH2 | ARG | A | 217 | 15.562 | −71.374 | 2.673 | 1.00 | 46.22 | N |
| ATOM | 126 | C | ARG | A | 217 | 18.903 | −66.489 | 4.505 | 1.00 | 52.60 | C |
| ATOM | 127 | O | ARG | A | 217 | 18.784 | −66.780 | 5.703 | 1.00 | 52.26 | O |
| ATOM | 129 | N | ASP | A | 218 | 20.049 | −66.594 | 3.843 | 1.00 | 52.51 | N |
| ATOM | 130 | CA | ASP | A | 218 | 21.301 | −66.974 | 4.510 | 1.00 | 53.21 | C |
| ATOM | 132 | CB | ASP | A | 218 | 22.477 | −66.844 | 3.538 | 1.00 | 53.69 | C |
| ATOM | 135 | CG | ASP | A | 218 | 23.762 | −67.419 | 4.096 | 1.00 | 54.40 | C |
| ATOM | 136 | OD1 | ASP | A | 218 | 23.982 | −68.621 | 3.875 | 1.00 | 55.35 | O |
| ATOM | 137 | OD2 | ASP | A | 218 | 24.564 | −66.674 | 4.727 | 1.00 | 58.00 | O |

TABLE 2-continued

| | | | | | | | | | | | |
|---|---|---|---|---|---|---|---|---|---|---|---|
| ATOM | 138 | C | ASP | A | 218 | 21.643 | −66.146 | 5.752 | 1.00 | 53.04 | C |
| ATOM | 139 | O | ASP | A | 218 | 22.199 | −66.680 | 6.718 | 1.00 | 52.74 | O |
| ATOM | 141 | N | GLU | A | 219 | 21.361 | −64.844 | 5.694 | 1.00 | 53.15 | N |
| ATOM | 142 | CA | GLU | A | 219 | 21.721 | −63.902 | 6.767 | 1.00 | 53.21 | C |
| ATOM | 144 | CB | GLU | A | 219 | 22.298 | −62.611 | 6.186 | 1.00 | 53.06 | C |
| ATOM | 147 | CG | GLU | A | 219 | 23.735 | −62.684 | 5.815 | 1.00 | 53.19 | C |
| ATOM | 150 | CD | GLU | A | 219 | 24.314 | −61.301 | 5.633 | 1.00 | 53.30 | C |
| ATOM | 151 | OE1 | GLU | A | 219 | 24.683 | −60.673 | 6.647 | 1.00 | 52.87 | O |
| ATOM | 152 | OE2 | GLU | A | 219 | 24.402 | −60.851 | 4.481 | 1.00 | 52.75 | O |
| ATOM | 153 | C | GLU | A | 219 | 20.559 | −63.491 | 7.627 | 1.00 | 53.33 | C |
| ATOM | 154 | O | GLU | A | 219 | 20.779 | −63.008 | 8.740 | 1.00 | 53.79 | O |
| ATOM | 156 | N | TYR | A | 220 | 19.343 | −63.639 | 7.107 | 1.00 | 53.55 | N |
| ATOM | 157 | CA | TYR | A | 220 | 18.156 | −63.122 | 7.754 | 1.00 | 54.35 | C |
| ATOM | 159 | CB | TYR | A | 220 | 17.707 | −61.830 | 7.056 | 1.00 | 54.15 | C |
| ATOM | 162 | CG | TYR | A | 220 | 18.751 | −60.715 | 7.062 | 1.00 | 53.15 | C |
| ATOM | 163 | CD1 | TYR | A | 220 | 18.892 | −59.862 | 8.159 | 1.00 | 53.30 | C |
| ATOM | 165 | CE1 | TYR | A | 220 | 19.838 | −58.833 | 8.172 | 1.00 | 51.77 | C |
| ATOM | 167 | CZ | TYR | A | 220 | 20.653 | −58.645 | 7.074 | 1.00 | 51.76 | C |
| ATOM | 168 | OH | TYR | A | 220 | 21.601 | −57.641 | 7.081 | 1.00 | 52.77 | O |
| ATOM | 170 | CE2 | TYR | A | 220 | 20.529 | −59.470 | 5.972 | 1.00 | 51.93 | C |
| ATOM | 172 | CD2 | TYR | A | 220 | 19.585 | −60.500 | 5.969 | 1.00 | 52.20 | C |
| ATOM | 174 | C | TYR | A | 220 | 17.002 | −64.125 | 7.758 | 1.00 | 55.63 | C |
| ATOM | 175 | O | TYR | A | 220 | 16.797 | −64.873 | 6.795 | 1.00 | 55.50 | O |
| ATOM | 177 | N | ILE | A | 221 | 16.269 | −64.137 | 8.867 | 1.00 | 57.44 | N |
| ATOM | 178 | CA | ILE | A | 221 | 14.982 | −64.809 | 8.973 | 1.00 | 59.07 | C |
| ATOM | 180 | CB | ILE | A | 221 | 14.742 | −65.392 | 10.359 | 1.00 | 59.12 | C |
| ATOM | 182 | CG1 | ILE | A | 221 | 15.752 | −66.486 | 10.679 | 1.00 | 57.77 | C |
| ATOM | 185 | CD1 | ILE | A | 221 | 15.931 | −66.670 | 12.175 | 1.00 | 57.33 | C |
| ATOM | 189 | CG2 | ILE | A | 221 | 13.304 | −65.891 | 10.472 | 1.00 | 58.21 | C |
| ATOM | 193 | C | ILE | A | 221 | 13.912 | −63.754 | 8.798 | 1.00 | 61.48 | C |
| ATOM | 194 | O | ILE | A | 221 | 13.863 | −62.773 | 9.550 | 1.00 | 60.93 | O |
| ATOM | 196 | N | MET | A | 222 | 13.039 | −63.972 | 7.822 | 1.00 | 64.73 | N |
| ATOM | 197 | CA | MET | A | 222 | 12.003 | −63.000 | 7.478 | 1.00 | 67.28 | C |
| ATOM | 199 | CB | MET | A | 222 | 11.690 | −63.050 | 5.981 | 1.00 | 67.73 | C |
| ATOM | 202 | CG | MET | A | 222 | 12.939 | −62.977 | 5.081 | 1.00 | 70.06 | C |
| ATOM | 205 | SD | MET | A | 222 | 13.810 | −61.407 | 5.173 | 1.00 | 75.87 | S |
| ATOM | 206 | CE | MET | A | 222 | 12.482 | −60.248 | 4.721 | 1.00 | 72.41 | C |
| ATOM | 210 | C | MET | A | 222 | 10.730 | −63.221 | 8.293 | 1.00 | 68.93 | C |
| ATOM | 211 | O | MET | A | 222 | 10.375 | −64.355 | 8.634 | 1.00 | 69.11 | O |
| ATOM | 213 | N | SER | A | 223 | 10.053 | −62.115 | 8.593 | 1.00 | 71.16 | N |
| ATOM | 214 | CA | SER | A | 223 | 8.869 | −62.123 | 9.436 | 1.00 | 72.72 | C |
| ATOM | 216 | CB | SER | A | 223 | 9.251 | −61.675 | 10.852 | 1.00 | 72.76 | C |
| ATOM | 219 | OG | SER | A | 223 | 8.222 | −61.947 | 11.784 | 1.00 | 72.89 | O |
| ATOM | 221 | C | SER | A | 223 | 7.774 | −61.233 | 8.831 | 1.00 | 74.35 | C |
| ATOM | 222 | O | SER | A | 223 | 7.682 | −61.103 | 7.605 | 1.00 | 74.25 | O |
| ATOM | 224 | N | LYS | A | 224 | 6.968 | −60.617 | 9.701 | 1.00 | 76.37 | N |
| ATOM | 225 | CA | LYS | A | 224 | 5.709 | −59.976 | 9.311 | 1.00 | 77.89 | C |
| ATOM | 227 | CB | LYS | A | 224 | 4.846 | −59.700 | 10.557 | 1.00 | 78.21 | C |
| ATOM | 230 | CG | LYS | A | 224 | 5.287 | −58.499 | 11.409 | 1.00 | 79.48 | C |
| ATOM | 233 | CD | LYS | A | 224 | 4.624 | −58.499 | 12.791 | 1.00 | 80.57 | C |
| ATOM | 236 | CE | LYS | A | 224 | 5.099 | −57.331 | 13.650 | 1.00 | 80.78 | C |
| ATOM | 239 | NZ | LYS | A | 224 | 4.758 | −56.019 | 13.022 | 1.00 | 81.60 | N |
| ATOM | 243 | C | LYS | A | 224 | 5.888 | −58.683 | 8.534 | 1.00 | 78.85 | C |
| ATOM | 244 | O | LYS | A | 224 | 6.977 | −58.108 | 8.493 | 1.00 | 79.38 | O |
| ATOM | 246 | N | THR | A | 225 | 4.792 | −58.237 | 7.926 | 1.00 | 79.95 | N |
| ATOM | 247 | CA | THR | A | 225 | 4.736 | −56.962 | 7.224 | 1.00 | 80.64 | C |
| ATOM | 249 | CB | THR | A | 225 | 3.646 | −56.979 | 6.140 | 1.00 | 80.64 | C |
| ATOM | 251 | OG1 | THR | A | 225 | 3.884 | −58.080 | 5.256 | 1.00 | 80.64 | O |
| ATOM | 253 | CG2 | THR | A | 225 | 3.639 | −55.661 | 5.338 | 1.00 | 80.64 | C |
| ATOM | 257 | C | THR | A | 225 | 4.454 | −55.832 | 8.209 | 1.00 | 81.30 | C |
| ATOM | 258 | O | THR | A | 225 | 3.713 | −56.011 | 9.173 | 1.00 | 81.52 | O |
| ATOM | 260 | N | LEU | A | 226 | 5.066 | −54.677 | 7.964 | 1.00 | 82.26 | N |
| ATOM | 261 | CA | LEU | A | 226 | 4.903 | −53.492 | 8.812 | 1.00 | 82.89 | C |
| ATOM | 263 | CB | LEU | A | 226 | 6.276 | −53.001 | 9.283 | 1.00 | 82.80 | C |
| ATOM | 266 | CG | LEU | A | 226 | 7.013 | −53.974 | 10.215 | 1.00 | 82.80 | C |
| ATOM | 268 | CD1 | LEU | A | 226 | 8.507 | −53.651 | 10.329 | 1.00 | 82.21 | C |
| ATOM | 272 | CD2 | LEU | A | 226 | 6.353 | −53.991 | 11.587 | 1.00 | 82.54 | C |
| ATOM | 276 | C | LEU | A | 226 | 4.135 | −52.381 | 8.076 | 1.00 | 83.57 | C |
| ATOM | 277 | O | LEU | A | 226 | 3.347 | −51.664 | 8.689 | 1.00 | 83.23 | O |
| ATOM | 279 | N | GLY | A | 227 | 4.373 | −52.250 | 6.769 | 1.00 | 84.56 | N |
| ATOM | 280 | CA | GLY | A | 227 | 3.577 | −51.375 | 5.903 | 1.00 | 85.41 | C |
| ATOM | 283 | C | GLY | A | 227 | 3.666 | −51.734 | 4.421 | 1.00 | 86.33 | C |
| ATOM | 284 | O | GLY | A | 227 | 4.271 | −52.751 | 4.042 | 1.00 | 86.12 | O |
| ATOM | 286 | N | SER | A | 228 | 3.047 | −50.896 | 3.585 | 1.00 | 87.47 | N |
| ATOM | 287 | CA | SER | A | 228 | 3.185 | −50.990 | 2.114 | 1.00 | 88.36 | C |
| ATOM | 289 | CB | SER | A | 228 | 2.328 | −52.135 | 1.546 | 1.00 | 88.37 | C |
| ATOM | 292 | OG | SER | A | 228 | 0.957 | −51.935 | 1.829 | 1.00 | 88.44 | O |
| ATOM | 294 | C | SER | A | 228 | 2.833 | −49.663 | 1.426 | 1.00 | 88.90 | C |
| ATOM | 295 | O | SER | A | 228 | 2.424 | −48.699 | 2.088 | 1.00 | 89.00 | O |
| ATOM | 297 | N | GLY | A | 229 | 3.015 | −49.616 | 0.103 | 1.00 | 89.40 | N |

TABLE 2-continued

| | | | | | | | | | | |
|---|---|---|---|---|---|---|---|---|---|---|
| ATOM | 298 | CA | GLY | A | 229 | 2.649 | −48.440 | −0.696 | 1.00 | 89.53 | C |
| ATOM | 301 | C | GLY | A | 229 | 2.643 | −48.742 | −2.184 | 1.00 | 89.79 | C |
| ATOM | 302 | O | GLY | A | 229 | 2.528 | −49.909 | −2.590 | 1.00 | 90.11 | O |
| ATOM | 304 | N | ALA | A | 230 | 2.751 | −47.696 | −3.003 | 1.00 | 89.68 | N |
| ATOM | 305 | CA | ALA | A | 230 | 2.987 | −47.884 | −4.430 | 1.00 | 89.48 | C |
| ATOM | 307 | CB | ALA | A | 230 | 2.856 | −46.554 | −5.190 | 1.00 | 89.35 | C |
| ATOM | 311 | C | ALA | A | 230 | 4.395 | −48.494 | −4.596 | 1.00 | 89.31 | C |
| ATOM | 312 | O | ALA | A | 230 | 5.358 | −48.028 | −3.965 | 1.00 | 89.33 | O |
| ATOM | 314 | N | CYS | A | 231 | 4.483 | −49.570 | −5.389 | 1.00 | 88.81 | N |
| ATOM | 315 | CA | CYS | A | 231 | 5.751 | −50.258 | −5.763 | 1.00 | 88.31 | C |
| ATOM | 317 | CB | CYS | A | 231 | 6.805 | −49.265 | −6.328 | 1.00 | 88.65 | C |
| ATOM | 320 | SG | CYS | A | 231 | 6.395 | −48.463 | −7.955 | 1.00 | 90.98 | S |
| ATOM | 322 | C | CYS | A | 231 | 6.410 | −51.187 | −4.695 | 1.00 | 86.89 | C |
| ATOM | 323 | O | CYS | A | 231 | 7.030 | −52.188 | −5.067 | 1.00 | 86.84 | O |
| ATOM | 325 | N | GLY | A | 232 | 6.286 | −50.880 | −3.400 | 1.00 | 85.15 | N |
| ATOM | 326 | CA | GLY | A | 232 | 7.008 | −51.644 | −2.369 | 1.00 | 83.63 | C |
| ATOM | 329 | C | GLY | A | 232 | 6.314 | −51.919 | −1.043 | 1.00 | 82.13 | C |
| ATOM | 330 | O | GLY | A | 232 | 5.110 | −51.689 | −0.883 | 1.00 | 81.95 | O |
| ATOM | 332 | N | GLU | A | 233 | 7.114 | −52.406 | −0.090 | 1.00 | 80.29 | N |
| ATOM | 333 | CA | GLU | A | 233 | 6.632 | −52.963 | 1.180 | 1.00 | 78.67 | C |
| ATOM | 335 | CB | GLU | A | 233 | 6.101 | −54.372 | 0.930 | 1.00 | 78.75 | C |
| ATOM | 338 | CG | GLU | A | 233 | 5.300 | −54.984 | 2.066 | 1.00 | 80.04 | C |
| ATOM | 341 | CD | GLU | A | 233 | 5.094 | −56.498 | 1.893 | 1.00 | 81.89 | C |
| ATOM | 342 | OE1 | GLU | A | 233 | 5.456 | −57.033 | 0.817 | 1.00 | 82.69 | O |
| ATOM | 343 | OE2 | GLU | A | 233 | 4.576 | −57.156 | 2.835 | 1.00 | 82.47 | O |
| ATOM | 344 | C | GLU | A | 233 | 7.766 | −53.014 | 2.224 | 1.00 | 76.64 | C |
| ATOM | 345 | O | GLU | A | 233 | 8.942 | −53.141 | 1.871 | 1.00 | 76.15 | O |
| ATOM | 347 | N | VAL | A | 234 | 7.405 | −52.916 | 3.503 | 1.00 | 74.24 | N |
| ATOM | 348 | CA | VAL | A | 234 | 8.372 | −53.026 | 4.585 | 1.00 | 72.31 | C |
| ATOM | 350 | CB | VAL | A | 234 | 8.365 | −51.774 | 5.468 | 1.00 | 72.25 | C |
| ATOM | 352 | CG1 | VAL | A | 234 | 9.567 | −51.781 | 6.383 | 1.00 | 71.92 | C |
| ATOM | 356 | CG2 | VAL | A | 234 | 8.370 | −50.540 | 4.623 | 1.00 | 72.34 | C |
| ATOM | 360 | C | VAL | A | 234 | 8.086 | −54.253 | 5.457 | 1.00 | 70.71 | C |
| ATOM | 361 | O | VAL | A | 234 | 6.998 | −54.369 | 6.028 | 1.00 | 69.97 | O |
| ATOM | 363 | N | LYS | A | 235 | 9.077 | −55.151 | 5.547 | 1.00 | 68.82 | N |
| ATOM | 364 | CA | LYS | A | 235 | 9.000 | −56.382 | 6.356 | 1.00 | 67.28 | C |
| ATOM | 366 | CB | LYS | A | 235 | 9.474 | −57.589 | 5.540 | 1.00 | 67.57 | C |
| ATOM | 369 | CG | LYS | A | 235 | 8.467 | −58.117 | 4.518 | 1.00 | 69.04 | C |
| ATOM | 372 | CD | LYS | A | 235 | 7.541 | −59.179 | 5.125 | 1.00 | 71.23 | C |
| ATOM | 375 | CE | LYS | A | 235 | 6.432 | −59.613 | 4.152 | 1.00 | 72.35 | C |
| ATOM | 378 | NZ | LYS | A | 235 | 6.939 | −59.790 | 2.739 | 1.00 | 72.71 | N |
| ATOM | 382 | C | LYS | A | 235 | 9.838 | −56.304 | 7.627 | 1.00 | 65.41 | C |
| ATOM | 383 | O | LYS | A | 235 | 10.804 | −55.561 | 7.721 | 1.00 | 64.96 | O |
| ATOM | 385 | N | LEU | A | 236 | 9.455 | −57.093 | 8.615 | 1.00 | 63.85 | N |
| ATOM | 386 | CA | LEU | A | 236 | 10.290 | −57.304 | 9.794 | 1.00 | 62.20 | C |
| ATOM | 388 | CB | LEU | A | 236 | 9.436 | −57.581 | 11.034 | 1.00 | 62.14 | C |
| ATOM | 391 | CG | LEU | A | 236 | 10.199 | −57.880 | 12.335 | 1.00 | 62.51 | C |
| ATOM | 393 | CD1 | LEU | A | 236 | 10.922 | −56.627 | 12.868 | 1.00 | 60.92 | C |
| ATOM | 397 | CD2 | LEU | A | 236 | 9.288 | −58.481 | 13.411 | 1.00 | 60.30 | C |
| ATOM | 401 | C | LEU | A | 236 | 11.184 | −58.498 | 9.498 | 1.00 | 60.71 | C |
| ATOM | 402 | O | LEU | A | 236 | 10.742 | −59.479 | 8.875 | 1.00 | 60.24 | O |
| ATOM | 404 | N | ALA | A | 237 | 12.445 | −58.398 | 9.918 | 1.00 | 58.82 | N |
| ATOM | 405 | CA | ALA | A | 237 | 13.373 | −59.513 | 9.825 | 1.00 | 57.67 | C |
| ATOM | 407 | CB | ALA | A | 237 | 14.110 | −59.456 | 8.513 | 1.00 | 57.41 | C |
| ATOM | 411 | C | ALA | A | 237 | 14.345 | −59.525 | 11.012 | 1.00 | 56.66 | C |
| ATOM | 412 | O | ALA | A | 237 | 14.464 | −58.536 | 11.752 | 1.00 | 56.37 | O |
| ATOM | 414 | N | PHE | A | 238 | 15.017 | −60.653 | 11.210 | 1.00 | 55.52 | N |
| ATOM | 415 | CA | PHE | A | 238 | 16.030 | −60.771 | 12.261 | 1.00 | 55.20 | C |
| ATOM | 417 | CB | PHE | A | 238 | 15.675 | −61.873 | 13.253 | 1.00 | 55.71 | C |
| ATOM | 420 | CG | PHE | A | 238 | 14.365 | −61.682 | 13.903 | 1.00 | 56.62 | C |
| ATOM | 421 | CD1 | PHE | A | 238 | 14.281 | −61.076 | 15.141 | 1.00 | 59.36 | C |
| ATOM | 423 | CE1 | PHE | A | 238 | 13.047 | −60.889 | 15.756 | 1.00 | 60.39 | C |
| ATOM | 425 | CZ | PHE | A | 238 | 11.894 | −61.316 | 15.116 | 1.00 | 59.69 | C |
| ATOM | 427 | CE2 | PHE | A | 238 | 11.983 | −61.931 | 13.874 | 1.00 | 59.53 | C |
| ATOM | 429 | CD2 | PHE | A | 238 | 13.209 | −62.104 | 13.277 | 1.00 | 57.92 | C |
| ATOM | 431 | C | PHE | A | 238 | 17.348 | −61.125 | 11.651 | 1.00 | 53.79 | C |
| ATOM | 432 | O | PHE | A | 238 | 17.422 | −62.050 | 10.873 | 1.00 | 53.07 | O |
| ATOM | 434 | N | GLU | A | 239 | 18.392 | −60.416 | 12.026 | 1.00 | 53.11 | N |
| ATOM | 435 | CA | GLU | A | 239 | 19.720 | −60.772 | 11.562 | 1.00 | 53.36 | C |
| ATOM | 437 | CB | GLU | A | 239 | 20.670 | −59.607 | 11.780 | 1.00 | 53.56 | C |
| ATOM | 440 | CG | GLU | A | 239 | 22.005 | −59.711 | 11.059 | 1.00 | 55.35 | C |
| ATOM | 443 | CD | GLU | A | 239 | 22.933 | −58.571 | 11.472 | 1.00 | 58.46 | C |
| ATOM | 444 | OE1 | GLU | A | 239 | 22.382 | −57.510 | 11.879 | 1.00 | 59.16 | O |
| ATOM | 445 | OE2 | GLU | A | 239 | 24.185 | −58.742 | 11.398 | 1.00 | 58.56 | O |
| ATOM | 446 | C | GLU | A | 239 | 20.198 | −62.026 | 12.302 | 1.00 | 52.68 | C |
| ATOM | 447 | O | GLU | A | 239 | 20.225 | −62.074 | 13.521 | 1.00 | 51.90 | O |
| ATOM | 449 | N | ARG | A | 240 | 20.543 | −63.056 | 11.553 | 1.00 | 52.84 | N |
| ATOM | 450 | CA | ARG | A | 240 | 20.932 | −64.326 | 12.158 | 1.00 | 53.23 | C |
| ATOM | 452 | CB | ARG | A | 240 | 21.216 | −65.368 | 11.081 | 1.00 | 52.90 | C |
| ATOM | 455 | CG | ARG | A | 240 | 19.955 | −65.799 | 10.334 | 1.00 | 51.69 | C |

TABLE 2-continued

| ATOM | 458 | CD | ARG | A | 240 | 20.286 | −66.765 | 9.232 | 1.00 | 50.76 | C |
|---|---|---|---|---|---|---|---|---|---|---|---|
| ATOM | 461 | NE | ARG | A | 240 | 19.139 | −66.983 | 8.349 | 1.00 | 50.02 | N |
| ATOM | 463 | CZ | ARG | A | 240 | 18.214 | −67.934 | 8.501 | 1.00 | 49.70 | C |
| ATOM | 464 | NH1 | ARG | A | 240 | 18.262 | −68.790 | 9.509 | 1.00 | 49.42 | N |
| ATOM | 467 | NH2 | ARG | A | 240 | 17.221 | −68.022 | 7.633 | 1.00 | 49.65 | N |
| ATOM | 470 | C | ARG | A | 240 | 22.134 | −64.159 | 13.077 | 1.00 | 54.12 | C |
| ATOM | 471 | O | ARG | A | 240 | 22.142 | −64.686 | 14.185 | 1.00 | 54.74 | O |
| ATOM | 473 | N | LYS | A | 241 | 23.125 | −63.388 | 12.648 | 1.00 | 54.86 | N |
| ATOM | 474 | CA | LYS | A | 241 | 24.331 | −63.200 | 13.448 | 1.00 | 55.86 | C |
| ATOM | 476 | CB | LYS | A | 241 | 25.360 | −62.335 | 12.688 | 1.00 | 56.93 | C |
| ATOM | 479 | CG | LYS | A | 241 | 26.798 | −62.455 | 13.231 | 1.00 | 59.58 | C |
| ATOM | 482 | CD | LYS | A | 241 | 27.842 | −61.801 | 12.312 | 1.00 | 63.23 | C |
| ATOM | 485 | CE | LYS | A | 241 | 27.811 | −60.265 | 12.381 | 1.00 | 65.01 | C |
| ATOM | 488 | NZ | LYS | A | 241 | 28.757 | −59.656 | 11.383 | 1.00 | 66.35 | N |
| ATOM | 492 | C | LYS | A | 241 | 24.109 | −62.596 | 14.825 | 1.00 | 55.46 | C |
| ATOM | 493 | O | LYS | A | 241 | 24.903 | −62.851 | 15.704 | 1.00 | 55.12 | O |
| ATOM | 495 | N | THR | A | 242 | 23.068 | −61.774 | 15.007 | 1.00 | 55.69 | N |
| ATOM | 496 | CA | THR | A | 242 | 22.864 | −61.053 | 16.277 | 1.00 | 55.89 | C |
| ATOM | 498 | CB | THR | A | 242 | 22.957 | −59.514 | 16.064 | 1.00 | 56.33 | C |
| ATOM | 500 | OG1 | THR | A | 242 | 21.863 | −59.071 | 15.232 | 1.00 | 56.30 | O |
| ATOM | 502 | CG2 | THR | A | 242 | 24.339 | −59.101 | 15.471 | 1.00 | 53.37 | C |
| ATOM | 506 | C | THR | A | 242 | 21.521 | −61.268 | 16.948 | 1.00 | 56.68 | C |
| ATOM | 507 | O | THR | A | 242 | 21.327 | −60.868 | 18.088 | 1.00 | 56.11 | O |
| ATOM | 509 | N | CYS | A | 243 | 20.573 | −61.849 | 16.229 | 1.00 | 57.80 | N |
| ATOM | 510 | CA | CYS | A | 243 | 19.209 | −61.948 | 16.710 | 1.00 | 58.80 | C |
| ATOM | 512 | CB | CYS | A | 243 | 19.141 | −62.852 | 17.935 | 1.00 | 58.56 | C |
| ATOM | 515 | SG | CYS | A | 243 | 19.704 | −64.479 | 17.564 | 1.00 | 59.76 | S |
| ATOM | 517 | C | CYS | A | 243 | 18.598 | −60.591 | 17.023 | 1.00 | 59.69 | C |
| ATOM | 518 | O | CYS | A | 243 | 17.820 | −60.461 | 17.972 | 1.00 | 60.65 | O |
| ATOM | 520 | N | LYS | A | 244 | 18.941 | −59.587 | 16.228 | 1.00 | 60.16 | N |
| ATOM | 521 | CA | LYS | A | 244 | 18.373 | −58.273 | 16.413 | 1.00 | 60.73 | C |
| ATOM | 523 | CB | LYS | A | 244 | 19.461 | −57.192 | 16.469 | 1.00 | 61.42 | C |
| ATOM | 526 | CG | LYS | A | 244 | 20.251 | −57.118 | 17.809 | 1.00 | 63.19 | C |
| ATOM | 529 | CD | LYS | A | 244 | 19.399 | −56.559 | 18.978 | 1.00 | 65.45 | C |
| ATOM | 532 | CE | LYS | A | 244 | 20.243 | −55.851 | 20.072 | 1.00 | 66.52 | C |
| ATOM | 535 | NZ | LYS | A | 244 | 20.891 | −56.802 | 21.036 | 1.00 | 66.32 | N |
| ATOM | 539 | C | LYS | A | 244 | 17.413 | −58.007 | 15.266 | 1.00 | 60.83 | C |
| ATOM | 540 | O | LYS | A | 244 | 17.661 | −58.381 | 14.104 | 1.00 | 60.86 | O |
| ATOM | 542 | N | LYS | A | 245 | 16.307 | −57.364 | 15.612 | 1.00 | 60.45 | N |
| ATOM | 543 | CA | LYS | A | 245 | 15.317 | −56.962 | 14.650 | 1.00 | 60.56 | C |
| ATOM | 545 | CB | LYS | A | 245 | 14.152 | −56.295 | 15.374 | 1.00 | 61.00 | C |
| ATOM | 548 | CG | LYS | A | 245 | 13.379 | −57.218 | 16.349 | 1.00 | 62.98 | C |
| ATOM | 551 | CD | LYS | A | 245 | 12.198 | −56.453 | 16.990 | 1.00 | 65.29 | C |
| ATOM | 554 | CE | LYS | A | 245 | 11.545 | −57.219 | 18.134 | 1.00 | 66.40 | C |
| ATOM | 557 | NZ | LYS | A | 245 | 10.325 | −56.509 | 18.634 | 1.00 | 66.86 | N |
| ATOM | 561 | C | LYS | A | 245 | 15.935 | −55.999 | 13.629 | 1.00 | 59.94 | C |
| ATOM | 562 | O | LYS | A | 245 | 16.765 | −55.165 | 13.982 | 1.00 | 59.48 | O |
| ATOM | 564 | N | VAL | A | 246 | 15.570 | −56.170 | 12.363 | 1.00 | 59.25 | N |
| ATOM | 565 | CA | VAL | A | 246 | 15.942 | −55.239 | 11.305 | 1.00 | 58.95 | C |
| ATOM | 567 | CB | VAL | A | 246 | 17.127 | −55.744 | 10.432 | 1.00 | 58.86 | C |
| ATOM | 569 | CG1 | VAL | A | 246 | 18.401 | −55.977 | 11.255 | 1.00 | 56.91 | C |
| ATOM | 573 | CG2 | VAL | A | 246 | 16.723 | −56.982 | 9.657 | 1.00 | 56.99 | C |
| ATOM | 577 | C | VAL | A | 246 | 14.716 | −55.052 | 10.399 | 1.00 | 59.82 | C |
| ATOM | 578 | O | VAL | A | 246 | 13.777 | −55.843 | 10.421 | 1.00 | 59.34 | O |
| ATOM | 580 | N | ALA | A | 247 | 14.716 | −53.994 | 9.608 | 1.00 | 60.50 | N |
| ATOM | 581 | CA | ALA | A | 247 | 13.620 | −53.765 | 8.696 | 1.00 | 61.12 | C |
| ATOM | 583 | CB | ALA | A | 247 | 13.103 | −52.343 | 8.852 | 1.00 | 61.11 | C |
| ATOM | 587 | C | ALA | A | 247 | 14.156 | −54.002 | 7.304 | 1.00 | 61.70 | C |
| ATOM | 588 | O | ALA | A | 247 | 15.312 | −53.709 | 7.030 | 1.00 | 61.34 | O |
| ATOM | 590 | N | ILE | A | 248 | 13.325 | −54.548 | 6.431 | 1.00 | 62.75 | N |
| ATOM | 591 | CA | ILE | A | 248 | 13.746 | −54.823 | 5.059 | 1.00 | 63.81 | C |
| ATOM | 593 | CB | ILE | A | 248 | 13.925 | −56.332 | 4.821 | 1.00 | 63.85 | C |
| ATOM | 595 | CG1 | ILE | A | 248 | 15.112 | −56.847 | 5.634 | 1.00 | 63.43 | C |
| ATOM | 598 | CD1 | ILE | A | 248 | 15.448 | −58.304 | 5.363 | 1.00 | 61.87 | C |
| ATOM | 602 | CG2 | ILE | A | 248 | 14.150 | −56.616 | 3.339 | 1.00 | 63.80 | C |
| ATOM | 606 | C | ILE | A | 248 | 12.760 | −54.263 | 4.035 | 1.00 | 64.51 | C |
| ATOM | 607 | O | ILE | A | 248 | 11.656 | −54.785 | 3.892 | 1.00 | 64.61 | O |
| ATOM | 609 | N | LYS | A | 249 | 13.178 | −53.209 | 3.326 | 1.00 | 65.57 | N |
| ATOM | 610 | CA | LYS | A | 249 | 12.359 | −52.575 | 2.286 | 1.00 | 66.27 | C |
| ATOM | 612 | CB | LYS | A | 249 | 12.725 | −51.091 | 2.106 | 1.00 | 66.49 | C |
| ATOM | 615 | CG | LYS | A | 249 | 11.936 | −50.335 | 1.022 | 1.00 | 66.47 | C |
| ATOM | 618 | CD | LYS | A | 249 | 10.677 | −49.669 | 1.578 | 1.00 | 68.07 | C |
| ATOM | 621 | CE | LYS | A | 249 | 9.875 | −48.937 | 0.481 | 1.00 | 69.24 | C |
| ATOM | 624 | NZ | LYS | A | 249 | 8.454 | −48.611 | 0.890 | 1.00 | 71.19 | N |
| ATOM | 628 | C | LYS | A | 249 | 12.555 | −53.312 | 0.975 | 1.00 | 66.70 | C |
| ATOM | 629 | O | LYS | A | 249 | 13.679 | −53.481 | 0.507 | 1.00 | 66.44 | O |
| ATOM | 631 | N | ILE | A | 250 | 11.438 | −53.738 | 0.399 | 1.00 | 67.51 | N |
| ATOM | 632 | CA | ILE | A | 250 | 11.424 | −54.430 | −0.865 | 1.00 | 68.46 | C |
| ATOM | 634 | CB | ILE | A | 250 | 10.501 | −55.687 | −0.809 | 1.00 | 68.77 | C |
| ATOM | 636 | CG1 | ILE | A | 250 | 10.708 | −56.445 | 0.513 | 1.00 | 69.23 | C |

TABLE 2-continued

| | | | | | | | | | | | |
|---|---|---|---|---|---|---|---|---|---|---|---|
| ATOM | 639 | CD1 | ILE | A | 250 | 9.952 | −57.745 | 0.610 | 1.00 | 70.43 | C |
| ATOM | 643 | CG2 | ILE | A | 250 | 10.751 | −56.593 | −2.019 | 1.00 | 67.98 | C |
| ATOM | 647 | C | ILE | A | 250 | 10.896 | −53.455 | −1.906 | 1.00 | 69.21 | C |
| ATOM | 648 | O | ILE | A | 250 | 9.810 | −52.898 | −1.744 | 1.00 | 68.88 | O |
| ATOM | 650 | N | ILE | A | 251 | 11.681 | −53.214 | −2.947 | 1.00 | 70.25 | N |
| ATOM | 651 | CA | ILE | A | 251 | 11.218 | −52.426 | −4.072 | 1.00 | 71.13 | C |
| ATOM | 653 | CB | ILE | A | 251 | 12.084 | −51.173 | −4.347 | 1.00 | 71.33 | C |
| ATOM | 655 | CG1 | ILE | A | 251 | 12.475 | −50.463 | −3.053 | 1.00 | 71.35 | C |
| ATOM | 658 | CD1 | ILE | A | 251 | 13.696 | −49.546 | −3.238 | 1.00 | 71.11 | C |
| ATOM | 662 | CG2 | ILE | A | 251 | 11.336 | −50.210 | −5.274 | 1.00 | 70.48 | C |
| ATOM | 666 | C | ILE | A | 251 | 11.267 | −53.317 | −5.296 | 1.00 | 72.00 | C |
| ATOM | 667 | O | ILE | A | 251 | 12.349 | −53.771 | −5.714 | 1.00 | 71.58 | O |
| ATOM | 669 | N | SER | A | 252 | 10.087 | −53.553 | −5.866 | 1.00 | 73.24 | N |
| ATOM | 670 | CA | SER | A | 252 | 9.941 | −54.391 | −7.059 | 1.00 | 74.18 | C |
| ATOM | 672 | CB | SER | A | 252 | 8.481 | −54.813 | −7.242 | 1.00 | 74.34 | C |
| ATOM | 675 | OG | SER | A | 252 | 7.701 | −53.747 | −7.750 | 1.00 | 74.43 | O |
| ATOM | 677 | C | SER | A | 252 | 10.403 | −53.648 | −8.303 | 1.00 | 74.62 | C |
| ATOM | 678 | O | SER | A | 252 | 10.321 | −52.421 | −8.361 | 1.00 | 74.70 | O |
| ATOM | 680 | N | LYS | A | 253 | 10.856 | −54.405 | −9.297 | 1.00 | 75.20 | N |
| ATOM | 681 | CA | LYS | A | 253 | 11.352 | −53.837 | −10.548 | 1.00 | 75.62 | C |
| ATOM | 683 | CB | LYS | A | 253 | 12.426 | −54.745 | −11.131 | 1.00 | 75.58 | C |
| ATOM | 686 | CG | LYS | A | 253 | 13.458 | −55.164 | −10.116 | 1.00 | 75.54 | C |
| ATOM | 689 | CD | LYS | A | 253 | 14.715 | −55.637 | −10.792 | 1.00 | 75.90 | C |
| ATOM | 692 | CE | LYS | A | 253 | 15.825 | −55.808 | −9.783 | 1.00 | 76.35 | C |
| ATOM | 695 | NZ | LYS | A | 253 | 17.142 | −55.981 | −10.443 | 1.00 | 75.89 | N |
| ATOM | 699 | C | LYS | A | 253 | 10.212 | −53.648 | −11.559 | 1.00 | 75.89 | C |
| ATOM | 700 | O | LYS | A | 253 | 10.443 | −53.285 | −12.717 | 1.00 | 76.23 | O |
| ATOM | 702 | N | ASN | A | 269 | 17.249 | −44.062 | −9.764 | 1.00 | 75.30 | N |
| ATOM | 703 | CA | ASN | A | 269 | 17.488 | −45.492 | −9.610 | 1.00 | 75.65 | C |
| ATOM | 705 | CB | ASN | A | 269 | 18.483 | −46.009 | −10.665 | 1.00 | 75.83 | C |
| ATOM | 708 | CG | ASN | A | 269 | 18.131 | −47.422 | −11.170 | 1.00 | 76.90 | C |
| ATOM | 709 | OD1 | ASN | A | 269 | 17.815 | −48.330 | −10.388 | 1.00 | 77.75 | O |
| ATOM | 710 | ND2 | ASN | A | 269 | 18.189 | −47.603 | −12.478 | 1.00 | 77.63 | N |
| ATOM | 713 | C | ASN | A | 269 | 17.966 | −45.889 | −8.204 | 1.00 | 75.30 | C |
| ATOM | 714 | O | ASN | A | 269 | 18.396 | −45.064 | −7.387 | 1.00 | 75.29 | O |
| ATOM | 716 | N | VAL | A | 270 | 17.901 | −47.184 | −7.951 | 1.00 | 74.60 | N |
| ATOM | 717 | CA | VAL | A | 270 | 18.065 | −47.707 | −6.618 | 1.00 | 74.06 | C |
| ATOM | 719 | CB | VAL | A | 270 | 17.386 | −49.071 | −6.519 | 1.00 | 74.08 | C |
| ATOM | 721 | CG1 | VAL | A | 270 | 17.506 | −49.636 | −5.112 | 1.00 | 73.80 | C |
| ATOM | 725 | CG2 | VAL | A | 270 | 15.916 | −48.931 | −6.941 | 1.00 | 73.96 | C |
| ATOM | 729 | C | VAL | A | 270 | 19.533 | −47.795 | −6.242 | 1.00 | 73.65 | C |
| ATOM | 730 | O | VAL | A | 270 | 19.902 | −47.530 | −5.094 | 1.00 | 73.33 | O |
| ATOM | 732 | N | GLU | A | 271 | 20.372 | −48.138 | −7.215 | 1.00 | 73.37 | N |
| ATOM | 733 | CA | GLU | A | 271 | 21.817 | −48.217 | −6.979 | 1.00 | 73.17 | C |
| ATOM | 735 | CB | GLU | A | 271 | 22.561 | −48.776 | −8.217 | 1.00 | 73.98 | C |
| ATOM | 738 | CG | GLU | A | 271 | 22.796 | −50.337 | −8.159 | 1.00 | 76.01 | C |
| ATOM | 741 | CD | GLU | A | 271 | 22.609 | −51.064 | −9.508 | 1.00 | 78.36 | C |
| ATOM | 742 | OE1 | GLU | A | 271 | 23.243 | −50.659 | −10.516 | 1.00 | 79.71 | O |
| ATOM | 743 | OE2 | GLU | A | 271 | 21.836 | −52.057 | −9.547 | 1.00 | 79.28 | O |
| ATOM | 744 | C | GLU | A | 271 | 22.366 | −46.865 | −6.532 | 1.00 | 71.90 | C |
| ATOM | 745 | O | GLU | A | 271 | 23.255 | −46.796 | −5.690 | 1.00 | 72.40 | O |
| ATOM | 747 | N | THR | A | 272 | 21.807 | −45.787 | −7.059 | 1.00 | 70.36 | N |
| ATOM | 748 | CA | THR | A | 272 | 22.149 | −44.454 | −6.577 | 1.00 | 69.00 | C |
| ATOM | 750 | CB | THR | A | 272 | 21.452 | −43.386 | −7.409 | 1.00 | 69.38 | C |
| ATOM | 752 | OG1 | THR | A | 272 | 22.034 | −43.392 | −8.715 | 1.00 | 70.35 | O |
| ATOM | 754 | CG2 | THR | A | 272 | 21.588 | −41.981 | −6.777 | 1.00 | 69.58 | C |
| ATOM | 758 | C | THR | A | 272 | 21.763 | −44.282 | −5.127 | 1.00 | 67.28 | C |
| ATOM | 759 | O | THR | A | 272 | 22.593 | −43.917 | −4.290 | 1.00 | 67.23 | O |
| ATOM | 761 | N | GLU | A | 273 | 20.501 | −44.552 | −4.829 | 1.00 | 65.42 | N |
| ATOM | 762 | CA | GLU | A | 273 | 20.027 | −44.464 | −3.458 | 1.00 | 63.93 | C |
| ATOM | 764 | CB | GLU | A | 273 | 18.591 | −44.968 | −3.371 | 1.00 | 63.50 | C |
| ATOM | 767 | CG | GLU | A | 273 | 18.019 | −45.028 | −1.952 | 1.00 | 62.42 | C |
| ATOM | 770 | CD | GLU | A | 273 | 16.539 | −45.382 | −1.938 | 1.00 | 61.38 | C |
| ATOM | 771 | OE1 | GLU | A | 273 | 16.052 | −45.912 | −2.978 | 1.00 | 59.63 | O |
| ATOM | 772 | OE2 | GLU | A | 273 | 15.868 | −45.140 | −0.896 | 1.00 | 57.75 | O |
| ATOM | 773 | C | GLU | A | 273 | 20.953 | −45.230 | −2.508 | 1.00 | 63.40 | C |
| ATOM | 774 | O | GLU | A | 273 | 21.333 | −44.713 | −1.464 | 1.00 | 62.38 | O |
| ATOM | 776 | N | ILE | A | 274 | 21.342 | −46.444 | −2.889 | 1.00 | 63.37 | N |
| ATOM | 777 | CA | ILE | A | 274 | 22.251 | −47.250 | −2.062 | 1.00 | 63.54 | C |
| ATOM | 779 | CB | ILE | A | 274 | 22.630 | −48.611 | −2.745 | 1.00 | 63.67 | C |
| ATOM | 781 | CG1 | ILE | A | 274 | 21.392 | −49.497 | −2.987 | 1.00 | 63.32 | C |
| ATOM | 784 | CD1 | ILE | A | 274 | 20.383 | −49.462 | −1.872 | 1.00 | 62.22 | C |
| ATOM | 788 | CG2 | ILE | A | 274 | 23.663 | −49.370 | −1.911 | 1.00 | 62.45 | C |
| ATOM | 792 | C | ILE | A | 274 | 23.540 | −46.495 | −1.784 | 1.00 | 64.08 | C |
| ATOM | 793 | O | ILE | A | 274 | 23.951 | −46.333 | −0.625 | 1.00 | 63.61 | O |
| ATOM | 795 | N | GLU | A | 275 | 24.168 | −46.033 | −2.863 | 1.00 | 64.88 | N |
| ATOM | 796 | CA | GLU | A | 275 | 25.462 | −45.362 | −2.781 | 1.00 | 65.81 | C |
| ATOM | 798 | CB | GLU | A | 275 | 26.015 | −45.089 | −4.187 | 1.00 | 66.49 | C |
| ATOM | 801 | CG | GLU | A | 275 | 26.363 | −46.376 | −4.970 | 1.00 | 69.87 | C |
| ATOM | 804 | CD | GLU | A | 275 | 26.091 | −46.258 | −6.478 | 1.00 | 74.80 | C |

TABLE 2-continued

| | | | | | | | | | | | |
|---|---|---|---|---|---|---|---|---|---|---|---|
| ATOM | 805 | OE1 | GLU | A | 275 | 26.212 | −45.130 | −7.013 | 1.00 | 76.85 | O |
| ATOM | 806 | OE2 | GLU | A | 275 | 25.749 | −47.294 | −7.127 | 1.00 | 78.18 | O |
| ATOM | 807 | C | GLU | A | 275 | 25.367 | −44.076 | −1.972 | 1.00 | 65.43 | C |
| ATOM | 808 | O | GLU | A | 275 | 26.289 | −43.746 | −1.239 | 1.00 | 65.64 | O |
| ATOM | 810 | N | ILE | A | 276 | 24.259 | −43.351 | −2.095 | 1.00 | 65.27 | N |
| ATOM | 811 | CA | ILE | A | 276 | 24.026 | −42.199 | −1.229 | 1.00 | 65.16 | C |
| ATOM | 813 | CB | ILE | A | 276 | 22.697 | −41.507 | −1.541 | 1.00 | 65.40 | C |
| ATOM | 815 | CG1 | ILE | A | 276 | 22.788 | −40.726 | −2.854 | 1.00 | 65.41 | C |
| ATOM | 818 | CD1 | ILE | A | 276 | 21.499 | −40.006 | −3.215 | 1.00 | 64.13 | C |
| ATOM | 822 | CG2 | ILE | A | 276 | 22.306 | −40.574 | −0.400 | 1.00 | 65.41 | C |
| ATOM | 826 | C | ILE | A | 276 | 24.002 | −42.637 | 0.232 | 1.00 | 64.98 | C |
| ATOM | 827 | O | ILE | A | 276 | 24.780 | −42.145 | 1.055 | 1.00 | 65.02 | O |
| ATOM | 829 | N | LEU | A | 277 | 23.122 | −43.580 | 0.549 | 1.00 | 64.76 | N |
| ATOM | 830 | CA | LEU | A | 277 | 22.981 | −44.039 | 1.923 | 1.00 | 64.96 | C |
| ATOM | 832 | CB | LEU | A | 277 | 21.860 | −45.070 | 2.027 | 1.00 | 65.20 | C |
| ATOM | 835 | CG | LEU | A | 277 | 20.460 | −44.531 | 1.732 | 1.00 | 65.79 | C |
| ATOM | 837 | CD1 | LEU | A | 277 | 19.416 | −45.537 | 2.209 | 1.00 | 66.56 | C |
| ATOM | 841 | CD2 | LEU | A | 277 | 20.245 | −43.150 | 2.382 | 1.00 | 66.41 | C |
| ATOM | 845 | C | LEU | A | 277 | 24.268 | −44.609 | 2.518 | 1.00 | 65.06 | C |
| ATOM | 846 | O | LEU | A | 277 | 24.511 | −44.483 | 3.714 | 1.00 | 64.79 | O |
| ATOM | 848 | N | LYS | A | 278 | 25.100 | −45.235 | 1.697 | 1.00 | 65.16 | N |
| ATOM | 849 | CA | LYS | A | 278 | 26.378 | −45.713 | 2.201 | 1.00 | 65.51 | C |
| ATOM | 851 | CB | LYS | A | 278 | 27.030 | −46.697 | 1.214 | 1.00 | 65.65 | C |
| ATOM | 854 | CG | LYS | A | 278 | 26.365 | −48.109 | 1.171 | 1.00 | 67.14 | C |
| ATOM | 857 | CD | LYS | A | 278 | 26.585 | −48.949 | 2.488 | 1.00 | 68.52 | C |
| ATOM | 860 | CE | LYS | A | 278 | 26.232 | −50.472 | 2.313 | 1.00 | 69.53 | C |
| ATOM | 863 | NZ | LYS | A | 278 | 25.883 | −51.207 | 3.589 | 1.00 | 66.93 | N |
| ATOM | 867 | C | LYS | A | 278 | 27.319 | −44.545 | 2.567 | 1.00 | 65.52 | C |
| ATOM | 868 | O | LYS | A | 278 | 28.085 | −44.654 | 3.517 | 1.00 | 65.55 | O |
| ATOM | 870 | N | LYS | A | 279 | 27.249 | −43.424 | 1.849 | 1.00 | 65.49 | N |
| ATOM | 871 | CA | LYS | A | 279 | 28.157 | −42.293 | 2.130 | 1.00 | 65.64 | C |
| ATOM | 873 | CB | LYS | A | 279 | 28.318 | −41.389 | 0.895 | 1.00 | 66.19 | C |
| ATOM | 876 | CG | LYS | A | 279 | 29.099 | −42.051 | −0.270 | 1.00 | 68.19 | C |
| ATOM | 879 | CD | LYS | A | 279 | 29.383 | −41.078 | −1.440 | 1.00 | 70.45 | C |
| ATOM | 882 | CE | LYS | A | 279 | 29.501 | −41.815 | −2.797 | 1.00 | 71.15 | C |
| ATOM | 885 | NZ | LYS | A | 279 | 28.167 | −42.023 | −3.483 | 1.00 | 72.27 | N |
| ATOM | 889 | C | LYS | A | 279 | 27.691 | −41.456 | 3.323 | 1.00 | 64.79 | C |
| ATOM | 890 | O | LYS | A | 279 | 28.497 | −41.012 | 4.133 | 1.00 | 64.19 | O |
| ATOM | 892 | N | LEU | A | 280 | 26.379 | −41.254 | 3.425 | 1.00 | 64.20 | N |
| ATOM | 893 | CA | LEU | A | 280 | 25.805 | −40.404 | 4.484 | 1.00 | 63.37 | C |
| ATOM | 895 | CB | LEU | A | 280 | 24.319 | −40.122 | 4.228 | 1.00 | 63.30 | C |
| ATOM | 898 | CG | LEU | A | 280 | 23.939 | −39.537 | 2.870 | 1.00 | 63.06 | C |
| ATOM | 900 | CD1 | LEU | A | 280 | 22.442 | −39.301 | 2.842 | 1.00 | 61.64 | C |
| ATOM | 904 | CD2 | LEU | A | 280 | 24.748 | −38.267 | 2.571 | 1.00 | 63.81 | C |
| ATOM | 908 | C | LEU | A | 280 | 25.926 | −41.019 | 5.872 | 1.00 | 62.45 | C |
| ATOM | 909 | O | LEU | A | 280 | 25.796 | −42.239 | 6.056 | 1.00 | 62.82 | O |
| ATOM | 911 | N | ASN | A | 281 | 26.109 | −40.154 | 6.854 | 1.00 | 60.97 | N |
| ATOM | 912 | CA | ASN | A | 281 | 26.350 | −40.604 | 8.197 | 1.00 | 60.17 | C |
| ATOM | 914 | CB | ASN | A | 281 | 27.850 | −40.848 | 8.373 | 1.00 | 60.71 | C |
| ATOM | 917 | CG | ASN | A | 281 | 28.191 | −41.332 | 9.749 | 1.00 | 60.94 | C |
| ATOM | 918 | OD1 | ASN | A | 281 | 27.373 | −41.980 | 10.418 | 1.00 | 62.72 | O |
| ATOM | 919 | ND2 | ASN | A | 281 | 29.392 | −41.012 | 10.194 | 1.00 | 61.44 | N |
| ATOM | 922 | C | ASN | A | 281 | 25.862 | −39.583 | 9.193 | 1.00 | 58.60 | C |
| ATOM | 923 | O | ASN | A | 281 | 26.612 | −38.710 | 9.617 | 1.00 | 58.84 | O |
| ATOM | 925 | N | HIS | A | 282 | 24.593 | −39.687 | 9.555 | 1.00 | 56.95 | N |
| ATOM | 926 | CA | HIS | A | 282 | 23.970 | −38.698 | 10.418 | 1.00 | 55.47 | C |
| ATOM | 928 | CB | HIS | A | 282 | 23.331 | −37.594 | 9.563 | 1.00 | 55.48 | C |
| ATOM | 931 | CG | HIS | A | 282 | 22.928 | −36.374 | 10.335 | 1.00 | 54.30 | C |
| ATOM | 932 | ND1 | HIS | A | 282 | 21.685 | −36.236 | 10.907 | 1.00 | 53.37 | N |
| ATOM | 934 | CE1 | HIS | A | 282 | 21.613 | −35.066 | 11.522 | 1.00 | 54.59 | C |
| ATOM | 936 | NE2 | HIS | A | 282 | 22.765 | −34.439 | 11.367 | 1.00 | 52.80 | N |
| ATOM | 938 | CD2 | HIS | A | 282 | 23.598 | −35.231 | 10.615 | 1.00 | 54.22 | C |
| ATOM | 940 | C | HIS | A | 282 | 22.928 | −39.367 | 11.302 | 1.00 | 54.79 | C |
| ATOM | 941 | O | HIS | A | 282 | 22.216 | −40.251 | 10.864 | 1.00 | 53.78 | O |
| ATOM | 943 | N | PRO | A | 283 | 22.821 | −38.923 | 12.561 | 1.00 | 55.22 | N |
| ATOM | 944 | CA | PRO | A | 283 | 21.868 | −39.558 | 13.475 | 1.00 | 55.16 | C |
| ATOM | 946 | CB | PRO | A | 283 | 22.078 | −38.796 | 14.776 | 1.00 | 55.49 | C |
| ATOM | 949 | CG | PRO | A | 283 | 22.753 | −37.516 | 14.383 | 1.00 | 55.31 | C |
| ATOM | 952 | CD | PRO | A | 283 | 23.591 | −37.853 | 13.227 | 1.00 | 54.79 | C |
| ATOM | 955 | C | PRO | A | 283 | 20.405 | −39.481 | 13.031 | 1.00 | 55.23 | C |
| ATOM | 956 | O | PRO | A | 283 | 19.606 | −40.336 | 13.437 | 1.00 | 55.74 | O |
| ATOM | 957 | N | CYS | A | 284 | 20.067 | −38.511 | 12.178 | 1.00 | 54.62 | N |
| ATOM | 958 | CA | CYS | A | 284 | 18.686 | −38.345 | 11.704 | 1.00 | 54.42 | C |
| ATOM | 960 | CB | CYS | A | 284 | 18.241 | −36.882 | 11.909 | 1.00 | 54.83 | C |
| ATOM | 963 | SG | CYS | A | 284 | 18.454 | −36.288 | 13.620 | 1.00 | 53.38 | S |
| ATOM | 965 | C | CYS | A | 284 | 18.416 | −38.801 | 10.256 | 1.00 | 53.91 | C |
| ATOM | 966 | O | CYS | A | 284 | 17.399 | −38.446 | 9.669 | 1.00 | 52.91 | O |
| ATOM | 968 | N | ILE | A | 285 | 19.316 | −39.600 | 9.698 | 1.00 | 53.94 | N |
| ATOM | 969 | CA | ILE | A | 285 | 19.091 | −40.232 | 8.405 | 1.00 | 53.88 | C |
| ATOM | 971 | CB | ILE | A | 285 | 20.065 | −39.642 | 7.359 | 1.00 | 53.90 | C |

TABLE 2-continued

| | | | | | | | | | | |
|---|---|---|---|---|---|---|---|---|---|---|
| ATOM | 973 | CG1 | ILE | A | 285 | 19.758 | −38.143 | 7.172 | 1.00 | 53.23 | C |
| ATOM | 976 | CD1 | ILE | A | 285 | 20.760 | −37.385 | 6.417 | 1.00 | 51.89 | C |
| ATOM | 980 | CG2 | ILE | A | 285 | 19.981 | −40.427 | 6.039 | 1.00 | 51.62 | C |
| ATOM | 984 | C | ILE | A | 285 | 19.329 | −41.726 | 8.585 | 1.00 | 54.47 | C |
| ATOM | 985 | O | ILE | A | 285 | 20.377 | −42.097 | 9.092 | 1.00 | 54.41 | O |
| ATOM | 987 | N | ILE | A | 286 | 18.382 | −42.588 | 8.205 | 1.00 | 55.22 | N |
| ATOM | 988 | CA | ILE | A | 286 | 18.606 | −44.052 | 8.391 | 1.00 | 55.88 | C |
| ATOM | 990 | CB | ILE | A | 286 | 17.502 | −45.023 | 7.853 | 1.00 | 55.96 | C |
| ATOM | 992 | CG1 | ILE | A | 286 | 16.816 | −44.464 | 6.615 | 1.00 | 56.03 | C |
| ATOM | 995 | CD1 | ILE | A | 286 | 17.769 | −44.228 | 5.470 | 1.00 | 56.00 | C |
| ATOM | 999 | CG2 | ILE | A | 286 | 16.529 | −45.444 | 8.959 | 1.00 | 56.11 | C |
| ATOM | 1003 | C | ILE | A | 286 | 19.861 | −44.510 | 7.695 | 1.00 | 56.02 | C |
| ATOM | 1004 | O | ILE | A | 286 | 20.241 | −43.967 | 6.665 | 1.00 | 56.13 | O |
| ATOM | 1006 | N | LYS | A | 287 | 20.473 | −45.540 | 8.269 | 1.00 | 56.44 | N |
| ATOM | 1007 | CA | LYS | A | 287 | 21.625 | −46.194 | 7.684 | 1.00 | 56.19 | C |
| ATOM | 1009 | CB | LYS | A | 287 | 22.681 | −46.436 | 8.757 | 1.00 | 56.54 | C |
| ATOM | 1012 | CG | LYS | A | 287 | 23.626 | −45.250 | 8.958 | 1.00 | 56.84 | C |
| ATOM | 1015 | CD | LYS | A | 287 | 23.902 | −44.958 | 10.436 | 1.00 | 58.07 | C |
| ATOM | 1018 | CE | LYS | A | 287 | 24.607 | −43.580 | 10.593 | 1.00 | 58.98 | C |
| ATOM | 1021 | NZ | LYS | A | 287 | 24.099 | −42.824 | 11.759 | 1.00 | 57.94 | N |
| ATOM | 1025 | C | LYS | A | 287 | 21.184 | −47.501 | 7.053 | 1.00 | 56.10 | C |
| ATOM | 1026 | O | LYS | A | 287 | 20.240 | −48.148 | 7.516 | 1.00 | 56.40 | O |
| ATOM | 1028 | N | ILE | A | 288 | 21.856 | −47.867 | 5.972 | 1.00 | 55.95 | N |
| ATOM | 1029 | CA | ILE | A | 288 | 21.597 | −49.123 | 5.286 | 1.00 | 55.64 | C |
| ATOM | 1031 | CB | ILE | A | 288 | 21.819 | −48.977 | 3.778 | 1.00 | 55.51 | C |
| ATOM | 1033 | CG1 | ILE | A | 288 | 21.792 | −50.342 | 3.082 | 1.00 | 54.98 | C |
| ATOM | 1036 | CD1 | ILE | A | 288 | 21.897 | −50.242 | 1.600 | 1.00 | 53.83 | C |
| ATOM | 1040 | CG2 | ILE | A | 288 | 23.149 | −48.309 | 3.511 | 1.00 | 55.89 | C |
| ATOM | 1044 | C | ILE | A | 288 | 22.539 | −50.168 | 5.873 | 1.00 | 55.72 | C |
| ATOM | 1045 | O | ILE | A | 288 | 23.715 | −49.917 | 6.004 | 1.00 | 55.45 | O |
| ATOM | 1047 | N | LYS | A | 289 | 22.014 | −51.331 | 6.246 | 1.00 | 56.07 | N |
| ATOM | 1048 | CA | LYS | A | 289 | 22.824 | −52.388 | 6.864 | 1.00 | 56.14 | C |
| ATOM | 1050 | CB | LYS | A | 289 | 22.047 | −53.062 | 8.005 | 1.00 | 56.24 | C |
| ATOM | 1053 | CG | LYS | A | 289 | 21.971 | −52.208 | 9.272 | 1.00 | 57.32 | C |
| ATOM | 1056 | CD | LYS | A | 289 | 21.032 | −52.788 | 10.326 | 1.00 | 59.72 | C |
| ATOM | 1059 | CE | LYS | A | 289 | 21.619 | −54.041 | 11.035 | 1.00 | 61.28 | C |
| ATOM | 1062 | NZ | LYS | A | 289 | 22.683 | −53.752 | 12.070 | 1.00 | 61.20 | N |
| ATOM | 1066 | C | LYS | A | 289 | 23.261 | −53.408 | 5.830 | 1.00 | 56.18 | C |
| ATOM | 1067 | O | LYS | A | 289 | 24.289 | −54.012 | 5.968 | 1.00 | 56.47 | O |
| ATOM | 1069 | N | ASN | A | 290 | 22.476 | −53.587 | 4.783 | 1.00 | 56.61 | N |
| ATOM | 1070 | CA | ASN | A | 290 | 22.771 | −54.570 | 3.768 | 1.00 | 56.87 | C |
| ATOM | 1072 | CB | ASN | A | 290 | 22.583 | −55.986 | 4.341 | 1.00 | 57.09 | C |
| ATOM | 1075 | CG | ASN | A | 290 | 23.464 | −57.027 | 3.661 | 1.00 | 56.76 | C |
| ATOM | 1076 | OD1 | ASN | A | 290 | 23.904 | −56.838 | 2.531 | 1.00 | 56.75 | O |
| ATOM | 1077 | ND2 | ASN | A | 290 | 23.703 | −58.140 | 4.346 | 1.00 | 55.84 | N |
| ATOM | 1080 | C | ASN | A | 290 | 21.857 | −54.370 | 2.557 | 1.00 | 57.22 | C |
| ATOM | 1081 | O | ASN | A | 290 | 20.869 | −53.641 | 2.633 | 1.00 | 56.77 | O |
| ATOM | 1083 | N | PHE | A | 291 | 22.173 | −55.045 | 1.457 | 1.00 | 58.14 | N |
| ATOM | 1084 | CA | PHE | A | 291 | 21.460 | −54.844 | 0.206 | 1.00 | 58.77 | C |
| ATOM | 1086 | CB | PHE | A | 291 | 22.100 | −53.682 | −0.529 | 1.00 | 58.89 | C |
| ATOM | 1089 | CG | PHE | A | 291 | 21.480 | −53.404 | −1.860 | 1.00 | 60.09 | C |
| ATOM | 1090 | CD1 | PHE | A | 291 | 20.144 | −53.011 | −1.950 | 1.00 | 60.98 | C |
| ATOM | 1092 | CE1 | PHE | A | 291 | 19.545 | −52.745 | −3.181 | 1.00 | 61.25 | C |
| ATOM | 1094 | CZ | PHE | A | 291 | 20.285 | −52.860 | −4.344 | 1.00 | 62.75 | C |
| ATOM | 1096 | CE2 | PHE | A | 291 | 21.635 | −53.244 | −4.271 | 1.00 | 63.59 | C |
| ATOM | 1098 | CD2 | PHE | A | 291 | 22.223 | −53.516 | −3.024 | 1.00 | 62.17 | C |
| ATOM | 1100 | C | PHE | A | 291 | 21.488 | −56.065 | −0.692 | 1.00 | 59.06 | C |
| ATOM | 1101 | O | PHE | A | 291 | 22.520 | −56.703 | −0.849 | 1.00 | 58.99 | O |
| ATOM | 1103 | N | PHE | A | 292 | 20.352 | −56.382 | −1.297 | 1.00 | 59.94 | N |
| ATOM | 1104 | CA | PHE | A | 292 | 20.266 | −57.525 | −2.211 | 1.00 | 60.65 | C |
| ATOM | 1106 | CB | PHE | A | 292 | 19.630 | −58.746 | −1.533 | 1.00 | 60.43 | C |
| ATOM | 1109 | CG | PHE | A | 292 | 20.347 | −59.179 | −0.290 | 1.00 | 58.34 | C |
| ATOM | 1110 | CD1 | PHE | A | 292 | 19.956 | −58.690 | 0.955 | 1.00 | 54.84 | C |
| ATOM | 1112 | CE1 | PHE | A | 292 | 20.642 | −59.069 | 2.107 | 1.00 | 55.59 | C |
| ATOM | 1114 | CZ | PHE | A | 292 | 21.745 | −59.955 | 2.014 | 1.00 | 54.34 | C |
| ATOM | 1116 | CE2 | PHE | A | 292 | 22.127 | −60.442 | 0.776 | 1.00 | 54.43 | C |
| ATOM | 1118 | CD2 | PHE | A | 292 | 21.436 | −60.053 | −0.367 | 1.00 | 55.22 | C |
| ATOM | 1120 | C | PHE | A | 292 | 19.464 | −57.157 | −3.438 | 1.00 | 62.08 | C |
| ATOM | 1121 | O | PHE | A | 292 | 18.294 | −56.819 | −3.346 | 1.00 | 62.08 | O |
| ATOM | 1123 | N | ASP | A | 293 | 20.128 | −57.245 | −4.584 | 1.00 | 64.11 | N |
| ATOM | 1124 | CA | ASP | A | 293 | 19.556 | −56.986 | −5.897 | 1.00 | 65.31 | C |
| ATOM | 1126 | CB | ASP | A | 293 | 20.543 | −56.117 | −6.706 | 1.00 | 65.60 | C |
| ATOM | 1129 | CG | ASP | A | 293 | 20.204 | −56.027 | −8.189 | 1.00 | 66.04 | C |
| ATOM | 1130 | OD1 | ASP | A | 293 | 19.004 | −56.033 | −8.556 | 1.00 | 67.97 | O |
| ATOM | 1131 | OD2 | ASP | A | 293 | 21.154 | −55.927 | −8.987 | 1.00 | 67.09 | O |
| ATOM | 1132 | C | ASP | A | 293 | 19.353 | −58.334 | −6.565 | 1.00 | 66.19 | C |
| ATOM | 1133 | O | ASP | A | 293 | 20.315 | −58.958 | −7.018 | 1.00 | 65.94 | O |
| ATOM | 1135 | N | ALA | A | 294 | 18.097 | −58.768 | −6.614 | 1.00 | 67.46 | N |
| ATOM | 1136 | CA | ALA | A | 294 | 17.723 | −60.069 | −7.164 | 1.00 | 68.36 | C |
| ATOM | 1138 | CB | ALA | A | 294 | 17.543 | −61.070 | −6.026 | 1.00 | 68.32 | C |

TABLE 2-continued

| | | | | | | | | | | |
|---|---|---|---|---|---|---|---|---|---|---|
| ATOM | 1142 | C | ALA | A | 294 | 16.435 | −59.897 | −7.970 | 1.00 | 69.19 | C |
| ATOM | 1143 | O | ALA | A | 294 | 16.266 | −58.885 | −8.641 | 1.00 | 69.35 | O |
| ATOM | 1145 | N | GLU | A | 295 | 15.514 | −60.853 | −7.901 | 1.00 | 70.28 | N |
| ATOM | 1146 | CA | GLU | A | 295 | 14.225 | −60.702 | −8.586 | 1.00 | 71.17 | C |
| ATOM | 1148 | CB | GLU | A | 295 | 13.219 | −61.762 | −8.111 | 1.00 | 71.91 | C |
| ATOM | 1151 | CG | GLU | A | 295 | 13.583 | −63.241 | −8.397 | 1.00 | 73.91 | C |
| ATOM | 1154 | CD | GLU | A | 295 | 13.519 | −63.596 | −9.879 | 1.00 | 77.38 | C |
| ATOM | 1155 | OE1 | GLU | A | 295 | 13.028 | −64.707 | −10.212 | 1.00 | 80.75 | O |
| ATOM | 1156 | OE2 | GLU | A | 295 | 13.948 | −62.766 | −10.715 | 1.00 | 78.25 | O |
| ATOM | 1157 | C | GLU | A | 295 | 13.658 | −59.302 | −8.325 | 1.00 | 71.10 | C |
| ATOM | 1158 | O | GLU | A | 295 | 13.089 | −58.667 | −9.213 | 1.00 | 71.56 | O |
| ATOM | 1160 | N | ASP | A | 296 | 13.805 | −58.846 | −7.083 | 1.00 | 70.85 | N |
| ATOM | 1161 | CA | ASP | A | 296 | 13.545 | −57.464 | −6.692 | 1.00 | 70.55 | C |
| ATOM | 1163 | CB | ASP | A | 296 | 12.342 | −57.394 | −5.757 | 1.00 | 70.83 | C |
| ATOM | 1166 | CG | ASP | A | 296 | 11.108 | −58.023 | −6.357 | 1.00 | 73.35 | C |
| ATOM | 1167 | OD1 | ASP | A | 296 | 11.246 | −58.783 | −7.348 | 1.00 | 75.95 | O |
| ATOM | 1168 | OD2 | ASP | A | 296 | 9.997 | −57.756 | −5.843 | 1.00 | 75.01 | O |
| ATOM | 1169 | C | ASP | A | 296 | 14.775 | −56.928 | −5.975 | 1.00 | 69.63 | C |
| ATOM | 1170 | O | ASP | A | 296 | 15.795 | −57.630 | −5.872 | 1.00 | 69.58 | O |
| ATOM | 1172 | N | TYR | A | 297 | 14.683 | −55.681 | −5.502 | 1.00 | 68.55 | N |
| ATOM | 1173 | CA | TYR | A | 297 | 15.694 | −55.093 | −4.613 | 1.00 | 67.57 | C |
| ATOM | 1175 | CB | TYR | A | 297 | 15.913 | −53.608 | −4.922 | 1.00 | 68.20 | C |
| ATOM | 1178 | CG | TYR | A | 297 | 16.317 | −53.242 | −6.346 | 1.00 | 70.05 | C |
| ATOM | 1179 | CD1 | TYR | A | 297 | 17.653 | −53.347 | −6.767 | 1.00 | 72.08 | C |
| ATOM | 1181 | CE1 | TYR | A | 297 | 18.045 | −52.980 | −8.065 | 1.00 | 73.13 | C |
| ATOM | 1183 | CZ | TYR | A | 297 | 17.085 | −52.485 | −8.959 | 1.00 | 74.77 | C |
| ATOM | 1184 | OH | TYR | A | 297 | 17.460 | −52.124 | −10.239 | 1.00 | 77.08 | O |
| ATOM | 1186 | CE2 | TYR | A | 297 | 15.746 | −52.356 | −8.563 | 1.00 | 73.21 | C |
| ATOM | 1188 | CD2 | TYR | A | 297 | 15.373 | −52.721 | −7.252 | 1.00 | 71.78 | C |
| ATOM | 1190 | C | TYR | A | 297 | 15.219 | −55.217 | −3.166 | 1.00 | 65.65 | C |
| ATOM | 1191 | O | TYR | A | 297 | 14.023 | −55.056 | −2.888 | 1.00 | 65.16 | O |
| ATOM | 1193 | N | TYR | A | 298 | 16.156 | −55.496 | −2.256 | 1.00 | 63.96 | N |
| ATOM | 1194 | CA | TYR | A | 298 | 15.873 | −55.598 | −0.808 | 1.00 | 62.61 | C |
| ATOM | 1196 | CB | TYR | A | 298 | 15.963 | −57.048 | −0.309 | 1.00 | 62.37 | C |
| ATOM | 1199 | CG | TYR | A | 298 | 15.056 | −58.009 | −1.051 | 1.00 | 62.71 | C |
| ATOM | 1200 | CD1 | TYR | A | 298 | 15.369 | −58.429 | −2.341 | 1.00 | 62.68 | C |
| ATOM | 1202 | CE1 | TYR | A | 298 | 14.544 | −59.312 | −3.047 | 1.00 | 63.17 | C |
| ATOM | 1204 | CZ | TYR | A | 298 | 13.376 | −59.790 | −2.475 | 1.00 | 63.52 | C |
| ATOM | 1205 | OH | TYR | A | 298 | 12.585 | −60.658 | −3.217 | 1.00 | 64.14 | O |
| ATOM | 1207 | CE2 | TYR | A | 298 | 13.031 | −59.396 | −1.184 | 1.00 | 63.13 | C |
| ATOM | 1209 | CD2 | TYR | A | 298 | 13.882 | −58.502 | −0.472 | 1.00 | 63.61 | C |
| ATOM | 1211 | C | TYR | A | 298 | 16.896 | −54.755 | −0.088 | 1.00 | 61.30 | C |
| ATOM | 1212 | O | TYR | A | 298 | 18.082 | −54.893 | −0.339 | 1.00 | 61.05 | O |
| ATOM | 1214 | N | ILE | A | 299 | 16.443 | −53.888 | 0.803 | 1.00 | 60.15 | N |
| ATOM | 1215 | CA | ILE | A | 299 | 17.330 | −52.981 | 1.508 | 1.00 | 59.57 | C |
| ATOM | 1217 | CB | ILE | A | 299 | 17.015 | −51.511 | 1.169 | 1.00 | 59.54 | C |
| ATOM | 1219 | CG1 | ILE | A | 299 | 17.165 | −51.269 | −0.334 | 1.00 | 60.63 | C |
| ATOM | 1222 | CD1 | ILE | A | 299 | 16.438 | −50.057 | −0.828 | 1.00 | 61.22 | C |
| ATOM | 1226 | CG2 | ILE | A | 299 | 17.943 | −50.578 | 1.917 | 1.00 | 58.97 | C |
| ATOM | 1230 | C | ILE | A | 299 | 17.139 | −53.185 | 2.992 | 1.00 | 59.20 | C |
| ATOM | 1231 | O | ILE | A | 299 | 16.065 | −52.944 | 3.509 | 1.00 | 58.79 | O |
| ATOM | 1233 | N | VAL | A | 300 | 18.194 | −53.614 | 3.677 | 1.00 | 59.15 | N |
| ATOM | 1234 | CA | VAL | A | 300 | 18.140 | −53.864 | 5.109 | 1.00 | 58.89 | C |
| ATOM | 1236 | CB | VAL | A | 300 | 19.118 | −55.002 | 5.519 | 1.00 | 58.69 | C |
| ATOM | 1238 | CG1 | VAL | A | 300 | 18.942 | −55.384 | 6.998 | 1.00 | 57.87 | C |
| ATOM | 1242 | CG2 | VAL | A | 300 | 18.907 | −56.208 | 4.631 | 1.00 | 57.62 | C |
| ATOM | 1246 | C | VAL | A | 300 | 18.492 | −52.567 | 5.840 | 1.00 | 59.51 | C |
| ATOM | 1247 | O | VAL | A | 300 | 19.546 | −51.967 | 5.575 | 1.00 | 59.35 | O |
| ATOM | 1249 | N | LEU | A | 301 | 17.619 | −52.147 | 6.757 | 1.00 | 60.01 | N |
| ATOM | 1250 | CA | LEU | A | 301 | 17.807 | −50.907 | 7.503 | 1.00 | 60.84 | C |
| ATOM | 1252 | CB | LEU | A | 301 | 16.788 | −49.869 | 7.061 | 1.00 | 60.86 | C |
| ATOM | 1255 | CG | LEU | A | 301 | 16.766 | −49.484 | 5.571 | 1.00 | 61.82 | C |
| ATOM | 1257 | CD1 | LEU | A | 301 | 15.345 | −49.183 | 5.118 | 1.00 | 59.88 | C |
| ATOM | 1261 | CD2 | LEU | A | 301 | 17.724 | −48.296 | 5.246 | 1.00 | 63.88 | C |
| ATOM | 1265 | C | LEU | A | 301 | 17.647 | −51.141 | 8.992 | 1.00 | 61.68 | C |
| ATOM | 1266 | O | LEU | A | 301 | 17.120 | −52.171 | 9.408 | 1.00 | 61.80 | O |
| ATOM | 1268 | N | GLU | A | 302 | 18.120 | −50.185 | 9.789 | 1.00 | 62.73 | N |
| ATOM | 1269 | CA | GLU | A | 302 | 17.807 | −50.141 | 11.220 | 1.00 | 63.85 | C |
| ATOM | 1271 | CB | GLU | A | 302 | 18.289 | −48.817 | 11.855 | 1.00 | 64.43 | C |
| ATOM | 1274 | CG | GLU | A | 302 | 19.770 | −48.440 | 11.618 | 1.00 | 66.78 | C |
| ATOM | 1277 | CD | GLU | A | 302 | 20.087 | −46.974 | 11.999 | 1.00 | 69.99 | C |
| ATOM | 1278 | OE1 | GLU | A | 302 | 19.490 | −46.036 | 11.403 | 1.00 | 71.14 | O |
| ATOM | 1279 | OE2 | GLU | A | 302 | 20.956 | −46.766 | 12.884 | 1.00 | 70.22 | O |
| ATOM | 1280 | C | GLU | A | 302 | 16.282 | −50.216 | 11.332 | 1.00 | 63.83 | C |
| ATOM | 1281 | O | GLU | A | 302 | 15.593 | −49.616 | 10.513 | 1.00 | 63.67 | O |
| ATOM | 1283 | N | LEU | A | 303 | 15.746 | −50.948 | 12.308 | 1.00 | 64.09 | N |
| ATOM | 1284 | CA | LEU | A | 303 | 14.289 | −50.932 | 12.558 | 1.00 | 64.10 | C |
| ATOM | 1286 | CB | LEU | A | 303 | 13.807 | −52.194 | 13.277 | 1.00 | 64.15 | C |
| ATOM | 1289 | CG | LEU | A | 303 | 12.299 | −52.220 | 13.613 | 1.00 | 64.76 | C |
| ATOM | 1291 | CD1 | LEU | A | 303 | 11.425 | −52.292 | 12.345 | 1.00 | 64.22 | C |

TABLE 2-continued

| | | | | | | | | | | |
|---|---|---|---|---|---|---|---|---|---|---|
| ATOM | 1295 | CD2 | LEU | A | 303 | 11.974 | −53.372 | 14.548 | 1.00 | 64.56 | C |
| ATOM | 1299 | C | LEU | A | 303 | 13.944 | −49.729 | 13.412 | 1.00 | 63.96 | C |
| ATOM | 1300 | O | LEU | A | 303 | 14.552 | −49.515 | 14.455 | 1.00 | 64.07 | O |
| ATOM | 1302 | N | MET | A | 304 | 12.963 | −48.953 | 12.976 | 1.00 | 64.32 | N |
| ATOM | 1303 | CA | MET | A | 304 | 12.513 | −47.773 | 13.724 | 1.00 | 64.35 | C |
| ATOM | 1305 | CB | MET | A | 304 | 12.436 | −46.519 | 12.839 | 1.00 | 63.90 | C |
| ATOM | 1308 | CG | MET | A | 304 | 13.748 | −46.062 | 12.290 | 1.00 | 63.44 | C |
| ATOM | 1311 | SD | MET | A | 304 | 14.957 | −45.565 | 13.510 | 1.00 | 62.40 | S |
| ATOM | 1312 | CE | MET | A | 304 | 14.285 | −44.011 | 14.078 | 1.00 | 64.56 | C |
| ATOM | 1316 | C | MET | A | 304 | 11.153 | −48.114 | 14.259 | 1.00 | 64.47 | C |
| ATOM | 1317 | O | MET | A | 304 | 10.175 | −48.111 | 13.526 | 1.00 | 63.93 | O |
| ATOM | 1319 | N | GLU | A | 305 | 11.092 | −48.395 | 15.547 | 1.00 | 65.30 | N |
| ATOM | 1320 | CA | GLU | A | 305 | 9.909 | −49.028 | 16.097 | 1.00 | 66.36 | C |
| ATOM | 1322 | CB | GLU | A | 305 | 10.270 | −49.749 | 17.397 | 1.00 | 66.97 | C |
| ATOM | 1325 | CG | GLU | A | 305 | 11.023 | −51.076 | 17.097 | 1.00 | 69.38 | C |
| ATOM | 1328 | CD | GLU | A | 305 | 11.585 | −51.748 | 18.339 | 1.00 | 72.88 | C |
| ATOM | 1329 | OE1 | GLU | A | 305 | 12.483 | −51.137 | 18.972 | 1.00 | 74.64 | O |
| ATOM | 1330 | OE2 | GLU | A | 305 | 11.132 | −52.879 | 18.669 | 1.00 | 73.96 | O |
| ATOM | 1331 | C | GLU | A | 305 | 8.695 | −48.095 | 16.219 | 1.00 | 66.20 | C |
| ATOM | 1332 | O | GLU | A | 305 | 7.558 | −48.556 | 16.166 | 1.00 | 65.92 | O |
| ATOM | 1334 | N | GLY | A | 306 | 8.937 | −46.788 | 16.294 | 1.00 | 66.25 | N |
| ATOM | 1335 | CA | GLY | A | 306 | 7.856 | −45.792 | 16.299 | 1.00 | 66.14 | C |
| ATOM | 1338 | C | GLY | A | 306 | 7.036 | −45.695 | 15.017 | 1.00 | 65.68 | C |
| ATOM | 1339 | O | GLY | A | 306 | 5.951 | −45.104 | 15.001 | 1.00 | 65.47 | O |
| ATOM | 1341 | N | GLY | A | 307 | 7.555 | −46.264 | 13.937 | 1.00 | 65.50 | N |
| ATOM | 1342 | CA | GLY | A | 307 | 6.837 | −46.275 | 12.661 | 1.00 | 65.37 | C |
| ATOM | 1345 | C | GLY | A | 307 | 6.941 | −44.946 | 11.937 | 1.00 | 65.23 | C |
| ATOM | 1346 | O | GLY | A | 307 | 7.812 | −44.127 | 12.234 | 1.00 | 64.97 | O |
| ATOM | 1348 | N | GLU | A | 308 | 6.042 | −44.736 | 10.986 | 1.00 | 65.35 | N |
| ATOM | 1349 | CA | GLU | A | 308 | 6.033 | −43.516 | 10.193 | 1.00 | 65.65 | C |
| ATOM | 1351 | CB | GLU | A | 308 | 5.284 | −43.737 | 8.887 | 1.00 | 65.80 | C |
| ATOM | 1354 | CG | GLU | A | 308 | 5.854 | −44.823 | 7.991 | 1.00 | 66.14 | C |
| ATOM | 1357 | CD | GLU | A | 308 | 4.857 | −45.263 | 6.931 | 1.00 | 66.49 | C |
| ATOM | 1358 | OE1 | GLU | A | 308 | 3.846 | −44.551 | 6.717 | 1.00 | 67.49 | O |
| ATOM | 1359 | OE2 | GLU | A | 308 | 5.082 | −46.323 | 6.316 | 1.00 | 68.05 | O |
| ATOM | 1360 | C | GLU | A | 308 | 5.354 | −42.369 | 10.925 | 1.00 | 65.68 | C |
| ATOM | 1361 | O | GLU | A | 308 | 4.358 | −42.570 | 11.604 | 1.00 | 66.25 | O |
| ATOM | 1363 | N | LEU | A | 309 | 5.883 | −41.167 | 10.739 | 1.00 | 65.55 | N |
| ATOM | 1364 | CA | LEU | A | 309 | 5.278 | −39.939 | 11.225 | 1.00 | 65.53 | C |
| ATOM | 1366 | CB | LEU | A | 309 | 6.174 | −38.765 | 10.839 | 1.00 | 65.33 | C |
| ATOM | 1369 | CG | LEU | A | 309 | 5.747 | −37.353 | 11.213 | 1.00 | 64.88 | C |
| ATOM | 1371 | CD1 | LEU | A | 309 | 5.621 | −37.254 | 12.714 | 1.00 | 63.48 | C |
| ATOM | 1375 | CD2 | LEU | A | 309 | 6.750 | −36.321 | 10.675 | 1.00 | 62.86 | C |
| ATOM | 1379 | C | LEU | A | 309 | 3.878 | −39.730 | 10.646 | 1.00 | 66.04 | C |
| ATOM | 1380 | O | LEU | A | 309 | 3.044 | −39.063 | 11.249 | 1.00 | 66.15 | O |
| ATOM | 1382 | N | PHE | A | 310 | 3.630 | −40.288 | 9.474 | 1.00 | 66.59 | N |
| ATOM | 1383 | CA | PHE | A | 310 | 2.324 | −40.199 | 8.854 | 1.00 | 67.78 | C |
| ATOM | 1385 | CB | PHE | A | 310 | 2.308 | −41.023 | 7.570 | 1.00 | 67.63 | C |
| ATOM | 1388 | CG | PHE | A | 310 | 0.985 | −41.044 | 6.888 | 1.00 | 68.15 | C |
| ATOM | 1389 | CD1 | PHE | A | 310 | 0.520 | −39.922 | 6.232 | 1.00 | 68.67 | C |
| ATOM | 1391 | CE1 | PHE | A | 310 | −0.703 | −39.929 | 5.589 | 1.00 | 69.05 | C |
| ATOM | 1393 | CZ | PHE | A | 310 | −1.478 | −41.067 | 5.608 | 1.00 | 68.84 | C |
| ATOM | 1395 | CE2 | PHE | A | 310 | −1.024 | −42.195 | 6.267 | 1.00 | 68.74 | C |
| ATOM | 1397 | CD2 | PHE | A | 310 | 0.197 | −42.180 | 6.905 | 1.00 | 68.63 | C |
| ATOM | 1399 | C | PHE | A | 310 | 1.210 | −40.675 | 9.797 | 1.00 | 68.67 | C |
| ATOM | 1400 | O | PHE | A | 310 | 0.242 | −39.949 | 10.044 | 1.00 | 68.56 | O |
| ATOM | 1402 | N | ASP | A | 311 | 1.374 | −41.890 | 10.320 | 1.00 | 69.95 | N |
| ATOM | 1403 | CA | ASP | A | 311 | 0.405 | −42.523 | 11.228 | 1.00 | 71.01 | C |
| ATOM | 1405 | CB | ASP | A | 311 | 0.948 | −43.841 | 11.819 | 1.00 | 71.55 | C |
| ATOM | 1408 | CG | ASP | A | 311 | 1.412 | −44.843 | 10.751 | 1.00 | 73.42 | C |
| ATOM | 1409 | OD1 | ASP | A | 311 | 0.659 | −45.069 | 9.774 | 1.00 | 74.21 | O |
| ATOM | 1410 | OD2 | ASP | A | 311 | 2.536 | −45.407 | 10.906 | 1.00 | 76.34 | O |
| ATOM | 1411 | C | ASP | A | 311 | 0.016 | −41.630 | 12.402 | 1.00 | 71.20 | C |
| ATOM | 1412 | O | ASP | A | 311 | −1.096 | −41.734 | 12.897 | 1.00 | 71.28 | O |
| ATOM | 1414 | N | LYS | A | 312 | 0.927 | −40.776 | 12.863 | 1.00 | 71.64 | N |
| ATOM | 1415 | CA | LYS | A | 312 | 0.642 | −39.925 | 14.018 | 1.00 | 72.10 | C |
| ATOM | 1417 | CB | LYS | A | 312 | 1.882 | −39.820 | 14.925 | 1.00 | 72.08 | C |
| ATOM | 1420 | CG | LYS | A | 312 | 2.209 | −41.186 | 15.603 | 1.00 | 73.58 | C |
| ATOM | 1423 | CD | LYS | A | 312 | 3.321 | −41.152 | 16.671 | 1.00 | 75.07 | C |
| ATOM | 1426 | CE | LYS | A | 312 | 3.710 | −42.598 | 17.121 | 1.00 | 76.74 | C |
| ATOM | 1429 | NZ | LYS | A | 312 | 5.048 | −42.722 | 17.855 | 1.00 | 77.13 | N |
| ATOM | 1433 | C | LYS | A | 312 | 0.039 | −38.558 | 13.649 | 1.00 | 72.39 | C |
| ATOM | 1434 | O | LYS | A | 312 | −0.131 | −37.707 | 14.524 | 1.00 | 72.39 | O |
| ATOM | 1436 | N | VAL | A | 313 | −0.314 | −38.356 | 12.375 | 1.00 | 72.79 | N |
| ATOM | 1437 | CA | VAL | A | 313 | −1.009 | −37.123 | 11.942 | 1.00 | 73.32 | C |
| ATOM | 1439 | CB | VAL | A | 313 | −0.051 | −36.111 | 11.240 | 1.00 | 73.09 | C |
| ATOM | 1441 | CG1 | VAL | A | 313 | 1.144 | −35.815 | 12.105 | 1.00 | 72.77 | C |
| ATOM | 1445 | CG2 | VAL | A | 313 | 0.373 | −36.619 | 9.870 | 1.00 | 71.98 | C |
| ATOM | 1449 | C | VAL | A | 313 | −2.202 | −37.321 | 10.991 | 1.00 | 74.45 | C |
| ATOM | 1450 | O | VAL | A | 313 | −2.827 | −36.339 | 10.591 | 1.00 | 74.43 | O |

TABLE 2-continued

| | | | | | | | | | | |
|---|---|---|---|---|---|---|---|---|---|---|
| ATOM | 1452 | N | VAL | A | 314 | −2.504 | −38.560 | 10.614 | 1.00 | 75.73 N |
| ATOM | 1453 | CA | VAL | A | 314 | −3.651 | −38.849 | 9.766 | 1.00 | 76.84 C |
| ATOM | 1455 | CB | VAL | A | 314 | −3.606 | −40.301 | 9.252 | 1.00 | 77.14 C |
| ATOM | 1457 | CG1 | VAL | A | 314 | −3.862 | −41.282 | 10.403 | 1.00 | 76.34 C |
| ATOM | 1461 | CG2 | VAL | A | 314 | −4.600 | −40.494 | 8.093 | 1.00 | 77.06 C |
| ATOM | 1465 | C | VAL | A | 314 | −4.975 | −38.621 | 10.518 | 1.00 | 77.93 C |
| ATOM | 1466 | O | VAL | A | 314 | −5.029 | −38.702 | 11.754 | 1.00 | 77.76 O |
| ATOM | 1468 | N | GLY | A | 315 | −6.029 | −38.328 | 9.750 | 1.00 | 79.21 N |
| ATOM | 1469 | CA | GLY | A | 315 | −7.370 | −38.050 | 10.288 | 1.00 | 80.06 C |
| ATOM | 1472 | C | GLY | A | 315 | −7.431 | −36.861 | 11.241 | 1.00 | 80.73 C |
| ATOM | 1473 | O | GLY | A | 315 | −8.006 | −36.966 | 12.326 | 1.00 | 81.18 O |
| ATOM | 1475 | N | ASN | A | 316 | −6.825 | −35.736 | 10.852 | 1.00 | 81.18 N |
| ATOM | 1476 | CA | ASN | A | 316 | −6.795 | −34.525 | 11.695 | 1.00 | 81.52 C |
| ATOM | 1478 | CB | ASN | A | 316 | −8.189 | −33.901 | 11.762 | 1.00 | 81.69 C |
| ATOM | 1481 | CG | ASN | A | 316 | −8.792 | −33.705 | 10.385 | 1.00 | 83.03 C |
| ATOM | 1482 | OD1 | ASN | A | 316 | −8.272 | −32.929 | 9.577 | 1.00 | 84.21 O |
| ATOM | 1483 | ND2 | ASN | A | 316 | −9.880 | −34.428 | 10.097 | 1.00 | 84.79 N |
| ATOM | 1486 | C | ASN | A | 316 | −6.213 | −34.737 | 13.107 | 1.00 | 81.37 C |
| ATOM | 1487 | O | ASN | A | 316 | −6.389 | −33.901 | 14.011 | 1.00 | 81.11 O |
| ATOM | 1489 | N | LYS | A | 317 | −5.510 | −35.857 | 13.277 | 1.00 | 81.21 N |
| ATOM | 1490 | CA | LYS | A | 317 | −4.805 | −36.156 | 14.517 | 1.00 | 81.15 C |
| ATOM | 1492 | CB | LYS | A | 317 | −4.335 | −37.622 | 14.520 | 1.00 | 81.28 C |
| ATOM | 1495 | CG | LYS | A | 317 | −4.127 | −38.265 | 15.898 | 1.00 | 81.67 C |
| ATOM | 1498 | CD | LYS | A | 317 | −3.506 | −39.675 | 15.771 | 1.00 | 81.68 C |
| ATOM | 1501 | CE | LYS | A | 317 | −4.494 | −40.691 | 15.204 | 1.00 | 81.48 C |
| ATOM | 1504 | NZ | LYS | A | 317 | −3.933 | −41.407 | 14.029 | 1.00 | 81.24 N |
| ATOM | 1508 | C | LYS | A | 317 | −3.640 | −35.177 | 14.489 | 1.00 | 80.75 C |
| ATOM | 1509 | O | LYS | A | 317 | −3.103 | −34.904 | 13.410 | 1.00 | 80.96 O |
| ATOM | 1511 | N | ARG | A | 318 | −3.273 | −34.605 | 15.632 | 1.00 | 80.02 N |
| ATOM | 1512 | CA | ARG | A | 318 | −2.195 | −33.624 | 15.628 | 1.00 | 79.43 C |
| ATOM | 1514 | CB | ARG | A | 318 | −2.698 | −32.227 | 15.206 | 1.00 | 79.71 C |
| ATOM | 1517 | CG | ARG | A | 318 | −3.850 | −31.632 | 16.010 | 1.00 | 80.36 C |
| ATOM | 1520 | CD | ARG | A | 318 | −3.352 | −30.834 | 17.206 | 1.00 | 80.59 C |
| ATOM | 1523 | NE | ARG | A | 318 | −4.353 | −29.865 | 17.640 | 1.00 | 81.01 N |
| ATOM | 1525 | CZ | ARG | A | 318 | −4.524 | −28.650 | 17.117 | 1.00 | 81.29 C |
| ATOM | 1526 | NH1 | ARG | A | 318 | −3.754 | −28.207 | 16.129 | 1.00 | 80.27 N |
| ATOM | 1529 | NH2 | ARG | A | 318 | −5.480 | −27.861 | 17.600 | 1.00 | 82.20 N |
| ATOM | 1532 | C | ARG | A | 318 | −1.439 | −33.597 | 16.940 | 1.00 | 78.57 C |
| ATOM | 1533 | O | ARG | A | 318 | −2.004 | −33.888 | 17.995 | 1.00 | 79.12 O |
| ATOM | 1535 | N | LEU | A | 319 | −0.153 | −33.245 | 16.838 | 1.00 | 77.05 N |
| ATOM | 1536 | CA | LEU | A | 319 | 0.832 | −33.441 | 17.896 | 1.00 | 75.52 C |
| ATOM | 1538 | CB | LEU | A | 319 | 2.202 | −33.746 | 17.274 | 1.00 | 75.70 C |
| ATOM | 1541 | CG | LEU | A | 319 | 2.483 | −35.029 | 16.466 | 1.00 | 75.81 C |
| ATOM | 1543 | CD1 | LEU | A | 319 | 1.258 | −35.556 | 15.737 | 1.00 | 76.76 C |
| ATOM | 1547 | CD2 | LEU | A | 319 | 3.633 | −34.803 | 15.472 | 1.00 | 74.78 C |
| ATOM | 1551 | C | LEU | A | 319 | 0.980 | −32.186 | 18.733 | 1.00 | 74.16 C |
| ATOM | 1552 | O | LEU | A | 319 | 0.812 | −31.081 | 18.235 | 1.00 | 74.10 O |
| ATOM | 1554 | N | LYS | A | 320 | 1.355 | −32.356 | 19.994 | 1.00 | 72.57 N |
| ATOM | 1555 | CA | LYS | A | 320 | 1.634 | −31.219 | 20.862 | 1.00 | 71.41 C |
| ATOM | 1557 | CB | LYS | A | 320 | 2.195 | −31.682 | 22.211 | 1.00 | 71.71 C |
| ATOM | 1560 | CG | LYS | A | 320 | 1.325 | −32.709 | 22.981 | 1.00 | 72.56 C |
| ATOM | 1563 | CD | LYS | A | 320 | 1.876 | −33.038 | 24.397 | 1.00 | 73.53 C |
| ATOM | 1566 | CE | LYS | A | 320 | 3.413 | −33.184 | 24.409 | 1.00 | 74.42 C |
| ATOM | 1569 | NZ | LYS | A | 320 | 3.957 | −33.974 | 25.563 | 1.00 | 73.81 N |
| ATOM | 1573 | C | LYS | A | 320 | 2.659 | −30.338 | 20.166 | 1.00 | 70.16 C |
| ATOM | 1574 | O | LYS | A | 320 | 3.507 | −30.843 | 19.448 | 1.00 | 70.05 O |
| ATOM | 1576 | N | GLU | A | 321 | 2.587 | −29.028 | 20.373 | 1.00 | 68.57 N |
| ATOM | 1577 | CA | GLU | A | 321 | 3.498 | −28.098 | 19.705 | 1.00 | 67.18 C |
| ATOM | 1579 | CB | GLU | A | 321 | 3.180 | −26.643 | 20.077 | 1.00 | 66.94 C |
| ATOM | 1582 | CG | GLU | A | 321 | 4.245 | −25.639 | 19.625 | 1.00 | 67.62 C |
| ATOM | 1585 | CD | GLU | A | 321 | 3.758 | −24.192 | 19.468 | 1.00 | 67.87 C |
| ATOM | 1586 | OE1 | GLU | A | 321 | 2.552 | −23.953 | 19.230 | 1.00 | 68.38 O |
| ATOM | 1587 | OE2 | GLU | A | 321 | 4.614 | −23.287 | 19.546 | 1.00 | 67.61 O |
| ATOM | 1588 | C | GLU | A | 321 | 4.967 | −28.433 | 20.003 | 1.00 | 66.07 C |
| ATOM | 1589 | O | GLU | A | 321 | 5.839 | −28.297 | 19.129 | 1.00 | 65.70 O |
| ATOM | 1591 | N | ALA | A | 322 | 5.225 | −28.877 | 21.232 | 1.00 | 64.58 N |
| ATOM | 1592 | CA | ALA | A | 322 | 6.578 | −29.188 | 21.693 | 1.00 | 63.25 C |
| ATOM | 1594 | CB | ALA | A | 322 | 6.593 | −29.380 | 23.215 | 1.00 | 62.92 C |
| ATOM | 1598 | C | ALA | A | 322 | 7.110 | −30.440 | 21.007 | 1.00 | 62.33 C |
| ATOM | 1599 | O | ALA | A | 322 | 8.309 | −30.557 | 20.783 | 1.00 | 61.76 O |
| ATOM | 1601 | N | THR | A | 323 | 6.215 | −31.381 | 20.715 | 1.00 | 61.27 N |
| ATOM | 1602 | CA | THR | A | 323 | 6.567 | −32.558 | 19.950 | 1.00 | 60.86 C |
| ATOM | 1604 | CB | THR | A | 323 | 5.417 | −33.571 | 19.903 | 1.00 | 60.91 C |
| ATOM | 1606 | OG1 | THR | A | 323 | 4.996 | −33.891 | 21.235 | 1.00 | 61.77 O |
| ATOM | 1608 | CG2 | THR | A | 323 | 5.847 | −34.843 | 19.185 | 1.00 | 60.69 C |
| ATOM | 1612 | C | THR | A | 323 | 6.933 | −32.137 | 18.525 | 1.00 | 60.40 C |
| ATOM | 1613 | O | THR | A | 323 | 7.965 | −32.561 | 18.002 | 1.00 | 60.46 O |
| ATOM | 1615 | N | CYS | A | 324 | 6.092 | −31.300 | 17.914 | 1.00 | 59.84 N |
| ATOM | 1616 | CA | CYS | A | 324 | 6.337 | −30.760 | 16.575 | 1.00 | 59.40 C |
| ATOM | 1618 | CB | CYS | A | 324 | 5.315 | −29.671 | 16.189 | 1.00 | 59.18 C |

TABLE 2-continued

| | | | | | | | | | | |
|---|---|---|---|---|---|---|---|---|---|---|
| ATOM | 1621 | SG | CYS | A | 324 | 3.607 | −30.242 | 15.940 | 1.00 | 60.83 | S |
| ATOM | 1623 | C | CYS | A | 324 | 7.731 | −30.162 | 16.506 | 1.00 | 59.02 | C |
| ATOM | 1624 | O | CYS | A | 324 | 8.444 | −30.398 | 15.535 | 1.00 | 59.73 | O |
| ATOM | 1626 | N | LYS | A | 325 | 8.116 | −29.398 | 17.529 | 1.00 | 57.66 | N |
| ATOM | 1627 | CA | LYS | A | 325 | 9.397 | −28.735 | 17.526 | 1.00 | 56.89 | C |
| ATOM | 1629 | CB | LYS | A | 325 | 9.529 | −27.759 | 18.704 | 1.00 | 56.78 | C |
| ATOM | 1632 | CG | LYS | A | 325 | 10.670 | −26.757 | 18.533 | 1.00 | 56.87 | C |
| ATOM | 1635 | CD | LYS | A | 325 | 10.938 | −25.917 | 19.792 | 1.00 | 57.08 | C |
| ATOM | 1638 | CE | LYS | A | 325 | 9.830 | −24.878 | 20.034 | 1.00 | 58.00 | C |
| ATOM | 1641 | NZ | LYS | A | 325 | 10.330 | −23.657 | 20.742 | 1.00 | 57.03 | N |
| ATOM | 1645 | C | LYS | A | 325 | 10.508 | −29.763 | 17.574 | 1.00 | 56.36 | C |
| ATOM | 1646 | O | LYS | A | 325 | 11.402 | −29.755 | 16.739 | 1.00 | 56.55 | O |
| ATOM | 1648 | N | LEU | A | 326 | 10.452 | −30.652 | 18.554 | 1.00 | 55.82 | N |
| ATOM | 1649 | CA | LEU | A | 326 | 11.501 | −31.642 | 18.729 | 1.00 | 55.11 | C |
| ATOM | 1651 | CB | LEU | A | 326 | 11.122 | −32.689 | 19.790 | 1.00 | 54.72 | C |
| ATOM | 1654 | CG | LEU | A | 326 | 12.138 | −33.839 | 19.963 | 1.00 | 55.43 | C |
| ATOM | 1656 | CD1 | LEU | A | 326 | 13.541 | −33.288 | 20.261 | 1.00 | 55.66 | C |
| ATOM | 1660 | CD2 | LEU | A | 326 | 11.739 | −34.874 | 21.034 | 1.00 | 55.01 | C |
| ATOM | 1664 | C | LEU | A | 326 | 11.769 | −32.319 | 17.385 | 1.00 | 54.43 | C |
| ATOM | 1665 | O | LEU | A | 326 | 12.905 | −32.395 | 16.943 | 1.00 | 54.95 | O |
| ATOM | 1667 | N | TYR | A | 327 | 10.716 | −32.795 | 16.737 | 1.00 | 53.42 | N |
| ATOM | 1668 | CA | TYR | A | 327 | 10.864 | −33.550 | 15.510 | 1.00 | 52.70 | C |
| ATOM | 1670 | CB | TYR | A | 327 | 9.533 | −34.161 | 15.081 | 1.00 | 52.77 | C |
| ATOM | 1673 | CG | TYR | A | 327 | 8.943 | −35.226 | 15.974 | 1.00 | 52.81 | C |
| ATOM | 1674 | CD1 | TYR | A | 327 | 9.658 | −35.798 | 17.022 | 1.00 | 52.65 | C |
| ATOM | 1676 | CE1 | TYR | A | 327 | 9.097 | −36.798 | 17.811 | 1.00 | 52.07 | C |
| ATOM | 1678 | CZ | TYR | A | 327 | 7.808 | −37.228 | 17.543 | 1.00 | 53.30 | C |
| ATOM | 1679 | OH | TYR | A | 327 | 7.200 | −38.201 | 18.308 | 1.00 | 54.03 | O |
| ATOM | 1681 | CE2 | TYR | A | 327 | 7.091 | −36.671 | 16.510 | 1.00 | 53.65 | C |
| ATOM | 1683 | CD2 | TYR | A | 327 | 7.659 | −35.688 | 15.731 | 1.00 | 53.59 | C |
| ATOM | 1685 | C | TYR | A | 327 | 11.349 | −32.672 | 14.361 | 1.00 | 51.79 | C |
| ATOM | 1686 | O | TYR | A | 327 | 12.142 | −33.112 | 13.541 | 1.00 | 52.23 | O |
| ATOM | 1688 | N | PHE | A | 328 | 10.843 | −31.448 | 14.284 | 1.00 | 50.11 | N |
| ATOM | 1689 | CA | PHE | A | 328 | 11.142 | −30.603 | 13.160 | 1.00 | 48.88 | C |
| ATOM | 1691 | CB | PHE | A | 328 | 10.224 | −29.394 | 13.123 | 1.00 | 48.38 | C |
| ATOM | 1694 | CG | PHE | A | 328 | 10.307 | −28.656 | 11.838 | 1.00 | 46.12 | C |
| ATOM | 1695 | CD1 | PHE | A | 328 | 9.809 | −29.226 | 10.684 | 1.00 | 44.74 | C |
| ATOM | 1697 | CE1 | PHE | A | 328 | 9.914 | −28.562 | 9.467 | 1.00 | 45.53 | C |
| ATOM | 1699 | CZ | PHE | A | 328 | 10.540 | −27.316 | 9.421 | 1.00 | 45.64 | C |
| ATOM | 1701 | CE2 | PHE | A | 328 | 11.052 | −26.760 | 10.581 | 1.00 | 45.80 | C |
| ATOM | 1703 | CD2 | PHE | A | 328 | 10.938 | −27.430 | 11.768 | 1.00 | 45.48 | C |
| ATOM | 1705 | C | PHE | A | 328 | 12.585 | −30.152 | 13.184 | 1.00 | 48.57 | C |
| ATOM | 1706 | O | PHE | A | 328 | 13.238 | −30.001 | 12.154 | 1.00 | 48.18 | O |
| ATOM | 1708 | N | TYR | A | 329 | 13.059 | −29.901 | 14.383 | 1.00 | 48.20 | N |
| ATOM | 1709 | CA | TYR | A | 329 | 14.447 | −29.603 | 14.615 | 1.00 | 47.95 | C |
| ATOM | 1711 | CB | TYR | A | 329 | 14.678 | −29.545 | 16.140 | 1.00 | 47.63 | C |
| ATOM | 1714 | CG | TYR | A | 329 | 16.094 | −29.254 | 16.511 | 1.00 | 46.45 | C |
| ATOM | 1715 | CD1 | TYR | A | 329 | 16.660 | −28.025 | 16.208 | 1.00 | 46.71 | C |
| ATOM | 1717 | CE1 | TYR | A | 329 | 17.958 | −27.736 | 16.541 | 1.00 | 48.16 | C |
| ATOM | 1719 | CZ | TYR | A | 329 | 18.717 | −28.684 | 17.181 | 1.00 | 49.47 | C |
| ATOM | 1720 | OH | TYR | A | 329 | 20.025 | −28.398 | 17.498 | 1.00 | 52.55 | O |
| ATOM | 1722 | CE2 | TYR | A | 329 | 18.168 | −29.922 | 17.507 | 1.00 | 49.23 | C |
| ATOM | 1724 | CD2 | TYR | A | 329 | 16.863 | −30.193 | 17.165 | 1.00 | 46.47 | C |
| ATOM | 1726 | C | TYR | A | 329 | 15.334 | −30.679 | 13.966 | 1.00 | 47.74 | C |
| ATOM | 1727 | O | TYR | A | 329 | 16.298 | −30.368 | 13.272 | 1.00 | 48.59 | O |
| ATOM | 1729 | N | GLN | A | 330 | 14.995 | −31.941 | 14.180 | 1.00 | 47.10 | N |
| ATOM | 1730 | CA | GLN | A | 330 | 15.810 | −33.047 | 13.668 | 1.00 | 47.43 | C |
| ATOM | 1732 | CB | GLN | A | 330 | 15.374 | −34.375 | 14.280 | 1.00 | 47.47 | C |
| ATOM | 1735 | CG | GLN | A | 330 | 15.683 | −34.484 | 15.751 | 1.00 | 49.80 | C |
| ATOM | 1738 | CD | GLN | A | 330 | 15.045 | −35.687 | 16.380 | 1.00 | 51.80 | C |
| ATOM | 1739 | OE1 | GLN | A | 330 | 15.421 | −36.832 | 16.095 | 1.00 | 53.09 | O |
| ATOM | 1740 | NE2 | GLN | A | 330 | 14.067 | −35.443 | 17.244 | 1.00 | 53.40 | N |
| ATOM | 1743 | C | GLN | A | 330 | 15.728 | −33.155 | 12.150 | 1.00 | 47.41 | C |
| ATOM | 1744 | O | GLN | A | 330 | 16.737 | −33.468 | 11.493 | 1.00 | 47.37 | O |
| ATOM | 1746 | N | MET | A | 331 | 14.532 | −32.915 | 11.609 | 1.00 | 46.95 | N |
| ATOM | 1747 | CA | MET | A | 331 | 14.328 | −32.839 | 10.161 | 1.00 | 47.05 | C |
| ATOM | 1749 | CB | MET | A | 331 | 12.849 | −32.566 | 9.820 | 1.00 | 47.42 | C |
| ATOM | 1752 | CG | MET | A | 331 | 11.888 | −33.737 | 10.108 | 1.00 | 47.36 | C |
| ATOM | 1755 | SD | MET | A | 331 | 10.161 | −33.355 | 9.674 | 1.00 | 50.19 | S |
| ATOM | 1756 | CE | MET | A | 331 | 9.447 | −33.237 | 11.313 | 1.00 | 50.50 | C |
| ATOM | 1760 | C | MET | A | 331 | 15.221 | −31.755 | 9.571 | 1.00 | 46.37 | C |
| ATOM | 1761 | O | MET | A | 331 | 15.870 | −31.968 | 8.546 | 1.00 | 47.50 | O |
| ATOM | 1763 | N | LEU | A | 332 | 15.310 | −30.617 | 10.240 | 1.00 | 45.37 | N |
| ATOM | 1764 | CA | LEU | A | 332 | 16.112 | −29.516 | 9.716 | 1.00 | 44.73 | C |
| ATOM | 1766 | CB | LEU | A | 332 | 15.911 | −28.232 | 10.516 | 1.00 | 44.06 | C |
| ATOM | 1769 | CG | LEU | A | 332 | 14.635 | −27.448 | 10.277 | 1.00 | 42.42 | C |
| ATOM | 1771 | CD1 | LEU | A | 332 | 14.544 | −26.320 | 11.314 | 1.00 | 39.75 | C |
| ATOM | 1775 | CD2 | LEU | A | 332 | 14.605 | −26.895 | 8.840 | 1.00 | 41.89 | C |
| ATOM | 1779 | C | LEU | A | 332 | 17.582 | −29.891 | 9.739 | 1.00 | 44.97 | C |
| ATOM | 1780 | O | LEU | A | 332 | 18.315 | −29.591 | 8.796 | 1.00 | 44.68 | O |

TABLE 2-continued

| | | | | | | | | | | |
|---|---|---|---|---|---|---|---|---|---|---|
| ATOM | 1782 | N | LEU | A | 333 | 18.024 | −30.527 | 10.823 | 1.00 | 45.01 | N |
| ATOM | 1783 | CA | LEU | A | 333 | 19.427 | −30.947 | 10.903 | 1.00 | 44.72 | C |
| ATOM | 1785 | CB | LEU | A | 333 | 19.740 | −31.564 | 12.259 | 1.00 | 44.76 | C |
| ATOM | 1788 | CG | LEU | A | 333 | 19.789 | −30.627 | 13.473 | 1.00 | 44.99 | C |
| ATOM | 1790 | CD1 | LEU | A | 333 | 19.975 | −31.486 | 14.704 | 1.00 | 45.77 | C |
| ATOM | 1794 | CD2 | LEU | A | 333 | 20.908 | −29.556 | 13.376 | 1.00 | 42.11 | C |
| ATOM | 1798 | C | LEU | A | 333 | 19.729 | −31.944 | 9.790 | 1.00 | 44.41 | C |
| ATOM | 1799 | O | LEU | A | 333 | 20.795 | −31.875 | 9.162 | 1.00 | 44.99 | O |
| ATOM | 1801 | N | ALA | A | 334 | 18.769 | −32.828 | 9.517 | 1.00 | 43.57 | N |
| ATOM | 1802 | CA | ALA | A | 334 | 18.954 | −33.867 | 8.529 | 1.00 | 43.35 | C |
| ATOM | 1804 | CB | ALA | A | 334 | 17.841 | −34.883 | 8.593 | 1.00 | 43.16 | C |
| ATOM | 1808 | C | ALA | A | 334 | 19.020 | −33.239 | 7.158 | 1.00 | 43.11 | C |
| ATOM | 1809 | O | ALA | A | 334 | 19.982 | −33.421 | 6.430 | 1.00 | 43.54 | O |
| ATOM | 1811 | N | VAL | A | 335 | 18.022 | −32.447 | 6.818 | 1.00 | 43.17 | N |
| ATOM | 1812 | CA | VAL | A | 335 | 18.026 | −31.822 | 5.512 | 1.00 | 42.44 | C |
| ATOM | 1814 | CB | VAL | A | 335 | 16.694 | −31.143 | 5.219 | 1.00 | 42.60 | C |
| ATOM | 1816 | CG1 | VAL | A | 335 | 16.706 | −30.411 | 3.847 | 1.00 | 39.84 | C |
| ATOM | 1820 | CG2 | VAL | A | 335 | 15.601 | −32.190 | 5.274 | 1.00 | 40.69 | C |
| ATOM | 1824 | C | VAL | A | 335 | 19.217 | −30.901 | 5.384 | 1.00 | 42.93 | C |
| ATOM | 1825 | O | VAL | A | 335 | 19.819 | −30.838 | 4.318 | 1.00 | 43.83 | O |
| ATOM | 1827 | N | GLN | A | 336 | 19.585 | −30.208 | 6.445 | 1.00 | 43.44 | N |
| ATOM | 1828 | CA | GLN | A | 336 | 20.793 | −29.369 | 6.418 | 1.00 | 44.97 | C |
| ATOM | 1830 | CB | GLN | A | 336 | 21.067 | −28.744 | 7.791 | 1.00 | 45.12 | C |
| ATOM | 1833 | CG | GLN | A | 336 | 22.268 | −27.786 | 7.770 | 1.00 | 46.48 | C |
| ATOM | 1836 | CD | GLN | A | 336 | 22.574 | −27.139 | 9.100 | 1.00 | 47.30 | C |
| ATOM | 1837 | OE1 | GLN | A | 336 | 22.680 | −25.917 | 9.185 | 1.00 | 51.31 | O |
| ATOM | 1838 | NE2 | GLN | A | 336 | 22.738 | −27.947 | 10.140 | 1.00 | 48.53 | N |
| ATOM | 1841 | C | GLN | A | 336 | 22.058 | −30.142 | 5.998 | 1.00 | 45.82 | C |
| ATOM | 1842 | O | GLN | A | 336 | 22.819 | −29.717 | 5.121 | 1.00 | 45.88 | O |
| ATOM | 1844 | N | TYR | A | 337 | 22.281 | −31.263 | 6.672 | 1.00 | 46.64 | N |
| ATOM | 1845 | CA | TYR | A | 337 | 23.405 | −32.145 | 6.377 | 1.00 | 46.89 | C |
| ATOM | 1847 | CB | TYR | A | 337 | 23.404 | −33.296 | 7.393 | 1.00 | 47.51 | C |
| ATOM | 1850 | CG | TYR | A | 337 | 24.348 | −34.435 | 7.078 | 1.00 | 49.20 | C |
| ATOM | 1851 | CD1 | TYR | A | 337 | 25.697 | −34.391 | 7.477 | 1.00 | 50.00 | C |
| ATOM | 1853 | CE1 | TYR | A | 337 | 26.551 | −35.434 | 7.195 | 1.00 | 48.96 | C |
| ATOM | 1855 | CZ | TYR | A | 337 | 26.064 | −36.536 | 6.518 | 1.00 | 49.55 | C |
| ATOM | 1856 | OH | TYR | A | 337 | 26.885 | −37.590 | 6.234 | 1.00 | 51.72 | O |
| ATOM | 1858 | CE2 | TYR | A | 337 | 24.746 | −36.602 | 6.113 | 1.00 | 49.78 | C |
| ATOM | 1860 | CD2 | TYR | A | 337 | 23.894 | −35.561 | 6.402 | 1.00 | 48.92 | C |
| ATOM | 1862 | C | TYR | A | 337 | 23.323 | −32.654 | 4.929 | 1.00 | 46.37 | C |
| ATOM | 1863 | O | TYR | A | 337 | 24.343 | −32.737 | 4.227 | 1.00 | 46.14 | O |
| ATOM | 1865 | N | LEU | A | 338 | 22.119 | −32.965 | 4.463 | 1.00 | 45.26 | N |
| ATOM | 1866 | CA | LEU | A | 338 | 21.988 | −33.372 | 3.067 | 1.00 | 45.20 | C |
| ATOM | 1868 | CB | LEU | A | 338 | 20.548 | −33.740 | 2.722 | 1.00 | 44.79 | C |
| ATOM | 1871 | CG | LEU | A | 338 | 20.036 | −35.033 | 3.321 | 1.00 | 43.89 | C |
| ATOM | 1873 | CD1 | LEU | A | 338 | 18.720 | −35.400 | 2.628 | 1.00 | 44.37 | C |
| ATOM | 1877 | CD2 | LEU | A | 338 | 21.021 | −36.192 | 3.178 | 1.00 | 43.52 | C |
| ATOM | 1881 | C | LEU | A | 338 | 22.514 | −32.286 | 2.117 | 1.00 | 44.65 | C |
| ATOM | 1882 | O | LEU | A | 338 | 23.380 | −32.545 | 1.284 | 1.00 | 45.12 | O |
| ATOM | 1884 | N | HIS | A | 339 | 22.031 | −31.068 | 2.286 | 1.00 | 44.54 | N |
| ATOM | 1885 | CA | HIS | A | 339 | 22.437 | −29.944 | 1.428 | 1.00 | 44.54 | C |
| ATOM | 1887 | CB | HIS | A | 339 | 21.538 | −28.713 | 1.666 | 1.00 | 43.43 | C |
| ATOM | 1890 | CG | HIS | A | 339 | 20.090 | −28.968 | 1.371 | 1.00 | 43.49 | C |
| ATOM | 1891 | ND1 | HIS | A | 339 | 19.085 | −28.093 | 1.723 | 1.00 | 42.10 | N |
| ATOM | 1893 | CE1 | HIS | A | 339 | 17.921 | −28.593 | 1.346 | 1.00 | 42.21 | C |
| ATOM | 1895 | NE2 | HIS | A | 339 | 18.129 | −29.781 | 0.797 | 1.00 | 41.76 | N |
| ATOM | 1897 | CD2 | HIS | A | 339 | 19.476 | −30.033 | 0.789 | 1.00 | 41.52 | C |
| ATOM | 1899 | C | HIS | A | 339 | 23.923 | −29.623 | 1.635 | 1.00 | 45.65 | C |
| ATOM | 1900 | O | HIS | A | 339 | 24.645 | −29.376 | 0.681 | 1.00 | 45.85 | O |
| ATOM | 1902 | N | GLU | A | 340 | 24.395 | −29.678 | 2.873 | 1.00 | 46.76 | N |
| ATOM | 1903 | CA | GLU | A | 340 | 25.826 | −29.570 | 3.118 | 1.00 | 47.97 | C |
| ATOM | 1905 | CB | GLU | A | 340 | 26.163 | −29.806 | 4.612 | 1.00 | 48.13 | C |
| ATOM | 1908 | CG | GLU | A | 340 | 25.986 | −28.543 | 5.504 | 1.00 | 50.25 | C |
| ATOM | 1911 | CD | GLU | A | 340 | 26.147 | −28.794 | 7.025 | 1.00 | 53.30 | C |
| ATOM | 1912 | OE1 | GLU | A | 340 | 26.012 | −29.948 | 7.502 | 1.00 | 54.76 | O |
| ATOM | 1913 | OE2 | GLU | A | 340 | 26.407 | −27.809 | 7.760 | 1.00 | 57.21 | O |
| ATOM | 1914 | C | GLU | A | 340 | 26.615 | −30.533 | 2.217 | 1.00 | 48.19 | C |
| ATOM | 1915 | O | GLU | A | 340 | 27.678 | −30.166 | 1.747 | 1.00 | 48.82 | O |
| ATOM | 1917 | N | ASN | A | 341 | 26.071 | −31.730 | 1.967 | 1.00 | 48.19 | N |
| ATOM | 1918 | CA | ASN | A | 341 | 26.766 | −32.815 | 1.260 | 1.00 | 48.05 | C |
| ATOM | 1920 | CB | ASN | A | 341 | 26.556 | −34.138 | 2.024 | 1.00 | 47.72 | C |
| ATOM | 1923 | CG | ASN | A | 341 | 27.456 | −34.245 | 3.256 | 1.00 | 49.22 | C |
| ATOM | 1924 | OD1 | ASN | A | 341 | 28.655 | −34.469 | 3.119 | 1.00 | 53.48 | O |
| ATOM | 1925 | ND2 | ASN | A | 341 | 26.892 | −34.102 | 4.452 | 1.00 | 46.44 | N |
| ATOM | 1928 | C | ASN | A | 341 | 26.348 | −32.985 | −0.216 | 1.00 | 48.08 | C |
| ATOM | 1929 | O | ASN | A | 341 | 26.583 | −34.049 | −0.811 | 1.00 | 47.55 | O |
| ATOM | 1931 | N | GLY | A | 342 | 25.718 | −31.953 | −0.802 | 1.00 | 47.76 | N |
| ATOM | 1932 | CA | GLY | A | 342 | 25.279 | −31.981 | −2.226 | 1.00 | 46.70 | C |
| ATOM | 1935 | C | GLY | A | 342 | 24.105 | −32.898 | −2.562 | 1.00 | 46.21 | C |
| ATOM | 1936 | O | GLY | A | 342 | 23.933 | −33.314 | −3.713 | 1.00 | 45.79 | O |

TABLE 2-continued

| | | | | | | | | | | |
|---|---|---|---|---|---|---|---|---|---|---|
| ATOM | 1938 | N | ILE | A | 343 | 23.275 | −33.214 | −1.578 | 1.00 | 45.51 | N |
| ATOM | 1939 | CA | ILE | A | 343 | 22.114 | −34.060 | −1.841 | 1.00 | 45.28 | C |
| ATOM | 1941 | CB | ILE | A | 343 | 22.108 | −35.329 | −0.951 | 1.00 | 44.95 | C |
| ATOM | 1943 | CG1 | ILE | A | 343 | 23.410 | −36.124 | −1.127 | 1.00 | 46.08 | C |
| ATOM | 1946 | CD1 | ILE | A | 343 | 23.671 | −36.568 | −2.550 | 1.00 | 46.29 | C |
| ATOM | 1950 | CG2 | ILE | A | 343 | 20.892 | −36.196 | −1.266 | 1.00 | 42.48 | C |
| ATOM | 1954 | C | ILE | A | 343 | 20.798 | −33.333 | −1.596 | 1.00 | 45.36 | C |
| ATOM | 1955 | O | ILE | A | 343 | 20.587 | −32.751 | −0.547 | 1.00 | 45.72 | O |
| ATOM | 1957 | N | ILE | A | 344 | 19.892 | −33.452 | −2.546 | 1.00 | 45.73 | N |
| ATOM | 1958 | CA | ILE | A | 344 | 18.548 | −32.949 | −2.413 | 1.00 | 46.09 | C |
| ATOM | 1960 | CB | ILE | A | 344 | 18.190 | −32.104 | −3.672 | 1.00 | 46.67 | C |
| ATOM | 1962 | CG1 | ILE | A | 344 | 19.145 | −30.913 | −3.818 | 1.00 | 47.52 | C |
| ATOM | 1965 | CD1 | ILE | A | 344 | 19.073 | −30.277 | −5.244 | 1.00 | 49.76 | C |
| ATOM | 1969 | CG2 | ILE | A | 344 | 16.759 | −31.583 | −3.623 | 1.00 | 46.72 | C |
| ATOM | 1973 | C | ILE | A | 344 | 17.648 | −34.172 | −2.309 | 1.00 | 46.07 | C |
| ATOM | 1974 | O | ILE | A | 344 | 17.776 | −35.083 | −3.116 | 1.00 | 46.69 | O |
| ATOM | 1976 | N | HIS | A | 345 | 16.741 | −34.199 | −1.340 | 1.00 | 45.43 | N |
| ATOM | 1977 | CA | HIS | A | 345 | 15.917 | −35.368 | −1.123 | 1.00 | 45.30 | C |
| ATOM | 1979 | CB | HIS | A | 345 | 15.318 | −35.352 | 0.268 | 1.00 | 44.91 | C |
| ATOM | 1982 | CG | HIS | A | 345 | 14.582 | −36.604 | 0.615 | 1.00 | 44.33 | C |
| ATOM | 1983 | ND1 | HIS | A | 345 | 13.308 | −36.869 | 0.164 | 1.00 | 44.50 | N |
| ATOM | 1985 | CE1 | HIS | A | 345 | 12.899 | −38.026 | 0.651 | 1.00 | 45.09 | C |
| ATOM | 1987 | NE2 | HIS | A | 345 | 13.885 | −38.551 | 1.356 | 1.00 | 45.83 | N |
| ATOM | 1989 | CD2 | HIS | A | 345 | 14.948 | −37.677 | 1.355 | 1.00 | 45.41 | C |
| ATOM | 1991 | C | HIS | A | 345 | 14.793 | −35.511 | −2.136 | 1.00 | 45.95 | C |
| ATOM | 1992 | O | HIS | A | 345 | 14.660 | −36.563 | −2.748 | 1.00 | 46.59 | O |
| ATOM | 1994 | N | ARG | A | 346 | 13.962 | −34.475 | −2.257 | 1.00 | 46.66 | N |
| ATOM | 1995 | CA | ARG | A | 346 | 12.906 | −34.357 | −3.267 | 1.00 | 46.99 | C |
| ATOM | 1997 | CB | ARG | A | 346 | 13.414 | −34.661 | −4.678 | 1.00 | 47.38 | C |
| ATOM | 2000 | CG | ARG | A | 346 | 14.596 | −33.840 | −5.075 | 1.00 | 50.14 | C |
| ATOM | 2003 | CD | ARG | A | 346 | 14.494 | −33.335 | −6.491 | 1.00 | 53.73 | C |
| ATOM | 2006 | NE | ARG | A | 346 | 14.691 | −34.425 | −7.423 | 1.00 | 58.00 | N |
| ATOM | 2008 | CZ | ARG | A | 346 | 13.743 | −35.005 | −8.166 | 1.00 | 62.37 | C |
| ATOM | 2009 | NH1 | ARG | A | 346 | 12.479 | −34.600 | −8.139 | 1.00 | 61.80 | N |
| ATOM | 2012 | NH2 | ARG | A | 346 | 14.086 | −36.009 | −8.977 | 1.00 | 65.64 | N |
| ATOM | 2015 | C | ARG | A | 346 | 11.686 | −35.191 | −3.022 | 1.00 | 47.13 | C |
| ATOM | 2016 | O | ARG | A | 346 | 10.893 | −35.355 | −3.909 | 1.00 | 47.86 | O |
| ATOM | 2018 | N | ASP | A | 347 | 11.499 | −35.696 | −1.827 | 1.00 | 47.76 | N |
| ATOM | 2019 | CA | ASP | A | 347 | 10.325 | −36.498 | −1.540 | 1.00 | 48.57 | C |
| ATOM | 2021 | CB | ASP | A | 347 | 10.544 | −37.935 | −2.059 | 1.00 | 49.46 | C |
| ATOM | 2024 | CG | ASP | A | 347 | 9.240 | −38.749 | −2.194 | 1.00 | 51.98 | C |
| ATOM | 2025 | OD1 | ASP | A | 347 | 8.146 | −38.139 | −2.233 | 1.00 | 54.15 | O |
| ATOM | 2026 | OD2 | ASP | A | 347 | 9.340 | −40.010 | −2.270 | 1.00 | 56.77 | O |
| ATOM | 2027 | C | ASP | A | 347 | 10.038 | −36.491 | −0.046 | 1.00 | 48.43 | C |
| ATOM | 2028 | O | ASP | A | 347 | 9.551 | −37.476 | 0.506 | 1.00 | 48.53 | O |
| ATOM | 2030 | N | LEU | A | 348 | 10.348 | −35.376 | 0.616 | 1.00 | 47.86 | N |
| ATOM | 2031 | CA | LEU | A | 348 | 10.079 | −35.272 | 2.021 | 1.00 | 47.45 | C |
| ATOM | 2033 | CB | LEU | A | 348 | 10.766 | −34.050 | 2.614 | 1.00 | 46.99 | C |
| ATOM | 2036 | CG | LEU | A | 348 | 12.279 | −34.181 | 2.662 | 1.00 | 46.68 | C |
| ATOM | 2038 | CD1 | LEU | A | 348 | 12.926 | −32.905 | 3.181 | 1.00 | 46.29 | C |
| ATOM | 2042 | CD2 | LEU | A | 348 | 12.676 | −35.348 | 3.525 | 1.00 | 47.53 | C |
| ATOM | 2046 | C | LEU | A | 348 | 8.574 | −35.241 | 2.226 | 1.00 | 47.57 | C |
| ATOM | 2047 | O | LEU | A | 348 | 7.890 | −34.379 | 1.721 | 1.00 | 46.95 | O |
| ATOM | 2049 | N | LYS | A | 349 | 8.061 | −36.256 | 2.904 | 1.00 | 49.13 | N |
| ATOM | 2050 | CA | LYS | A | 349 | 6.656 | −36.294 | 3.361 | 1.00 | 50.29 | C |
| ATOM | 2052 | CB | LYS | A | 349 | 5.696 | −36.831 | 2.279 | 1.00 | 50.38 | C |
| ATOM | 2055 | CG | LYS | A | 349 | 6.354 | −37.661 | 1.193 | 1.00 | 52.63 | C |
| ATOM | 2058 | CD | LYS | A | 349 | 5.345 | −38.225 | 0.178 | 1.00 | 56.26 | C |
| ATOM | 2061 | CE | LYS | A | 349 | 5.834 | −39.602 | −0.341 | 1.00 | 59.11 | C |
| ATOM | 2064 | NZ | LYS | A | 349 | 4.928 | −40.241 | −1.362 | 1.00 | 62.69 | N |
| ATOM | 2068 | C | LYS | A | 349 | 6.583 | −37.122 | 4.641 | 1.00 | 50.86 | C |
| ATOM | 2069 | O | LYS | A | 349 | 7.551 | −37.818 | 4.995 | 1.00 | 50.72 | O |
| ATOM | 2071 | N | PRO | A | 350 | 5.451 | −37.041 | 5.363 | 1.00 | 51.63 | N |
| ATOM | 2072 | CA | PRO | A | 350 | 5.301 | −37.768 | 6.622 | 1.00 | 52.12 | C |
| ATOM | 2074 | CB | PRO | A | 350 | 3.863 | −37.478 | 7.001 | 1.00 | 52.29 | C |
| ATOM | 2077 | CG | PRO | A | 350 | 3.612 | −36.140 | 6.410 | 1.00 | 51.71 | C |
| ATOM | 2080 | CD | PRO | A | 350 | 4.283 | −36.200 | 5.095 | 1.00 | 51.56 | C |
| ATOM | 2083 | C | PRO | A | 350 | 5.561 | −39.280 | 6.521 | 1.00 | 52.88 | C |
| ATOM | 2084 | O | PRO | A | 350 | 6.114 | −39.858 | 7.459 | 1.00 | 52.82 | O |
| ATOM | 2085 | N | GLU | A | 351 | 5.214 | −39.879 | 5.380 | 1.00 | 53.73 | N |
| ATOM | 2086 | CA | GLU | A | 351 | 5.533 | −41.294 | 5.058 | 1.00 | 55.09 | C |
| ATOM | 2088 | CB | GLU | A | 351 | 5.070 | −41.663 | 3.620 | 1.00 | 55.57 | C |
| ATOM | 2091 | CG | GLU | A | 351 | 3.568 | −41.488 | 3.251 | 1.00 | 57.24 | C |
| ATOM | 2094 | CD | GLU | A | 351 | 3.123 | −40.032 | 3.067 | 1.00 | 59.54 | C |
| ATOM | 2095 | OE1 | GLU | A | 351 | 3.539 | −39.167 | 3.868 | 1.00 | 61.16 | O |
| ATOM | 2096 | OE2 | GLU | A | 351 | 2.320 | −39.745 | 2.148 | 1.00 | 63.53 | O |
| ATOM | 2097 | C | GLU | A | 351 | 7.047 | −41.612 | 5.139 | 1.00 | 55.45 | C |
| ATOM | 2098 | O | GLU | A | 351 | 7.449 | −42.763 | 5.381 | 1.00 | 55.42 | O |
| ATOM | 2100 | N | ASN | A | 352 | 7.884 | −40.599 | 4.903 | 1.00 | 55.39 | N |
| ATOM | 2101 | CA | ASN | A | 352 | 9.312 | −40.815 | 4.778 | 1.00 | 55.22 | C |

TABLE 2-continued

| | | | | | | | | | | |
|---|---|---|---|---|---|---|---|---|---|---|
| ATOM | 2103 | CB | ASN | A | 352 | 9.819 | −40.172 | 3.486 | 1.00 | 55.15 | C |
| ATOM | 2106 | CG | ASN | A | 352 | 9.365 | −40.924 | 2.255 | 1.00 | 56.59 | C |
| ATOM | 2107 | OD1 | ASN | A | 352 | 9.265 | −42.147 | 2.274 | 1.00 | 60.88 | O |
| ATOM | 2108 | ND2 | ASN | A | 352 | 9.104 | −40.208 | 1.173 | 1.00 | 57.72 | N |
| ATOM | 2111 | C | ASN | A | 352 | 10.055 | −40.313 | 5.996 | 1.00 | 55.19 | C |
| ATOM | 2112 | O | ASN | A | 352 | 11.277 | −40.225 | 5.985 | 1.00 | 55.11 | O |
| ATOM | 2114 | N | VAL | A | 353 | 9.317 | −40.013 | 7.060 | 1.00 | 55.36 | N |
| ATOM | 2115 | CA | VAL | A | 353 | 9.919 | −39.668 | 8.346 | 1.00 | 55.41 | C |
| ATOM | 2117 | CB | VAL | A | 353 | 9.420 | −38.317 | 8.826 | 1.00 | 55.10 | C |
| ATOM | 2119 | CG1 | VAL | A | 353 | 9.973 | −38.000 | 10.177 | 1.00 | 54.49 | C |
| ATOM | 2123 | CG2 | VAL | A | 353 | 9.776 | −37.250 | 7.818 | 1.00 | 52.21 | C |
| ATOM | 2127 | C | VAL | A | 353 | 9.545 | −40.780 | 9.343 | 1.00 | 56.84 | C |
| ATOM | 2128 | O | VAL | A | 353 | 8.360 | −41.014 | 9.615 | 1.00 | 56.79 | O |
| ATOM | 2130 | N | LEU | A | 354 | 10.564 | −41.486 | 9.844 | 1.00 | 57.94 | N |
| ATOM | 2131 | CA | LEU | A | 354 | 10.389 | −42.626 | 10.740 | 1.00 | 58.20 | C |
| ATOM | 2133 | CB | LEU | A | 354 | 11.254 | −43.796 | 10.267 | 1.00 | 58.09 | C |
| ATOM | 2136 | CG | LEU | A | 354 | 11.130 | −44.208 | 8.793 | 1.00 | 58.07 | C |
| ATOM | 2138 | CD1 | LEU | A | 354 | 12.216 | −45.192 | 8.401 | 1.00 | 56.66 | C |
| ATOM | 2142 | CD2 | LEU | A | 354 | 9.779 | −44.803 | 8.504 | 1.00 | 57.80 | C |
| ATOM | 2146 | C | LEU | A | 354 | 10.779 | −42.221 | 12.165 | 1.00 | 58.82 | C |
| ATOM | 2147 | O | LEU | A | 354 | 11.706 | −41.432 | 12.356 | 1.00 | 57.76 | O |
| ATOM | 2149 | N | LEU | A | 355 | 10.068 | −42.778 | 13.150 | 1.00 | 60.04 | N |
| ATOM | 2150 | CA | LEU | A | 355 | 10.321 | −42.507 | 14.579 | 1.00 | 61.15 | C |
| ATOM | 2152 | CB | LEU | A | 355 | 9.000 | −42.163 | 15.275 | 1.00 | 61.08 | C |
| ATOM | 2155 | CG | LEU | A | 355 | 7.998 | −41.293 | 14.504 | 1.00 | 60.70 | C |
| ATOM | 2157 | CD1 | LEU | A | 355 | 6.676 | −41.105 | 15.265 | 1.00 | 59.30 | C |
| ATOM | 2161 | CD2 | LEU | A | 355 | 8.627 | −39.964 | 14.227 | 1.00 | 60.79 | C |
| ATOM | 2165 | C | LEU | A | 355 | 10.987 | −43.722 | 15.273 | 1.00 | 62.23 | C |
| ATOM | 2166 | O | LEU | A | 355 | 10.646 | −44.873 | 14.991 | 1.00 | 61.85 | O |
| ATOM | 2168 | N | SER | A | 356 | 11.914 | −43.467 | 16.190 | 1.00 | 63.94 | N |
| ATOM | 2169 | CA | SER | A | 356 | 12.656 | −44.565 | 16.860 | 1.00 | 65.74 | C |
| ATOM | 2171 | CB | SER | A | 356 | 13.930 | −44.024 | 17.517 | 1.00 | 65.28 | C |
| ATOM | 2174 | OG | SER | A | 356 | 13.672 | −42.802 | 18.170 | 1.00 | 65.64 | O |
| ATOM | 2176 | C | SER | A | 356 | 11.848 | −45.405 | 17.884 | 1.00 | 67.21 | C |
| ATOM | 2177 | O | SER | A | 356 | 12.247 | −46.528 | 18.232 | 1.00 | 67.34 | O |
| ATOM | 2179 | N | SER | A | 357 | 10.722 | −44.877 | 18.358 | 1.00 | 68.95 | N |
| ATOM | 2180 | CA | SER | A | 357 | 9.895 | −45.605 | 19.324 | 1.00 | 70.25 | C |
| ATOM | 2182 | CB | SER | A | 357 | 10.519 | −45.555 | 20.718 | 1.00 | 70.25 | C |
| ATOM | 2185 | OG | SER | A | 357 | 10.555 | −44.222 | 21.200 | 1.00 | 70.69 | O |
| ATOM | 2187 | C | SER | A | 357 | 8.497 | −45.043 | 19.411 | 1.00 | 71.38 | C |
| ATOM | 2188 | O | SER | A | 357 | 8.183 | −43.985 | 18.845 | 1.00 | 72.02 | O |
| ATOM | 2190 | N | GLN | A | 358 | 7.658 | −45.761 | 20.140 | 1.00 | 72.38 | N |
| ATOM | 2191 | CA | GLN | A | 358 | 6.307 | −45.312 | 20.395 | 1.00 | 73.26 | C |
| ATOM | 2193 | CB | GLN | A | 358 | 5.463 | −46.497 | 20.830 | 1.00 | 73.92 | C |
| ATOM | 2196 | CG | GLN | A | 358 | 5.304 | −47.565 | 19.748 | 1.00 | 75.89 | C |
| ATOM | 2199 | CD | GLN | A | 358 | 4.743 | −48.882 | 20.296 | 1.00 | 79.35 | C |
| ATOM | 2200 | OE1 | GLN | A | 358 | 4.909 | −49.203 | 21.483 | 1.00 | 80.93 | O |
| ATOM | 2201 | NE2 | GLN | A | 358 | 4.081 | −49.656 | 19.426 | 1.00 | 80.44 | N |
| ATOM | 2204 | C | GLN | A | 358 | 6.277 | −44.201 | 21.449 | 1.00 | 73.21 | C |
| ATOM | 2205 | O | GLN | A | 358 | 5.256 | −43.550 | 21.628 | 1.00 | 73.00 | O |
| ATOM | 2207 | N | GLU | A | 359 | 7.397 | −43.989 | 22.137 | 1.00 | 73.47 | N |
| ATOM | 2208 | CA | GLU | A | 359 | 7.554 | −42.841 | 23.035 | 1.00 | 73.76 | C |
| ATOM | 2210 | CB | GLU | A | 359 | 8.937 | −42.837 | 23.717 | 1.00 | 73.91 | C |
| ATOM | 2213 | CG | GLU | A | 359 | 9.320 | −44.108 | 24.504 | 1.00 | 74.95 | C |
| ATOM | 2216 | CD | GLU | A | 359 | 9.252 | −43.947 | 26.024 | 1.00 | 76.20 | C |
| ATOM | 2217 | OE1 | GLU | A | 359 | 9.052 | −42.810 | 26.506 | 1.00 | 78.04 | O |
| ATOM | 2218 | OE2 | GLU | A | 359 | 9.415 | −44.960 | 26.739 | 1.00 | 74.69 | O |
| ATOM | 2219 | C | GLU | A | 359 | 7.421 | −41.560 | 22.207 | 1.00 | 73.60 | C |
| ATOM | 2220 | O | GLU | A | 359 | 8.036 | −41.439 | 21.143 | 1.00 | 73.59 | O |
| ATOM | 2222 | N | GLU | A | 360 | 6.615 | −40.615 | 22.685 | 1.00 | 73.25 | N |
| ATOM | 2223 | CA | GLU | A | 360 | 6.415 | −39.359 | 21.969 | 1.00 | 72.64 | C |
| ATOM | 2225 | CB | GLU | A | 360 | 5.516 | −38.392 | 22.751 | 1.00 | 73.00 | C |
| ATOM | 2228 | CG | GLU | A | 360 | 4.087 | −38.311 | 22.229 | 1.00 | 74.60 | C |
| ATOM | 2231 | CD | GLU | A | 360 | 3.344 | −37.105 | 22.786 | 1.00 | 77.02 | C |
| ATOM | 2232 | OE1 | GLU | A | 360 | 3.048 | −36.175 | 21.990 | 1.00 | 78.71 | O |
| ATOM | 2233 | OE2 | GLU | A | 360 | 3.084 | −37.076 | 24.018 | 1.00 | 77.12 | O |
| ATOM | 2234 | C | GLU | A | 360 | 7.750 | −38.692 | 21.705 | 1.00 | 71.51 | C |
| ATOM | 2235 | O | GLU | A | 360 | 8.072 | −38.369 | 20.568 | 1.00 | 71.13 | O |
| ATOM | 2237 | N | ASP | A | 361 | 8.519 | −38.486 | 22.765 | 1.00 | 70.15 | N |
| ATOM | 2238 | CA | ASP | A | 361 | 9.815 | −37.838 | 22.643 | 1.00 | 69.12 | C |
| ATOM | 2240 | CB | ASP | A | 361 | 10.239 | −37.259 | 23.985 | 1.00 | 69.49 | C |
| ATOM | 2243 | CG | ASP | A | 361 | 9.383 | −36.086 | 24.412 | 1.00 | 70.54 | C |
| ATOM | 2244 | OD1 | ASP | A | 361 | 8.234 | −35.980 | 23.909 | 1.00 | 70.30 | O |
| ATOM | 2245 | OD2 | ASP | A | 361 | 9.870 | −35.284 | 25.256 | 1.00 | 71.17 | O |
| ATOM | 2246 | C | ASP | A | 361 | 10.880 | −38.815 | 22.186 | 1.00 | 67.73 | C |
| ATOM | 2247 | O | ASP | A | 361 | 11.473 | −39.493 | 23.012 | 1.00 | 67.91 | O |
| ATOM | 2249 | N | CYS | A | 362 | 11.133 | −38.872 | 20.878 | 1.00 | 66.21 | N |
| ATOM | 2250 | CA | CYS | A | 362 | 12.096 | −39.828 | 20.310 | 1.00 | 64.77 | C |
| ATOM | 2252 | CB | CYS | A | 362 | 11.343 | −41.055 | 19.807 | 1.00 | 64.55 | C |
| ATOM | 2255 | SG | CYS | A | 362 | 10.347 | −40.709 | 18.412 | 1.00 | 65.24 | S |

TABLE 2-continued

| | | | | | | | | | | |
|---|---|---|---|---|---|---|---|---|---|---|
| ATOM | 2257 | C | CYS | A | 362 | 12.989 | −39.241 | 19.199 | 1.00 | 63.37 | C |
| ATOM | 2258 | O | CYS | A | 362 | 12.981 | −38.034 | 18.922 | 1.00 | 63.35 | O |
| ATOM | 2260 | N | LEU | A | 363 | 13.801 | −40.094 | 18.587 | 1.00 | 61.73 | N |
| ATOM | 2261 | CA | LEU | A | 363 | 14.628 | −39.664 | 17.465 | 1.00 | 60.17 | C |
| ATOM | 2263 | CB | LEU | A | 363 | 15.981 | −40.369 | 17.462 | 1.00 | 60.59 | C |
| ATOM | 2266 | CG | LEU | A | 363 | 16.924 | −40.012 | 18.627 | 1.00 | 60.04 | C |
| ATOM | 2268 | CD1 | LEU | A | 363 | 18.092 | −40.973 | 18.651 | 1.00 | 60.86 | C |
| ATOM | 2272 | CD2 | LEU | A | 363 | 17.426 | −38.598 | 18.518 | 1.00 | 58.93 | C |
| ATOM | 2276 | C | LEU | A | 363 | 13.876 | −39.957 | 16.194 | 1.00 | 58.54 | C |
| ATOM | 2277 | O | LEU | A | 363 | 13.199 | −40.981 | 16.080 | 1.00 | 57.95 | O |
| ATOM | 2279 | N | ILE | A | 364 | 13.957 | −39.025 | 15.256 | 1.00 | 56.96 | N |
| ATOM | 2280 | CA | ILE | A | 364 | 13.367 | −39.228 | 13.948 | 1.00 | 55.82 | C |
| ATOM | 2282 | CB | ILE | A | 364 | 12.478 | −38.020 | 13.504 | 1.00 | 55.93 | C |
| ATOM | 2284 | CG1 | ILE | A | 364 | 13.325 | −36.803 | 13.136 | 1.00 | 55.75 | C |
| ATOM | 2287 | CD1 | ILE | A | 364 | 13.782 | −36.806 | 11.649 | 1.00 | 54.84 | C |
| ATOM | 2291 | CG2 | ILE | A | 364 | 11.447 | −37.664 | 14.572 | 1.00 | 56.64 | C |
| ATOM | 2295 | C | ILE | A | 364 | 14.486 | −39.483 | 12.950 | 1.00 | 54.64 | C |
| ATOM | 2296 | O | ILE | A | 364 | 15.589 | −38.954 | 13.100 | 1.00 | 54.49 | O |
| ATOM | 2298 | N | LYS | A | 365 | 14.214 | −40.301 | 11.943 | 1.00 | 53.70 | N |
| ATOM | 2299 | CA | LYS | A | 365 | 15.153 | −40.484 | 10.841 | 1.00 | 53.25 | C |
| ATOM | 2301 | CB | LYS | A | 365 | 15.937 | −41.797 | 10.966 | 1.00 | 53.47 | C |
| ATOM | 2304 | CG | LYS | A | 365 | 17.010 | −41.765 | 12.076 | 1.00 | 55.49 | C |
| ATOM | 2307 | CD | LYS | A | 365 | 17.386 | −43.162 | 12.511 | 1.00 | 58.37 | C |
| ATOM | 2310 | CE | LYS | A | 365 | 18.316 | −43.166 | 13.731 | 1.00 | 60.12 | C |
| ATOM | 2313 | NZ | LYS | A | 365 | 19.743 | −43.384 | 13.341 | 1.00 | 61.38 | N |
| ATOM | 2317 | C | LYS | A | 365 | 14.423 | −40.396 | 9.510 | 1.00 | 52.19 | C |
| ATOM | 2318 | O | LYS | A | 365 | 13.307 | −40.891 | 9.368 | 1.00 | 51.38 | O |
| ATOM | 2320 | N | ILE | A | 366 | 15.079 | −39.734 | 8.560 | 1.00 | 51.17 | N |
| ATOM | 2321 | CA | ILE | A | 366 | 14.554 | −39.500 | 7.238 | 1.00 | 50.59 | C |
| ATOM | 2323 | CB | ILE | A | 366 | 15.067 | −38.166 | 6.659 | 1.00 | 50.65 | C |
| ATOM | 2325 | CG1 | ILE | A | 366 | 14.193 | −37.036 | 7.190 | 1.00 | 51.03 | C |
| ATOM | 2328 | CD1 | ILE | A | 366 | 14.996 | −35.956 | 7.812 | 1.00 | 53.52 | C |
| ATOM | 2332 | CG2 | ILE | A | 366 | 14.988 | −38.152 | 5.167 | 1.00 | 50.10 | C |
| ATOM | 2336 | C | ILE | A | 366 | 14.954 | −40.632 | 6.349 | 1.00 | 50.00 | C |
| ATOM | 2337 | O | ILE | A | 366 | 16.087 | −41.076 | 6.401 | 1.00 | 49.68 | O |
| ATOM | 2339 | N | THR | A | 367 | 14.008 | −41.071 | 5.527 | 1.00 | 49.89 | N |
| ATOM | 2340 | CA | THR | A | 367 | 14.218 | −42.177 | 4.625 | 1.00 | 50.22 | C |
| ATOM | 2342 | CB | THR | A | 367 | 13.560 | −43.433 | 5.182 | 1.00 | 50.18 | C |
| ATOM | 2344 | OG1 | THR | A | 367 | 14.126 | −44.569 | 4.531 | 1.00 | 50.46 | O |
| ATOM | 2346 | CG2 | THR | A | 367 | 12.045 | −43.408 | 4.974 | 1.00 | 49.66 | C |
| ATOM | 2350 | C | THR | A | 367 | 13.695 | −41.920 | 3.192 | 1.00 | 50.58 | C |
| ATOM | 2351 | O | THR | A | 367 | 13.281 | −40.802 | 2.842 | 1.00 | 49.35 | O |
| ATOM | 2353 | N | ASP | A | 368 | 13.732 | −42.983 | 2.388 | 1.00 | 50.89 | N |
| ATOM | 2354 | CA | ASP | A | 368 | 13.370 | −42.956 | 0.967 | 1.00 | 51.92 | C |
| ATOM | 2356 | CB | ASP | A | 368 | 11.874 | −42.694 | 0.752 | 1.00 | 52.48 | C |
| ATOM | 2359 | CG | ASP | A | 368 | 11.510 | −42.704 | −0.716 | 1.00 | 55.33 | C |
| ATOM | 2360 | OD1 | ASP | A | 368 | 12.474 | −42.872 | −1.512 | 1.00 | 55.24 | O |
| ATOM | 2361 | OD2 | ASP | A | 368 | 10.298 | −42.562 | −1.074 | 1.00 | 60.92 | O |
| ATOM | 2362 | C | ASP | A | 368 | 14.162 | −41.954 | 0.137 | 1.00 | 51.49 | C |
| ATOM | 2363 | O | ASP | A | 368 | 13.661 | −40.859 | −0.156 | 1.00 | 51.72 | O |
| ATOM | 2365 | N | PHE | A | 369 | 15.371 | −42.343 | −0.262 | 1.00 | 50.73 | N |
| ATOM | 2366 | CA | PHE | A | 369 | 16.183 | −41.533 | −1.133 | 1.00 | 50.21 | C |
| ATOM | 2368 | CB | PHE | A | 369 | 17.614 | −41.581 | −0.683 | 1.00 | 49.86 | C |
| ATOM | 2371 | CG | PHE | A | 369 | 17.861 | −40.801 | 0.570 | 1.00 | 49.46 | C |
| ATOM | 2372 | CD1 | PHE | A | 369 | 17.435 | −41.281 | 1.793 | 1.00 | 48.66 | C |
| ATOM | 2374 | CE1 | PHE | A | 369 | 17.670 | −40.561 | 2.951 | 1.00 | 47.57 | C |
| ATOM | 2376 | CZ | PHE | A | 369 | 18.327 | −39.379 | 2.887 | 1.00 | 46.10 | C |
| ATOM | 2378 | CE2 | PHE | A | 369 | 18.752 | −38.896 | 1.673 | 1.00 | 46.74 | C |
| ATOM | 2380 | CD2 | PHE | A | 369 | 18.519 | −39.583 | 0.529 | 1.00 | 45.50 | C |
| ATOM | 2382 | C | PHE | A | 369 | 16.067 | −41.907 | −2.597 | 1.00 | 50.84 | C |
| ATOM | 2383 | O | PHE | A | 369 | 16.971 | −41.631 | −3.358 | 1.00 | 50.68 | O |
| ATOM | 2385 | N | GLY | A | 370 | 14.932 | −42.483 | −2.989 | 1.00 | 52.02 | N |
| ATOM | 2386 | CA | GLY | A | 370 | 14.696 | −42.927 | −4.356 | 1.00 | 53.43 | C |
| ATOM | 2389 | C | GLY | A | 370 | 14.709 | −41.835 | −5.408 | 1.00 | 55.21 | C |
| ATOM | 2390 | O | GLY | A | 370 | 15.258 | −42.018 | −6.502 | 1.00 | 55.92 | O |
| ATOM | 2392 | N | HIS | A | 371 | 14.117 | −40.694 | −5.082 | 1.00 | 56.65 | N |
| ATOM | 2393 | CA | HIS | A | 371 | 14.025 | −39.583 | −6.012 | 1.00 | 57.75 | C |
| ATOM | 2395 | CB | HIS | A | 371 | 12.698 | −38.847 | −5.837 | 1.00 | 58.16 | C |
| ATOM | 2398 | CG | HIS | A | 371 | 11.494 | −39.716 | −5.973 | 1.00 | 61.57 | C |
| ATOM | 2399 | ND1 | HIS | A | 371 | 10.566 | −39.543 | −6.978 | 1.00 | 64.03 | N |
| ATOM | 2401 | CE1 | HIS | A | 371 | 9.616 | −40.449 | −6.850 | 1.00 | 65.75 | C |
| ATOM | 2403 | NE2 | HIS | A | 371 | 9.880 | −41.188 | −5.787 | 1.00 | 65.34 | N |
| ATOM | 2405 | CD2 | HIS | A | 371 | 11.051 | −40.751 | −5.220 | 1.00 | 64.54 | C |
| ATOM | 2407 | C | HIS | A | 371 | 15.121 | −38.561 | −5.777 | 1.00 | 57.99 | C |
| ATOM | 2408 | O | HIS | A | 371 | 15.074 | −37.491 | −6.346 | 1.00 | 57.95 | O |
| ATOM | 2410 | N | SER | A | 372 | 16.098 | −38.837 | −4.934 | 1.00 | 58.63 | N |
| ATOM | 2411 | CA | SER | A | 372 | 17.002 | −37.750 | −4.576 | 1.00 | 59.64 | C |
| ATOM | 2413 | CB | SER | A | 372 | 17.718 | −38.025 | −3.254 | 1.00 | 59.50 | C |
| ATOM | 2416 | OG | SER | A | 372 | 18.297 | −39.298 | −3.242 | 1.00 | 60.20 | O |
| ATOM | 2418 | C | SER | A | 372 | 17.960 | −37.436 | −5.720 | 1.00 | 60.37 | C |

TABLE 2-continued

| ATOM | 2419 | O | SER | A | 372 | 17.992 | −38.140 | −6.702 | 1.00 | 61.25 | O |
|---|---|---|---|---|---|---|---|---|---|---|---|
| ATOM | 2421 | N | LYS | A | 373 | 18.696 | −36.344 | −5.623 | 1.00 | 61.74 | N |
| ATOM | 2422 | CA | LYS | A | 373 | 19.573 | −35.919 | −6.704 | 1.00 | 63.04 | C |
| ATOM | 2424 | CB | LYS | A | 373 | 18.934 | −34.783 | −7.517 | 1.00 | 63.54 | C |
| ATOM | 2427 | CG | LYS | A | 373 | 18.001 | −35.241 | −8.654 | 1.00 | 66.39 | C |
| ATOM | 2430 | CD | LYS | A | 373 | 17.311 | −34.015 | −9.351 | 1.00 | 69.30 | C |
| ATOM | 2433 | CE | LYS | A | 373 | 16.399 | −34.401 | −10.563 | 1.00 | 69.79 | C |
| ATOM | 2436 | NZ | LYS | A | 373 | 16.972 | −33.950 | −11.891 | 1.00 | 68.96 | N |
| ATOM | 2440 | C | LYS | A | 373 | 20.864 | −35.432 | −6.115 | 1.00 | 63.56 | C |
| ATOM | 2441 | O | LYS | A | 373 | 20.882 | −34.934 | −4.997 | 1.00 | 63.29 | O |
| ATOM | 2443 | N | ILE | A | 374 | 21.939 | −35.559 | −6.879 | 1.00 | 64.99 | N |
| ATOM | 2444 | CA | ILE | A | 374 | 23.238 | −35.068 | −6.454 | 1.00 | 66.47 | C |
| ATOM | 2446 | CB | ILE | A | 374 | 24.357 | −36.079 | −6.742 | 1.00 | 66.34 | C |
| ATOM | 2448 | CG1 | ILE | A | 374 | 23.940 | −37.481 | −6.280 | 1.00 | 66.90 | C |
| ATOM | 2451 | CD1 | ILE | A | 374 | 24.946 | −38.601 | −6.609 | 1.00 | 67.97 | C |
| ATOM | 2455 | CG2 | ILE | A | 374 | 25.627 | −35.644 | −6.039 | 1.00 | 65.93 | C |
| ATOM | 2459 | C | ILE | A | 374 | 23.536 | −33.749 | −7.155 | 1.00 | 67.83 | C |
| ATOM | 2460 | O | ILE | A | 374 | 23.488 | −33.675 | −8.381 | 1.00 | 68.04 | O |
| ATOM | 2462 | N | LEU | A | 375 | 23.791 | −32.700 | −6.378 | 1.00 | 69.39 | N |
| ATOM | 2463 | CA | LEU | A | 375 | 24.337 | −31.478 | −6.945 | 1.00 | 70.74 | C |
| ATOM | 2465 | CB | LEU | A | 375 | 24.391 | −30.346 | −5.933 | 1.00 | 70.59 | C |
| ATOM | 2468 | CG | LEU | A | 375 | 23.052 | −29.802 | −5.468 | 1.00 | 70.20 | C |
| ATOM | 2470 | CD1 | LEU | A | 375 | 21.998 | −30.183 | −6.481 | 1.00 | 68.60 | C |
| ATOM | 2474 | CD2 | LEU | A | 375 | 22.712 | −30.300 | −4.067 | 1.00 | 68.62 | C |
| ATOM | 2478 | C | LEU | A | 375 | 25.742 | −31.792 | −7.382 | 1.00 | 72.23 | C |
| ATOM | 2479 | O | LEU | A | 375 | 26.467 | −32.505 | −6.679 | 1.00 | 72.51 | O |
| ATOM | 2481 | N | GLY | A | 376 | 26.105 | −31.259 | −8.545 | 1.00 | 73.89 | N |
| ATOM | 2482 | CA | GLY | A | 376 | 27.417 | −31.470 | −9.164 | 1.00 | 74.95 | C |
| ATOM | 2485 | C | GLY | A | 376 | 27.555 | −30.547 | −10.372 | 1.00 | 76.05 | C |
| ATOM | 2486 | O | GLY | A | 376 | 26.622 | −29.771 | −10.668 | 1.00 | 76.67 | O |
| ATOM | 2488 | N | GLU | A | 377 | 28.700 | −30.622 | −11.067 | 1.00 | 76.87 | N |
| ATOM | 2489 | CA | GLU | A | 377 | 28.968 | −29.735 | −12.212 | 1.00 | 77.36 | C |
| ATOM | 2491 | CB | GLU | A | 377 | 30.291 | −30.049 | −12.943 | 1.00 | 77.88 | C |
| ATOM | 2494 | CG | GLU | A | 377 | 30.512 | −29.183 | −14.222 | 1.00 | 79.59 | C |
| ATOM | 2497 | CD | GLU | A | 377 | 31.992 | −29.047 | −14.664 | 1.00 | 81.28 | C |
| ATOM | 2498 | OE1 | GLU | A | 377 | 32.569 | −30.016 | −15.226 | 1.00 | 81.70 | O |
| ATOM | 2499 | OE2 | GLU | A | 377 | 32.559 | −27.943 | −14.475 | 1.00 | 82.09 | O |
| ATOM | 2500 | C | GLU | A | 377 | 27.797 | −29.800 | −13.179 | 1.00 | 76.82 | C |
| ATOM | 2501 | O | GLU | A | 377 | 27.482 | −30.849 | −13.733 | 1.00 | 77.21 | O |
| ATOM | 2503 | N | THR | A | 378 | 27.136 | −28.663 | −13.325 | 1.00 | 76.13 | N |
| ATOM | 2504 | CA | THR | A | 378 | 25.991 | −28.543 | −14.178 | 1.00 | 75.58 | C |
| ATOM | 2506 | CB | THR | A | 378 | 25.173 | −27.325 | −13.747 | 1.00 | 75.78 | C |
| ATOM | 2508 | OG1 | THR | A | 378 | 26.057 | −26.201 | −13.640 | 1.00 | 75.38 | O |
| ATOM | 2510 | CG2 | THR | A | 378 | 24.495 | −27.573 | −12.381 | 1.00 | 74.99 | C |
| ATOM | 2514 | C | THR | A | 378 | 26.512 | −28.345 | −15.593 | 1.00 | 75.09 | C |
| ATOM | 2515 | O | THR | A | 378 | 27.664 | −27.905 | −15.791 | 1.00 | 74.86 | O |
| ATOM | 2517 | N | SER | A | 379 | 25.693 | −28.707 | −16.576 | 1.00 | 74.28 | N |
| ATOM | 2518 | CA | SER | A | 379 | 26.000 | −28.328 | −17.947 | 1.00 | 74.12 | C |
| ATOM | 2520 | CB | SER | A | 379 | 25.151 | −29.082 | −19.000 | 1.00 | 74.08 | C |
| ATOM | 2523 | OG | SER | A | 379 | 23.824 | −29.353 | −18.587 | 1.00 | 73.75 | O |
| ATOM | 2525 | C | SER | A | 379 | 25.891 | −26.804 | −18.101 | 1.00 | 73.69 | C |
| ATOM | 2526 | O | SER | A | 379 | 26.483 | −26.243 | −19.013 | 1.00 | 73.69 | O |
| ATOM | 2528 | N | LEU | A | 380 | 25.165 | −26.145 | −17.194 | 1.00 | 73.30 | N |
| ATOM | 2529 | CA | LEU | A | 380 | 25.072 | −24.688 | −17.190 | 1.00 | 72.81 | C |
| ATOM | 2531 | CB | LEU | A | 380 | 24.083 | −24.171 | −16.130 | 1.00 | 72.30 | C |
| ATOM | 2534 | CG | LEU | A | 380 | 23.642 | −22.704 | −16.313 | 1.00 | 71.47 | C |
| ATOM | 2536 | CD1 | LEU | A | 380 | 22.887 | −22.548 | −17.610 | 1.00 | 70.50 | C |
| ATOM | 2540 | CD2 | LEU | A | 380 | 22.792 | −22.164 | −15.164 | 1.00 | 68.86 | C |
| ATOM | 2544 | C | LEU | A | 380 | 26.447 | −24.097 | −16.960 | 1.00 | 73.16 | C |
| ATOM | 2545 | O | LEU | A | 380 | 26.861 | −23.210 | −17.691 | 1.00 | 73.06 | O |
| ATOM | 2547 | N | MET | A | 381 | 27.165 | −24.602 | −15.961 | 1.00 | 73.70 | N |
| ATOM | 2548 | CA | MET | A | 381 | 28.493 | −24.075 | −15.650 | 1.00 | 74.08 | C |
| ATOM | 2550 | CB | MET | A | 381 | 29.094 | −24.784 | −14.418 | 1.00 | 74.25 | C |
| ATOM | 2553 | CG | MET | A | 381 | 28.435 | −24.360 | −13.051 | 1.00 | 75.07 | C |
| ATOM | 2556 | SD | MET | A | 381 | 28.696 | −25.452 | −11.581 | 1.00 | 76.15 | S |
| ATOM | 2557 | CE | MET | A | 381 | 27.423 | −24.933 | −10.408 | 1.00 | 73.78 | C |
| ATOM | 2561 | C | MET | A | 381 | 29.393 | −24.165 | −16.895 | 1.00 | 74.29 | C |
| ATOM | 2562 | O | MET | A | 381 | 29.954 | −23.153 | −17.335 | 1.00 | 74.27 | O |
| ATOM | 2564 | N | ARG | A | 382 | 29.473 | −25.352 | −17.499 | 1.00 | 74.49 | N |
| ATOM | 2565 | CA | ARG | A | 382 | 30.334 | −25.573 | −18.674 | 1.00 | 74.86 | C |
| ATOM | 2567 | CB | ARG | A | 382 | 30.442 | −27.078 | −19.006 | 1.00 | 75.57 | C |
| ATOM | 2570 | CG | ARG | A | 382 | 31.717 | −27.507 | −19.786 | 1.00 | 78.25 | C |
| ATOM | 2573 | CD | ARG | A | 382 | 32.989 | −27.432 | −18.913 | 1.00 | 81.68 | C |
| ATOM | 2576 | NE | ARG | A | 382 | 34.194 | −27.984 | −19.558 | 1.00 | 84.37 | N |
| ATOM | 2578 | CZ | ARG | A | 382 | 34.876 | −29.071 | −19.161 | 1.00 | 86.53 | C |
| ATOM | 2579 | NH1 | ARG | A | 382 | 34.507 | −29.794 | −18.095 | 1.00 | 86.72 | N |
| ATOM | 2582 | NH2 | ARG | A | 382 | 35.963 | −29.440 | −19.836 | 1.00 | 86.11 | N |
| ATOM | 2585 | C | ARG | A | 382 | 29.845 | −24.774 | −19.894 | 1.00 | 74.02 | C |
| ATOM | 2586 | O | ARG | A | 382 | 30.645 | −24.209 | −20.644 | 1.00 | 73.32 | O |
| ATOM | 2588 | N | THR | A | 383 | 28.531 | −24.717 | −20.079 | 1.00 | 73.57 | N |

TABLE 2-continued

| | | | | | | | | | | |
|---|---|---|---|---|---|---|---|---|---|---|
| ATOM | 2589 | CA | THR | A | 383 | 27.946 | −23.906 | −21.149 | 1.00 | 73.31 | C |
| ATOM | 2591 | CB | THR | A | 383 | 26.396 | −23.916 | −21.120 | 1.00 | 73.37 | C |
| ATOM | 2593 | OG1 | THR | A | 383 | 25.906 | −25.229 | −21.432 | 1.00 | 72.99 | O |
| ATOM | 2595 | CG2 | THR | A | 383 | 25.827 | −22.925 | −22.133 | 1.00 | 73.52 | C |
| ATOM | 2599 | C | THR | A | 383 | 28.431 | −22.470 | −21.047 | 1.00 | 73.06 | C |
| ATOM | 2600 | O | THR | A | 383 | 28.774 | −21.875 | −22.046 | 1.00 | 72.91 | O |
| ATOM | 2602 | N | LEU | A | 384 | 28.492 | −21.941 | −19.831 | 1.00 | 73.25 | N |
| ATOM | 2603 | CA | LEU | A | 384 | 28.885 | −20.558 | −19.612 | 1.00 | 73.59 | C |
| ATOM | 2605 | CB | LEU | A | 384 | 28.488 | −20.089 | −18.206 | 1.00 | 73.14 | C |
| ATOM | 2608 | CG | LEU | A | 384 | 27.007 | −20.030 | −17.841 | 1.00 | 72.28 | C |
| ATOM | 2610 | CD1 | LEU | A | 384 | 26.836 | −19.411 | −16.459 | 1.00 | 70.01 | C |
| ATOM | 2614 | CD2 | LEU | A | 384 | 26.203 | −19.278 | −18.890 | 1.00 | 70.90 | C |
| ATOM | 2618 | C | LEU | A | 384 | 30.380 | −20.283 | −19.807 | 1.00 | 74.49 | C |
| ATOM | 2619 | O | LEU | A | 384 | 30.768 | −19.120 | −19.924 | 1.00 | 74.87 | O |
| ATOM | 2621 | N | CYS | A | 385 | 31.232 | −21.306 | −19.825 | 1.00 | 75.27 | N |
| ATOM | 2622 | CA | CYS | A | 385 | 32.678 | −21.043 | −20.002 | 1.00 | 75.89 | C |
| ATOM | 2624 | CB | CYS | A | 385 | 33.523 | −22.240 | −19.584 | 1.00 | 75.95 | C |
| ATOM | 2627 | SG | CYS | A | 385 | 33.556 | −22.422 | −17.781 | 1.00 | 78.97 | S |
| ATOM | 2629 | C | CYS | A | 385 | 33.025 | −20.590 | −21.423 | 1.00 | 75.60 | C |
| ATOM | 2630 | O | CYS | A | 385 | 33.980 | −19.818 | −21.614 | 1.00 | 75.75 | O |
| ATOM | 2632 | N | GLY | A | 386 | 32.242 | −21.046 | −22.405 | 1.00 | 74.84 | N |
| ATOM | 2633 | CA | GLY | A | 386 | 32.369 | −20.553 | −23.782 | 1.00 | 74.47 | C |
| ATOM | 2636 | C | GLY | A | 386 | 31.617 | −19.244 | −23.984 | 1.00 | 73.79 | C |
| ATOM | 2637 | O | GLY | A | 386 | 30.912 | −18.789 | −23.086 | 1.00 | 74.13 | O |
| ATOM | 2639 | N | THR | A | 387 | 31.776 | −18.626 | −25.153 | 1.00 | 72.88 | N |
| ATOM | 2640 | CA | THR | A | 387 | 30.977 | −17.454 | −25.516 | 1.00 | 72.16 | C |
| ATOM | 2642 | CB | THR | A | 387 | 31.539 | −16.676 | −26.725 | 1.00 | 72.42 | C |
| ATOM | 2644 | OG1 | THR | A | 387 | 32.931 | −16.436 | −26.536 | 1.00 | 73.70 | O |
| ATOM | 2646 | CG2 | THR | A | 387 | 30.835 | −15.317 | −26.895 | 1.00 | 73.31 | C |
| ATOM | 2650 | C | THR | A | 387 | 29.595 | −17.953 | −25.897 | 1.00 | 70.89 | C |
| ATOM | 2651 | O | THR | A | 387 | 29.465 | −19.043 | −26.477 | 1.00 | 70.82 | O |
| ATOM | 2653 | N | PRO | A | 388 | 28.563 | −17.170 | −25.551 | 1.00 | 68.94 | N |
| ATOM | 2654 | CA | PRO | A | 388 | 27.199 | −17.471 | −25.916 | 1.00 | 67.62 | C |
| ATOM | 2656 | CB | PRO | A | 388 | 26.399 | −16.892 | −24.747 | 1.00 | 67.72 | C |
| ATOM | 2659 | CG | PRO | A | 388 | 27.173 | −15.727 | −24.336 | 1.00 | 68.59 | C |
| ATOM | 2662 | CD | PRO | A | 388 | 28.622 | −16.079 | −24.562 | 1.00 | 69.15 | C |
| ATOM | 2665 | C | PRO | A | 388 | 26.802 | −16.837 | −27.240 | 1.00 | 65.94 | C |
| ATOM | 2666 | O | PRO | A | 388 | 25.627 | −16.600 | −27.485 | 1.00 | 65.83 | O |
| ATOM | 2667 | N | THR | A | 389 | 27.777 | −16.591 | −28.105 | 1.00 | 64.11 | N |
| ATOM | 2668 | CA | THR | A | 389 | 27.483 | −16.263 | −29.483 | 1.00 | 62.60 | C |
| ATOM | 2670 | CB | THR | A | 389 | 28.682 | −16.621 | −30.394 | 1.00 | 62.45 | C |
| ATOM | 2672 | OG1 | THR | A | 389 | 29.877 | −16.074 | −29.832 | 1.00 | 63.70 | O |
| ATOM | 2674 | CG2 | THR | A | 389 | 28.507 | −16.080 | −31.825 | 1.00 | 61.74 | C |
| ATOM | 2678 | C | THR | A | 389 | 26.228 | −17.031 | −29.925 | 1.00 | 61.08 | C |
| ATOM | 2679 | O | THR | A | 389 | 25.367 | −16.462 | −30.603 | 1.00 | 61.74 | O |
| ATOM | 2681 | N | TYR | A | 390 | 26.133 | −18.306 | −29.525 | 1.00 | 58.96 | N |
| ATOM | 2682 | CA | TYR | A | 390 | 25.076 | −19.220 | −29.968 | 1.00 | 57.09 | C |
| ATOM | 2684 | CB | TYR | A | 390 | 25.701 | −20.475 | −30.591 | 1.00 | 57.06 | C |
| ATOM | 2687 | CG | TYR | A | 390 | 26.638 | −20.160 | −31.737 | 1.00 | 56.98 | C |
| ATOM | 2688 | CD1 | TYR | A | 390 | 26.158 | −20.033 | −33.023 | 1.00 | 56.74 | C |
| ATOM | 2690 | CE1 | TYR | A | 390 | 27.002 | −19.710 | −34.074 | 1.00 | 57.62 | C |
| ATOM | 2692 | CZ | TYR | A | 390 | 28.343 | −19.508 | −33.838 | 1.00 | 57.75 | C |
| ATOM | 2693 | OH | TYR | A | 390 | 29.149 | −19.195 | −34.899 | 1.00 | 60.22 | O |
| ATOM | 2695 | CE2 | TYR | A | 390 | 28.864 | −19.619 | −32.566 | 1.00 | 56.62 | C |
| ATOM | 2697 | CD2 | TYR | A | 390 | 28.009 | −19.944 | −31.518 | 1.00 | 58.02 | C |
| ATOM | 2699 | C | TYR | A | 390 | 24.141 | −19.633 | −28.846 | 1.00 | 55.58 | C |
| ATOM | 2700 | O | TYR | A | 390 | 23.200 | −20.338 | −29.081 | 1.00 | 56.20 | O |
| ATOM | 2702 | N | LEU | A | 391 | 24.385 | −19.192 | −27.629 | 1.00 | 53.40 | N |
| ATOM | 2703 | CA | LEU | A | 391 | 23.577 | −19.612 | −26.522 | 1.00 | 52.11 | C |
| ATOM | 2705 | CB | LEU | A | 391 | 24.285 | −19.234 | −25.237 | 1.00 | 52.19 | C |
| ATOM | 2708 | CG | LEU | A | 391 | 24.018 | −20.128 | −24.050 | 1.00 | 53.31 | C |
| ATOM | 2710 | CD1 | LEU | A | 391 | 23.843 | −21.619 | −24.518 | 1.00 | 55.41 | C |
| ATOM | 2714 | CD2 | LEU | A | 391 | 25.162 | −19.948 | −23.034 | 1.00 | 52.32 | C |
| ATOM | 2718 | C | LEU | A | 391 | 22.160 | −19.014 | −26.540 | 1.00 | 50.87 | C |
| ATOM | 2719 | O | LEU | A | 391 | 21.966 | −17.842 | −26.843 | 1.00 | 51.39 | O |
| ATOM | 2721 | N | ALA | A | 392 | 21.184 | −19.836 | −26.179 | 1.00 | 48.95 | N |
| ATOM | 2722 | CA | ALA | A | 392 | 19.777 | −19.508 | −26.298 | 1.00 | 46.87 | C |
| ATOM | 2724 | CB | ALA | A | 392 | 18.968 | −20.781 | −26.318 | 1.00 | 45.79 | C |
| ATOM | 2728 | C | ALA | A | 392 | 19.358 | −18.656 | −25.123 | 1.00 | 45.35 | C |
| ATOM | 2729 | O | ALA | A | 392 | 19.828 | −18.877 | −24.024 | 1.00 | 46.11 | O |
| ATOM | 2731 | N | PRO | A | 393 | 18.438 | −17.702 | −25.329 | 1.00 | 43.92 | N |
| ATOM | 2732 | CA | PRO | A | 393 | 17.952 | −16.819 | −24.275 | 1.00 | 42.86 | C |
| ATOM | 2734 | CB | PRO | A | 393 | 16.739 | −16.141 | −24.902 | 1.00 | 43.34 | C |
| ATOM | 2737 | CG | PRO | A | 393 | 16.835 | −16.342 | −26.360 | 1.00 | 43.91 | C |
| ATOM | 2740 | CD | PRO | A | 393 | 17.899 | −17.341 | −26.647 | 1.00 | 44.23 | C |
| ATOM | 2743 | C | PRO | A | 393 | 17.490 | −17.531 | −23.026 | 1.00 | 42.30 | C |
| ATOM | 2744 | O | PRO | A | 393 | 17.758 | −17.074 | −21.912 | 1.00 | 42.30 | O |
| ATOM | 2745 | N | GLU | A | 394 | 16.763 | −18.627 | −23.195 | 1.00 | 41.33 | N |
| ATOM | 2746 | CA | GLU | A | 394 | 16.180 | −19.290 | −22.038 | 1.00 | 41.04 | C |
| ATOM | 2748 | CB | GLU | A | 394 | 15.124 | −20.345 | −22.434 | 1.00 | 40.54 | C |

TABLE 2-continued

| | | | | | | | | | | |
|---|---|---|---|---|---|---|---|---|---|---|
| ATOM | 2751 | CG | GLU | A | 394 | 15.568 | −21.479 | −23.398 | 1.00 | 41.14 | C |
| ATOM | 2754 | CD | GLU | A | 394 | 15.529 | −21.104 | −24.878 | 1.00 | 41.67 | C |
| ATOM | 2755 | OE1 | GLU | A | 394 | 15.673 | −19.896 | −25.242 | 1.00 | 41.71 | O |
| ATOM | 2756 | OE2 | GLU | A | 394 | 15.359 | −22.034 | −25.684 | 1.00 | 39.55 | O |
| ATOM | 2757 | C | GLU | A | 394 | 17.272 | −19.855 | −21.134 | 1.00 | 40.97 | C |
| ATOM | 2758 | O | GLU | A | 394 | 17.115 | −19.925 | −19.916 | 1.00 | 41.23 | O |
| ATOM | 2760 | N | VAL | A | 395 | 18.402 | −20.233 | −21.716 | 1.00 | 40.74 | N |
| ATOM | 2761 | CA | VAL | A | 395 | 19.458 | −20.780 | −20.892 | 1.00 | 40.47 | C |
| ATOM | 2763 | CB | VAL | A | 395 | 20.541 | −21.513 | −21.743 | 1.00 | 40.76 | C |
| ATOM | 2765 | CG1 | VAL | A | 395 | 21.686 | −21.977 | −20.882 | 1.00 | 38.79 | C |
| ATOM | 2769 | CG2 | VAL | A | 395 | 19.897 | −22.713 | −22.477 | 1.00 | 38.93 | C |
| ATOM | 2773 | C | VAL | A | 395 | 20.006 | −19.642 | −20.056 | 1.00 | 40.54 | C |
| ATOM | 2774 | O | VAL | A | 395 | 20.178 | −19.778 | −18.848 | 1.00 | 39.07 | O |
| ATOM | 2776 | N | LEU | A | 396 | 20.239 | −18.506 | −20.697 | 1.00 | 41.60 | N |
| ATOM | 2777 | CA | LEU | A | 396 | 20.714 | −17.321 | −19.972 | 1.00 | 42.68 | C |
| ATOM | 2779 | CB | LEU | A | 396 | 21.100 | −16.202 | −20.934 | 1.00 | 42.97 | C |
| ATOM | 2782 | CG | LEU | A | 396 | 22.355 | −16.461 | −21.802 | 1.00 | 43.25 | C |
| ATOM | 2784 | CD1 | LEU | A | 396 | 22.581 | −15.341 | −22.806 | 1.00 | 44.53 | C |
| ATOM | 2788 | CD2 | LEU | A | 396 | 23.572 | −16.625 | −20.966 | 1.00 | 42.41 | C |
| ATOM | 2792 | C | LEU | A | 396 | 19.713 | −16.830 | −18.924 | 1.00 | 43.37 | C |
| ATOM | 2793 | O | LEU | A | 396 | 20.108 | −16.433 | −17.833 | 1.00 | 43.85 | O |
| ATOM | 2795 | N | VAL | A | 397 | 18.421 | −16.913 | −19.208 | 1.00 | 44.11 | N |
| ATOM | 2796 | CA | VAL | A | 397 | 17.425 | −16.518 | −18.221 | 1.00 | 44.38 | C |
| ATOM | 2798 | CB | VAL | A | 397 | 15.996 | −16.483 | −18.832 | 1.00 | 45.56 | C |
| ATOM | 2800 | CG1 | VAL | A | 397 | 14.927 | −16.380 | −17.737 | 1.00 | 44.34 | C |
| ATOM | 2804 | CG2 | VAL | A | 397 | 15.878 | −15.366 | −19.898 | 1.00 | 42.24 | C |
| ATOM | 2808 | C | VAL | A | 397 | 17.430 | −17.438 | −17.024 | 1.00 | 45.00 | C |
| ATOM | 2809 | O | VAL | A | 397 | 17.151 | −16.992 | −15.919 | 1.00 | 46.57 | O |
| ATOM | 2811 | N | SER | A | 398 | 17.767 | −18.705 | −17.227 | 1.00 | 45.19 | N |
| ATOM | 2812 | CA | SER | A | 398 | 17.756 | −19.711 | −16.159 | 1.00 | 45.53 | C |
| ATOM | 2814 | CB | SER | A | 398 | 17.794 | −21.116 | −16.760 | 1.00 | 45.57 | C |
| ATOM | 2817 | OG | SER | A | 398 | 19.110 | −21.484 | −17.138 | 1.00 | 45.64 | O |
| ATOM | 2819 | C | SER | A | 398 | 18.906 | −19.561 | −15.173 | 1.00 | 46.68 | C |
| ATOM | 2820 | O | SER | A | 398 | 18.878 | −20.094 | −14.056 | 1.00 | 46.69 | O |
| ATOM | 2822 | N | VAL | A | 399 | 19.935 | −18.836 | −15.581 | 1.00 | 48.01 | N |
| ATOM | 2823 | CA | VAL | A | 399 | 21.034 | −18.495 | −14.678 | 1.00 | 48.40 | C |
| ATOM | 2825 | CB | VAL | A | 399 | 22.084 | −17.637 | −15.397 | 1.00 | 48.50 | C |
| ATOM | 2827 | CG1 | VAL | A | 399 | 23.065 | −17.003 | −14.391 | 1.00 | 48.78 | C |
| ATOM | 2831 | CG2 | VAL | A | 399 | 22.826 | −18.493 | −16.452 | 1.00 | 47.62 | C |
| ATOM | 2835 | C | VAL | A | 399 | 20.552 | −17.764 | −13.422 | 1.00 | 49.45 | C |
| ATOM | 2836 | O | VAL | A | 399 | 21.135 | −17.929 | −12.347 | 1.00 | 49.64 | O |
| ATOM | 2838 | N | GLY | A | 400 | 19.494 | −16.959 | −13.544 | 1.00 | 50.27 | N |
| ATOM | 2839 | CA | GLY | A | 400 | 18.987 | −16.234 | −12.393 | 1.00 | 50.67 | C |
| ATOM | 2842 | C | GLY | A | 400 | 18.715 | −17.150 | −11.211 | 1.00 | 51.33 | C |
| ATOM | 2843 | O | GLY | A | 400 | 18.957 | −16.749 | −10.079 | 1.00 | 52.05 | O |
| ATOM | 2845 | N | THR | A | 401 | 18.235 | −18.381 | −11.470 | 1.00 | 51.53 | N |
| ATOM | 2846 | CA | THR | A | 401 | 17.792 | −19.308 | −10.404 | 1.00 | 51.64 | C |
| ATOM | 2848 | CB | THR | A | 401 | 16.297 | −19.616 | −10.553 | 1.00 | 51.98 | C |
| ATOM | 2850 | OG1 | THR | A | 401 | 15.998 | −19.949 | −11.923 | 1.00 | 53.59 | O |
| ATOM | 2852 | CG2 | THR | A | 401 | 15.489 | −18.370 | −10.168 | 1.00 | 51.82 | C |
| ATOM | 2856 | C | THR | A | 401 | 18.563 | −20.625 | −10.265 | 1.00 | 51.24 | C |
| ATOM | 2857 | O | THR | A | 401 | 18.437 | −21.310 | −9.265 | 1.00 | 52.12 | O |
| ATOM | 2859 | N | ALA | A | 402 | 19.361 | −20.999 | −11.249 | 1.00 | 50.44 | N |
| ATOM | 2860 | CA | ALA | A | 402 | 20.260 | −22.130 | −11.088 | 1.00 | 49.38 | C |
| ATOM | 2862 | CB | ALA | A | 402 | 21.439 | −22.008 | −12.062 | 1.00 | 48.67 | C |
| ATOM | 2866 | C | ALA | A | 402 | 20.791 | −22.202 | −9.656 | 1.00 | 48.66 | C |
| ATOM | 2867 | O | ALA | A | 402 | 21.223 | −21.203 | −9.119 | 1.00 | 49.38 | O |
| ATOM | 2869 | N | GLY | A | 403 | 20.801 | −23.387 | −9.056 | 1.00 | 47.59 | N |
| ATOM | 2870 | CA | GLY | A | 403 | 21.515 | −23.598 | −7.795 | 1.00 | 46.67 | C |
| ATOM | 2873 | C | GLY | A | 403 | 20.621 | −23.535 | −6.583 | 1.00 | 46.21 | C |
| ATOM | 2874 | O | GLY | A | 403 | 21.110 | −23.613 | −5.456 | 1.00 | 46.21 | O |
| ATOM | 2876 | N | TYR | A | 404 | 19.310 | −23.428 | −6.834 | 1.00 | 45.04 | N |
| ATOM | 2877 | CA | TYR | A | 404 | 18.278 | −23.380 | −5.816 | 1.00 | 44.20 | C |
| ATOM | 2879 | CB | TYR | A | 404 | 17.476 | −22.062 | −5.936 | 1.00 | 44.30 | C |
| ATOM | 2882 | CG | TYR | A | 404 | 18.202 | −20.918 | −5.298 | 1.00 | 44.77 | C |
| ATOM | 2883 | CD1 | TYR | A | 404 | 19.160 | −20.199 | −6.006 | 1.00 | 48.10 | C |
| ATOM | 2885 | CE1 | TYR | A | 404 | 19.879 | −19.150 | −5.389 | 1.00 | 48.41 | C |
| ATOM | 2887 | CZ | TYR | A | 404 | 19.626 | −18.838 | −4.066 | 1.00 | 45.56 | C |
| ATOM | 2888 | OH | TYR | A | 404 | 20.322 | −17.826 | −3.474 | 1.00 | 47.93 | O |
| ATOM | 2890 | CE2 | TYR | A | 404 | 18.679 | −19.534 | −3.358 | 1.00 | 44.85 | C |
| ATOM | 2892 | CD2 | TYR | A | 404 | 17.981 | −20.582 | −3.974 | 1.00 | 44.11 | C |
| ATOM | 2894 | C | TYR | A | 404 | 17.320 | −24.570 | −5.882 | 1.00 | 43.74 | C |
| ATOM | 2895 | O | TYR | A | 404 | 16.239 | −24.529 | −5.279 | 1.00 | 43.41 | O |
| ATOM | 2897 | N | ASN | A | 405 | 17.678 | −25.624 | −6.607 | 1.00 | 43.18 | N |
| ATOM | 2898 | CA | ASN | A | 405 | 16.847 | −26.836 | −6.582 | 1.00 | 43.07 | C |
| ATOM | 2900 | CB | ASN | A | 405 | 17.487 | −27.999 | −7.344 | 1.00 | 43.67 | C |
| ATOM | 2903 | CG | ASN | A | 405 | 17.735 | −27.701 | −8.788 | 1.00 | 45.40 | C |
| ATOM | 2904 | OD1 | ASN | A | 405 | 17.279 | −26.709 | −9.320 | 1.00 | 51.30 | O |
| ATOM | 2905 | ND2 | ASN | A | 405 | 18.461 | −28.586 | −9.447 | 1.00 | 51.39 | N |
| ATOM | 2908 | C | ASN | A | 405 | 16.577 | −27.292 | −5.146 | 1.00 | 42.04 | C |

TABLE 2-continued

| ATOM | 2909 | O | ASN | A | 405 | 15.495 | −27.770 | −4.834 | 1.00 | 42.99 | O |
|------|------|------|-----|---|-----|--------|---------|--------|------|-------|---|
| ATOM | 2911 | N | ARG | A | 406 | 17.567 | −27.135 | −4.273 | 1.00 | 41.43 | N |
| ATOM | 2912 | CA | ARG | A | 406 | 17.444 | −27.529 | −2.855 | 1.00 | 40.89 | C |
| ATOM | 2914 | CB | ARG | A | 406 | 18.732 | −27.231 | −2.079 | 1.00 | 41.15 | C |
| ATOM | 2917 | CG | ARG | A | 406 | 18.978 | −25.767 | −1.673 | 1.00 | 42.83 | C |
| ATOM | 2920 | CD | ARG | A | 406 | 20.433 | −25.565 | −1.179 | 1.00 | 43.63 | C |
| ATOM | 2923 | NE | ARG | A | 406 | 21.356 | −25.802 | −2.292 | 1.00 | 47.26 | N |
| ATOM | 2925 | CZ | ARG | A | 406 | 22.688 | −25.728 | −2.226 | 1.00 | 47.25 | C |
| ATOM | 2926 | NH1 | ARG | A | 406 | 23.319 | −25.430 | −1.101 | 1.00 | 46.98 | N |
| ATOM | 2929 | NH2 | ARG | A | 406 | 23.389 | −25.940 | −3.318 | 1.00 | 47.87 | N |
| ATOM | 2932 | C | ARG | A | 406 | 16.297 | −26.878 | −2.120 | 1.00 | 40.15 | C |
| ATOM | 2933 | O | ARG | A | 406 | 15.797 | −27.442 | −1.174 | 1.00 | 40.13 | O |
| ATOM | 2935 | N | ALA | A | 407 | 15.909 | −25.670 | −2.523 | 1.00 | 38.94 | N |
| ATOM | 2936 | CA | ALA | A | 407 | 14.777 | −25.018 | −1.908 | 1.00 | 37.74 | C |
| ATOM | 2938 | CB | ALA | A | 407 | 14.538 | −23.682 | −2.541 | 1.00 | 35.93 | C |
| ATOM | 2942 | C | ALA | A | 407 | 13.496 | −25.908 | −1.931 | 1.00 | 37.54 | C |
| ATOM | 2943 | O | ALA | A | 407 | 12.646 | −25.741 | −1.077 | 1.00 | 37.24 | O |
| ATOM | 2945 | N | VAL | A | 408 | 13.359 | −26.868 | −2.852 | 1.00 | 37.48 | N |
| ATOM | 2946 | CA | VAL | A | 408 | 12.102 | −27.661 | −2.900 | 1.00 | 37.20 | C |
| ATOM | 2948 | CB | VAL | A | 408 | 11.996 | −28.590 | −4.174 | 1.00 | 37.55 | C |
| ATOM | 2950 | CG1 | VAL | A | 408 | 12.259 | −27.815 | −5.461 | 1.00 | 35.10 | C |
| ATOM | 2954 | CG2 | VAL | A | 408 | 12.964 | −29.734 | −4.083 | 1.00 | 36.52 | C |
| ATOM | 2958 | C | VAL | A | 408 | 11.972 | −28.510 | −1.645 | 1.00 | 37.77 | C |
| ATOM | 2959 | O | VAL | A | 408 | 10.874 | −28.844 | −1.229 | 1.00 | 38.37 | O |
| ATOM | 2961 | N | ASP | A | 409 | 13.103 | −28.858 | −1.036 | 1.00 | 38.23 | N |
| ATOM | 2962 | CA | ASP | A | 409 | 13.118 | −29.533 | 0.256 | 1.00 | 38.49 | C |
| ATOM | 2964 | CB | ASP | A | 409 | 14.530 | −30.022 | 0.586 | 1.00 | 38.54 | C |
| ATOM | 2967 | CG | ASP | A | 409 | 14.913 | −31.344 | −0.121 | 1.00 | 39.97 | C |
| ATOM | 2968 | OD1 | ASP | A | 409 | 14.029 | −32.048 | −0.681 | 1.00 | 37.42 | O |
| ATOM | 2969 | OD2 | ASP | A | 409 | 16.135 | −31.679 | −0.074 | 1.00 | 40.55 | O |
| ATOM | 2970 | C | ASP | A | 409 | 12.624 | −28.618 | 1.385 | 1.00 | 39.12 | C |
| ATOM | 2971 | O | ASP | A | 409 | 12.028 | −29.072 | 2.374 | 1.00 | 39.10 | O |
| ATOM | 2973 | N | CYS | A | 410 | 12.885 | −27.330 | 1.266 | 1.00 | 39.98 | N |
| ATOM | 2974 | CA | CYS | A | 410 | 12.471 | −26.412 | 2.320 | 1.00 | 40.84 | C |
| ATOM | 2976 | CB | CYS | A | 410 | 13.291 | −25.131 | 2.286 | 1.00 | 41.09 | C |
| ATOM | 2979 | SG | CYS | A | 410 | 15.032 | −25.442 | 2.851 | 1.00 | 41.18 | S |
| ATOM | 2981 | C | CYS | A | 410 | 10.974 | −26.179 | 2.227 | 1.00 | 41.43 | C |
| ATOM | 2982 | O | CYS | A | 410 | 10.302 | −26.140 | 3.242 | 1.00 | 41.27 | O |
| ATOM | 2984 | N | TRP | A | 411 | 10.443 | −26.109 | 1.011 | 1.00 | 42.36 | N |
| ATOM | 2985 | CA | TRP | A | 411 | 9.009 | −26.041 | 0.812 | 1.00 | 43.21 | C |
| ATOM | 2987 | CB | TRP | A | 411 | 8.670 | −26.042 | −0.674 | 1.00 | 43.89 | C |
| ATOM | 2990 | CG | TRP | A | 411 | 7.168 | −25.986 | −0.922 | 1.00 | 45.03 | C |
| ATOM | 2991 | CD1 | TRP | A | 411 | 6.315 | −27.049 | −1.020 | 1.00 | 46.43 | C |
| ATOM | 2993 | NE1 | TRP | A | 411 | 5.032 | −26.607 | −1.216 | 1.00 | 46.64 | N |
| ATOM | 2995 | CE2 | TRP | A | 411 | 5.038 | −25.243 | −1.264 | 1.00 | 44.12 | C |
| ATOM | 2996 | CD2 | TRP | A | 411 | 6.372 | −24.818 | −1.073 | 1.00 | 43.38 | C |
| ATOM | 2997 | CE3 | TRP | A | 411 | 6.652 | −23.447 | −1.063 | 1.00 | 44.77 | C |
| ATOM | 2999 | CZ3 | TRP | A | 411 | 5.607 | −22.550 | −1.266 | 1.00 | 45.34 | C |
| ATOM | 3001 | CH2 | TRP | A | 411 | 4.285 | −23.014 | −1.455 | 1.00 | 45.72 | C |
| ATOM | 3003 | CZ2 | TRP | A | 411 | 3.987 | −24.353 | −1.446 | 1.00 | 43.97 | C |
| ATOM | 3005 | C | TRP | A | 411 | 8.298 | −27.215 | 1.490 | 1.00 | 43.79 | C |
| ATOM | 3006 | O | TRP | A | 411 | 7.411 | −27.011 | 2.336 | 1.00 | 43.19 | O |
| ATOM | 3008 | N | SER | A | 412 | 8.702 | −28.438 | 1.122 | 1.00 | 43.89 | N |
| ATOM | 3009 | CA | SER | A | 412 | 8.152 | −29.657 | 1.744 | 1.00 | 43.75 | C |
| ATOM | 3011 | CB | SER | A | 412 | 8.868 | −30.902 | 1.217 | 1.00 | 43.71 | C |
| ATOM | 3014 | OG | SER | A | 412 | 8.909 | −30.883 | −0.202 | 1.00 | 44.41 | O |
| ATOM | 3016 | C | SER | A | 412 | 8.225 | −29.636 | 3.261 | 1.00 | 43.69 | C |
| ATOM | 3017 | O | SER | A | 412 | 7.274 | −30.008 | 3.940 | 1.00 | 44.02 | O |
| ATOM | 3019 | N | LEU | A | 413 | 9.356 | −29.227 | 3.824 | 1.00 | 44.18 | N |
| ATOM | 3020 | CA | LEU | A | 413 | 9.438 | −29.173 | 5.286 | 1.00 | 44.11 | C |
| ATOM | 3022 | CB | LEU | A | 413 | 10.819 | −28.740 | 5.754 | 1.00 | 43.89 | C |
| ATOM | 3025 | CG | LEU | A | 413 | 11.942 | −29.779 | 5.640 | 1.00 | 44.19 | C |
| ATOM | 3027 | CD1 | LEU | A | 413 | 13.296 | −29.166 | 5.875 | 1.00 | 40.72 | C |
| ATOM | 3031 | CD2 | LEU | A | 413 | 11.713 | −30.950 | 6.603 | 1.00 | 44.60 | C |
| ATOM | 3035 | C | LEU | A | 413 | 8.371 | −28.191 | 5.761 | 1.00 | 44.88 | C |
| ATOM | 3036 | O | LEU | A | 413 | 7.682 | −28.436 | 6.745 | 1.00 | 45.07 | O |
| ATOM | 3038 | N | GLY | A | 414 | 8.226 | −27.088 | 5.025 | 1.00 | 45.47 | N |
| ATOM | 3039 | CA | GLY | A | 414 | 7.165 | −26.131 | 5.257 | 1.00 | 45.73 | C |
| ATOM | 3042 | C | GLY | A | 414 | 5.817 | −26.807 | 5.350 | 1.00 | 46.41 | C |
| ATOM | 3043 | O | GLY | A | 414 | 5.104 | −26.640 | 6.352 | 1.00 | 46.96 | O |
| ATOM | 3045 | N | VAL | A | 415 | 5.474 | −27.567 | 4.316 | 1.00 | 46.53 | N |
| ATOM | 3046 | CA | VAL | A | 415 | 4.210 | −28.270 | 4.277 | 1.00 | 47.31 | C |
| ATOM | 3048 | CB | VAL | A | 415 | 3.962 | −28.994 | 2.935 | 1.00 | 47.46 | C |
| ATOM | 3050 | CG1 | VAL | A | 415 | 2.753 | −29.878 | 3.047 | 1.00 | 46.40 | C |
| ATOM | 3054 | CG2 | VAL | A | 415 | 3.787 | −27.983 | 1.792 | 1.00 | 46.46 | C |
| ATOM | 3058 | C | VAL | A | 415 | 4.109 | −29.280 | 5.410 | 1.00 | 48.55 | C |
| ATOM | 3059 | O | VAL | A | 415 | 3.050 | −29.391 | 6.040 | 1.00 | 49.95 | O |
| ATOM | 3061 | N | ILE | A | 416 | 5.186 | −30.010 | 5.688 | 1.00 | 48.88 | N |
| ATOM | 3062 | CA | ILE | A | 416 | 5.173 | −30.997 | 6.780 | 1.00 | 48.60 | C |
| ATOM | 3064 | CB | ILE | A | 416 | 6.528 | −31.767 | 6.841 | 1.00 | 48.40 | C |

TABLE 2-continued

| | | | | | | | | | | |
|---|---|---|---|---|---|---|---|---|---|---|
| ATOM | 3066 | CG1 | ILE | A | 416 | 6.613 | −32.784 | 5.692 | 1.00 | 47.72 | C |
| ATOM | 3069 | CD1 | ILE | A | 416 | 7.991 | −33.448 | 5.558 | 1.00 | 44.52 | C |
| ATOM | 3073 | CG2 | ILE | A | 416 | 6.706 | −32.491 | 8.185 | 1.00 | 47.39 | C |
| ATOM | 3077 | C | ILE | A | 416 | 4.891 | −30.344 | 8.145 | 1.00 | 48.97 | C |
| ATOM | 3078 | O | ILE | A | 416 | 4.133 | −30.874 | 8.964 | 1.00 | 48.10 | O |
| ATOM | 3080 | N | LEU | A | 417 | 5.544 | −29.214 | 8.403 | 1.00 | 49.89 | N |
| ATOM | 3081 | CA | LEU | A | 417 | 5.387 | −28.525 | 9.681 | 1.00 | 51.00 | C |
| ATOM | 3083 | CB | LEU | A | 417 | 6.364 | −27.379 | 9.786 | 1.00 | 50.44 | C |
| ATOM | 3086 | CG | LEU | A | 417 | 6.325 | −26.591 | 11.083 | 1.00 | 50.45 | C |
| ATOM | 3088 | CD1 | LEU | A | 417 | 6.566 | −27.505 | 12.273 | 1.00 | 48.96 | C |
| ATOM | 3092 | CD2 | LEU | A | 417 | 7.357 | −25.489 | 11.024 | 1.00 | 50.19 | C |
| ATOM | 3096 | C | LEU | A | 417 | 3.943 | −28.013 | 9.837 | 1.00 | 52.24 | C |
| ATOM | 3097 | O | LEU | A | 417 | 3.329 | −28.186 | 10.873 | 1.00 | 52.75 | O |
| ATOM | 3099 | N | PHE | A | 418 | 3.410 | −27.416 | 8.786 | 1.00 | 53.54 | N |
| ATOM | 3100 | CA | PHE | A | 418 | 2.005 | −27.014 | 8.742 | 1.00 | 55.13 | C |
| ATOM | 3102 | CB | PHE | A | 418 | 1.663 | −26.578 | 7.314 | 1.00 | 55.27 | C |
| ATOM | 3105 | CG | PHE | A | 418 | 0.307 | −25.957 | 7.155 | 1.00 | 56.07 | C |
| ATOM | 3106 | CD1 | PHE | A | 418 | −0.837 | −26.756 | 7.074 | 1.00 | 57.49 | C |
| ATOM | 3108 | CE1 | PHE | A | 418 | −2.102 | −26.188 | 6.886 | 1.00 | 56.24 | C |
| ATOM | 3110 | CZ | PHE | A | 418 | −2.223 | −24.821 | 6.754 | 1.00 | 56.24 | C |
| ATOM | 3112 | CE2 | PHE | A | 418 | −1.081 | −24.006 | 6.812 | 1.00 | 56.64 | C |
| ATOM | 3114 | CD2 | PHE | A | 418 | 0.177 | −24.580 | 6.996 | 1.00 | 55.63 | C |
| ATOM | 3116 | C | PHE | A | 418 | 1.109 | −28.168 | 9.193 | 1.00 | 55.76 | C |
| ATOM | 3117 | O | PHE | A | 418 | 0.436 | −28.061 | 10.217 | 1.00 | 56.47 | O |
| ATOM | 3119 | N | ILE | A | 419 | 1.146 | −29.272 | 8.451 | 1.00 | 56.11 | N |
| ATOM | 3120 | CA | ILE | A | 419 | 0.380 | −30.475 | 8.766 | 1.00 | 56.41 | C |
| ATOM | 3122 | CB | ILE | A | 419 | 0.805 | −31.653 | 7.864 | 1.00 | 56.61 | C |
| ATOM | 3124 | CG1 | ILE | A | 419 | 0.214 | −31.469 | 6.466 | 1.00 | 56.42 | C |
| ATOM | 3127 | CD1 | ILE | A | 419 | 0.753 | −32.440 | 5.436 | 1.00 | 56.52 | C |
| ATOM | 3131 | CG2 | ILE | A | 419 | 0.364 | −33.001 | 8.438 | 1.00 | 56.53 | C |
| ATOM | 3135 | C | ILE | A | 419 | 0.529 | −30.882 | 10.213 | 1.00 | 57.00 | C |
| ATOM | 3136 | O | ILE | A | 419 | −0.463 | −31.038 | 10.915 | 1.00 | 57.28 | O |
| ATOM | 3138 | N | CYS | A | 420 | 1.766 | −31.029 | 10.664 | 1.00 | 57.65 | N |
| ATOM | 3139 | CA | CYS | A | 420 | 2.043 | −31.457 | 12.035 | 1.00 | 58.05 | C |
| ATOM | 3141 | CB | CYS | A | 420 | 3.548 | −31.476 | 12.283 | 1.00 | 58.22 | C |
| ATOM | 3144 | SG | CYS | A | 420 | 4.347 | −32.928 | 11.633 | 1.00 | 59.26 | S |
| ATOM | 3146 | C | CYS | A | 420 | 1.439 | −30.549 | 13.079 | 1.00 | 58.71 | C |
| ATOM | 3147 | O | CYS | A | 420 | 0.931 | −31.022 | 14.093 | 1.00 | 59.38 | O |
| ATOM | 3149 | N | LEU | A | 421 | 1.546 | −29.241 | 12.844 | 1.00 | 59.35 | N |
| ATOM | 3150 | CA | LEU | A | 421 | 1.089 | −28.218 | 13.797 | 1.00 | 59.60 | C |
| ATOM | 3152 | CB | LEU | A | 421 | 1.644 | −26.830 | 13.415 | 1.00 | 59.24 | C |
| ATOM | 3155 | CG | LEU | A | 421 | 3.104 | −26.487 | 13.760 | 1.00 | 58.85 | C |
| ATOM | 3157 | CD1 | LEU | A | 421 | 3.498 | −25.088 | 13.239 | 1.00 | 56.81 | C |
| ATOM | 3161 | CD2 | LEU | A | 421 | 3.371 | −26.580 | 15.265 | 1.00 | 58.40 | C |
| ATOM | 3165 | C | LEU | A | 421 | −0.448 | −28.153 | 13.895 | 1.00 | 59.82 | C |
| ATOM | 3166 | O | LEU | A | 421 | −0.982 | −27.886 | 14.955 | 1.00 | 59.45 | O |
| ATOM | 3168 | N | SER | A | 422 | −1.126 | −28.440 | 12.786 | 1.00 | 60.46 | N |
| ATOM | 3169 | CA | SER | A | 422 | −2.543 | −28.127 | 12.598 | 1.00 | 60.58 | C |
| ATOM | 3171 | CB | SER | A | 422 | −2.681 | −27.278 | 11.348 | 1.00 | 60.19 | C |
| ATOM | 3174 | OG | SER | A | 422 | −2.666 | −28.127 | 10.204 | 1.00 | 59.49 | O |
| ATOM | 3176 | C | SER | A | 422 | −3.448 | −29.329 | 12.386 | 1.00 | 61.17 | C |
| ATOM | 3177 | O | SER | A | 422 | −4.646 | −29.172 | 12.390 | 1.00 | 61.93 | O |
| ATOM | 3179 | N | GLY | A | 423 | −2.895 | −30.508 | 12.114 | 1.00 | 61.91 | N |
| ATOM | 3180 | CA | GLY | A | 423 | −3.700 | −31.701 | 11.843 | 1.00 | 61.68 | C |
| ATOM | 3183 | C | GLY | A | 423 | −4.249 | −31.775 | 10.438 | 1.00 | 62.09 | C |
| ATOM | 3184 | O | GLY | A | 423 | −4.795 | −32.810 | 10.053 | 1.00 | 61.95 | O |
| ATOM | 3186 | N | TYR | A | 424 | −4.094 | −30.697 | 9.660 | 1.00 | 62.86 | N |
| ATOM | 3187 | CA | TYR | A | 424 | −4.637 | −30.632 | 8.287 | 1.00 | 63.28 | C |
| ATOM | 3189 | CB | TYR | A | 424 | −5.977 | −29.831 | 8.274 | 1.00 | 63.23 | C |
| ATOM | 3192 | CG | TYR | A | 424 | −5.845 | −28.316 | 8.271 | 1.00 | 61.08 | C |
| ATOM | 3193 | CD1 | TYR | A | 424 | −5.732 | −27.606 | 9.457 | 1.00 | 59.53 | C |
| ATOM | 3195 | CE1 | TYR | A | 424 | −5.600 | −26.228 | 9.467 | 1.00 | 58.10 | C |
| ATOM | 3197 | CZ | TYR | A | 424 | −5.593 | −25.533 | 8.287 | 1.00 | 58.52 | C |
| ATOM | 3198 | OH | TYR | A | 424 | −5.444 | −24.152 | 8.325 | 1.00 | 60.25 | O |
| ATOM | 3200 | CE2 | TYR | A | 424 | −5.712 | −26.206 | 7.085 | 1.00 | 58.95 | C |
| ATOM | 3202 | CD2 | TYR | A | 424 | −5.840 | −27.599 | 7.083 | 1.00 | 60.35 | C |
| ATOM | 3204 | C | TYR | A | 424 | −3.633 | −30.054 | 7.245 | 1.00 | 64.16 | C |
| ATOM | 3205 | O | TYR | A | 424 | −2.758 | −29.253 | 7.595 | 1.00 | 63.66 | O |
| ATOM | 3207 | N | PRO | A | 425 | −3.782 | −30.452 | 5.957 | 1.00 | 65.03 | N |
| ATOM | 3208 | CA | PRO | A | 425 | −2.926 | −29.988 | 4.864 | 1.00 | 65.60 | C |
| ATOM | 3210 | CB | PRO | A | 425 | −3.262 | −30.949 | 3.722 | 1.00 | 65.60 | C |
| ATOM | 3213 | CG | PRO | A | 425 | −4.667 | −31.323 | 3.968 | 1.00 | 65.51 | C |
| ATOM | 3216 | CD | PRO | A | 425 | −4.773 | −31.429 | 5.472 | 1.00 | 64.99 | C |
| ATOM | 3219 | C | PRO | A | 425 | −3.238 | −28.583 | 4.411 | 1.00 | 66.19 | C |
| ATOM | 3220 | O | PRO | A | 425 | −4.401 | −28.225 | 4.333 | 1.00 | 66.80 | O |
| ATOM | 3221 | N | PRO | A | 426 | −2.207 | −27.798 | 4.077 | 1.00 | 66.99 | N |
| ATOM | 3222 | CA | PRO | A | 426 | −2.374 | −26.426 | 3.641 | 1.00 | 67.39 | C |
| ATOM | 3224 | CB | PRO | A | 426 | −0.944 | −25.895 | 3.670 | 1.00 | 67.75 | C |
| ATOM | 3227 | CG | PRO | A | 426 | −0.114 | −27.065 | 3.418 | 1.00 | 66.98 | C |
| ATOM | 3230 | CD | PRO | A | 426 | −0.791 | −28.200 | 4.075 | 1.00 | 66.70 | C |

TABLE 2-continued

| | | | | | | | | | | |
|---|---|---|---|---|---|---|---|---|---|---|
| ATOM | 3233 | C | PRO | A | 426 | −2.916 | −26.280 | 2.235 | 1.00 | 68.08 | C |
| ATOM | 3234 | O | PRO | A | 426 | −3.491 | −25.250 | 1.914 | 1.00 | 68.23 | O |
| ATOM | 3235 | N | PHE | A | 427 | −2.677 | −27.269 | 1.389 | 1.00 | 69.04 | N |
| ATOM | 3236 | CA | PHE | A | 427 | −3.204 | −27.267 | 0.047 | 1.00 | 70.14 | C |
| ATOM | 3238 | CB | PHE | A | 427 | −2.079 | −27.113 | −0.961 | 1.00 | 70.17 | C |
| ATOM | 3241 | CG | PHE | A | 427 | −1.124 | −26.030 | −0.621 | 1.00 | 69.52 | C |
| ATOM | 3242 | CD1 | PHE | A | 427 | −1.453 | −24.711 | −0.850 | 1.00 | 68.89 | C |
| ATOM | 3244 | CE1 | PHE | A | 427 | −0.573 | −23.703 | −0.520 | 1.00 | 68.15 | C |
| ATOM | 3246 | CZ | PHE | A | 427 | 0.645 | −24.014 | 0.038 | 1.00 | 67.52 | C |
| ATOM | 3248 | CE2 | PHE | A | 427 | 0.981 | −25.327 | 0.266 | 1.00 | 67.49 | C |
| ATOM | 3250 | CD2 | PHE | A | 427 | 0.104 | −26.323 | −0.054 | 1.00 | 68.46 | C |
| ATOM | 3252 | C | PHE | A | 427 | −3.908 | −28.572 | −0.206 | 1.00 | 71.56 | C |
| ATOM | 3253 | O | PHE | A | 427 | −3.306 | −29.619 | −0.108 | 1.00 | 71.96 | O |
| ATOM | 3255 | N | SER | A | 428 | −5.193 | −28.502 | −0.507 | 1.00 | 73.56 | N |
| ATOM | 3256 | CA | SER | A | 428 | −5.948 | −29.653 | −0.987 | 1.00 | 74.95 | C |
| ATOM | 3258 | CB | SER | A | 428 | −6.370 | −30.569 | 0.160 | 1.00 | 75.15 | C |
| ATOM | 3261 | OG | SER | A | 428 | −7.155 | −29.876 | 1.101 | 1.00 | 75.42 | O |
| ATOM | 3263 | C | SER | A | 428 | −7.175 | −29.177 | −1.735 | 1.00 | 76.27 | C |
| ATOM | 3264 | O | SER | A | 428 | −7.504 | −27.990 | −1.735 | 1.00 | 76.12 | O |
| ATOM | 3266 | N | GLU | A | 429 | −7.852 | −30.115 | −2.379 | 1.00 | 78.09 | N |
| ATOM | 3267 | CA | GLU | A | 429 | −9.076 | −29.802 | −3.100 | 1.00 | 79.46 | C |
| ATOM | 3269 | CB | GLU | A | 429 | −9.111 | −30.626 | −4.389 | 1.00 | 79.70 | C |
| ATOM | 3272 | CG | GLU | A | 429 | −7.876 | −30.324 | −5.274 | 1.00 | 80.16 | C |
| ATOM | 3275 | CD | GLU | A | 429 | −7.780 | −31.149 | −6.549 | 1.00 | 80.27 | C |
| ATOM | 3276 | OE1 | GLU | A | 429 | −8.103 | −32.353 | −6.507 | 1.00 | 80.90 | O |
| ATOM | 3277 | OE2 | GLU | A | 429 | −7.347 | −30.592 | −7.588 | 1.00 | 79.70 | O |
| ATOM | 3278 | C | GLU | A | 429 | −10.334 | −29.964 | −2.206 | 1.00 | 80.53 | C |
| ATOM | 3279 | O | GLU | A | 429 | −11.454 | −29.717 | −2.662 | 1.00 | 80.66 | O |
| ATOM | 3281 | N | HIS | A | 430 | −10.123 | −30.318 | −0.928 | 1.00 | 81.63 | N |
| ATOM | 3282 | CA | HIS | A | 430 | −11.188 | −30.438 | 0.081 | 1.00 | 82.67 | C |
| ATOM | 3284 | CB | HIS | A | 430 | −10.666 | −31.180 | 1.328 | 1.00 | 83.11 | C |
| ATOM | 3287 | CG | HIS | A | 430 | −11.684 | −31.350 | 2.429 | 1.00 | 85.22 | C |
| ATOM | 3288 | ND1 | HIS | A | 430 | −12.459 | −32.487 | 2.566 | 1.00 | 86.32 | N |
| ATOM | 3290 | CE1 | HIS | A | 430 | −13.239 | −32.366 | 3.627 | 1.00 | 86.71 | C |
| ATOM | 3292 | NE2 | HIS | A | 430 | −12.994 | −31.197 | 4.193 | 1.00 | 87.13 | N |
| ATOM | 3294 | CD2 | HIS | A | 430 | −12.025 | −30.542 | 3.465 | 1.00 | 86.69 | C |
| ATOM | 3296 | C | HIS | A | 430 | −11.717 | −29.071 | 0.501 | 1.00 | 83.07 | C |
| ATOM | 3297 | O | HIS | A | 430 | −11.036 | −28.334 | 1.226 | 1.00 | 83.17 | O |
| ATOM | 3299 | N | ARG | A | 431 | −12.942 | −28.762 | 0.064 | 1.00 | 83.42 | N |
| ATOM | 3300 | CA | ARG | A | 431 | −13.622 | −27.492 | 0.362 | 1.00 | 83.44 | C |
| ATOM | 3302 | CB | ARG | A | 431 | −13.842 | −27.296 | 1.883 | 1.00 | 83.82 | C |
| ATOM | 3305 | CG | ARG | A | 431 | −14.688 | −28.415 | 2.562 | 1.00 | 85.30 | C |
| ATOM | 3308 | CD | ARG | A | 431 | −15.776 | −27.870 | 3.536 | 1.00 | 87.34 | C |
| ATOM | 3311 | NE | ARG | A | 431 | −15.574 | −28.175 | 4.964 | 1.00 | 88.75 | N |
| ATOM | 3313 | CZ | ARG | A | 431 | −16.243 | −27.595 | 5.977 | 1.00 | 90.15 | C |
| ATOM | 3314 | NH1 | ARG | A | 431 | −17.159 | −26.648 | 5.763 | 1.00 | 90.54 | N |
| ATOM | 3317 | NH2 | ARG | A | 431 | −15.985 | −27.948 | 7.232 | 1.00 | 90.64 | N |
| ATOM | 3320 | C | ARG | A | 431 | −12.907 | −26.279 | −0.273 | 1.00 | 82.97 | C |
| ATOM | 3321 | O | ARG | A | 431 | −12.322 | −25.442 | 0.432 | 1.00 | 83.31 | O |
| ATOM | 3323 | N | THR | A | 432 | −12.941 | −26.233 | −1.608 | 1.00 | 81.92 | N |
| ATOM | 3324 | CA | THR | A | 432 | −12.619 | −25.040 | −2.415 | 1.00 | 81.04 | C |
| ATOM | 3326 | CB | THR | A | 432 | −11.147 | −24.557 | −2.306 | 1.00 | 81.16 | C |
| ATOM | 3328 | OG1 | THR | A | 432 | −10.294 | −25.668 | −1.999 | 1.00 | 82.51 | O |
| ATOM | 3330 | CG2 | THR | A | 432 | −10.988 | −23.452 | −1.254 | 1.00 | 81.57 | C |
| ATOM | 3334 | C | THR | A | 432 | −12.845 | −25.383 | −3.872 | 1.00 | 79.95 | C |
| ATOM | 3335 | O | THR | A | 432 | −12.871 | −26.561 | −4.251 | 1.00 | 79.64 | O |
| ATOM | 3337 | N | GLN | A | 433 | −12.998 | −24.349 | −4.687 | 1.00 | 78.65 | N |
| ATOM | 3338 | CA | GLN | A | 433 | −13.035 | −24.520 | −6.136 | 1.00 | 77.89 | C |
| ATOM | 3340 | CB | GLN | A | 433 | −14.074 | −23.578 | −6.777 | 1.00 | 78.29 | C |
| ATOM | 3343 | CG | GLN | A | 433 | −15.518 | −24.142 | −6.813 | 1.00 | 79.96 | C |
| ATOM | 3346 | CD | GLN | A | 433 | −16.387 | −23.723 | −5.606 | 1.00 | 82.44 | C |
| ATOM | 3347 | OE1 | GLN | A | 433 | −15.885 | −23.476 | −4.499 | 1.00 | 83.03 | O |
| ATOM | 3348 | NE2 | GLN | A | 433 | −17.706 | −23.654 | −5.828 | 1.00 | 83.17 | N |
| ATOM | 3351 | C | GLN | A | 433 | −11.648 | −24.308 | −6.753 | 1.00 | 76.18 | C |
| ATOM | 3352 | O | GLN | A | 433 | −11.374 | −24.808 | −7.846 | 1.00 | 75.99 | O |
| ATOM | 3354 | N | VAL | A | 434 | −10.778 | −23.577 | −6.050 | 1.00 | 74.33 | N |
| ATOM | 3355 | CA | VAL | A | 434 | −9.424 | −23.272 | −6.551 | 1.00 | 72.65 | C |
| ATOM | 3357 | CB | VAL | A | 434 | −8.634 | −22.318 | −5.558 | 1.00 | 72.89 | C |
| ATOM | 3359 | CG1 | VAL | A | 434 | −8.462 | −22.950 | −4.162 | 1.00 | 73.31 | C |
| ATOM | 3363 | CG2 | VAL | A | 434 | −7.286 | −21.873 | −6.152 | 1.00 | 72.29 | C |
| ATOM | 3367 | C | VAL | A | 434 | −8.663 | −24.568 | −6.853 | 1.00 | 70.67 | C |
| ATOM | 3368 | O | VAL | A | 434 | −8.648 | −25.484 | −6.033 | 1.00 | 70.10 | O |
| ATOM | 3370 | N | SER | A | 435 | −8.085 | −24.652 | −8.052 | 1.00 | 68.66 | N |
| ATOM | 3371 | CA | SER | A | 435 | −7.326 | −25.831 | −8.472 | 1.00 | 67.06 | C |
| ATOM | 3373 | CB | SER | A | 435 | −7.005 | −25.784 | −9.964 | 1.00 | 66.93 | C |
| ATOM | 3376 | OG | SER | A | 435 | −5.824 | −25.038 | −10.233 | 1.00 | 67.15 | O |
| ATOM | 3378 | C | SER | A | 435 | −6.026 | −25.906 | −7.690 | 1.00 | 66.12 | C |
| ATOM | 3379 | O | SER | A | 435 | −5.320 | −24.904 | −7.590 | 1.00 | 65.87 | O |
| ATOM | 3381 | N | LEU | A | 436 | −5.718 | −27.098 | −7.161 | 1.00 | 64.78 | N |
| ATOM | 3382 | CA | LEU | A | 436 | −4.554 | −27.347 | −6.297 | 1.00 | 63.53 | C |

TABLE 2-continued

| | | | | | | | | | |
|---|---|---|---|---|---|---|---|---|---|
| ATOM | 3384 | CB  | LEU | A | 436 | −4.376 | −28.856 | −6.094 | 1.00 63.63 C |
| ATOM | 3387 | CG  | LEU | A | 436 | −3.477 | −29.414 | −4.981 | 1.00 64.34 C |
| ATOM | 3389 | CD1 | LEU | A | 436 | −3.678 | −28.754 | −3.606 | 1.00 64.94 C |
| ATOM | 3393 | CD2 | LEU | A | 436 | −3.712 | −30.913 | −4.877 | 1.00 64.95 C |
| ATOM | 3397 | C   | LEU | A | 436 | −3.275 | −26.705 | −6.852 | 1.00 62.11 C |
| ATOM | 3398 | O   | LEU | A | 436 | −2.483 | −26.139 | −6.101 | 1.00 61.06 O |
| ATOM | 3400 | N   | LYS | A | 437 | −3.118 | −26.750 | −8.168 | 1.00 60.71 N |
| ATOM | 3401 | CA  | LYS | A | 437 | −2.026 | −26.064 | −8.826 | 1.00 60.41 C |
| ATOM | 3403 | CB  | LYS | A | 437 | −2.090 | −26.241 | −10.343 | 1.00 59.74 C |
| ATOM | 3406 | CG  | LYS | A | 437 | −0.895 | −25.644 | −11.064 | 1.00 60.54 C |
| ATOM | 3409 | CD  | LYS | A | 437 | −1.021 | −25.562 | −12.598 | 1.00 61.17 C |
| ATOM | 3412 | CE  | LYS | A | 437 | 0.338 | −25.202 | −13.220 | 1.00 61.82 C |
| ATOM | 3415 | NZ  | LYS | A | 437 | 0.338 | −24.799 | −14.663 | 1.00 62.92 N |
| ATOM | 3419 | C   | LYS | A | 437 | −2.051 | −24.575 | −8.495 | 1.00 60.64 C |
| ATOM | 3420 | O   | LYS | A | 437 | −1.033 | −23.979 | −8.168 | 1.00 60.95 O |
| ATOM | 3422 | N   | ASP | A | 438 | −3.218 | −23.960 | −8.595 | 1.00 60.83 N |
| ATOM | 3423 | CA  | ASP | A | 438 | −3.312 | −22.522 | −8.380 | 1.00 60.32 C |
| ATOM | 3425 | CB  | ASP | A | 438 | −4.652 | −22.001 | −8.905 | 1.00 60.32 C |
| ATOM | 3428 | CG  | ASP | A | 438 | −4.688 | −21.930 | −10.426 | 1.00 60.99 C |
| ATOM | 3429 | OD1 | ASP | A | 438 | −3.657 | −22.180 | −11.088 | 1.00 59.16 O |
| ATOM | 3430 | OD2 | ASP | A | 438 | −5.764 | −21.609 | −10.971 | 1.00 65.12 O |
| ATOM | 3431 | C   | ASP | A | 438 | −3.053 | −22.140 | −6.920 | 1.00 59.49 C |
| ATOM | 3432 | O   | ASP | A | 438 | −2.441 | −21.100 | −6.649 | 1.00 59.64 O |
| ATOM | 3434 | N   | GLN | A | 439 | −3.464 | −22.995 | −5.988 | 1.00 58.54 N |
| ATOM | 3435 | CA  | GLN | A | 439 | −3.223 | −22.726 | −4.570 | 1.00 57.88 C |
| ATOM | 3437 | CB  | GLN | A | 439 | −3.863 | −23.784 | −3.651 | 1.00 57.98 C |
| ATOM | 3440 | CG  | GLN | A | 439 | −5.308 | −24.182 | −3.988 | 1.00 58.93 C |
| ATOM | 3443 | CD  | GLN | A | 439 | −5.909 | −25.163 | −2.973 | 1.00 59.83 C |
| ATOM | 3444 | OE1 | GLN | A | 439 | −5.430 | −25.300 | −1.836 | 1.00 58.68 O |
| ATOM | 3445 | NE2 | GLN | A | 439 | −6.959 | −25.852 | −3.390 | 1.00 58.65 N |
| ATOM | 3448 | C   | GLN | A | 439 | −1.713 | −22.689 | −4.322 | 1.00 56.94 C |
| ATOM | 3449 | O   | GLN | A | 439 | −1.203 | −21.760 | −3.695 | 1.00 57.60 O |
| ATOM | 3451 | N   | ILE | A | 440 | −1.001 | −23.691 | −4.832 | 1.00 55.00 N |
| ATOM | 3452 | CA  | ILE | A | 440 | 0.406 | −23.830 | −4.534 | 1.00 53.55 C |
| ATOM | 3454 | CB  | ILE | A | 440 | 0.953 | −25.232 | −4.953 | 1.00 53.04 C |
| ATOM | 3456 | CG1 | ILE | A | 440 | 0.335 | −26.320 | −4.091 | 1.00 49.96 C |
| ATOM | 3459 | CD1 | ILE | A | 440 | 0.445 | −27.651 | −4.729 | 1.00 47.57 C |
| ATOM | 3463 | CG2 | ILE | A | 440 | 2.455 | −25.316 | −4.810 | 1.00 51.53 C |
| ATOM | 3467 | C   | ILE | A | 440 | 1.177 | −22.689 | −5.184 | 1.00 53.77 C |
| ATOM | 3468 | O   | ILE | A | 440 | 1.921 | −21.986 | −4.507 | 1.00 52.55 O |
| ATOM | 3470 | N   | THR | A | 441 | 0.983 | −22.467 | −6.477 | 1.00 54.53 N |
| ATOM | 3471 | CA  | THR | A | 441 | 1.766 | −21.427 | −7.160 | 1.00 56.00 C |
| ATOM | 3473 | CB  | THR | A | 441 | 1.595 | −21.456 | −8.674 | 1.00 55.87 C |
| ATOM | 3475 | OG1 | THR | A | 441 | 0.207 | −21.393 | −8.980 | 1.00 57.84 O |
| ATOM | 3477 | CG2 | THR | A | 441 | 2.193 | −22.707 | −9.250 | 1.00 54.58 C |
| ATOM | 3481 | C   | THR | A | 441 | 1.488 | −20.000 | −6.674 | 1.00 57.06 C |
| ATOM | 3482 | O   | THR | A | 441 | 2.366 | −19.148 | −6.741 | 1.00 56.89 O |
| ATOM | 3484 | N   | SER | A | 442 | 0.279 | −19.742 | −6.191 | 1.00 58.94 N |
| ATOM | 3485 | CA  | SER | A | 442 | −0.025 | −18.450 | −5.582 | 1.00 60.26 C |
| ATOM | 3487 | CB  | SER | A | 442 | −1.532 | −18.189 | −5.586 | 1.00 60.01 C |
| ATOM | 3490 | OG  | SER | A | 442 | −2.166 | −18.782 | −4.459 | 1.00 60.26 O |
| ATOM | 3492 | C   | SER | A | 442 | 0.531 | −18.410 | −4.149 | 1.00 61.69 C |
| ATOM | 3493 | O   | SER | A | 442 | 0.999 | −17.369 | −3.688 | 1.00 62.08 O |
| ATOM | 3495 | N   | GLY | A | 443 | 0.481 | −19.548 | −3.457 | 1.00 63.15 N |
| ATOM | 3496 | CA  | GLY | A | 443 | 0.868 | −19.633 | −2.036 | 1.00 64.24 C |
| ATOM | 3499 | C   | GLY | A | 443 | −0.272 | −19.393 | −1.054 | 1.00 65.51 C |
| ATOM | 3500 | O   | GLY | A | 443 | −0.066 | −19.339 | 0.157 | 1.00 65.49 O |
| ATOM | 3502 | N   | LYS | A | 444 | −1.488 | −19.251 | −1.566 | 1.00 67.13 N |
| ATOM | 3503 | CA  | LYS | A | 444 | −2.641 | −19.005 | −0.720 | 1.00 68.14 C |
| ATOM | 3505 | CB  | LYS | A | 444 | −3.788 | −18.418 | −1.549 | 1.00 68.59 C |
| ATOM | 3508 | CG  | LYS | A | 444 | −3.504 | −16.997 | −2.093 | 1.00 69.14 C |
| ATOM | 3511 | CD  | LYS | A | 444 | −4.504 | −16.596 | −3.198 | 1.00 70.30 C |
| ATOM | 3514 | CE  | LYS | A | 444 | −4.738 | −15.076 | −3.282 | 1.00 71.05 C |
| ATOM | 3517 | NZ  | LYS | A | 444 | −3.530 | −14.308 | −3.715 | 1.00 70.57 N |
| ATOM | 3521 | C   | LYS | A | 444 | −3.037 | −20.318 | −0.056 | 1.00 68.76 C |
| ATOM | 3522 | O   | LYS | A | 444 | −3.804 | −21.101 | −0.603 | 1.00 68.82 O |
| ATOM | 3524 | N   | TYR | A | 445 | −2.477 | −20.552 | 1.123 | 1.00 69.26 N |
| ATOM | 3525 | CA  | TYR | A | 445 | −2.726 | −21.779 | 1.869 | 1.00 69.63 C |
| ATOM | 3527 | CB  | TYR | A | 445 | −1.554 | −22.087 | 2.817 | 1.00 69.79 C |
| ATOM | 3530 | CG  | TYR | A | 445 | −1.065 | −20.887 | 3.605 | 1.00 69.19 C |
| ATOM | 3531 | CD1 | TYR | A | 445 | −1.762 | −20.416 | 4.720 | 1.00 69.61 C |
| ATOM | 3533 | CE1 | TYR | A | 445 | −1.324 | −19.314 | 5.435 | 1.00 69.55 C |
| ATOM | 3535 | CZ  | TYR | A | 445 | −0.170 | −18.658 | 5.041 | 1.00 70.95 C |
| ATOM | 3536 | OH  | TYR | A | 445 | 0.296 | −17.552 | 5.735 | 1.00 71.08 O |
| ATOM | 3538 | CE2 | TYR | A | 445 | 0.538 | −19.113 | 3.937 | 1.00 70.28 C |
| ATOM | 3540 | CD2 | TYR | A | 445 | 0.084 | −20.223 | 3.229 | 1.00 68.92 C |
| ATOM | 3542 | C   | TYR | A | 445 | −3.996 | −21.665 | 2.685 | 1.00 70.10 C |
| ATOM | 3543 | O   | TYR | A | 445 | −4.337 | −20.595 | 3.160 | 1.00 69.71 O |
| ATOM | 3545 | N   | ASN | A | 446 | −4.660 | −22.797 | 2.886 | 1.00 71.08 N |
| ATOM | 3546 | CA  | ASN | A | 446 | −5.865 | −22.861 | 3.696 | 1.00 71.63 C |

TABLE 2-continued

| | | | | | | | | | | |
|---|---|---|---|---|---|---|---|---|---|---|
| ATOM | 3548 | CB | ASN | A | 446 | −6.524 | −24.224 | 3.511 | 1.00 | 71.71 | C |
| ATOM | 3551 | CG | ASN | A | 446 | −7.997 | −24.214 | 3.854 | 1.00 | 72.24 | C |
| ATOM | 3552 | OD1 | ASN | A | 446 | −8.830 | −24.058 | 2.968 | 1.00 | 73.35 | O |
| ATOM | 3553 | ND2 | ASN | A | 446 | −8.328 | −24.379 | 5.136 | 1.00 | 71.49 | N |
| ATOM | 3556 | C | ASN | A | 446 | −5.582 | −22.580 | 5.184 | 1.00 | 72.35 | C |
| ATOM | 3557 | O | ASN | A | 446 | −5.228 | −23.477 | 5.940 | 1.00 | 71.86 | O |
| ATOM | 3559 | N | PHE | A | 447 | −5.729 | −21.318 | 5.582 | 1.00 | 73.47 | N |
| ATOM | 3560 | CA | PHE | A | 447 | −5.599 | −20.900 | 6.984 | 1.00 | 74.56 | C |
| ATOM | 3562 | CB | PHE | A | 447 | −5.083 | −19.474 | 7.036 | 1.00 | 74.58 | C |
| ATOM | 3565 | CG | PHE | A | 447 | −4.834 | −18.985 | 8.417 | 1.00 | 75.74 | C |
| ATOM | 3566 | CD1 | PHE | A | 447 | −3.925 | −19.637 | 9.238 | 1.00 | 77.05 | C |
| ATOM | 3568 | CE1 | PHE | A | 447 | −3.681 | −19.188 | 10.534 | 1.00 | 77.94 | C |
| ATOM | 3570 | CZ | PHE | A | 447 | −4.346 | −18.073 | 11.007 | 1.00 | 77.80 | C |
| ATOM | 3572 | CE2 | PHE | A | 447 | −5.252 | −17.408 | 10.181 | 1.00 | 77.25 | C |
| ATOM | 3574 | CD2 | PHE | A | 447 | −5.490 | −17.865 | 8.900 | 1.00 | 76.65 | C |
| ATOM | 3576 | C | PHE | A | 447 | −6.927 | −20.973 | 7.747 | 1.00 | 75.24 | C |
| ATOM | 3577 | O | PHE | A | 447 | −7.941 | −20.519 | 7.248 | 1.00 | 75.85 | O |
| ATOM | 3579 | N | ILE | A | 448 | −6.913 | −21.533 | 8.954 | 1.00 | 76.05 | N |
| ATOM | 3580 | CA | ILE | A | 448 | −8.130 | −21.739 | 9.749 | 1.00 | 76.78 | C |
| ATOM | 3582 | CB | ILE | A | 448 | −8.575 | −23.211 | 9.744 | 1.00 | 76.67 | C |
| ATOM | 3584 | CG1 | ILE | A | 448 | −8.990 | −23.646 | 8.335 | 1.00 | 76.17 | C |
| ATOM | 3587 | CD1 | ILE | A | 448 | −9.447 | −25.085 | 8.258 | 1.00 | 75.25 | C |
| ATOM | 3591 | CG2 | ILE | A | 448 | −9.722 | −23.414 | 10.722 | 1.00 | 76.47 | C |
| ATOM | 3595 | C | ILE | A | 448 | −7.885 | −21.316 | 11.197 | 1.00 | 77.87 | C |
| ATOM | 3596 | O | ILE | A | 448 | −7.384 | −22.107 | 12.002 | 1.00 | 78.10 | O |
| ATOM | 3598 | N | PRO | A | 449 | −8.253 | −20.070 | 11.545 | 1.00 | 79.21 | N |
| ATOM | 3599 | CA | PRO | A | 449 | −7.814 | −19.520 | 12.842 | 1.00 | 79.97 | C |
| ATOM | 3601 | CB | PRO | A | 449 | −8.489 | −18.135 | 12.888 | 1.00 | 80.05 | C |
| ATOM | 3604 | CG | PRO | A | 449 | −8.720 | −17.772 | 11.437 | 1.00 | 79.51 | C |
| ATOM | 3607 | CD | PRO | A | 449 | −9.000 | −19.075 | 10.741 | 1.00 | 79.13 | C |
| ATOM | 3610 | C | PRO | A | 449 | −8.145 | −20.342 | 14.106 | 1.00 | 80.64 | C |
| ATOM | 3611 | O | PRO | A | 449 | −7.317 | −20.393 | 15.022 | 1.00 | 81.26 | O |
| ATOM | 3612 | N | GLU | A | 450 | −9.313 | −20.980 | 14.169 | 1.00 | 81.17 | N |
| ATOM | 3613 | CA | GLU | A | 450 | −9.707 | −21.711 | 15.393 | 1.00 | 81.71 | C |
| ATOM | 3615 | CB | GLU | A | 450 | −11.217 | −22.033 | 15.464 | 1.00 | 81.99 | C |
| ATOM | 3618 | CG | GLU | A | 450 | −11.841 | −22.668 | 14.208 | 1.00 | 83.45 | C |
| ATOM | 3621 | CD | GLU | A | 450 | −12.314 | −21.631 | 13.173 | 1.00 | 84.96 | C |
| ATOM | 3622 | OE1 | GLU | A | 450 | −11.941 | −20.439 | 13.295 | 1.00 | 84.92 | O |
| ATOM | 3623 | OE2 | GLU | A | 450 | −13.048 | −22.013 | 12.228 | 1.00 | 85.98 | O |
| ATOM | 3624 | C | GLU | A | 450 | −8.905 | −22.978 | 15.586 | 1.00 | 81.74 | C |
| ATOM | 3625 | O | GLU | A | 450 | −8.828 | −23.498 | 16.702 | 1.00 | 82.06 | O |
| ATOM | 3627 | N | VAL | A | 451 | −8.325 | −23.497 | 14.508 | 1.00 | 81.59 | N |
| ATOM | 3628 | CA | VAL | A | 451 | −7.385 | −24.596 | 14.647 | 1.00 | 81.43 | C |
| ATOM | 3630 | CB | VAL | A | 451 | −7.376 | −25.496 | 13.405 | 1.00 | 81.67 | C |
| ATOM | 3632 | CG1 | VAL | A | 451 | −6.375 | −26.634 | 13.574 | 1.00 | 81.63 | C |
| ATOM | 3636 | CG2 | VAL | A | 451 | −8.769 | −26.066 | 13.164 | 1.00 | 81.69 | C |
| ATOM | 3640 | C | VAL | A | 451 | −5.989 | −24.049 | 14.995 | 1.00 | 81.02 | C |
| ATOM | 3641 | O | VAL | A | 451 | −5.286 | −24.653 | 15.802 | 1.00 | 81.00 | O |
| ATOM | 3643 | N | TRP | A | 452 | −5.621 | −22.891 | 14.438 | 1.00 | 80.50 | N |
| ATOM | 3644 | CA | TRP | A | 452 | −4.299 | −22.274 | 14.685 | 1.00 | 80.35 | C |
| ATOM | 3646 | CB | TRP | A | 452 | −3.892 | −21.373 | 13.512 | 1.00 | 80.27 | C |
| ATOM | 3649 | CG | TRP | A | 452 | −3.405 | −22.175 | 12.367 | 1.00 | 80.45 | C |
| ATOM | 3650 | CD1 | TRP | A | 452 | −4.129 | −22.597 | 11.299 | 1.00 | 80.94 | C |
| ATOM | 3652 | NE1 | TRP | A | 452 | −3.347 | −23.351 | 10.459 | 1.00 | 80.66 | N |
| ATOM | 3654 | CE2 | TRP | A | 452 | −2.087 | −23.435 | 10.987 | 1.00 | 80.06 | C |
| ATOM | 3655 | CD2 | TRP | A | 452 | −2.089 | −22.708 | 12.194 | 1.00 | 79.74 | C |
| ATOM | 3656 | CE3 | TRP | A | 452 | −0.910 | −22.636 | 12.938 | 1.00 | 79.12 | C |
| ATOM | 3658 | CZ3 | TRP | A | 452 | 0.217 | −23.283 | 12.459 | 1.00 | 78.79 | C |
| ATOM | 3660 | CH2 | TRP | A | 452 | 0.190 | −23.987 | 11.249 | 1.00 | 78.09 | C |
| ATOM | 3662 | CZ2 | TRP | A | 452 | −0.948 | −24.078 | 10.502 | 1.00 | 79.05 | C |
| ATOM | 3664 | C | TRP | A | 452 | −4.151 | −21.475 | 15.977 | 1.00 | 80.44 | C |
| ATOM | 3665 | O | TRP | A | 452 | −3.026 | −21.289 | 16.462 | 1.00 | 80.41 | O |
| ATOM | 3667 | N | ALA | A | 453 | −5.267 | −20.971 | 16.509 | 1.00 | 80.32 | N |
| ATOM | 3668 | CA | ALA | A | 453 | −5.274 | −20.236 | 17.780 | 1.00 | 79.90 | C |
| ATOM | 3670 | CB | ALA | A | 453 | −6.709 | −19.984 | 18.232 | 1.00 | 79.89 | C |
| ATOM | 3674 | C | ALA | A | 453 | −4.503 | −21.003 | 18.854 | 1.00 | 79.42 | C |
| ATOM | 3675 | O | ALA | A | 453 | −3.779 | −20.404 | 19.648 | 1.00 | 79.41 | O |
| ATOM | 3677 | N | GLU | A | 454 | −4.670 | −22.327 | 18.862 | 1.00 | 78.97 | N |
| ATOM | 3678 | CA | GLU | A | 454 | −3.826 | −23.242 | 19.660 | 1.00 | 78.65 | C |
| ATOM | 3680 | CB | GLU | A | 454 | −4.025 | −24.708 | 19.221 | 1.00 | 78.87 | C |
| ATOM | 3683 | CG | GLU | A | 454 | −5.171 | −25.444 | 19.910 | 1.00 | 79.73 | C |
| ATOM | 3686 | CD | GLU | A | 454 | −6.516 | −25.170 | 19.271 | 1.00 | 81.49 | C |
| ATOM | 3687 | OE1 | GLU | A | 454 | −7.426 | −26.019 | 19.416 | 1.00 | 82.42 | O |
| ATOM | 3688 | OE2 | GLU | A | 454 | −6.667 | −24.112 | 18.619 | 1.00 | 82.36 | O |
| ATOM | 3689 | C | GLU | A | 454 | −2.333 | −22.929 | 19.553 | 1.00 | 77.59 | C |
| ATOM | 3690 | O | GLU | A | 454 | −1.626 | −22.920 | 20.553 | 1.00 | 77.58 | O |
| ATOM | 3692 | N | VAL | A | 455 | −1.863 | −22.672 | 18.335 | 1.00 | 76.41 | N |
| ATOM | 3693 | CA | VAL | A | 455 | −0.423 | −22.612 | 18.040 | 1.00 | 75.31 | C |
| ATOM | 3695 | CB | VAL | A | 455 | −0.174 | −23.112 | 16.597 | 1.00 | 75.16 | C |
| ATOM | 3697 | CG1 | VAL | A | 455 | 1.314 | −23.147 | 16.269 | 1.00 | 75.38 | C |

TABLE 2-continued

| ATOM | 3701 | CG2 | VAL | A | 455 | −0.794 | −24.482 | 16.420 | 1.00 | 74.75 | C |
|---|---|---|---|---|---|---|---|---|---|---|---|
| ATOM | 3705 | C | VAL | A | 455 | 0.198 | −21.212 | 18.249 | 1.00 | 74.21 | C |
| ATOM | 3706 | O | VAL | A | 455 | −0.455 | −20.192 | 18.043 | 1.00 | 74.16 | O |
| ATOM | 3708 | N | SER | A | 456 | 1.465 | −21.183 | 18.652 | 1.00 | 73.01 | N |
| ATOM | 3709 | CA | SER | A | 456 | 2.176 | −19.934 | 18.894 | 1.00 | 72.31 | C |
| ATOM | 3711 | CB | SER | A | 456 | 3.545 | −20.205 | 19.536 | 1.00 | 72.27 | C |
| ATOM | 3714 | OG | SER | A | 456 | 4.556 | −20.429 | 18.560 | 1.00 | 71.70 | O |
| ATOM | 3716 | C | SER | A | 456 | 2.369 | −19.147 | 17.606 | 1.00 | 71.90 | C |
| ATOM | 3717 | O | SER | A | 456 | 2.256 | −19.698 | 16.511 | 1.00 | 71.81 | O |
| ATOM | 3719 | N | GLU | A | 457 | 2.669 | −17.858 | 17.747 | 1.00 | 71.42 | N |
| ATOM | 3720 | CA | GLU | A | 457 | 2.956 | −16.988 | 16.599 | 1.00 | 70.91 | C |
| ATOM | 3722 | CB | GLU | A | 457 | 3.038 | −15.513 | 17.020 | 1.00 | 71.26 | C |
| ATOM | 3725 | CG | GLU | A | 457 | 1.777 | −14.908 | 17.609 | 1.00 | 74.10 | C |
| ATOM | 3728 | CD | GLU | A | 457 | 2.090 | −13.757 | 18.585 | 1.00 | 77.16 | C |
| ATOM | 3729 | OE1 | GLU | A | 457 | 1.618 | −12.617 | 18.343 | 1.00 | 78.32 | O |
| ATOM | 3730 | OE2 | GLU | A | 457 | 2.821 | −13.999 | 19.588 | 1.00 | 77.62 | O |
| ATOM | 3731 | C | GLU | A | 457 | 4.288 | −17.335 | 15.938 | 1.00 | 69.45 | C |
| ATOM | 3732 | O | GLU | A | 457 | 4.406 | −17.242 | 14.714 | 1.00 | 69.10 | O |
| ATOM | 3734 | N | LYS | A | 458 | 5.294 | −17.674 | 16.755 | 1.00 | 67.93 | N |
| ATOM | 3735 | CA | LYS | A | 458 | 6.642 | −18.011 | 16.259 | 1.00 | 66.84 | C |
| ATOM | 3737 | CB | LYS | A | 458 | 7.599 | −18.290 | 17.419 | 1.00 | 66.96 | C |
| ATOM | 3740 | CG | LYS | A | 458 | 7.885 | −17.108 | 18.324 | 1.00 | 67.37 | C |
| ATOM | 3743 | CD | LYS | A | 458 | 8.794 | −17.539 | 19.457 | 1.00 | 68.52 | C |
| ATOM | 3746 | CE | LYS | A | 458 | 9.059 | −16.439 | 20.488 | 1.00 | 69.47 | C |
| ATOM | 3749 | NZ | LYS | A | 458 | 10.282 | −15.633 | 20.194 | 1.00 | 70.38 | N |
| ATOM | 3753 | C | LYS | A | 458 | 6.591 | −19.237 | 15.333 | 1.00 | 65.32 | C |
| ATOM | 3754 | O | LYS | A | 458 | 7.110 | −19.199 | 14.223 | 1.00 | 64.20 | O |
| ATOM | 3756 | N | ALA | A | 459 | 5.926 | −20.299 | 15.797 | 1.00 | 64.03 | N |
| ATOM | 3757 | CA | ALA | A | 459 | 5.685 | −21.519 | 14.999 | 1.00 | 62.98 | C |
| ATOM | 3759 | CB | ALA | A | 459 | 4.845 | −22.497 | 15.773 | 1.00 | 62.81 | C |
| ATOM | 3763 | C | ALA | A | 459 | 5.026 | −21.233 | 13.655 | 1.00 | 62.13 | C |
| ATOM | 3764 | O | ALA | A | 459 | 5.403 | −21.814 | 12.624 | 1.00 | 62.18 | O |
| ATOM | 3766 | N | LEU | A | 460 | 4.047 | −20.339 | 13.661 | 1.00 | 61.02 | N |
| ATOM | 3767 | CA | LEU | A | 460 | 3.373 | −19.933 | 12.424 | 1.00 | 60.18 | C |
| ATOM | 3769 | CB | LEU | A | 460 | 2.045 | −19.223 | 12.720 | 1.00 | 60.37 | C |
| ATOM | 3772 | CG | LEU | A | 460 | 1.178 | −18.721 | 11.545 | 1.00 | 61.36 | C |
| ATOM | 3774 | CD1 | LEU | A | 460 | 0.794 | −19.856 | 10.561 | 1.00 | 60.72 | C |
| ATOM | 3778 | CD2 | LEU | A | 460 | −0.074 | −18.033 | 12.093 | 1.00 | 60.57 | C |
| ATOM | 3782 | C | LEU | A | 460 | 4.260 | −19.038 | 11.584 | 1.00 | 58.95 | C |
| ATOM | 3783 | O | LEU | A | 460 | 4.186 | −19.077 | 10.366 | 1.00 | 59.20 | O |
| ATOM | 3785 | N | ASP | A | 461 | 5.092 | −18.228 | 12.223 | 1.00 | 58.21 | N |
| ATOM | 3786 | CA | ASP | A | 461 | 6.012 | −17.342 | 11.494 | 1.00 | 57.65 | C |
| ATOM | 3788 | CB | ASP | A | 461 | 6.742 | −16.389 | 12.445 | 1.00 | 57.66 | C |
| ATOM | 3791 | CG | ASP | A | 461 | 7.592 | −15.380 | 11.708 | 1.00 | 59.03 | C |
| ATOM | 3792 | OD1 | ASP | A | 461 | 7.003 | −14.480 | 11.072 | 1.00 | 59.94 | O |
| ATOM | 3793 | OD2 | ASP | A | 461 | 8.845 | −15.493 | 11.755 | 1.00 | 60.28 | O |
| ATOM | 3794 | C | ASP | A | 461 | 7.032 | −18.143 | 10.682 | 1.00 | 56.90 | C |
| ATOM | 3795 | O | ASP | A | 461 | 7.352 | −17.775 | 9.560 | 1.00 | 57.73 | O |
| ATOM | 3797 | N | LEU | A | 462 | 7.542 | −19.233 | 11.247 | 1.00 | 55.92 | N |
| ATOM | 3798 | CA | LEU | A | 462 | 8.441 | −20.128 | 10.516 | 1.00 | 55.25 | C |
| ATOM | 3800 | CB | LEU | A | 462 | 8.945 | −21.229 | 11.433 | 1.00 | 55.27 | C |
| ATOM | 3803 | CG | LEU | A | 462 | 10.099 | −22.077 | 10.903 | 1.00 | 55.00 | C |
| ATOM | 3805 | CD1 | LEU | A | 462 | 11.276 | −21.221 | 10.458 | 1.00 | 51.17 | C |
| ATOM | 3809 | CD2 | LEU | A | 462 | 10.506 | −23.071 | 12.004 | 1.00 | 54.50 | C |
| ATOM | 3813 | C | LEU | A | 462 | 7.767 | −20.765 | 9.300 | 1.00 | 54.69 | C |
| ATOM | 3814 | O | LEU | A | 462 | 8.327 | −20.740 | 8.205 | 1.00 | 53.99 | O |
| ATOM | 3816 | N | VAL | A | 463 | 6.569 | −21.318 | 9.512 | 1.00 | 54.28 | N |
| ATOM | 3817 | CA | VAL | A | 463 | 5.796 | −21.953 | 8.465 | 1.00 | 53.99 | C |
| ATOM | 3819 | CB | VAL | A | 463 | 4.410 | −22.461 | 8.975 | 1.00 | 54.39 | C |
| ATOM | 3821 | CG1 | VAL | A | 463 | 3.542 | −22.982 | 7.826 | 1.00 | 53.31 | C |
| ATOM | 3825 | CG2 | VAL | A | 463 | 4.562 | −23.557 | 10.041 | 1.00 | 53.72 | C |
| ATOM | 3829 | C | VAL | A | 463 | 5.601 | −20.961 | 7.348 | 1.00 | 54.63 | C |
| ATOM | 3830 | O | VAL | A | 463 | 5.741 | −21.314 | 6.190 | 1.00 | 54.51 | O |
| ATOM | 3832 | N | LYS | A | 464 | 5.304 | −19.703 | 7.680 | 1.00 | 55.63 | N |
| ATOM | 3833 | CA | LYS | A | 464 | 5.107 | −18.672 | 6.631 | 1.00 | 55.86 | C |
| ATOM | 3835 | CB | LYS | A | 464 | 4.630 | −17.324 | 7.209 | 1.00 | 56.28 | C |
| ATOM | 3838 | CG | LYS | A | 464 | 3.121 | −17.253 | 7.565 | 1.00 | 58.04 | C |
| ATOM | 3841 | CD | LYS | A | 464 | 2.672 | −15.827 | 8.009 | 1.00 | 60.49 | C |
| ATOM | 3844 | CE | LYS | A | 464 | 1.194 | −15.810 | 8.509 | 1.00 | 62.97 | C |
| ATOM | 3847 | NZ | LYS | A | 464 | 0.561 | −14.437 | 8.612 | 1.00 | 63.20 | N |
| ATOM | 3851 | C | LYS | A | 464 | 6.387 | −18.448 | 5.846 | 1.00 | 55.30 | C |
| ATOM | 3852 | O | LYS | A | 464 | 6.339 | −18.187 | 4.659 | 1.00 | 56.07 | O |
| ATOM | 3854 | N | LYS | A | 465 | 7.538 | −18.553 | 6.501 | 1.00 | 54.46 | N |
| ATOM | 3855 | CA | LYS | A | 465 | 8.811 | −18.250 | 5.828 | 1.00 | 53.72 | C |
| ATOM | 3857 | CB | LYS | A | 465 | 9.857 | −17.751 | 6.842 | 1.00 | 54.01 | C |
| ATOM | 3860 | CG | LYS | A | 465 | 9.795 | −16.201 | 7.084 | 1.00 | 55.87 | C |
| ATOM | 3863 | CD | LYS | A | 465 | 9.944 | −15.840 | 8.581 | 1.00 | 58.67 | C |
| ATOM | 3866 | CE | LYS | A | 465 | 10.260 | −14.350 | 8.860 | 1.00 | 57.68 | C |
| ATOM | 3869 | NZ | LYS | A | 465 | 10.588 | −14.212 | 10.311 | 1.00 | 57.74 | N |
| ATOM | 3873 | C | LYS | A | 465 | 9.326 | −19.428 | 4.987 | 1.00 | 52.49 | C |

TABLE 2-continued

| | | | | | | | | | | |
|---|---|---|---|---|---|---|---|---|---|---|
| ATOM | 3874 | O | LYS | A | 465 | 10.194 | −19.237 | 4.119 | 1.00 | 51.40 | O |
| ATOM | 3876 | N | LEU | A | 466 | 8.768 | −20.624 | 5.226 | 1.00 | 50.63 | N |
| ATOM | 3877 | CA | LEU | A | 466 | 9.101 | −21.806 | 4.436 | 1.00 | 49.58 | C |
| ATOM | 3879 | CB | LEU | A | 466 | 9.087 | −23.089 | 5.287 | 1.00 | 49.23 | C |
| ATOM | 3882 | CG | LEU | A | 466 | 10.213 | −23.203 | 6.313 | 1.00 | 48.53 | C |
| ATOM | 3884 | CD1 | LEU | A | 466 | 9.963 | −24.308 | 7.293 | 1.00 | 48.55 | C |
| ATOM | 3888 | CD2 | LEU | A | 466 | 11.526 | −23.424 | 5.651 | 1.00 | 48.08 | C |
| ATOM | 3892 | C | LEU | A | 466 | 8.151 | −21.944 | 3.256 | 1.00 | 49.24 | C |
| ATOM | 3893 | O | LEU | A | 466 | 8.546 | −22.426 | 2.181 | 1.00 | 48.61 | O |
| ATOM | 3895 | N | LEU | A | 467 | 6.905 | −21.513 | 3.436 | 1.00 | 48.81 | N |
| ATOM | 3896 | CA | LEU | A | 467 | 5.935 | −21.594 | 2.361 | 1.00 | 48.58 | C |
| ATOM | 3898 | CB | LEU | A | 467 | 4.551 | −21.966 | 2.901 | 1.00 | 48.50 | C |
| ATOM | 3901 | CG | LEU | A | 467 | 4.379 | −23.326 | 3.599 | 1.00 | 48.69 | C |
| ATOM | 3903 | CD1 | LEU | A | 467 | 2.907 | −23.533 | 3.954 | 1.00 | 47.86 | C |
| ATOM | 3907 | CD2 | LEU | A | 467 | 4.860 | −24.500 | 2.770 | 1.00 | 46.46 | C |
| ATOM | 3911 | C | LEU | A | 467 | 5.926 | −20.279 | 1.583 | 1.00 | 48.49 | C |
| ATOM | 3912 | O | LEU | A | 467 | 4.879 | −19.673 | 1.380 | 1.00 | 48.93 | O |
| ATOM | 3914 | N | VAL | A | 468 | 7.109 | −19.863 | 1.132 | 1.00 | 48.45 | N |
| ATOM | 3915 | CA | VAL | A | 468 | 7.279 | −18.721 | 0.251 | 1.00 | 48.04 | C |
| ATOM | 3917 | CB | VAL | A | 468 | 8.515 | −17.865 | 0.654 | 1.00 | 48.13 | C |
| ATOM | 3919 | CG1 | VAL | A | 468 | 8.954 | −16.935 | −0.505 | 1.00 | 47.61 | C |
| ATOM | 3923 | CG2 | VAL | A | 468 | 8.218 | −17.082 | 1.914 | 1.00 | 46.10 | C |
| ATOM | 3927 | C | VAL | A | 468 | 7.462 | −19.201 | −1.175 | 1.00 | 48.34 | C |
| ATOM | 3928 | O | VAL | A | 468 | 8.329 | −20.017 | −1.458 | 1.00 | 48.69 | O |
| ATOM | 3930 | N | VAL | A | 469 | 6.678 | −18.621 | −2.072 | 1.00 | 48.54 | N |
| ATOM | 3931 | CA | VAL | A | 469 | 6.613 | −19.004 | −3.475 | 1.00 | 48.12 | C |
| ATOM | 3933 | CB | VAL | A | 469 | 5.482 | −18.191 | −4.166 | 1.00 | 48.00 | C |
| ATOM | 3935 | CG1 | VAL | A | 469 | 5.635 | −18.162 | −5.673 | 1.00 | 45.59 | C |
| ATOM | 3939 | CG2 | VAL | A | 469 | 4.118 | −18.783 | −3.726 | 1.00 | 47.99 | C |
| ATOM | 3943 | C | VAL | A | 469 | 7.941 | −18.846 | −4.206 | 1.00 | 48.45 | C |
| ATOM | 3944 | O | VAL | A | 469 | 8.299 | −19.681 | −5.053 | 1.00 | 49.04 | O |
| ATOM | 3946 | N | ASP | A | 470 | 8.668 | −17.787 | −3.879 | 1.00 | 47.94 | N |
| ATOM | 3947 | CA | ASP | A | 470 | 9.948 | −17.471 | −4.528 | 1.00 | 47.53 | C |
| ATOM | 3949 | CB | ASP | A | 470 | 10.259 | −15.998 | −4.266 | 1.00 | 47.37 | C |
| ATOM | 3952 | CG | ASP | A | 470 | 11.530 | −15.552 | −4.880 | 1.00 | 47.86 | C |
| ATOM | 3953 | OD1 | ASP | A | 470 | 12.318 | −16.359 | −5.405 | 1.00 | 50.10 | O |
| ATOM | 3954 | OD2 | ASP | A | 470 | 11.754 | −14.340 | −4.842 | 1.00 | 54.22 | O |
| ATOM | 3955 | C | ASP | A | 470 | 11.084 | −18.318 | −3.937 | 1.00 | 47.15 | C |
| ATOM | 3956 | O | ASP | A | 470 | 11.487 | −18.091 | −2.799 | 1.00 | 46.88 | O |
| ATOM | 3958 | N | PRO | A | 471 | 11.638 | −19.256 | −4.721 | 1.00 | 46.92 | N |
| ATOM | 3959 | CA | PRO | A | 471 | 12.618 | −20.176 | −4.132 | 1.00 | 46.91 | C |
| ATOM | 3961 | CB | PRO | A | 471 | 12.965 | −21.144 | −5.286 | 1.00 | 47.03 | C |
| ATOM | 3964 | CG | PRO | A | 471 | 12.547 | −20.457 | −6.549 | 1.00 | 47.10 | C |
| ATOM | 3967 | CD | PRO | A | 471 | 11.489 | −19.436 | −6.181 | 1.00 | 47.26 | C |
| ATOM | 3970 | C | PRO | A | 471 | 13.868 | −19.475 | −3.584 | 1.00 | 47.02 | C |
| ATOM | 3971 | O | PRO | A | 471 | 14.478 | −19.987 | −2.638 | 1.00 | 47.05 | O |
| ATOM | 3972 | N | LYS | A | 472 | 14.229 | −18.320 | −4.155 | 1.00 | 46.81 | N |
| ATOM | 3973 | CA | LYS | A | 472 | 15.402 | −17.575 | −3.718 | 1.00 | 46.47 | C |
| ATOM | 3975 | CB | LYS | A | 472 | 15.877 | −16.588 | −4.779 | 1.00 | 46.68 | C |
| ATOM | 3978 | CG | LYS | A | 472 | 16.300 | −17.258 | −6.066 | 1.00 | 48.98 | C |
| ATOM | 3981 | CD | LYS | A | 472 | 16.899 | −16.286 | −7.067 | 1.00 | 49.15 | C |
| ATOM | 3984 | CE | LYS | A | 472 | 18.319 | −15.960 | −6.668 | 1.00 | 51.37 | C |
| ATOM | 3987 | NZ | LYS | A | 472 | 19.011 | −15.193 | −7.758 | 1.00 | 53.15 | N |
| ATOM | 3991 | C | LYS | A | 472 | 15.143 | −16.826 | −2.440 | 1.00 | 45.81 | C |
| ATOM | 3992 | O | LYS | A | 472 | 16.080 | −16.585 | −1.704 | 1.00 | 46.33 | O |
| ATOM | 3994 | N | ALA | A | 473 | 13.898 | −16.456 | −2.166 | 1.00 | 45.22 | N |
| ATOM | 3995 | CA | ALA | A | 473 | 13.549 | −15.822 | −0.887 | 1.00 | 44.97 | C |
| ATOM | 3997 | CB | ALA | A | 473 | 12.351 | −14.869 | −1.060 | 1.00 | 44.55 | C |
| ATOM | 4001 | C | ALA | A | 473 | 13.230 | −16.870 | 0.181 | 1.00 | 44.94 | C |
| ATOM | 4002 | O | ALA | A | 473 | 13.308 | −16.595 | 1.367 | 1.00 | 45.69 | O |
| ATOM | 4004 | N | ARG | A | 474 | 12.874 | −18.086 | −0.226 | 1.00 | 44.43 | N |
| ATOM | 4005 | CA | ARG | A | 474 | 12.497 | −19.110 | 0.746 | 1.00 | 43.55 | C |
| ATOM | 4007 | CB | ARG | A | 474 | 12.221 | −20.452 | 0.045 | 1.00 | 43.23 | C |
| ATOM | 4010 | CG | ARG | A | 474 | 11.536 | −21.478 | 0.938 | 1.00 | 43.06 | C |
| ATOM | 4013 | CD | ARG | A | 474 | 10.890 | −22.654 | 0.169 | 1.00 | 45.19 | C |
| ATOM | 4016 | NE | ARG | A | 474 | 10.131 | −22.211 | −1.004 | 1.00 | 44.70 | N |
| ATOM | 4018 | CZ | ARG | A | 474 | 10.290 | −22.677 | −2.236 | 1.00 | 45.05 | C |
| ATOM | 4019 | NH1 | ARG | A | 474 | 11.139 | −23.674 | −2.509 | 1.00 | 45.04 | N |
| ATOM | 4022 | NH2 | ARG | A | 474 | 9.569 | −22.152 | −3.206 | 1.00 | 45.27 | N |
| ATOM | 4025 | C | ARG | A | 474 | 13.575 | −19.305 | 1.794 | 1.00 | 43.28 | C |
| ATOM | 4026 | O | ARG | A | 474 | 14.768 | −19.237 | 1.494 | 1.00 | 42.80 | O |
| ATOM | 4028 | N | PHE | A | 475 | 13.153 | −19.605 | 3.011 | 1.00 | 43.08 | N |
| ATOM | 4029 | CA | PHE | A | 475 | 14.090 | −19.913 | 4.062 | 1.00 | 43.61 | C |
| ATOM | 4031 | CB | PHE | A | 475 | 13.376 | −20.060 | 5.412 | 1.00 | 43.68 | C |
| ATOM | 4034 | CG | PHE | A | 475 | 13.542 | −18.865 | 6.330 | 1.00 | 45.19 | C |
| ATOM | 4035 | CD1 | PHE | A | 475 | 13.550 | −17.550 | 5.831 | 1.00 | 47.37 | C |
| ATOM | 4037 | CE1 | PHE | A | 475 | 13.701 | −16.443 | 6.707 | 1.00 | 47.15 | C |
| ATOM | 4039 | CZ | PHE | A | 475 | 13.850 | −16.652 | 8.071 | 1.00 | 45.77 | C |
| ATOM | 4041 | CE2 | PHE | A | 475 | 13.845 | −17.942 | 8.576 | 1.00 | 46.83 | C |
| ATOM | 4043 | CD2 | PHE | A | 475 | 13.682 | −19.045 | 7.709 | 1.00 | 47.18 | C |

TABLE 2-continued

| ATOM | 4045 | C | PHE | A | 475 | 14.941 | −21.147 | 3.758 | 1.00 | 44.21 | C |
|---|---|---|---|---|---|---|---|---|---|---|---|
| ATOM | 4046 | O | PHE | A | 475 | 14.459 | −22.188 | 3.267 | 1.00 | 43.61 | O |
| ATOM | 4048 | N | THR | A | 476 | 16.231 | −21.012 | 4.046 | 1.00 | 44.74 | N |
| ATOM | 4049 | CA | THR | A | 476 | 17.126 | −22.150 | 3.984 | 1.00 | 45.20 | C |
| ATOM | 4051 | CB | THR | A | 476 | 18.583 | −21.716 | 3.838 | 1.00 | 45.28 | C |
| ATOM | 4053 | OG1 | THR | A | 476 | 18.951 | −20.951 | 4.996 | 1.00 | 44.24 | O |
| ATOM | 4055 | CG2 | THR | A | 476 | 18.766 | −20.917 | 2.554 | 1.00 | 42.77 | C |
| ATOM | 4059 | C | THR | A | 476 | 16.975 | −22.926 | 5.280 | 1.00 | 46.22 | C |
| ATOM | 4060 | O | THR | A | 476 | 16.265 | −22.493 | 6.186 | 1.00 | 46.18 | O |
| ATOM | 4062 | N | THR | A | 477 | 17.618 | −24.088 | 5.351 | 1.00 | 47.15 | N |
| ATOM | 4063 | CA | THR | A | 477 | 17.693 | −24.842 | 6.586 | 1.00 | 48.13 | C |
| ATOM | 4065 | CB | THR | A | 477 | 18.396 | −26.216 | 6.390 | 1.00 | 48.11 | C |
| ATOM | 4067 | OG1 | THR | A | 477 | 19.559 | −26.053 | 5.570 | 1.00 | 49.36 | O |
| ATOM | 4069 | CG2 | THR | A | 477 | 17.490 | −27.200 | 5.695 | 1.00 | 47.76 | C |
| ATOM | 4073 | C | THR | A | 477 | 18.418 | −23.991 | 7.628 | 1.00 | 49.12 | C |
| ATOM | 4074 | O | THR | A | 477 | 17.972 | −23.893 | 8.757 | 1.00 | 49.32 | O |
| ATOM | 4076 | N | GLU | A | 478 | 19.506 | −23.331 | 7.248 | 1.00 | 50.57 | N |
| ATOM | 4077 | CA | GLU | A | 478 | 20.275 | −22.532 | 8.225 | 1.00 | 51.68 | C |
| ATOM | 4079 | CB | GLU | A | 478 | 21.537 | −21.917 | 7.591 | 1.00 | 52.02 | C |
| ATOM | 4082 | CG | GLU | A | 478 | 22.740 | −22.885 | 7.418 | 1.00 | 54.69 | C |
| ATOM | 4085 | CD | GLU | A | 478 | 22.641 | −23.882 | 6.200 | 1.00 | 59.11 | C |
| ATOM | 4086 | OE1 | GLU | A | 478 | 21.904 | −23.604 | 5.199 | 1.00 | 57.86 | O |
| ATOM | 4087 | OE2 | GLU | A | 478 | 23.324 | −24.958 | 6.280 | 1.00 | 59.87 | O |
| ATOM | 4088 | C | GLU | A | 478 | 19.396 | −21.444 | 8.879 | 1.00 | 51.84 | C |
| ATOM | 4089 | O | GLU | A | 478 | 19.387 | −21.293 | 10.110 | 1.00 | 51.67 | O |
| ATOM | 4091 | N | GLU | A | 479 | 18.641 | −20.724 | 8.047 | 1.00 | 51.84 | N |
| ATOM | 4092 | CA | GLU | A | 479 | 17.715 | −19.689 | 8.519 | 1.00 | 51.52 | C |
| ATOM | 4094 | CB | GLU | A | 479 | 17.113 | −18.953 | 7.336 | 1.00 | 51.17 | C |
| ATOM | 4097 | CG | GLU | A | 479 | 18.121 | −18.153 | 6.488 | 1.00 | 51.34 | C |
| ATOM | 4100 | CD | GLU | A | 479 | 17.453 | −17.515 | 5.282 | 1.00 | 52.15 | C |
| ATOM | 4101 | OE1 | GLU | A | 479 | 17.025 | −18.244 | 4.356 | 1.00 | 50.84 | O |
| ATOM | 4102 | OE2 | GLU | A | 479 | 17.319 | −16.279 | 5.280 | 1.00 | 52.68 | O |
| ATOM | 4103 | C | GLU | A | 479 | 16.584 | −20.238 | 9.398 | 1.00 | 52.20 | C |
| ATOM | 4104 | O | GLU | A | 479 | 16.100 | −19.532 | 10.300 | 1.00 | 52.47 | O |
| ATOM | 4106 | N | ALA | A | 480 | 16.151 | −21.473 | 9.128 | 1.00 | 52.01 | N |
| ATOM | 4107 | CA | ALA | A | 480 | 15.097 | −22.106 | 9.914 | 1.00 | 52.26 | C |
| ATOM | 4109 | CB | ALA | A | 480 | 14.598 | −23.356 | 9.227 | 1.00 | 51.60 | C |
| ATOM | 4113 | C | ALA | A | 480 | 15.634 | −22.448 | 11.304 | 1.00 | 53.02 | C |
| ATOM | 4114 | O | ALA | A | 480 | 14.976 | −22.224 | 12.320 | 1.00 | 52.62 | O |
| ATOM | 4116 | N | LEU | A | 481 | 16.848 | −22.981 | 11.321 | 1.00 | 54.43 | N |
| ATOM | 4117 | CA | LEU | A | 481 | 17.526 | −23.421 | 12.540 | 1.00 | 55.43 | C |
| ATOM | 4119 | CB | LEU | A | 481 | 18.855 | −24.097 | 12.179 | 1.00 | 54.98 | C |
| ATOM | 4122 | CG | LEU | A | 481 | 19.001 | −25.614 | 12.189 | 1.00 | 54.85 | C |
| ATOM | 4124 | CD1 | LEU | A | 481 | 17.706 | −26.346 | 12.368 | 1.00 | 55.30 | C |
| ATOM | 4128 | CD2 | LEU | A | 481 | 19.727 | −26.066 | 10.926 | 1.00 | 54.39 | C |
| ATOM | 4132 | C | LEU | A | 481 | 17.802 | −22.257 | 13.494 | 1.00 | 57.12 | C |
| ATOM | 4133 | O | LEU | A | 481 | 17.926 | −22.479 | 14.708 | 1.00 | 57.74 | O |
| ATOM | 4135 | N | ARG | A | 482 | 17.921 | −21.041 | 12.943 | 1.00 | 58.35 | N |
| ATOM | 4136 | CA | ARG | A | 482 | 18.126 | −19.820 | 13.734 | 1.00 | 59.67 | C |
| ATOM | 4138 | CB | ARG | A | 482 | 19.108 | −18.889 | 13.036 | 1.00 | 59.60 | C |
| ATOM | 4141 | CG | ARG | A | 482 | 20.494 | −19.484 | 12.938 | 1.00 | 62.22 | C |
| ATOM | 4144 | CD | ARG | A | 482 | 21.452 | −18.444 | 12.468 | 1.00 | 65.02 | C |
| ATOM | 4147 | NE | ARG | A | 482 | 20.943 | −17.800 | 11.258 | 1.00 | 68.45 | N |
| ATOM | 4149 | CZ | ARG | A | 482 | 21.459 | −17.936 | 10.031 | 1.00 | 71.42 | C |
| ATOM | 4150 | NH1 | ARG | A | 482 | 22.546 | −18.691 | 9.804 | 1.00 | 72.48 | N |
| ATOM | 4153 | NH2 | ARG | A | 482 | 20.891 | −17.285 | 9.016 | 1.00 | 71.66 | N |
| ATOM | 4156 | C | ARG | A | 482 | 16.845 | −19.030 | 14.003 | 1.00 | 60.27 | C |
| ATOM | 4157 | O | ARG | A | 482 | 16.874 | −18.029 | 14.716 | 1.00 | 61.13 | O |
| ATOM | 4159 | N | HIS | A | 483 | 15.729 | −19.450 | 13.429 | 1.00 | 60.43 | N |
| ATOM | 4160 | CA | HIS | A | 483 | 14.482 | −18.781 | 13.708 | 1.00 | 60.79 | C |
| ATOM | 4162 | CB | HIS | A | 483 | 13.373 | −19.438 | 12.905 | 1.00 | 60.56 | C |
| ATOM | 4165 | CG | HIS | A | 483 | 12.052 | −18.755 | 13.024 | 1.00 | 59.44 | C |
| ATOM | 4166 | ND1 | HIS | A | 483 | 11.186 | −18.997 | 14.066 | 1.00 | 59.23 | N |
| ATOM | 4168 | CE1 | HIS | A | 483 | 10.094 | −18.269 | 13.907 | 1.00 | 58.54 | C |
| ATOM | 4170 | NE2 | HIS | A | 483 | 10.219 | −17.570 | 12.794 | 1.00 | 57.64 | N |
| ATOM | 4172 | CD2 | HIS | A | 483 | 11.438 | −17.853 | 12.224 | 1.00 | 58.36 | C |
| ATOM | 4174 | C | HIS | A | 483 | 14.179 | −18.831 | 15.224 | 1.00 | 61.36 | C |
| ATOM | 4175 | O | HIS | A | 483 | 14.520 | −19.803 | 15.902 | 1.00 | 61.83 | O |
| ATOM | 4177 | N | PRO | A | 484 | 13.542 | −17.782 | 15.763 | 1.00 | 61.94 | N |
| ATOM | 4178 | CA | PRO | A | 484 | 13.269 | −17.769 | 17.207 | 1.00 | 62.22 | C |
| ATOM | 4180 | CB | PRO | A | 484 | 12.334 | −16.564 | 17.370 | 1.00 | 62.15 | C |
| ATOM | 4183 | CG | PRO | A | 484 | 12.697 | −15.662 | 16.260 | 1.00 | 61.97 | C |
| ATOM | 4186 | CD | PRO | A | 484 | 13.093 | −16.534 | 15.110 | 1.00 | 61.87 | C |
| ATOM | 4189 | C | PRO | A | 484 | 12.588 | −19.027 | 17.737 | 1.00 | 62.57 | C |
| ATOM | 4190 | O | PRO | A | 484 | 12.895 | −19.466 | 18.840 | 1.00 | 62.82 | O |
| ATOM | 4191 | N | TRP | A | 485 | 11.696 | −19.613 | 16.943 | 1.00 | 62.90 | N |
| ATOM | 4192 | CA | TRP | A | 485 | 10.934 | −20.777 | 17.370 | 1.00 | 63.04 | C |
| ATOM | 4194 | CB | TRP | A | 485 | 9.919 | −21.171 | 16.311 | 1.00 | 62.97 | C |
| ATOM | 4197 | CG | TRP | A | 485 | 8.954 | −22.214 | 16.777 | 1.00 | 63.14 | C |
| ATOM | 4198 | CD1 | TRP | A | 485 | 8.060 | −22.098 | 17.796 | 1.00 | 63.77 | C |

TABLE 2-continued

| | | | | | | | | | | |
|---|---|---|---|---|---|---|---|---|---|---|
| ATOM | 4200 | NE1 | TRP | A | 485 | 7.319 | −23.257 | 17.921 | 1.00 | 62.72 | N |
| ATOM | 4202 | CE2 | TRP | A | 485 | 7.746 | −24.155 | 16.979 | 1.00 | 62.42 | C |
| ATOM | 4203 | CD2 | TRP | A | 485 | 8.774 | −23.532 | 16.235 | 1.00 | 62.66 | C |
| ATOM | 4204 | CE3 | TRP | A | 485 | 9.373 | −24.241 | 15.193 | 1.00 | 61.41 | C |
| ATOM | 4206 | CZ3 | TRP | A | 485 | 8.938 | −25.526 | 14.933 | 1.00 | 61.04 | C |
| ATOM | 4208 | CH2 | TRP | A | 485 | 7.916 | −26.118 | 15.696 | 1.00 | 61.02 | C |
| ATOM | 4210 | CZ2 | TRP | A | 485 | 7.311 | −25.448 | 16.715 | 1.00 | 61.19 | C |
| ATOM | 4212 | C | TRP | A | 485 | 11.785 | −21.987 | 17.689 | 1.00 | 63.38 | C |
| ATOM | 4213 | O | TRP | A | 485 | 11.326 | −22.898 | 18.370 | 1.00 | 63.58 | O |
| ATOM | 4215 | N | LEU | A | 486 | 13.009 | −22.017 | 17.186 | 1.00 | 64.01 | N |
| ATOM | 4216 | CA | LEU | A | 486 | 13.902 | −23.160 | 17.435 | 1.00 | 64.66 | C |
| ATOM | 4218 | CB | LEU | A | 486 | 14.529 | −23.648 | 16.107 | 1.00 | 64.75 | C |
| ATOM | 4221 | CG | LEU | A | 486 | 13.598 | −24.560 | 15.304 | 1.00 | 64.10 | C |
| ATOM | 4223 | CD1 | LEU | A | 486 | 13.717 | −24.300 | 13.846 | 1.00 | 64.50 | C |
| ATOM | 4227 | CD2 | LEU | A | 486 | 13.890 | −26.009 | 15.607 | 1.00 | 64.61 | C |
| ATOM | 4231 | C | LEU | A | 486 | 14.990 | −22.849 | 18.459 | 1.00 | 64.90 | C |
| ATOM | 4232 | O | LEU | A | 486 | 15.809 | −23.704 | 18.769 | 1.00 | 64.60 | O |
| ATOM | 4234 | N | GLN | A | 487 | 15.004 | −21.624 | 18.968 | 1.00 | 65.83 | N |
| ATOM | 4235 | CA | GLN | A | 487 | 15.932 | −21.242 | 20.030 | 1.00 | 66.59 | C |
| ATOM | 4237 | CB | GLN | A | 487 | 16.223 | −19.732 | 19.979 | 1.00 | 66.60 | C |
| ATOM | 4240 | CG | GLN | A | 487 | 16.773 | −19.243 | 18.639 | 1.00 | 67.73 | C |
| ATOM | 4243 | CD | GLN | A | 487 | 17.667 | −20.268 | 17.945 | 1.00 | 69.74 | C |
| ATOM | 4244 | OE1 | GLN | A | 487 | 17.422 | −20.647 | 16.798 | 1.00 | 72.17 | O |
| ATOM | 4245 | NE2 | GLN | A | 487 | 18.685 | −20.738 | 18.646 | 1.00 | 70.27 | N |
| ATOM | 4248 | C | GLN | A | 487 | 15.295 | −21.657 | 21.352 | 1.00 | 66.71 | C |
| ATOM | 4249 | O | GLN | A | 487 | 14.732 | −20.844 | 22.075 | 1.00 | 66.47 | O |
| ATOM | 4251 | N | ASP | A | 488 | 15.361 | −22.948 | 21.629 | 1.00 | 67.26 | N |
| ATOM | 4252 | CA | ASP | A | 488 | 14.606 | −23.547 | 22.717 | 1.00 | 68.10 | C |
| ATOM | 4254 | CB | ASP | A | 488 | 13.277 | −24.113 | 22.207 | 1.00 | 67.46 | C |
| ATOM | 4257 | CG | ASP | A | 488 | 12.577 | −24.967 | 23.238 | 1.00 | 66.84 | C |
| ATOM | 4258 | OD1 | ASP | A | 488 | 13.278 | −25.497 | 24.133 | 1.00 | 67.27 | O |
| ATOM | 4259 | OD2 | ASP | A | 488 | 11.334 | −25.125 | 23.158 | 1.00 | 63.47 | O |
| ATOM | 4260 | C | ASP | A | 488 | 15.469 | −24.626 | 23.346 | 1.00 | 69.19 | C |
| ATOM | 4261 | O | ASP | A | 488 | 15.568 | −25.750 | 22.830 | 1.00 | 70.05 | O |
| ATOM | 4263 | N | GLU | A | 489 | 16.090 | −24.279 | 24.469 | 1.00 | 70.21 | N |
| ATOM | 4264 | CA | GLU | A | 489 | 17.151 | −25.106 | 25.056 | 1.00 | 70.94 | C |
| ATOM | 4266 | CB | GLU | A | 489 | 17.942 | −24.281 | 26.060 | 1.00 | 71.59 | C |
| ATOM | 4269 | CG | GLU | A | 489 | 18.630 | −23.100 | 25.374 | 1.00 | 74.55 | C |
| ATOM | 4272 | CD | GLU | A | 489 | 19.389 | −23.531 | 24.118 | 1.00 | 77.87 | C |
| ATOM | 4273 | OE1 | GLU | A | 489 | 20.248 | −24.441 | 24.254 | 1.00 | 80.21 | O |
| ATOM | 4274 | OE2 | GLU | A | 489 | 19.115 | −22.987 | 23.007 | 1.00 | 79.77 | O |
| ATOM | 4275 | C | GLU | A | 489 | 16.674 | −26.402 | 25.683 | 1.00 | 70.35 | C |
| ATOM | 4276 | O | GLU | A | 489 | 17.454 | −27.348 | 25.816 | 1.00 | 70.28 | O |
| ATOM | 4278 | N | ASP | A | 490 | 15.396 | −26.452 | 26.038 | 1.00 | 69.71 | N |
| ATOM | 4279 | CA | ASP | A | 490 | 14.819 | −27.667 | 26.576 | 1.00 | 69.50 | C |
| ATOM | 4281 | CB | ASP | A | 490 | 13.514 | −27.366 | 27.286 | 1.00 | 69.80 | C |
| ATOM | 4284 | CG | ASP | A | 490 | 13.740 | −26.850 | 28.669 | 1.00 | 70.54 | C |
| ATOM | 4285 | OD1 | ASP | A | 490 | 14.854 | −27.113 | 29.212 | 1.00 | 68.71 | O |
| ATOM | 4286 | OD2 | ASP | A | 490 | 12.809 | −26.183 | 29.189 | 1.00 | 71.34 | O |
| ATOM | 4287 | C | ASP | A | 490 | 14.565 | −28.687 | 25.514 | 1.00 | 68.81 | C |
| ATOM | 4288 | O | ASP | A | 490 | 14.719 | −29.892 | 25.755 | 1.00 | 68.52 | O |
| ATOM | 4290 | N | MET | A | 491 | 14.138 | −28.202 | 24.349 | 1.00 | 68.04 | N |
| ATOM | 4291 | CA | MET | A | 491 | 13.960 | −29.065 | 23.187 | 1.00 | 67.04 | C |
| ATOM | 4293 | CB | MET | A | 491 | 13.291 | −28.294 | 22.041 | 1.00 | 66.35 | C |
| ATOM | 4296 | CG | MET | A | 491 | 13.141 | −29.089 | 20.745 | 1.00 | 64.41 | C |
| ATOM | 4299 | SD | MET | A | 491 | 14.660 | −29.085 | 19.787 | 1.00 | 58.47 | S |
| ATOM | 4300 | CE | MET | A | 491 | 14.641 | −27.415 | 19.143 | 1.00 | 54.91 | C |
| ATOM | 4304 | C | MET | A | 491 | 15.328 | −29.648 | 22.789 | 1.00 | 67.12 | C |
| ATOM | 4305 | O | MET | A | 491 | 15.471 | −30.876 | 22.678 | 1.00 | 65.64 | O |
| ATOM | 4307 | N | LYS | A | 492 | 16.326 | −28.772 | 22.626 | 1.00 | 67.40 | N |
| ATOM | 4308 | CA | LYS | A | 492 | 17.682 | −29.212 | 22.272 | 1.00 | 68.42 | C |
| ATOM | 4310 | CB | LYS | A | 492 | 18.628 | −28.025 | 22.089 | 1.00 | 68.08 | C |
| ATOM | 4313 | CG | LYS | A | 492 | 18.265 | −27.206 | 20.845 | 1.00 | 68.30 | C |
| ATOM | 4316 | CD | LYS | A | 492 | 19.314 | −26.175 | 20.455 | 1.00 | 68.05 | C |
| ATOM | 4319 | CE | LYS | A | 492 | 18.899 | −25.394 | 19.209 | 1.00 | 67.32 | C |
| ATOM | 4322 | NZ | LYS | A | 492 | 19.448 | −24.017 | 19.226 | 1.00 | 66.78 | N |
| ATOM | 4326 | C | LYS | A | 492 | 18.252 | −30.226 | 23.261 | 1.00 | 69.48 | C |
| ATOM | 4327 | O | LYS | A | 492 | 18.806 | −31.260 | 22.835 | 1.00 | 70.01 | O |
| ATOM | 4329 | N | ARG | A | 493 | 18.078 | −29.968 | 24.564 | 1.00 | 70.30 | N |
| ATOM | 4330 | CA | ARG | A | 493 | 18.545 | −30.904 | 25.587 | 1.00 | 70.84 | C |
| ATOM | 4332 | CB | ARG | A | 493 | 18.272 | −30.394 | 27.000 | 1.00 | 71.56 | C |
| ATOM | 4335 | CG | ARG | A | 493 | 19.413 | −29.581 | 27.588 | 1.00 | 73.55 | C |
| ATOM | 4338 | CD | ARG | A | 493 | 19.540 | −29.831 | 29.088 | 1.00 | 76.82 | C |
| ATOM | 4341 | NE | ARG | A | 493 | 20.205 | −31.112 | 29.363 | 1.00 | 79.27 | N |
| ATOM | 4343 | CZ | ARG | A | 493 | 20.367 | −31.651 | 30.575 | 1.00 | 79.48 | C |
| ATOM | 4344 | NH1 | ARG | A | 493 | 19.896 | −31.037 | 31.665 | 1.00 | 79.97 | N |
| ATOM | 4347 | NH2 | ARG | A | 493 | 20.989 | −32.827 | 30.694 | 1.00 | 78.56 | N |
| ATOM | 4350 | C | ARG | A | 493 | 17.890 | −32.252 | 25.412 | 1.00 | 70.38 | C |
| ATOM | 4351 | O | ARG | A | 493 | 18.574 | −33.265 | 25.283 | 1.00 | 70.23 | O |
| ATOM | 4353 | N | LYS | A | 494 | 16.563 | −32.255 | 25.402 | 1.00 | 70.30 | N |

TABLE 2-continued

| | | | | | | | | | | |
|---|---|---|---|---|---|---|---|---|---|---|
| ATOM | 4354 | CA | LYS | A | 494 | 15.791 | −33.473 | 25.122 | 1.00 | 70.59 | C |
| ATOM | 4356 | CB | LYS | A | 494 | 14.318 | −33.128 | 24.867 | 1.00 | 70.68 | C |
| ATOM | 4359 | CG | LYS | A | 494 | 13.376 | −34.333 | 24.823 | 1.00 | 72.16 | C |
| ATOM | 4362 | CD | LYS | A | 494 | 12.796 | −34.663 | 26.207 | 1.00 | 74.04 | C |
| ATOM | 4365 | CE | LYS | A | 494 | 12.669 | −36.183 | 26.412 | 1.00 | 74.64 | C |
| ATOM | 4368 | NZ | LYS | A | 494 | 11.931 | −36.568 | 27.647 | 1.00 | 74.04 | N |
| ATOM | 4372 | C | LYS | A | 494 | 16.379 | −34.247 | 23.928 | 1.00 | 70.62 | C |
| ATOM | 4373 | O | LYS | A | 494 | 16.455 | −35.485 | 23.960 | 1.00 | 70.72 | O |
| ATOM | 4375 | N | PHE | A | 495 | 16.812 | −33.510 | 22.895 | 1.00 | 70.46 | N |
| ATOM | 4376 | CA | PHE | A | 495 | 17.428 | −34.115 | 21.710 | 1.00 | 70.24 | C |
| ATOM | 4378 | CB | PHE | A | 495 | 17.567 | −33.099 | 20.544 | 1.00 | 70.06 | C |
| ATOM | 4381 | CG | PHE | A | 495 | 18.370 | −33.625 | 19.367 | 1.00 | 67.41 | C |
| ATOM | 4382 | CD1 | PHE | A | 495 | 17.906 | −34.706 | 18.621 | 1.00 | 65.85 | C |
| ATOM | 4384 | CE1 | PHE | A | 495 | 18.643 | −35.209 | 17.567 | 1.00 | 65.61 | C |
| ATOM | 4386 | CZ | PHE | A | 495 | 19.863 | −34.617 | 17.243 | 1.00 | 65.54 | C |
| ATOM | 4388 | CE2 | PHE | A | 495 | 20.338 | −33.543 | 17.990 | 1.00 | 64.19 | C |
| ATOM | 4390 | CD2 | PHE | A | 495 | 19.596 | −33.060 | 19.036 | 1.00 | 65.09 | C |
| ATOM | 4392 | C | PHE | A | 495 | 18.782 | −34.740 | 22.045 | 1.00 | 70.63 | C |
| ATOM | 4393 | O | PHE | A | 495 | 18.995 | −35.926 | 21.796 | 1.00 | 69.99 | O |
| ATOM | 4395 | N | GLN | A | 496 | 19.690 | −33.947 | 22.600 | 1.00 | 71.49 | N |
| ATOM | 4396 | CA | GLN | A | 496 | 20.982 | −34.484 | 23.018 | 1.00 | 72.40 | C |
| ATOM | 4398 | CB | GLN | A | 496 | 21.808 | −33.428 | 23.740 | 1.00 | 72.53 | C |
| ATOM | 4401 | CG | GLN | A | 496 | 22.297 | −32.298 | 22.833 | 1.00 | 73.47 | C |
| ATOM | 4404 | CD | GLN | A | 496 | 23.076 | −32.803 | 21.604 | 1.00 | 74.99 | C |
| ATOM | 4405 | OE1 | GLN | A | 496 | 23.763 | −33.825 | 21.650 | 1.00 | 74.06 | O |
| ATOM | 4406 | NE2 | GLN | A | 496 | 22.960 | −32.076 | 20.501 | 1.00 | 75.88 | N |
| ATOM | 4409 | C | GLN | A | 496 | 20.846 | −35.736 | 23.891 | 1.00 | 73.06 | C |
| ATOM | 4410 | O | GLN | A | 496 | 21.618 | −36.677 | 23.724 | 1.00 | 73.38 | O |
| ATOM | 4412 | N | ASP | A | 497 | 19.857 | −35.772 | 24.785 | 1.00 | 73.69 | N |
| ATOM | 4413 | CA | ASP | A | 497 | 19.718 | −36.909 | 25.712 | 1.00 | 74.44 | C |
| ATOM | 4415 | CB | ASP | A | 497 | 18.746 | −36.598 | 26.861 | 1.00 | 74.35 | C |
| ATOM | 4418 | CG | ASP | A | 497 | 19.254 | −35.514 | 27.795 | 1.00 | 74.27 | C |
| ATOM | 4419 | OD1 | ASP | A | 497 | 20.456 | −35.145 | 27.753 | 1.00 | 73.03 | O |
| ATOM | 4420 | OD2 | ASP | A | 497 | 18.421 | −35.018 | 28.578 | 1.00 | 75.36 | O |
| ATOM | 4421 | C | ASP | A | 497 | 19.253 | −38.171 | 25.012 | 1.00 | 74.93 | C |
| ATOM | 4422 | O | ASP | A | 497 | 19.597 | −39.280 | 25.427 | 1.00 | 75.19 | O |
| ATOM | 4424 | N | LEU | A | 498 | 18.446 | −38.002 | 23.973 | 1.00 | 75.54 | N |
| ATOM | 4425 | CA | LEU | A | 498 | 17.981 | −39.128 | 23.170 | 1.00 | 76.01 | C |
| ATOM | 4427 | CB | LEU | A | 498 | 16.849 | −38.671 | 22.253 | 1.00 | 75.95 | C |
| ATOM | 4430 | CG | LEU | A | 498 | 15.551 | −38.314 | 22.975 | 1.00 | 75.90 | C |
| ATOM | 4432 | CD1 | LEU | A | 498 | 14.804 | −37.272 | 22.158 | 1.00 | 75.55 | C |
| ATOM | 4436 | CD2 | LEU | A | 498 | 14.682 | −39.564 | 23.248 | 1.00 | 73.60 | C |
| ATOM | 4440 | C | LEU | A | 498 | 19.112 | −39.720 | 22.338 | 1.00 | 76.40 | C |
| ATOM | 4441 | O | LEU | A | 498 | 19.159 | −40.925 | 22.063 | 1.00 | 75.87 | O |
| ATOM | 4443 | N | LEU | A | 499 | 20.021 | −38.841 | 21.947 | 1.00 | 77.51 | N |
| ATOM | 4444 | CA | LEU | A | 499 | 21.151 | −39.199 | 21.116 | 1.00 | 78.52 | C |
| ATOM | 4446 | CB | LEU | A | 499 | 21.860 | −37.930 | 20.643 | 1.00 | 78.41 | C |
| ATOM | 4449 | CG | LEU | A | 499 | 22.442 | −37.978 | 19.234 | 1.00 | 79.16 | C |
| ATOM | 4451 | CD1 | LEU | A | 499 | 22.830 | −36.554 | 18.820 | 1.00 | 78.37 | C |
| ATOM | 4455 | CD2 | LEU | A | 499 | 23.638 | −38.946 | 19.128 | 1.00 | 78.96 | C |
| ATOM | 4459 | C | LEU | A | 499 | 22.108 | −40.091 | 21.901 | 1.00 | 79.42 | C |
| ATOM | 4460 | O | LEU | A | 499 | 22.387 | −41.228 | 21.490 | 1.00 | 79.48 | O |
| ATOM | 4462 | N | SER | A | 500 | 22.587 | −39.579 | 23.037 | 1.00 | 80.45 | N |
| ATOM | 4463 | CA | SER | A | 500 | 23.525 | −40.323 | 23.882 | 1.00 | 81.37 | C |
| ATOM | 4465 | CB | SER | A | 500 | 24.042 | −39.460 | 25.041 | 1.00 | 81.46 | C |
| ATOM | 4468 | OG | SER | A | 500 | 23.151 | −38.407 | 25.351 | 1.00 | 81.99 | O |
| ATOM | 4470 | C | SER | A | 500 | 22.933 | −41.645 | 24.387 | 1.00 | 81.96 | C |
| ATOM | 4471 | O | SER | A | 500 | 23.653 | −42.636 | 24.519 | 1.00 | 81.83 | O |
| ATOM | 4473 | N | GLU | A | 501 | 21.629 | −41.678 | 24.627 | 1.00 | 82.78 | N |
| ATOM | 4474 | CA | GLU | A | 501 | 20.989 | −42.923 | 25.021 | 1.00 | 83.87 | C |
| ATOM | 4476 | CB | GLU | A | 501 | 19.624 | −42.667 | 25.693 | 1.00 | 84.11 | C |
| ATOM | 4479 | CG | GLU | A | 501 | 18.410 | −42.633 | 24.764 | 1.00 | 85.36 | C |
| ATOM | 4482 | CD | GLU | A | 501 | 17.082 | −42.555 | 25.518 | 1.00 | 86.97 | C |
| ATOM | 4483 | OE1 | GLU | A | 501 | 17.091 | −42.114 | 26.695 | 1.00 | 86.99 | O |
| ATOM | 4484 | OE2 | GLU | A | 501 | 16.034 | −42.932 | 24.928 | 1.00 | 87.22 | O |
| ATOM | 4485 | C | GLU | A | 501 | 20.891 | −43.934 | 23.853 | 1.00 | 84.48 | C |
| ATOM | 4486 | O | GLU | A | 501 | 20.897 | −45.145 | 24.084 | 1.00 | 84.45 | O |
| ATOM | 4488 | N | GLU | A | 502 | 20.806 | −43.460 | 22.610 | 1.00 | 85.32 | N |
| ATOM | 4489 | CA | GLU | A | 502 | 20.843 | −44.384 | 21.464 | 1.00 | 85.98 | C |
| ATOM | 4491 | CB | GLU | A | 502 | 20.445 | −43.697 | 20.148 | 1.00 | 85.98 | C |
| ATOM | 4494 | CG | GLU | A | 502 | 20.202 | −44.689 | 18.964 | 1.00 | 86.01 | C |
| ATOM | 4497 | CD | GLU | A | 502 | 20.561 | −44.115 | 17.577 | 1.00 | 86.02 | C |
| ATOM | 4498 | OE1 | GLU | A | 502 | 21.538 | −43.347 | 17.479 | 1.00 | 85.46 | O |
| ATOM | 4499 | OE2 | GLU | A | 502 | 19.872 | −44.439 | 16.575 | 1.00 | 85.60 | O |
| ATOM | 4500 | C | GLU | A | 502 | 22.226 | −45.034 | 21.296 | 1.00 | 86.54 | C |
| ATOM | 4501 | O | GLU | A | 502 | 22.302 | −46.201 | 20.932 | 1.00 | 86.75 | O |
| ATOM | 4503 | N | ASN | A | 503 | 23.303 | −44.289 | 21.561 | 1.00 | 87.14 | N |
| ATOM | 4504 | CA | ASN | A | 503 | 24.665 | −44.736 | 21.215 | 1.00 | 87.78 | C |
| ATOM | 4506 | CB | ASN | A | 503 | 25.574 | −43.515 | 20.958 | 1.00 | 88.00 | C |
| ATOM | 4509 | CG | ASN | A | 503 | 25.167 | −42.708 | 19.717 | 1.00 | 88.09 | C |

TABLE 2-continued

| | | | | | | | | | | |
|---|---|---|---|---|---|---|---|---|---|---|
| ATOM | 4510 | OD1 | ASN | A | 503 | 24.723 | −43.261 | 18.710 | 1.00 | 87.51 | O |
| ATOM | 4511 | ND2 | ASN | A | 503 | 25.343 | −41.391 | 19.789 | 1.00 | 87.81 | N |
| ATOM | 4514 | C | ASN | A | 503 | 25.358 | −45.676 | 22.239 | 1.00 | 88.06 | C |
| ATOM | 4515 | O | ASN | A | 503 | 25.685 | −45.257 | 23.356 | 1.00 | 87.79 | O |
| ATOM | 4517 | N | GLU | A | 504 | 25.571 | −46.936 | 21.835 | 1.00 | 88.40 | N |
| ATOM | 4518 | CA | GLU | A | 504 | 26.450 | −47.881 | 22.545 | 1.00 | 88.65 | C |
| ATOM | 4520 | CB | GLU | A | 504 | 25.764 | −49.225 | 22.784 | 1.00 | 88.63 | C |
| ATOM | 4523 | CG | GLU | A | 504 | 25.064 | −49.316 | 24.120 | 1.00 | 89.10 | C |
| ATOM | 4526 | CD | GLU | A | 504 | 24.237 | −48.081 | 24.423 | 1.00 | 90.07 | C |
| ATOM | 4527 | OE1 | GLU | A | 504 | 24.810 | −47.100 | 24.941 | 1.00 | 90.54 | O |
| ATOM | 4528 | OE2 | GLU | A | 504 | 23.018 | −48.091 | 24.145 | 1.00 | 89.81 | O |
| ATOM | 4529 | C | GLU | A | 504 | 27.731 | −48.093 | 21.750 | 1.00 | 88.84 | C |
| ATOM | 4530 | O | GLU | A | 504 | 27.715 | −48.698 | 20.677 | 1.00 | 88.58 | O |
| ATOM | 4532 | N | SER | A | 505 | 28.837 | −47.585 | 22.296 | 1.00 | 89.06 | N |
| ATOM | 4533 | CA | SER | A | 505 | 30.137 | −47.689 | 21.653 | 1.00 | 89.31 | C |
| ATOM | 4535 | CB | SER | A | 505 | 30.253 | −46.586 | 20.601 | 1.00 | 89.49 | C |
| ATOM | 4538 | OG | SER | A | 505 | 29.232 | −46.737 | 19.623 | 1.00 | 89.87 | O |
| ATOM | 4540 | C | SER | A | 505 | 31.336 | −47.694 | 22.654 | 1.00 | 89.29 | C |
| ATOM | 4541 | O | SER | A | 505 | 31.157 | −47.640 | 23.877 | 1.00 | 88.82 | O |
| ATOM | 4543 | N | THR | A | 506 | 32.547 | −47.770 | 22.103 | 1.00 | 89.34 | N |
| ATOM | 4544 | CA | THR | A | 506 | 33.741 | −48.215 | 22.829 | 1.00 | 89.44 | C |
| ATOM | 4546 | CB | THR | A | 506 | 34.850 | −48.614 | 21.802 | 1.00 | 89.43 | C |
| ATOM | 4548 | OG1 | THR | A | 506 | 35.013 | −47.569 | 20.837 | 1.00 | 90.10 | O |
| ATOM | 4550 | CG2 | THR | A | 506 | 34.458 | −49.872 | 21.042 | 1.00 | 89.22 | C |
| ATOM | 4554 | C | THR | A | 506 | 34.270 | −47.210 | 23.872 | 1.00 | 89.29 | C |
| ATOM | 4555 | O | THR | A | 506 | 33.873 | −46.043 | 23.879 | 1.00 | 89.59 | O |
| ATOM | 4557 | N | ALA | A | 507 | 35.140 | −47.677 | 24.769 | 1.00 | 89.27 | N |
| ATOM | 4558 | CA | ALA | A | 507 | 35.749 | −46.813 | 25.793 | 1.00 | 89.21 | C |
| ATOM | 4560 | CB | ALA | A | 507 | 36.520 | −47.653 | 26.793 | 1.00 | 88.97 | C |
| ATOM | 4564 | C | ALA | A | 507 | 36.661 | −45.774 | 25.136 | 1.00 | 89.23 | C |
| ATOM | 4565 | O | ALA | A | 507 | 37.346 | −46.097 | 24.174 | 1.00 | 89.23 | O |
| ATOM | 4567 | N | LEU | A | 508 | 36.647 | −44.530 | 25.626 | 1.00 | 89.36 | N |
| ATOM | 4568 | CA | LEU | A | 508 | 37.420 | −43.426 | 25.000 | 1.00 | 89.51 | C |
| ATOM | 4570 | CB | LEU | A | 508 | 36.580 | −42.128 | 24.935 | 1.00 | 89.25 | C |
| ATOM | 4573 | CG | LEU | A | 508 | 35.437 | −42.081 | 23.907 | 1.00 | 88.97 | C |
| ATOM | 4575 | CD1 | LEU | A | 508 | 34.213 | −42.865 | 24.385 | 1.00 | 88.65 | C |
| ATOM | 4579 | CD2 | LEU | A | 508 | 35.033 | −40.659 | 23.584 | 1.00 | 88.54 | C |
| ATOM | 4583 | C | LEU | A | 508 | 38.765 | −43.175 | 25.738 | 1.00 | 89.74 | C |
| ATOM | 4584 | O | LEU | A | 508 | 38.839 | −43.366 | 26.959 | 1.00 | 89.58 | O |
| ATOM | 4586 | N | PRO | A | 509 | 39.832 | −42.756 | 25.006 | 1.00 | 90.02 | N |
| ATOM | 4587 | CA | PRO | A | 509 | 41.123 | −42.594 | 25.694 | 1.00 | 90.13 | C |
| ATOM | 4589 | CB | PRO | A | 509 | 42.074 | −42.158 | 24.574 | 1.00 | 89.89 | C |
| ATOM | 4592 | CG | PRO | A | 509 | 41.489 | −42.754 | 23.368 | 1.00 | 90.03 | C |
| ATOM | 4595 | CD | PRO | A | 509 | 40.000 | −42.630 | 23.545 | 1.00 | 90.03 | C |
| ATOM | 4598 | C | PRO | A | 509 | 41.117 | −41.575 | 26.838 | 1.00 | 90.34 | C |
| ATOM | 4599 | O | PRO | A | 509 | 40.757 | −40.409 | 26.634 | 1.00 | 90.08 | O |
| ATOM | 4600 | N | GLN | A | 510 | 41.481 | −42.065 | 28.031 | 1.00 | 90.54 | N |
| ATOM | 4601 | CA | GLN | A | 510 | 41.797 | −41.251 | 29.211 | 1.00 | 90.53 | C |
| ATOM | 4603 | CB | GLN | A | 510 | 42.883 | −40.218 | 28.871 | 1.00 | 90.54 | C |
| ATOM | 4606 | CG | GLN | A | 510 | 43.648 | −39.669 | 30.081 | 1.00 | 90.88 | C |
| ATOM | 4609 | CD | GLN | A | 510 | 43.070 | −38.366 | 30.640 | 1.00 | 90.95 | C |
| ATOM | 4610 | OE1 | GLN | A | 510 | 42.095 | −37.821 | 30.111 | 1.00 | 91.20 | O |
| ATOM | 4611 | NE2 | GLN | A | 510 | 43.681 | −37.859 | 31.712 | 1.00 | 90.01 | N |
| ATOM | 4614 | C | GLN | A | 510 | 40.565 | −40.582 | 29.799 | 1.00 | 90.23 | C |
| ATOM | 4615 | O | GLN | A | 510 | 39.778 | −39.990 | 29.075 | 1.00 | 89.98 | O |
| ATOM | 4617 | CAL | DRG | X | 1 | 6.858 | −48.885 | 9.748 | 1.00 | 80.66 | C |
| ATOM | 4619 | CBA | DRG | X | 1 | 6.408 | −49.431 | 10.970 | 1.00 | 81.84 | C |
| ATOM | 4620 | CAI | DRG | X | 1 | 5.050 | −49.567 | 11.265 | 1.00 | 82.72 | C |
| ATOM | 4622 | CAF | DRG | X | 1 | 4.647 | −50.113 | 12.490 | 1.00 | 82.95 | C |
| ATOM | 4624 | CAW | DRG | X | 1 | 5.608 | −50.521 | 13.418 | 1.00 | 82.95 | C |
| ATOM | 4625 | CAB | DRG | X | 1 | 5.239 | −51.068 | 14.650 | 1.00 | 82.53 | C |
| ATOM | 4629 | NAP | DRG | X | 1 | 6.912 | −50.377 | 13.120 | 1.00 | 83.45 | N |
| ATOM | 4630 | CBC | DRG | X | 1 | 7.320 | −49.852 | 11.942 | 1.00 | 82.14 | C |
| ATOM | 4631 | CAJ | DRG | X | 1 | 8.675 | −49.739 | 11.690 | 1.00 | 81.02 | C |
| ATOM | 4633 | CAG | DRG | X | 1 | 9.124 | −49.203 | 10.485 | 1.00 | 80.72 | C |
| ATOM | 4635 | CAX | DRG | X | 1 | 8.238 | −48.758 | 9.481 | 1.00 | 80.00 | C |
| ATOM | 4636 | NAR | DRG | X | 1 | 8.652 | −48.231 | 8.279 | 1.00 | 78.44 | N |
| ATOM | 4638 | CAV | DRG | X | 1 | 9.980 | −48.286 | 7.857 | 1.00 | 75.21 | C |
| ATOM | 4639 | OAE | DRG | X | 1 | 10.873 | −48.829 | 8.510 | 1.00 | 74.14 | O |
| ATOM | 4640 | CAZ | DRG | X | 1 | 10.305 | −47.778 | 6.633 | 1.00 | 73.38 | C |
| ATOM | 4641 | NAS | DRG | X | 1 | 9.522 | −47.076 | 5.797 | 1.00 | 72.70 | N |
| ATOM | 4643 | CAN | DRG | X | 1 | 11.507 | −47.933 | 6.034 | 1.00 | 72.48 | C |
| ATOM | 4645 | CBB | DRG | X | 1 | 11.472 | −47.322 | 4.841 | 1.00 | 70.35 | C |
| ATOM | 4646 | CAM | DRG | X | 1 | 12.399 | −47.194 | 3.885 | 1.00 | 68.99 | C |
| ATOM | 4648 | CBD | DRG | X | 1 | 10.238 | −46.788 | 4.694 | 1.00 | 71.35 | C |
| ATOM | 4649 | CAK | DRG | X | 1 | 9.904 | −46.101 | 3.588 | 1.00 | 70.04 | C |
| ATOM | 4651 | CAH | DRG | X | 1 | 10.829 | −45.944 | 2.557 | 1.00 | 69.73 | C |
| ATOM | 4653 | CAY | DRG | X | 1 | 12.120 | −46.483 | 2.698 | 1.00 | 68.65 | C |
| ATOM | 4654 | CAU | DRG | X | 1 | 13.062 | −46.359 | 1.655 | 1.00 | 65.55 | C |
| ATOM | 4655 | CAA | DRG | X | 1 | 14.584 | −46.485 | 1.890 | 1.00 | 63.40 | C |

TABLE 2-continued

| ATOM | 4659 | NAO | DRG | X | 1 | 12.580 | −46.316 | 0.403 | 1.00 | 64.85 | N |
|---|---|---|---|---|---|---|---|---|---|---|---|
| ATOM | 4660 | NAQ | DRG | X | 1 | 13.390 | −46.274 | −0.687 | 1.00 | 65.79 | N |
| ATOM | 4662 | CAT | DRG | X | 1 | 12.771 | −46.168 | −1.900 | 1.00 | 65.39 | C |
| ATOM | 4663 | NAD | DRG | X | 1 | 13.474 | −46.101 | −3.044 | 1.00 | 64.35 | N |
| ATOM | 4666 | NAC | DRG | X | 1 | 11.432 | −46.108 | −1.988 | 1.00 | 65.90 | N |
| ATOM | 4669 | O | HOH | C | 1 | 20.930 | −26.484 | −5.467 | 1.00 | 37.35 | O |
| ATOM | 4672 | O | HOH | C | 2 | 11.241 | −67.537 | 0.693 | 1.00 | 52.17 | O |
| ATOM | 4675 | O | HOH | C | 3 | 11.866 | −13.585 | 19.362 | 1.00 | 66.67 | O |
| ATOM | 4678 | O | HOH | C | 4 | 21.551 | −24.045 | 2.097 | 1.00 | 53.00 | O |
| ATOM | 4681 | O | HOH | C | 5 | 15.849 | −68.979 | −1.703 | 1.00 | 47.22 | O |
| ATOM | 4684 | O | HOH | C | 6 | 19.141 | −25.650 | 2.896 | 1.00 | 41.05 | O |
| ATOM | 4687 | O | HOH | C | 7 | 15.162 | −48.681 | −10.570 | 1.00 | 77.34 | O |
| ATOM | 4690 | O | HOH | C | 8 | 8.238 | −43.990 | 1.181 | 1.00 | 55.79 | O |
| ATOM | 4693 | O | HOH | C | 9 | 23.345 | −32.040 | 13.063 | 1.00 | 45.27 | O |
| ATOM | 4696 | O | HOH | C | 10 | 5.313 | −40.618 | 25.009 | 1.00 | 70.54 | O |
| ATOM | 4699 | O | HOH | C | 11 | 14.643 | −20.120 | −18.788 | 1.00 | 52.15 | O |
| ATOM | 4702 | O | HOH | C | 12 | 13.131 | −16.510 | −7.994 | 1.00 | 49.32 | O |
| ATOM | 4705 | O | HOH | C | 13 | 24.923 | −71.081 | −1.533 | 1.00 | 61.12 | O |
| ATOM | 4708 | O | HOH | C | 14 | 27.904 | −26.745 | 9.990 | 1.00 | 64.30 | O |
| ATOM | 4711 | O | HOH | C | 15 | 24.202 | −45.754 | 5.931 | 1.00 | 60.23 | O |
| ATOM | 4714 | O | HOH | C | 16 | 11.295 | −32.748 | −0.676 | 1.00 | 47.49 | O |
| ATOM | 4717 | O | HOH | C | 17 | 5.143 | −16.239 | −1.389 | 1.00 | 49.61 | O |
| ATOM | 4720 | O | HOH | C | 18 | 14.008 | −24.975 | −6.302 | 1.00 | 44.88 | O |
| ATOM | 4723 | O | HOH | C | 19 | 24.591 | −60.631 | 9.238 | 1.00 | 63.84 | O |
| ATOM | 4726 | O | HOH | C | 20 | 23.249 | −62.769 | 9.802 | 1.00 | 62.08 | O |
| ATOM | 4729 | O | HOH | C | 21 | 1.344 | −44.323 | 3.749 | 1.00 | 57.24 | O |
| ATOM | 4732 | O | HOH | C | 22 | 14.938 | −23.179 | −8.497 | 1.00 | 48.63 | O |
| ATOM | 4735 | O | HOH | C | 23 | 12.315 | −45.744 | −5.727 | 1.00 | 62.98 | O |
| ATOM | 4738 | O | HOH | C | 24 | −1.044 | −20.065 | 21.638 | 1.00 | 67.43 | O |
| ATOM | 4741 | O | HOH | C | 25 | 7.123 | −15.123 | −2.722 | 1.00 | 50.52 | O |
| ATOM | 4744 | O | HOH | C | 26 | 22.377 | −58.926 | −5.005 | 1.00 | 69.12 | O |
| ATOM | 4747 | O | HOH | C | 27 | 17.716 | −27.416 | 29.164 | 1.00 | 58.71 | O |
| ATOM | 4750 | O | HOH | C | 28 | 21.799 | −61.267 | −4.095 | 1.00 | 62.77 | O |
| ATOM | 4753 | O | HOH | C | 29 | 19.416 | −51.379 | 13.861 | 1.00 | 66.09 | O |
| ATOM | 4756 | O | HOH | C | 30 | 20.031 | −29.184 | 33.548 | 1.00 | 51.93 | O |
| ATOM | 4759 | O | HOH | C | 31 | 7.546 | −48.748 | −2.331 | 1.00 | 66.88 | O |
| ATOM | 4762 | O | HOH | C | 32 | 8.097 | −37.892 | −6.319 | 1.00 | 66.69 | O |
| ATOM | 4765 | O | HOH | C | 33 | 16.004 | −20.218 | −0.585 | 1.00 | 48.10 | O |
| ATOM | 4768 | O | HOH | C | 34 | 17.264 | −22.295 | −12.830 | 1.00 | 60.90 | O |
| ATOM | 4771 | O | HOH | C | 35 | 2.962 | −47.830 | 6.211 | 1.00 | 67.47 | O |
| ATOM | 4774 | O | HOH | C | 36 | 20.468 | −64.851 | −3.672 | 1.00 | 60.63 | O |
| ATOM | 4777 | O | HOH | C | 37 | 2.823 | −16.881 | 20.692 | 1.00 | 65.77 | O |
| ATOM | 4780 | O | HOH | C | 38 | 19.443 | −55.271 | −11.289 | 1.00 | 70.17 | O |
| ATOM | 4783 | O | HOH | C | 39 | 17.373 | −14.509 | −14.627 | 1.00 | 66.09 | O |
| ATOM | 4786 | O | HOH | C | 40 | 17.414 | −12.269 | −17.448 | 1.00 | 53.14 | O |
| ATOM | 4789 | O | HOH | C | 41 | 22.605 | −66.406 | −3.102 | 1.00 | 71.61 | O |
| ATOM | 4792 | O | HOH | C | 42 | 16.408 | −16.870 | 10.741 | 1.00 | 49.77 | O |

What is claimed is:

1. A method of treating an Hepatitis C Virus infection in a patient, comprising providing a therapeutically effective amount, to a patient in need thereof, of a compound of Formula I

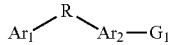

Formula I or a pharmaceutically acceptable salt thereof, wherein:

$G_1$ is a group of the formula

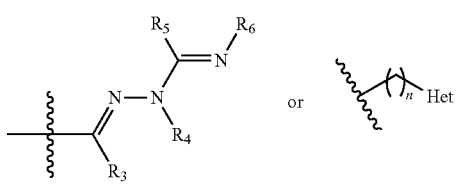

where n is 0, 1, 2, 3, or 4 and Het is a 5- or 6-membered heteroaryl group containing 1 to 4 heteroatoms independently chosen from N, O, and S, which Het is optionally substituted;

$Ar_1$ is a 6,6-fused or 6,5 bicyclic aromatic ring system containing only carbon ring atoms or containing 1, 2, or 3 nitrogen ring atoms with remaining atoms being carbon, which An is optionally substituted, $Ar_2$ is phenyl, a 6-membered heteroaryl ring containing 1 or 2 nitrogen ring atoms, or a 6,5 bicyclic aromatic ring system containing 1, 2, or 3, nitrogen atoms, with remaining atoms being carbon, which $Ar_2$ is optionally substituted;

R is a group of the formula —NH(C=O)— or —(O=C)NH—; $R_3$ is hydrogen or $C_1$-$C_6$alkyl;

$R_3$ is taken together with an $Ar_2$ substituent to form a 5- or 6-membered unsaturated or aromatic $R_3$/$Ar_2$ ring having 0, 1, or 2 heteroatoms independently chosen from N, O, and S, which $R_3$/$Ar_2$ ring is optionally substituted;

$R_4$ is hydrogen or $C_1$-$C_6$alkyl;

$R_5$ is amino, —NHOH, or optionally substituted mono- or di-alkylamino, and $R_6$ is hydrogen or hydroxyl; or $R_5$ and $R_6$ are taken together to form a 5 or 6-membered heterocyclic ring, which is unsaturated or aromatic and which contains 0, 1, or 2 additional heteroatoms chosen from N, S, and O, which 5 or 6-membered heterocyclic ring is optionally substituted.

2. A method of inhibiting Hepatitis C Virus replication comprising contacting the virus with a concentration of a compound sufficient to inhibit Hepatitis C Virus replication in vitro, wherein the compound is a compound of Formula I

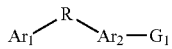

Formula I or a pharmaceutically acceptable salt thereof, wherein:
$G_1$ is a group of the formula

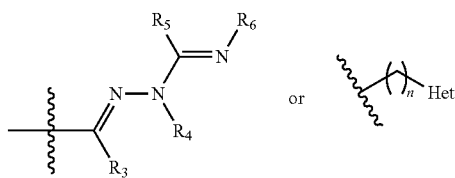

where n is 0, 1, 2, 3, or 4 and Het is a 5- or 6-membered heteroaryl group containing 1 to 4 heteroatoms independently chosen from N, O, and S; which Het is optionally substituted;

$Ar_1$ is a 6,6-fused or 6,5 bicyclic aromatic ring system containing only carbon ring atoms or containing 1, 2, or 3 nitrogen ring atoms with remaining atoms being carbon, which $Ar_1$ is optionally substituted, $Ar_2$ is phenyl, a 6-membered heteroaryl ring containing 1 or 2 nitrogen ring atoms, or a 6,5 bicyclic aromatic ring system containing 1, 2, or 3, nitrogen atoms, with remaining atoms being carbon, which $Ar_2$ is optionally substituted;

R is a group of the formula —NH(C=O)— or —(O=C)NH—; $R_3$ is hydrogen or $C_1$-$C_6$alkyl;

$R_3$ is taken together with an $Ar_2$ substituent to form a 5- or 6-membered unsaturated or aromatic $R_3$/$Ar_2$ ring having 0, 1, or 2 heteroatoms independently chosen from N, O, and S, which $R_3$/$Ar_2$ ring is optionally substituted;

$R_4$ is hydrogen or $C_1$-$C_6$alkyl;

$R_5$ is amino, —NHOH, or optionally substituted mono- or dialkylamino, and $R_6$ is hydrogen or hydroxyl; or $R_5$ and $R_6$ are taken together to form a 5 or 6-membered heterocyclic ring, which is unsaturated or aromatic and which contains 0, 1, or 2 additional heteroatoms chosen from N, S, and O, which 5 or 6-membered heterocyclic ring is optionally substituted.

3. The method of claim 1 wherein the compound of Formula I is administered together with a therapeutically effective amount of at least one additional active agent.

4. The method of claim 3, wherein the additional active agent is an interferon or an anti-HCV agent that is not a compound or salt of Formula I.

5. The method of claim 4, wherein the anti-HCV agent that is not a compound or salt of Formula I is an HCV protease inhibitor, an HCV NS3 inhibitor, and HCV NS4a inhibitor, an HCV NS5a, or an HCV NS5b inhibitor.

6. The method of claim 1, wherein R is —NH(C=O)—.

7. The method of claim 1, wherein R is —(C=O)NH—.

8. The method of claim 1, wherein $G_1$ is a group of the formula

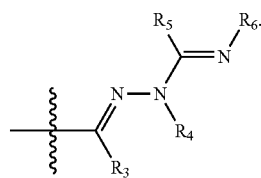

9. The method of claim 1, wherein $G_1$ is a group of the formula

where n is 0, 1, 2, 3, or 4 and Het is a 5- or 6-membered heteroaryl group containing 1 to 3 heteroatoms independently chosen from N, O, and S; which Het is optionally substituted.

10. The method of claim 9 where n is 0 or 1 and Het is an optionally substituted imidazolyl group.

11. The method of claim 1, wherein $Ar_1$ and $Ar_1$ are independently chosen from quinolinyl, isoquinolinyl, benzimidazolyl, indolyl, naphthyl, phenyl, pyridyl, and pyrimidinyl groups, wherein $Ar_1$ is unsubstituted or substituted with one or more substituents independently chosen from halogen, hydroxyl, amino, nitro, cyano, —COOH, —CONH$_2$, $C_1$-$C_6$alkyl, $C_1$-$C_6$alkoxy, $C_2$-$C_6$alkanoyl, $C_3$-$C_7$cycloalkyl, 5- to 7-membered heterocycloalkyl, (mono- or di-$C_1$-$C_4$alkylamino)$C_0$-$C_4$alkyl, $C_1$-$C_2$haloalkyl, and $C_1$-$C_2$haloalkoxy; and $Ar_2$ is unsubstituted or substituted with one or more substituents independently chosen from halogen, hydroxyl, amino, nitro, cyano, $C_1$-$C_4$alkyl, $C_1$-$C_4$alkoxy, (mono- or di-$C_1$-$C_4$alkylamino)$C_0$-$C_4$alkyl, $C_1$-$C_2$haloalkyl, and $C_1$-$C_2$haloalkoxy.

12. The method of claim 11, wherein $Ar_2$ is benzimidazolyl, which is unsubstituted or substituted with one or more substituents independently chosen from halogen, hydroxyl, nitro, amino, $C_1$-$C_2$alkyl, $C_1$-$C_2$alkoxy, (mono- or di-$C_1$-$C_2$alkylamino)$C_0$-$C_2$alkyl, $C_1$-$C_2$haloalkyl, and $C_1$-$C_2$haloalkoxy.

13. The method of claim 1, wherein the compound or salt of Formula I is a compound of the formula:

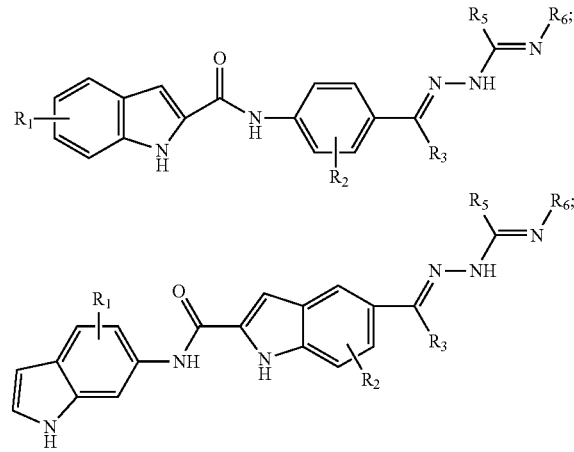

-continued or

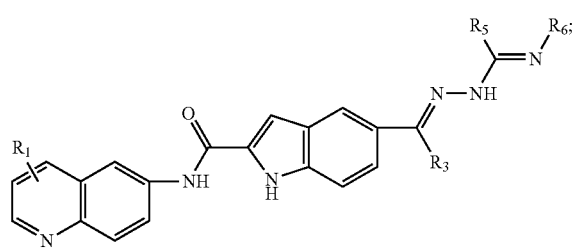

where
R₁ is absent or is 1 or more substituents bound to either ring of the bicyclic system and independently selected from halogen, hydroxyl, amino, nitro, cyano, —COOH, —CONH₂, $C_1$-$C_6$alkyl, $C_1$-$C_6$alkoxy, $C_2$-$C_6$alkanoyl, $C_3$-$C_7$cycloalkyl, 5- to 7-membered heterocycloalkyl, (mono- or di-$C_1$-$C_4$alkylamino)$C_0$-$C_4$alkyl, $C_1$-$C_2$haloalkyl, and $C_1$-$C_2$haloalkoxy; and R₂ is absent or is 1 or more substituents independently selected from halogen, hydroxyl, amino, nitro, cyano, —COOH, —CONH₂, $C_1$-$C_6$alkyl, $C_1$-$C_6$alkoxy, $C_2$-$C_6$alkanoyl, (mono- or di-$C_1$-$C_4$alkylamino)$C_0$-$C_4$alkyl, $C_1$-$C_2$haloalkyl, and $C_1$-$C_2$haloalkoxy.

14. The method of claim 13, wherein R₃ is methyl, R₅ is amino, and R₆ is hydrogen.

15. The method of claim 13, wherein R₁ is 1 or 2 substituents independently chosen from halogen, nitro, acetyl, $C_1$-$C_2$alkyl, and $C_1$-$C_2$alkoxy.

16. The method of claim 13, wherein R₂ is absent.

17. The method of claim 1, wherein the compound is

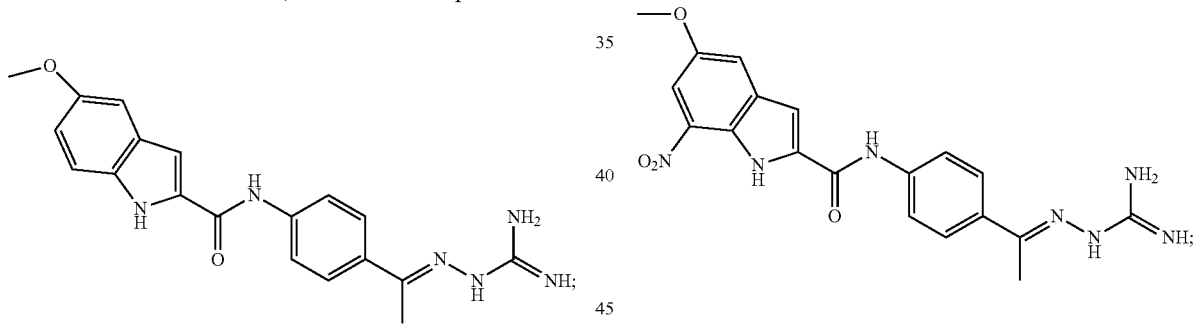

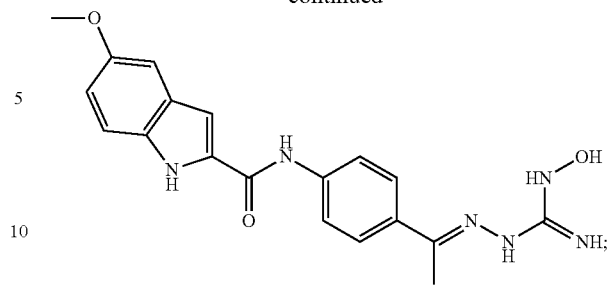

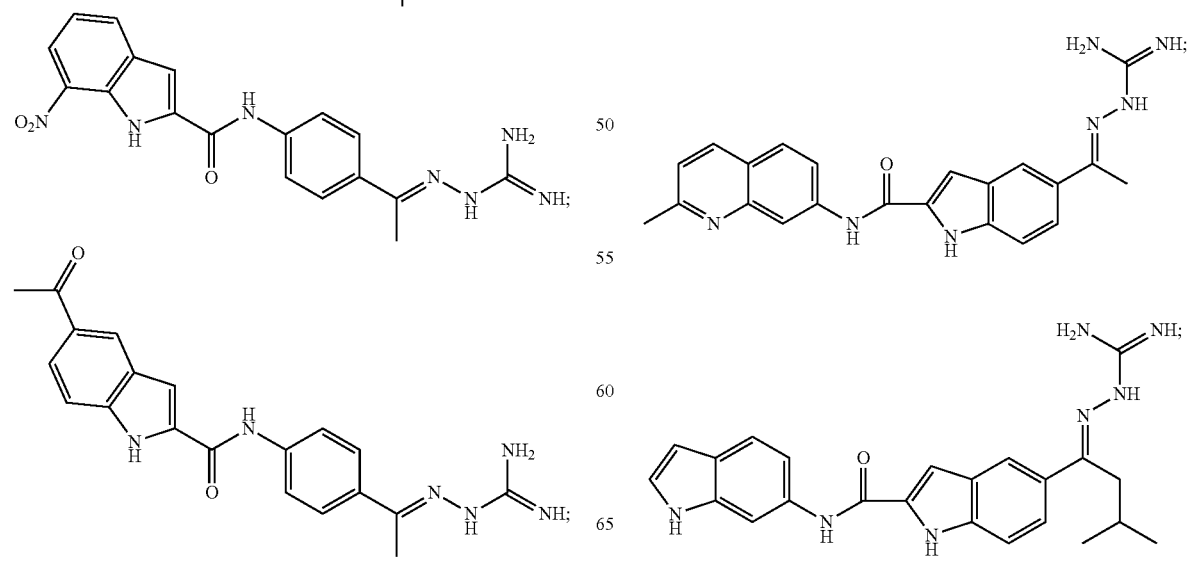

-continued

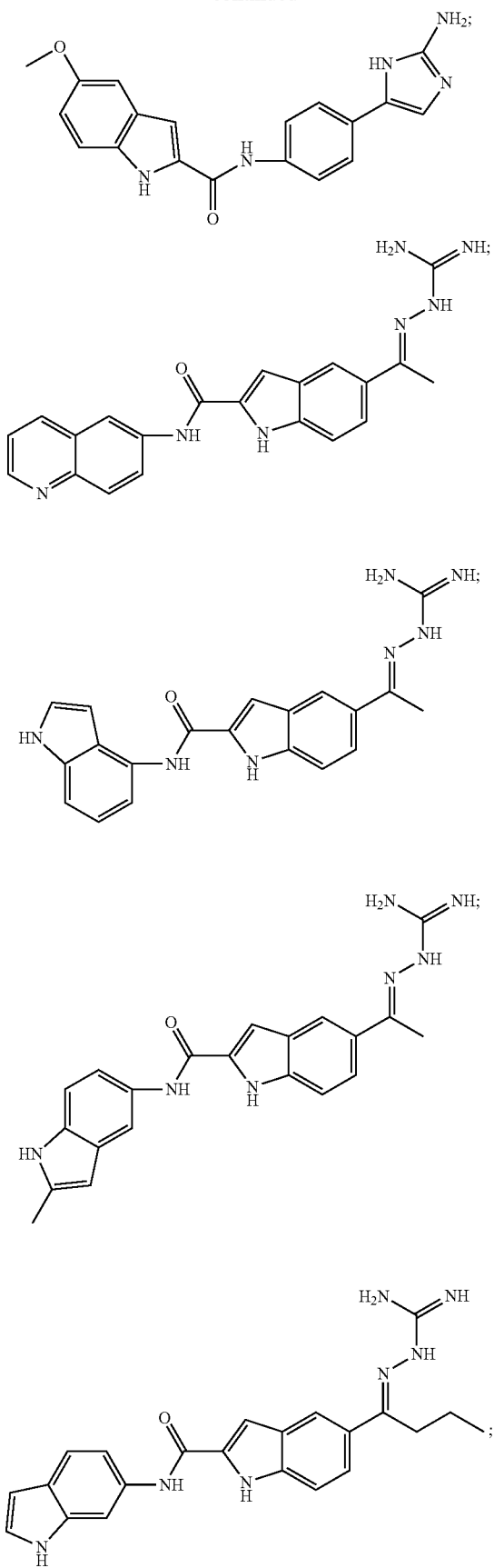

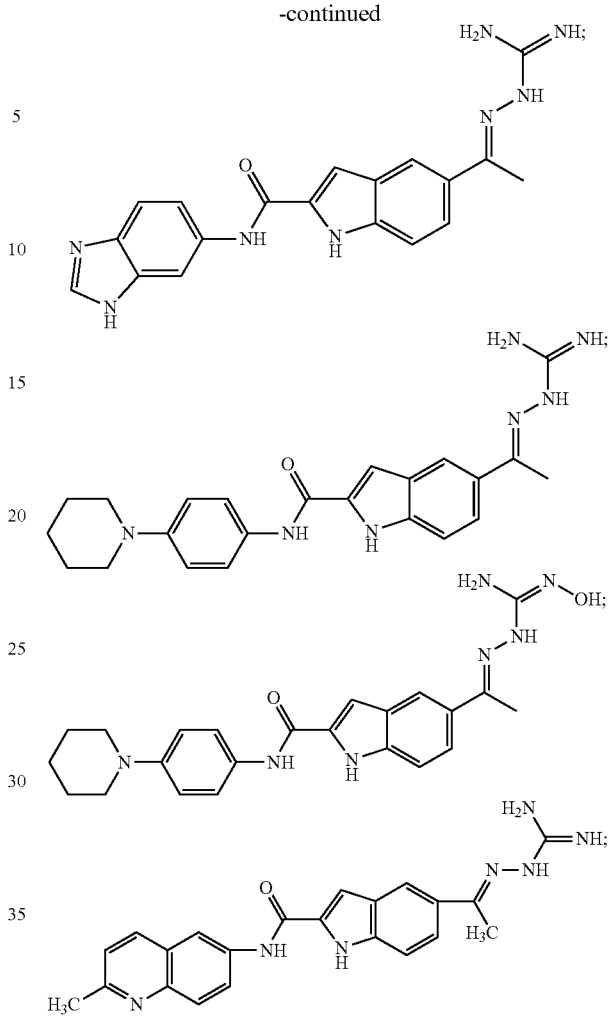

or a salt of any of the foregoing.

18. A method of treating Hepatitis C Virus infection comprising
(i) informing a patient that a compound of Formula I or a pharmaceutically acceptable salt thereof is useful for treating Hepatitis C Virus infection; and
(ii) providing the compound of Formula I in a container to the patient, wherein the compound of Formula I is

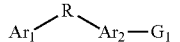

Formula I or a pharmaceutically acceptable salt thereof, wherein:
G$_1$ is a group of the formula

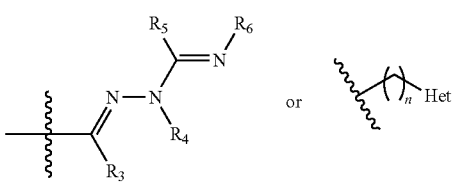

where n is 0, 1, 2, 3, or 4 and Het is a 5- or 6-membered heteroaryl group containing 1 to 4 heteroatoms independently chosen from N, O, and S; which Het is optionally substituted;

$Ar_1$ is a 6,6-fused or 6,5 bicyclic aromatic ring system containing only carbon ring atoms or containing 1, 2, or 3 nitrogen ring atoms with remaining atoms being carbon, which An is optionally substituted, $Ar_2$ is phenyl, a 6-membered heteroaryl ring containing 1 or 2 nitrogen ring atoms, or a 6,5 bicyclic aromatic ring system containing 1, 2, or 3, nitrogen atoms, with remaining atoms being carbon, which $Ar_2$ is optionally substituted;

R is a group of the formula —NH(C=O)— or —(O=C)NH—; $R_3$ is hydrogen or $C_1$-$C_6$alkyl;

$R_3$ is taken together with an $Ar_2$ substituent to form a 5- or 6-membered unsaturated or aromatic $R_3$/$Ar_2$ ring having 0, 1, or 2 heteroatoms independently chosen from N, O, and S, which $R_3$/$Ar_2$ ring is optionally substituted;

$R_4$ is hydrogen or $C_1$-$C_6$alkyl;

$R_5$ is amino, —NHOH, or optionally substituted mono- or di-alkylamino, and $R_6$ is hydrogen or hydroxyl; or $R_5$ and $R_6$ are taken together to form a 5 or 6-membered heterocyclic ring, which is unsaturated or aromatic and which contains 0, 1, or 2 additional heteroatoms chosen from N, S, and O, which 5 or 6-membered heterocyclic ring is optionally substituted.

19. The method of claim 1, wherein the compound or salt of Formula I is administered together with another active agent.

20. A crystal comprising a checkpoint kinase 2 in crystalline form, wherein the crystal comprises a chemical entity bound to the active site of the checkpoint kinase 2, wherein the chemical entity comprises a compound of Formula I

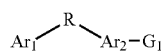

Formula I or a pharmaceutically acceptable salt thereof, wherein:
$G_1$ is a group of the formula

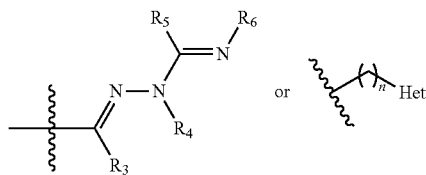

where n is 0, 1, 2, 3, or 4 and Het is a 5- or 6-membered heteroaryl group containing 1 to 4 heteroatoms independently chosen from N, O, and S, which Het is optionally substituted;

$Ar_1$ is a 6,6-fused or 6,5 bicyclic aromatic ring system containing only carbon ring atoms or containing 1, 2, or 3 nitrogen ring atoms with remaining atoms being carbon, which An is optionally substituted, $Ar_2$ is phenyl, a 6-membered heteroaryl ring containing 1 or 2 nitrogen ring atoms, or a 6,5 bicyclic aromatic ring system containing 1, 2, or 3, nitrogen atoms, with remaining atoms being carbon, which $Ar_2$ is optionally substituted;

R is a group of the formula —NH(C=O)— or —(O=C)NH—; $R_3$ is hydrogen or $C_1$-$C_6$alkyl;

$R_3$ is taken together with an $Ar_2$ substituent to form a 5- or 6-membered unsaturated or aromatic $R_3$/$Ar_2$ ring having 0, 1, or 2 heteroatoms independently chosen from N, O, and S, which $R_3$/$Ar_2$ ring is optionally substituted;

$R_4$ is hydrogen or $C_1$-$C_6$alkyl;

$R_5$ is amino, —NHOH, or optionally substituted mono- or di-alkylamino, and $R_6$ is hydrogen or hydroxyl; or $R_5$ and $R_6$ are taken together to form a 5 or 6-membered heterocyclic ring, which is unsaturated or aromatic and which contains 0, 1, or 2 additional heteroatoms chosen from N, S, and O, which 5 or 6-membered heterocyclic ring is optionally substituted.

21. The crystal of claim 20 wherein the chemical entity comprises:

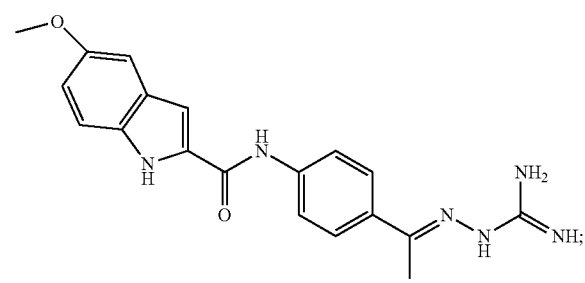

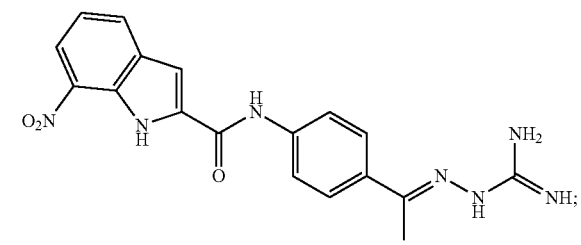

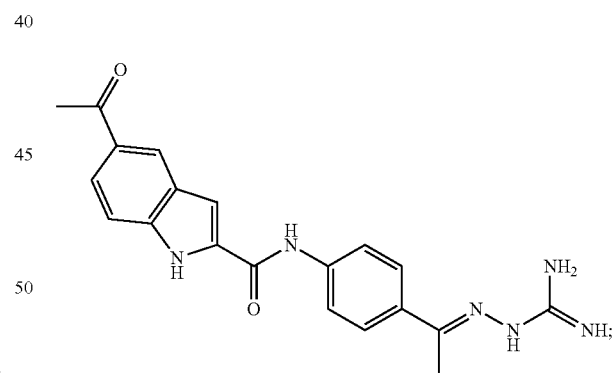

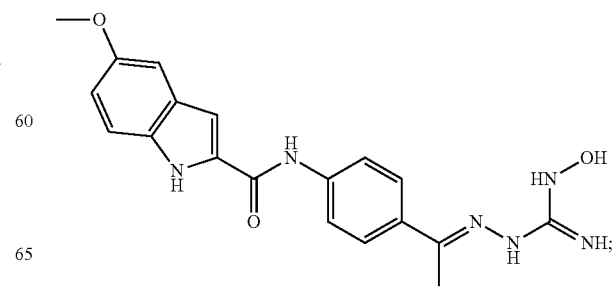

97
-continued
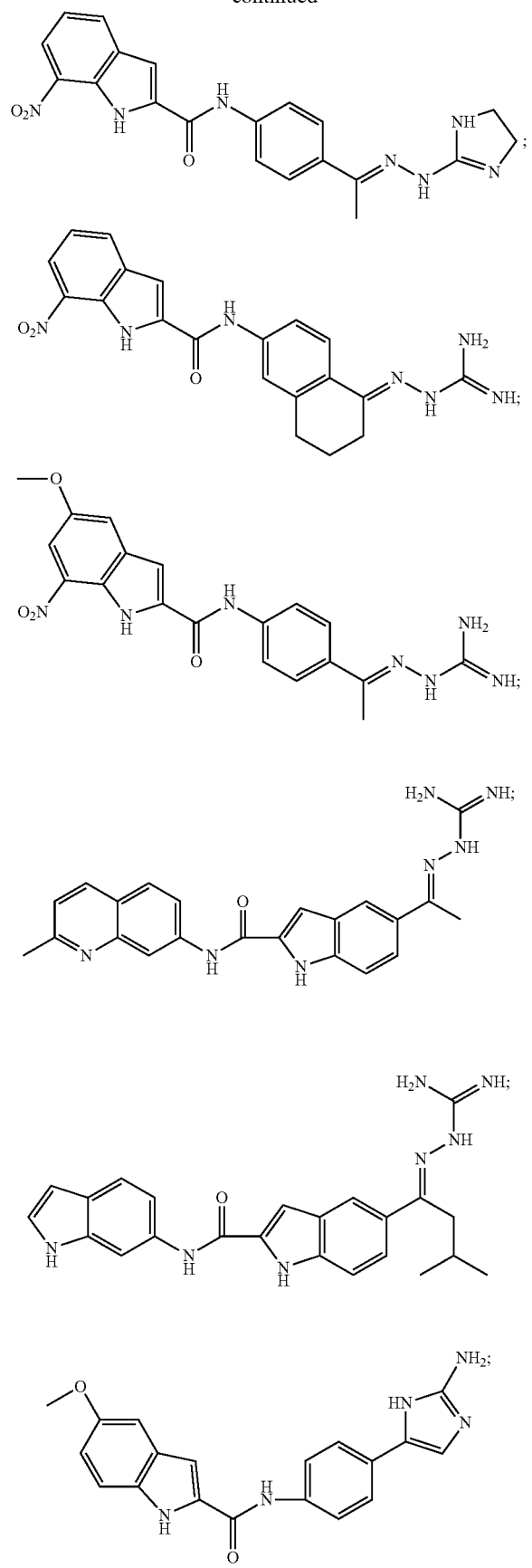
98
-continued
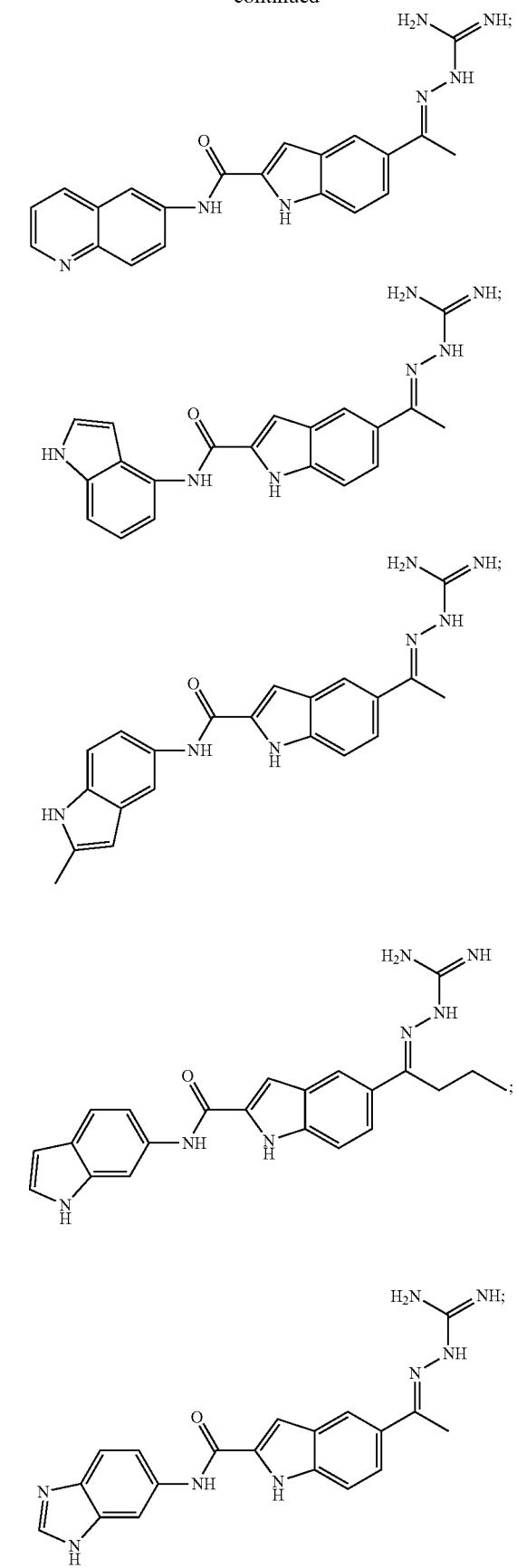

-continued
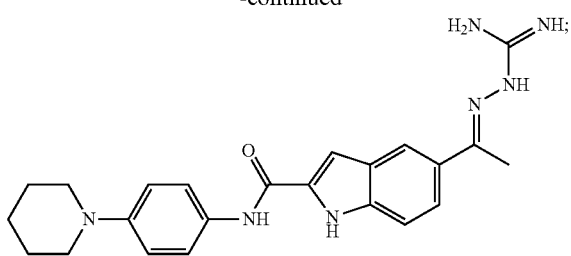
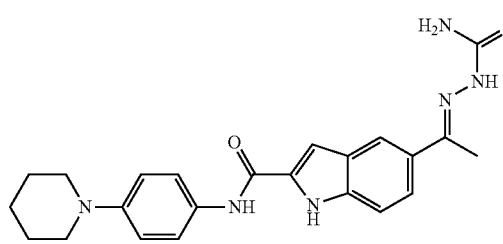
-continued
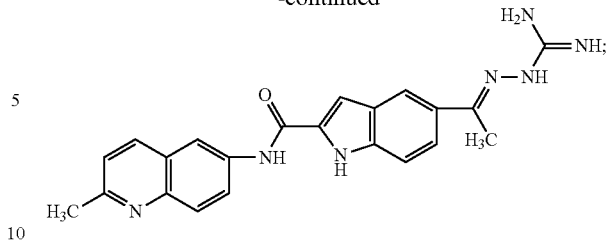
or a salt of any of the foregoing.
22. The crystal of claim 20 wherein the chemical entity comprises:
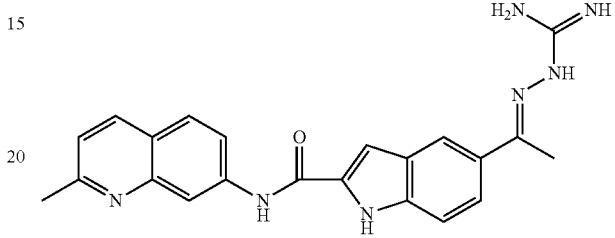
or a salt thereof.
23. The crystal of claim 20, further comprising a three-dimensional structure wherein the three-dimensional structure comprises atoms and atomic coordinates set forth in Table 2.
* * * * *